US009824179B2

(12) United States Patent
Sherwood et al.

(10) Patent No.: US 9,824,179 B2
(45) Date of Patent: Nov. 21, 2017

(54) DIAGNOSIS OF LYMPHOID MALIGNANCIES AND MINIMAL RESIDUAL DISEASE DETECTION

(71) Applicants: Adaptive Biotechnologies Corporation, Seattle, WA (US); Fred Hutchinson Cancer Research Center, Seattle, WA (US)

(72) Inventors: Anna M. Sherwood, Seattle, WA (US); Harlan S. Robins, Seattle, WA (US)

(73) Assignees: ADAPTIVE BIOTECHNOLOGIES CORP., Seattle, WA (US); FRED HUTCHINSON CANCER RESEARCH CENTER, Seattle, WA (US)

(*) Notice: Subject to any disclaimer, the term of this patent is extended or adjusted under 35 U.S.C. 154(b) by 0 days.

(21) Appl. No.: 13/708,847

(22) Filed: Dec. 7, 2012

(65) Prior Publication Data

US 2013/0253842 A1 Sep. 26, 2013

Related U.S. Application Data

(60) Provisional application No. 61/569,118, filed on Dec. 9, 2011, provisional application No. 61/644,294, filed on May 8, 2012, provisional application No. 61/726,489, filed on Nov. 14, 2012.

(51) Int. Cl.
*G01N 33/48* (2006.01)
*G06F 19/22* (2011.01)
*C12Q 1/68* (2006.01)

(52) U.S. Cl.
CPC .......... *G06F 19/22* (2013.01); *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 4,474,754 A | 10/1984 | Shimizu et al. |
| 4,683,195 A | 7/1987 | Mullis et al. |
| 4,683,202 A | 7/1987 | Mullis |
| 4,751,188 A | 6/1988 | Valet |
| 4,800,159 A | 1/1989 | Mullis et al. |
| 4,876,189 A | 10/1989 | Schetters |
| 4,942,124 A | 7/1990 | Church |
| 4,965,188 A | 10/1990 | Mullis et al. |
| 5,075,217 A | 12/1991 | Weber |
| 5,126,022 A | 6/1992 | Soane et al. |
| 5,149,625 A | 9/1992 | Church |
| 5,168,038 A | 12/1992 | Tecott et al. |
| 5,189,147 A | 2/1993 | Saito et al. |
| 5,210,015 A | 5/1993 | Gelfand et al. |
| 5,213,960 A | 5/1993 | Chang |
| 5,231,012 A | 7/1993 | Mosmann et al. |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,364,759 A | 11/1994 | Caskey |
| 5,399,491 A | 3/1995 | Kacian et al. |
| 5,418,134 A | 5/1995 | Morley |
| 5,449,752 A | 9/1995 | Fujii et al. |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

Kneba et al., "Analysis of Rearranged T-cell Receptor /?-Chain Genes by Polymerase Chain Reaction (PCR) DNA Sequencing and Automated High Resolution PCR Fragment Analysis" (Blood, vol. 86 (1995) pp. 3930-3937).*

Theodorou et al. "VJ Rearrangements of the TCRγ Locus in Peripheral T-Cell Lymphomas: Analysis by Polymerase Chain Reaction and Denaturing Gradient Gel Electrophoresis," (Journal of Pathology, vol. 178 (1996) 303-310).*

Rachlin et al. "MuPlex: multi-objective multiplex PCR assay design" (Nucleic Acids Research, vol. 33 (2005) pp. W544-W547).*

Dash et al. 'Paired analysis of TCR_ _and TCR_ _chains at the single-cell level in mice, Journal of Clinical Investigation vol. 121 (2011) pp. 288-295.*

(Continued)

*Primary Examiner* — Anna Skibinsky
(74) *Attorney, Agent, or Firm* — Cooley LLP

(57) ABSTRACT

Methods are described for diagnosis of a lymphoid hematological malignancy in a subject prior to treatment, and for detecting minimal residual disease (MRD) in the subject after treatment for the malignancy, by high throughput quantitative sequencing (HTS) of multiple unique adaptive immune receptor (TCR or Ig) encoding DNA molecules that have been amplified from DNA isolated from blood samples or other lymphoid cell-containing samples. Amplification employs oligonucleotide primer sets designed to amplify CDR3-encoding sequences within substantially all possible human VDJ or VJ combinations. Disease-characteristic adaptive immune receptor clonotypes occur, prior to treatment, at a relative frequency of at least 15-30% of rearranged receptor CDR3-encoding gene regions. Following treatment, persistence of at least one such clonotype at a detectable frequency of at least $10^{-6}$ or at least $10^{-5}$ receptor CDR3-encoding regions indicates MRD. Improved quantitative embodiments are provided by inclusion of a template composition for amplification factor determination and related methods.

21 Claims, 37 Drawing Sheets

(56) References Cited

U.S. PATENT DOCUMENTS

| | | |
|---|---|---|
| 5,498,392 A | 3/1996 | Wilding et al. |
| 5,506,126 A | 4/1996 | Seed et al. |
| 5,587,128 A | 12/1996 | Wilding et al. |
| 5,627,037 A | 5/1997 | Ward |
| 5,627,052 A | 5/1997 | Schrader |
| 5,635,354 A | 6/1997 | Kourilsky et al. |
| 5,667,967 A | 9/1997 | Steinman et al. |
| 5,698,396 A | 12/1997 | Pfreundschuh |
| 5,699,798 A | 12/1997 | Hochman et al. |
| 5,741,676 A | 4/1998 | Fuller |
| 5,742,598 A | 4/1998 | Dunn et al. |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner |
| 5,854,033 A | 12/1998 | Lizardi |
| 5,858,195 A | 1/1999 | Ramsey |
| 5,925,517 A | 7/1999 | Tyagi et al. |
| 5,935,793 A | 8/1999 | Wong |
| 5,969,108 A | 10/1999 | McCafferty et al. |
| 5,981,176 A | 11/1999 | Wallace |
| 5,981,179 A | 11/1999 | Lorinez et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,087,096 A | 7/2000 | Dau |
| 6,090,592 A | 7/2000 | Adams et al. |
| 6,143,496 A | 11/2000 | Brown et al. |
| 6,172,214 B1 | 1/2001 | Brenner |
| 6,174,670 B1 | 1/2001 | Wittwer et al. |
| 6,258,540 B1 | 7/2001 | Lo et al. |
| 6,258,568 B1 | 7/2001 | Nyren |
| 6,300,070 B1 | 10/2001 | Boles et al. |
| 6,416,948 B1 | 7/2002 | Pilarski |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seeger |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,792,355 B2 | 9/2004 | Hansen et al. |
| 6,794,499 B2 | 9/2004 | Wengel et al. |
| 6,806,079 B1 | 10/2004 | McCafferty et al. |
| 6,858,412 B2 | 2/2005 | Willis |
| 6,919,434 B1 | 7/2005 | Goto et al. |
| 6,964,850 B2 | 11/2005 | Bevilacqua et al. |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,566 B2 | 7/2008 | Miyata |
| 7,432,084 B2 | 10/2008 | Shoemaker |
| 7,537,897 B2 | 5/2009 | Brenner |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer |
| 7,700,323 B2 | 4/2010 | Willis et al. |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 8,883,418 B2 * | 11/2014 | Pasqual ............... C12Q 1/6883 |
| | | 435/6.12 |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 | 1/2016 | Faham et al. |
| 9,365,901 B2 | 6/2016 | Pepin et al. |
| 9,416,420 B2 | 8/2016 | Faham et al. |
| 9,512,487 B2 | 12/2016 | Faham et al. |
| 9,528,160 B2 | 12/2016 | Pepin et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0134326 A1 | 7/2003 | Hansen |
| 2003/0162197 A1 | 8/2003 | Morley |
| 2003/0207300 A1 | 11/2003 | Matray et al. |
| 2004/0033490 A1 | 2/2004 | Laird et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann |
| 2005/0142577 A1 | 6/2005 | Jones et al. |
| 2005/0250147 A1 | 11/2005 | Macevicz |
| 2005/0255482 A1 | 11/2005 | Morley |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus |

(56) References Cited

U.S. PATENT DOCUMENTS

| | | |
|---|---|---|
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1* | 1/2007 | Loken et al. .............. 435/6 |
| 2007/0105105 A1 | 5/2007 | Clelland |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski |
| 2008/0286777 A1 | 11/2008 | Candeias |
| 2009/0026082 A1 | 1/2009 | Rothberg et al. |
| 2009/0053184 A1 | 2/2009 | Morgan |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0253581 A1 | 10/2009 | Van Eijk et al. |
| 2009/0264299 A1 | 10/2009 | Drmanac et al. |
| 2009/0280489 A1 | 11/2009 | Devinder |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0063743 A1 | 3/2010 | Gordon et al. |
| 2010/0105886 A1 | 4/2010 | Woudenberg |
| 2010/0137143 A1 | 6/2010 | Rothberg et al. |
| 2010/0151471 A1 | 6/2010 | Faham |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0330571 A1 | 12/2010 | Robins |
| 2011/0003291 A1 | 1/2011 | Pasqual |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0195253 A1 | 8/2011 | Hinz et al. |
| 2011/0207134 A1 | 8/2011 | Faham |
| 2011/0207135 A1 | 8/2011 | Faham et al. |
| 2011/0207617 A1 | 8/2011 | Faham et al. |
| 2011/0223607 A1 | 9/2011 | Qu et al. |
| 2011/0251099 A1 | 10/2011 | Visvanathan et al. |
| 2012/0035062 A1 | 2/2012 | Schultz et al. |
| 2012/0058902 A1 | 3/2012 | Livingston et al. |
| 2012/0071331 A1 | 3/2012 | Casbon |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0202710 A1* | 8/2012 | Sharma .................. C07K 16/00 506/14 |
| 2012/0220466 A1 | 8/2012 | Fire |
| 2013/0005584 A1 | 1/2013 | Faham |
| 2013/0017957 A1 | 1/2013 | Faham et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0150252 A1 | 6/2013 | Faham |
| 2013/0195900 A1* | 8/2013 | Dornmair ............ C12Q 1/6883 424/184.1 |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0267427 A1 | 10/2013 | Faham |
| 2013/0288237 A1 | 10/2013 | Robins et al. |
| 2013/0288254 A1* | 10/2013 | Pollack ................ G01N 27/447 435/6.12 |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0094376 A1 | 4/2014 | Han |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017652 A1 | 1/2015 | Robins |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0133317 A1 | 5/2015 | Robinson et al. |
| 2015/0167080 A1 | 6/2015 | Moorhead et al. |
| 2015/0203897 A1 | 7/2015 | Robins et al. |
| 2015/0218656 A1 | 8/2015 | Kirsch et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |

(56) References Cited

U.S. PATENT DOCUMENTS

| | | |
|---|---|---|
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |
| 2015/0299785 A1 | 10/2015 | Livingston et al. |
| 2015/0299786 A1 | 10/2015 | Robins et al. |
| 2015/0299800 A1 | 10/2015 | Faham et al. |
| 2016/0115532 A1 | 4/2016 | Faham |
| 2016/0201133 A1 | 7/2016 | Faham et al. |
| 2016/0251721 A1 | 9/2016 | Robins et al. |
| 2016/0251728 A1 | 9/2016 | Faham et al. |

FOREIGN PATENT DOCUMENTS

| | | |
|---|---|---|
| EP | 0303459 A2 | 2/1989 |
| EP | 0799897 A1 | 10/1997 |
| EP | 1549764 B1 | 7/2005 |
| EP | 0972081 B1 | 6/2007 |
| EP | 1544308 B1 | 1/2009 |
| EP | 2062982 | 5/2009 |
| EP | 2088432 A1 | 8/2009 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2009-523226 A | 6/2009 |
| WO | WO 2012/083225 | 6/1920 |
| WO | WO 93/01838 A1 | 2/1993 |
| WO | WO 2005/059176 A1 | 6/1995 |
| WO | WO 95/28481 A1 | 10/1995 |
| WO | WO 97/13877 A1 | 4/1997 |
| WO | WO 97/18330 A1 | 5/1997 |
| WO | WO 97/46706 A1 | 12/1997 |
| WO | WO 98/01738 | 1/1998 |
| WO | WO 98/44151 A1 | 10/1998 |
| WO | WO 99/19717 A1 | 4/1999 |
| WO | WO 99/20798 A1 | 4/1999 |
| WO | WO 02/24322 A2 | 3/2002 |
| WO | WO 03/008624 A2 | 1/2003 |
| WO | WO 03/044225 A2 | 5/2003 |
| WO | WO 03/052101 A1 | 6/2003 |
| WO | WO 03/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 | 10/2006 |
| WO | WO 2006/116155 A2 | 11/2006 |
| WO | WO 2006/138284 A2 | 12/2006 |
| WO | WO 2007/008759 A2 | 1/2007 |
| WO | WO 2007/134220 A2 | 11/2007 |
| WO | WO 2008/026927 A3 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011-106738 A2 | 9/2011 |
| WO | WO 2011/107595 A1 | 9/2011 |
| WO | WO 2011/139371 | 10/2011 |
| WO | WO 2011/139372 A1 | 11/2011 |
| WO | WO 2011/140433 A2 | 11/2011 |
| WO | WO 2012/027503 | 3/2012 |
| WO | WO 2012/048340 | 4/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 | 6/2012 |
| WO | WO 2012/083225 | 6/2012 |
| WO | WO 2012/142213 A2 | 10/2012 |
| WO | WO 2012/148497 A2 | 11/2012 |
| WO | WO 2012/159754 A2 | 11/2012 |
| WO | WO 2013/033721 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/130512 | 9/2013 |
| WO | WO 2013/131074 A1 | 9/2013 |
| WO | WO 2013/134162 | 9/2013 |
| WO | WO 2013/134302 | 9/2013 |
| WO | WO 2013/155119 | 10/2013 |
| WO | WO 2013/158936 | 10/2013 |
| WO | WO 2013/169957 A1 | 11/2013 |
| WO | WO 2013/181428 | 12/2013 |
| WO | WO 2013/188471 | 12/2013 |
| WO | WO 2013/188831 A1 | 12/2013 |
| WO | WO 2014/018460 | 1/2014 |
| WO | WO 2014/026031 | 2/2014 |
| WO | WO 2014/062945 | 4/2014 |
| WO | WO 2014/062959 | 4/2014 |
| WO | WO 2014/066184 | 5/2014 |
| WO | WO 2014/130685 | 8/2014 |
| WO | WO 2015/002908 A1 | 1/2015 |
| WO | WO 2015/013461 A2 | 1/2015 |
| WO | WO 2015/058159 A1 | 4/2015 |
| WO | WO 2016/138122 A1 | 9/2016 |

OTHER PUBLICATIONS

Robins et al. "Comprehensive assessment of T-cell receptor beta-chain diversity in alpha-T cells," Blood, vol. 114 (2009) pp. 4099-4107.*

Margot et al. "Primary CD20+CD10+CD8+ T-Cell Lymphoma of the Skin With Dual IgH and TCRβ Gene Rearrangement," Hematopathology, vol. 126 (2006) pp. 14-22.*

Sherwood et al. 'Deep Sequencing of the Human TCRg and TCRb Repertoires Suggests that TCRb Rearranges After ab and gd T Cell Commitment, vol. 1 (2011) pp. 1-7).*

PCT International Search Report and Written Opinion for PCT/US2013/040221, dated Sep. 23, 2013, 16 pages.

(56) References Cited

OTHER PUBLICATIONS

Henegariu, O., et al., "Multiplex PCR: Critical Parameters and Step-By-Step Protocol," Biotechniques, Informa HealthCare, Sep. 1, 1997, pp. 504-511, vol. 23, No. 3.
Larimore, K., et al., "Shaping of Human Germline IgH Repertoires Revealed by Deep Sequencing," The Journal of Immunology, Sep. 15, 2012, pp. 3221-3230, vol. 189, No. 6.
Reischl, U., et al., "Quantitative PCR A Survey of the Present Technology," Molecular Biotechnology, 1995, pp. 55-71.
Sint, D., et al., "Advances in multiplex PCR: balancing primer efficiencies and improving detection success," Methods in Ecology and Evolution, Jun. 28, 2012, pp. 898-905, vol. 3, No. 5.
Al-Lazikani, B., et al., "Standard Conformations for the Canonical Structures of Immunoglobulins," J. Mol. Biol., 1997, vol. 273, pp. 927-948.
Bahloul, M., et al., "Clinical impact of molecular diagnostics in low-grade lymphoma," Best Pract Res Clin Haematol, 2005; vol. 18, No. 1, pp. 97-111.
Bernardin et al., 'Estimate of the total number of CD8+ clonal expansions in healthy adults using a new DNA heteroduplex-tracking assay for CDR3 repertoire analysis' Journal of Immunological Methods, Mar. 1, 2003, vol. 274, No. I-2, pp. 159-175.
Berquam-Vrieze, K., et al., "Cell of origin strongly influences genetic selection in a mouse model of T-ALL," Blood, 2011, vol. 118, pp. 4646-4656.
Boyd, S., et al., "Measurement and Clinical Monitoring of Human Lymphocyte Clonality by Massively Parallel V-D-J Pyrosequencing," Science Translational Medicine, 2009, vol. 1, 12ra23, pp. 1-8.
Bradfield, SM., "Graft-versus-leukemia effect in acute lymphoblastic leukemia: the importance of tumor burden and early detection," Leukemia Mar. 25, 2004; vol. 18, pp. 1156-1158.
Campana, D., "Progress of Minimal Residual Disease Studies in Childhood Acute Leukemia," Curr Hematol Malig Rep, 2010, vol. 5, pp. 169-176.
Cave, H, et al., "Clinical Significance of minimal residual disease in childhood acute lymphoblastic leukemia," The New England Journal of Medicine, Aug. 27, 1998, vol. 339, pp. 591-598.
Chothia, C., et al., "Canonical structures for the hypervariable regions of immunoglobulins," J. Mol. Biol., 1987, vol. 196, pp. 901-917, Abstract only.
Chothia, C., et al., "Conformation of immunoglobulin hypervariable regions," Nature, Dec. 21/28, 1989, vol. 342, pp. 877-883.
Ciudad, J., et al., "Detection of abnormalities in B-cell differentiation pattern is a useful tool to predict relapse in precursor-B-ALL," British Journal of Haematology, 1999, vol. 104, pp. 695-705.
Coustan-Smith, E., et al., "Clinical importance of minimal residual disease in childhood acute lymphoblastic leukemia," Blood, Oct. 15, 2000, pp. 2691-2696, vol. 96, No. 8.
Coustan-Smith, E., et al., "Prognostic importance of measuring early clearance of leukemic cells by flow cytometry in childhood acute lymphoblastic leukemia," Blood Jul. 1, 2002; vol. 100, No. 1, pp. 52-58.
Coustan-Smith, E., et al., "Early T-cell precursor leukaemia: a subtype of very high-risk acute lymphoblastic leukaemia," Lancet Oncology, Feb. 2009, vol. 10, pp. 147-156.
Flohr, T., et al., "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia," Leukemia, 2008, vol. 22, pp. 771-782.
Kalos, M., et al., "T Cells with Chimeric Antigen Receptors Have Potent Antitiumor Effects and Can Establish Memory in Patients with Advanced Leukemia," Sci Transl Med., 2011, vol. 3, 95ra73, pp. 1-11.
Lucio, P., et al., "Flow cytometric analysis of normal B cell differentiation: a frame of reference for the detection of minimal residual disease in precursor-B-ALL," Leukemia, 1999, pp. 419-27, vol. 13.
Monod, M.Y., et al., "IMGT/JunctionAnalysis: the first tool for the analysis of the immnoglublulin and T cell receptor complex V-J and V-D-J JUNCTIONs," Bioinformatics, 2004, vol. 20, Suppl 1, pp. i379-385.
Pohl, G., et al., "Principle and applications of digital PCR," Expert Rev. Mol. Diagn., 2004, pp. 41-47, vol. 4, No. 1.
Robin, H., et al., "Comprehensice assessment of T-cell receptor β-chain diversity in αβ T cells," Blood, Nov. 5, 2009, pp. 4099-4107, vol. 114, No. 19.
Robins, H., et al., "Overlap and Effective Size of the Human CD8+ T Cell Receptor Repertoire," Science Transitional Medicine, Sep. 1, 2010, pp. 1-9, vol. 2, Issue 47.
Robins, H., et al., "Ultra-sensitive detection of rare T cell clones," Journal of Immunological Methods, 2011, pp. 14-19, vol. 375.
Rock, E., et al., "CDR3 Length in Antigen-specific Immune Receptors," J. Exp. Med., 1994, vol. 179, pp. 323-328.
Roshal, M., et al., "Immaturity Associated Antigens Are Lost During Induction for T Cell Lymphoblastic Leukemia: Implications for Minimal Residual Disease Detection," Cytometry Part B Clin Cytom, 2010, vol. 78, pp. 139-146.
Saada, R., et al., "Models for antigen receptor gene rearrangement: CDR3 length," Immunol. Cell Biol., 2007, vol. 85, pp. 323-332.
Schrappe, M., et al., "Late MRD response determines relapse rish overall and in subsets of childhood T-cell ALL: results of the AIEOP-BFM-ALL 2000 study," Blood, Aug. 25, 2011, vol. 118, No. 8, pp. 2077-2084.
Sherwood, A., et al., "Deep Sequencing of the Human TCRγ and TCRβ Repertoires Suggests that TCR β Rearranges After αβ and γδ T Cell Commitment," Science Translational Medicine, Jul. 6, 2011, pp. 1-7, vol. 3, Issue 90.
Szczepanski, T., et al., "Minimal residual disease in leukaemea patients," The Lancet Oncology, Jul. 2001, pp. 409-417, vol. 2.
Tewhey, R., et al., "Microdroplet-based PCR enrichment for large-scale targeted sequencing," Nature Biotechnology, Nov. 2009, pp. 1025-1031, vol. 27, No. 11.
Tewhey, R., et al., "Corrigendum: Microdroplet-based PCR enrichment for large-scale targeted sequencing," Nature Biotechnology, Feb. 2010, p. 178, vol. 28, No. 2.
Van Dongen, J.J., et al., "Prognostic value of minimal residual disease in acute lymphoblastic leukaemia in childhood," The Lancet Nov. 28, 1998, vol. 352, pp. 1731-1738.
Van Der Velden, et al., "Optimization of PCT-based minimal residual disease diagnostics for childhood acute lymphoblastic leukemia in a multi-center setting," Leukemia, 2007, vol. 21, pp. 706-713.
Van Der Velden, et al., "Analysis of minimal residual disease by Ig/TCR gene rearrangements: guidelines for interpretation of real-time quantitative PCR data," Leukemia, 2007, vol. 21, pp. 604-611.
Wood, B., "9-Color and 10-Color Flow Cytometry in the Clinical Laboratory," Arch Pathol Lab Med, May 2006, vol. 130, pp. 680-690.
PCT International Search Report and Written Opinion, PCT/US2012/068617, dated Jun. 13, 2013, 10 pages.
Arstila, et al., "A Direct Estimate of the Human αβ T Cell Receptor Diversity," Science, Oct. 1999, pp. 958-961, vol. 286.
Kiianitsa, et al., "Development of tools for T cell repertoire analysis (TCRB spectratyping) for the canine model of hematopoietic cell transplantation," 49th Annual Meeting of the American Society of Hematology, Nov. 2007, p. 293B, vol. 110, No. 11.
Mariani, et al., "Comprehensive assessment of the TCRBV repertoire in small T-cell samples by means of an improved and convenient multiplex PCR method," Experimental Hematology, 2009, pp. 728-738, vol. 37, No. 6.
Maslanka, et al., "Molecular Analysis of T-Cell Repertoires: Spectratypes Generated byMultiplex Polymerase Chain Reaction and Evaluated by Radioactivity or Fluorescence", Human Technology, Apr. 1995, 44(1), 28-34.
Miqeu, P., et al., "Statistical analysis of CDR3 length distributions for the assessment of T and B cell repertoire biases," Molecular Immunology, 2007, pp. 1057-1064, vol. 44.

(56) References Cited

OTHER PUBLICATIONS

Van Dongen et al., 'Design and standardization of PCR primers and protocols for detection of clonal immunoglobulin and I-cell receptor gene recombinations in suspect lymphoproliferations: Report of the BIOMED-2 Concerted Action BMHC-CI98-3936, Leukemia, 2003, vol. 17, pp. 2257-2317.
Office Action for Canadian Patent Application No. 2,765,949, dated Apr. 3, 2014, 4 Pages.
Office Action for Chinese Patent Application No. 201080028875.2, dated Feb. 13, 2014, 9 pages.
Office Action for Israeli Patent Application No. 217200, dated Mar. 18, 2014, 8 pages.
Office Action for Russian Patent Application No. 2012101828/10(002474), dated Mar. 28, 2014, 5 pages.
Akatsuka, Y., et al., "Rapid screening of T-cell receptor (TCR) variable gene usage by multiplex PCR: Application for assessment of clonal composition," Tissue Antigens, 1999, vol. 53, pp. 122-134.
Bolotin, D., et al., "Next generation sequencing for TCR repertoire profiling: Platform-specific features and correction algorithms," Eur. J. Immunol., 2012, vol. 42, pp. 3073-3083.
de Jonge, H., et al., "Evidence Based Selection of Housekeeping Genes," PLoS One, Sep. 2007, Issue 9, e989, 5 pages.
Dheda, K., et al., "Validation of housekeeping genes for normalizing RNA expression in real-time PCR," Bio Techniques, Jul. 2004, vol. 37, pp. 112-119.
Dik, W., et al. "New insights on human T cell development by quantitative T cell receptor gene rearrangement studies and gene expression profiling," JEM, vol. 201, No. 11, Jun. 6, 2005 1715-1723.
Edwards, M.C., et al., "Multiplex PCR: advantages, development, and applications," Genome Research, 1994, vol. 3, pp. S65-S75.
Elnifro, E., et al., "Multiplex PCR: Optimization and Application in Diagnostic Virology," Clinical Microbiology Reviews, Oct. 2000, p. 559-570.
Kaplinski, L., et al., "MultiPLX Automatic Grouping and Evaluation of PCR Primers," in Methods in Molecular Biology, vol. 402: PCR Primer Design, Nov. 25, 2004, pp. 287-303.
Markoulatos, P., et al., "Multiplex Polymerase Chain Reaction: A Practical Approach," Journal of Clinical Laboratory Analysis, 2002, vol. 16, pp. 47-51.
Nicot, N., et al., "Housekeeping gene selection for real-time RT-PCR normalization in potato during biotic and abiotic stress," Journal of Experimental Botany, Nov. 2005, vol. 56, No. 421, pp. 2907-2914.
Perkel, J., "Overcoming the Challenges of Multiplex PCR," Biocompare Editorial Article, Oct. 23, 2012, 6 Pages, can be retrieved at <URL:http://www.biocompare.com/Editorial-Articles/117895-Multiplex-PCR/>.
Santalucia, J., "Physical Principles and Visual-OMP Software for Optimal PCR Design," in Methods in Molecular Biology, vol. 402: PCR Primer Design, Edited by Anton Yuryev, Aug. 23, 2007, pp. 3-33.
Silver, N., et al., "Selection of housekeeping genes for gene expression studies in human reticulocytes using real-time PCR," BMC Molecular Biology, Oct. 6, 2006, vol. 7, No. 33, pp. 1-9.
Xu, W., et al., "A Novel Universal Primer-Multiplex-PCR Method with Sequencing Gel Electrophoresis Analysis," PLoS One, vol. 7, issue 1, Jan. 2012, e22900, pp. 1-10.
Boyd, et al., "Measurement and clinical monitoring of human lymphocyte clonality by massively parallel VDJ pyrosequencing," Science Translational Medicene. 1(12):12ra23 (2009).
Rasmussen, "Quantitation of minimal residual disease in multiple myeloma using an allele-specific real-time PCR assay," Experimental Hematology, 28:1039-1045, (2000).
Van Der Velden, "Real-time quantitative PCR for detection of minimal residual disease before allogeneic stem cell transplantation predicts outcome in children with acute lymphoblastic leukemia," Leukemia, 15:1485-1487, (2001).

Van Der Velden, et al., "Detection of minimal residual disease in hematologic malignancies by real-time quantitative PCR: principles, approaches, and laboratory aspects," Leukemia, 17:1013-1034, (2003).
Freeman, et al., "Profiling the T-cell receptor beta-chain repertoire by massively parallel sequencing," Genome Res., 19:1817-1824, (2009).
Droese, et al., "Validation of BIOMED-2 multiplex PCR tubes for detection of TCRB gene rearrangements in T-cell malignancies," Leukemia, 18:1531-1538, (2004).
Casbon et al, "A method for counting PCR template molecules with application to nex-generation sequencing," Nucleic Acids Research 39(12): e81 (2011).
Craig et al, "Identification of genetic variants using bar-coded multiplex sequencing," Nature Methods, 5(10): 887-893 (2(308) and Supplemental Materials.
Eason et al, "Characterization of synthetic DNA bar codes in Saccharomyces cerevisiae acne-deletion strains," Proc. Natl. Acad. Sci., 101(30): 11046-11051 (2004).
Frank, "BARCRAWL and BARTAB: software tools for the design and implementation of barcoded primers for highly multiplexed DNA sequencing" BMC Bioinformatics, 10: 162 (Oct. 29, 2009).
Fu et al, "Counting individual DNA molecules by the stochastic attachment of diverse labels," Proc. Natl. Acad. Sci., 108(22): 9026-9031 (2011).
Gloor et al, "Microbiorne profiling by Illumina sequencing of combinatorial sequence-tagged PCR products," PLuS ONE 5(10): e15406 (2010).
Hamady, et al. Error-correcting barcoded pruners for pyrosequeneing hundreds of samples in multiplex. Nat Methods. Mar. 2008:5(3)1235-7. doi: 10.1038/nmeth.1184. Epub Feb. 10, 2008.
Hensel et al, "Simultaneous identification of bacterial virulence genes by negative selection," Science, 269(5222): 400-403 (1995).
Jabara et al, "Accurate sampling and deep sequencing of the HIV-1 protease gene using a primer ID," Proc. Natl. Acad. Sci. 108(50): 20166-20171 (2011).
Kinde et al, "Detection and quantification of mutations with massively parallel sequencing," Proc. Natl. Acad. Sci, 108: 9530-9535 (2011) and Supporting Information.
Kivioja et al, "Counting absolute numbers of molecules using unique molecular identifiers," Nature Methods, 9(1): 72-76 (2012).
Lennon et al, "A scalable, fully automated process for construction of sequence-ready barcoded libraries for 454," Genome Biology, 11 : R15 (2010).
McCloskey et al, "Encoding PCR products with batch-stamps and barcodes," Biochem. Genet., 45: 761-767 (2007).
Meyer et al, "Targeted high-throughput sequencing of tagged nucleic acid samples," Nucleic Acids Research, 35(15): e97 (2007).
Miner et al, "Molecular barcodes detect redundancy and contamination in hairpin-bisulfite PCR," Nucleic Acids Research, 32(17): e135 (2004).
Nguyen et al, "Identification of errors introduced during high throughput sequencing of the T cell receptor repertoire," BMC Genomics, 12: 106 (2011).
Parameswaran et al. "A pyrosequencing-tailored nucleotide barcode design unveils opportunities for large-scale sample multiplexing," Nucleic Acids Research, 35(19): e130 (2007).
Qiu et al, "DNA sequence-based "bar codes" for tracking the origins of expressed sequence tags from a maize cDNA library constructed using multiple mRNA sources," Plant Physiology, 133(2): 475-481 (2003).
Qu et al, "Efficient frequency-based de novo short-read clustering for error trimming in next-generation sequencing," Genome Research, 19: 1309-1315 (2009).
Robins et al, "Comprehensive assessment of T-cell receptor beta-chain diversity in alpha-beta T cells," Blood, 114(19): 4099-4107 (2009) (including supplemental materials).
Salzberg, "Mind the gaps," Nature Methods, 7(2):105-106 (2010).
Schmitt et al, "Detection of ultra-rare mutations by next-generation sequencing." Proc. Natl. Acad. Sci. 109(36): 14508-14513 (2012) and Supporting Informaton.

(56) References Cited

OTHER PUBLICATIONS

Shiroguchi et al, "Digital RNA sequencing minimizes sequence-dependent bias and amplification noise with optimized single-molecule barcodes," Proc. Natl. Acad. Sci., 109(4): 1347-1352 (2012).
Shoemaker, et al. Quantitative plienotypie analysis of yeast deletion mutants using a highly parallel molecular bar-coding strategy. Nat Genet. Dec. 14, 1996(4):450-6.
Smith et al, "Quantitative phenotyping via deep barcode sequencing" Genome Research, 19: 1836-1842 (2009).
Stiller et al., "Direct multiplex sequencing (DMPS)—a novel method for targeted high-throughput sequencing of ancient and highly degraded DNA," Genome Research, 19: 1843-1848 (2009).
Varley et al, "Nested patch PCR enables highly multiplexed mutation discovery in candidate genes," Genome Research, 18: 1844-1850 (2008).
Arstila et al, "A direct estimate of the human □β cell receptor diversity," Science, 286: 958-961 (1999).
Assaf et al, "High detection rate of T-cell receptor beta chain rearrangements in T-cell lymphoproliferations by family specific polymerase chain reaction in combination with the GeneScan technique and DNA sequencing," Blood, 96(2): 640-646 (2000).
Bentley et al, "Accurate whole human genome sequencing using reversible terminator chemistry," Nature, 456(7218); 53-59 (2008).
Bonarius et al, "Monitoring the T-cell receptor repertoire at single-clone resolution," PlosOne, 1(1): e55 (2006).
Bora et al, "Pinner sets for cloning the human repertoire of T cell receptor variable regions," BMC Immunology, 9: 50 (2008).
Boudinot et al, "New perspectives for large-scale repertoire analysis of immune receptors," Molecular Immunology, 45: 2437-2445 (2008).
Boyd et al, "Measurement and clinical monitoring of human lymphocyte clonality by massively parallel VDJ pyrosequencing," Science Transl. Med. 1(12): 12ra23 (2009)(including supplemental materials).
Buccisano et al, "Monitoring of minimal residual disease in acute myeloid leukemia," Current Opinion in Oncology, 21: 582-588 (2009).
Campbell et al, "Subclonal phylogenic structures in cancer revealed by ultra-deep sequencing," Proc. Natl. Acad. Sci. 105(35): 13081-13086 (2008).
Carlson et al, "Using synthetic templates to design an unbiased multiplex PCR," Nature Communications, 4:2680 (2013).
Compana, "Role of minimal residual disease monitoring in adult and pediatric acute lymphoblastic leukemia," Hematol. Oncol. Clin. North Am. 23(5): 1083-1098 (2009).
Decoste et al, "Relative and absolute gruantitative real-time PCR-based quantifications of hcnC and phlD gene transcripts in natural soil spiked with *Pseudomonas* sp. strain LBUM300," Applied Environmental Microbiol., 77(1): 41-47 (2011).
Dohm et al, "Substantial biases in ultra-short read data sets from high-throughput DNA sequencing." Nucleic Acids Research, 36(16): e105 (2008).
Freeman et al, "Profiling the T-cell receptor beta-chain repertoire by massively parallel sequencing," Genome Research, 19(10): 1817-1824(2009).
Garcia-Castillo et al, "Detection of clonal immunoglobulin and T-cell receptor gene recombination in hematological malignancies: monitoring minimal residual disease," Cardiovascular & Haematological Disorders-Drug Targets, 9: 124-135 (2009).
Gonzalez et al. "Incomplete DJH rearrangements as a novel tumor target for minimal residual disease quantitation in multiple myeloma using real-time PCR," Leukemia, 17: 1051-1057 (2003).
Gonzalez et al, "Incomplete DJH rearrangements of the IgH gene are frequent in multiple myeloma patients: immunobiological characteristics and clinical applications," Leukemia, 17: 1398-1403 (2003).

Han, et al. "Immunorepertoire analysis by multiplex PCR amplification and high throughput sequencing," Abstract. The 96 Annual Meeting of the American Association of Immunologists, Seattle, Washington, May 8-12, 2009.
Harris et al, "Single-molecule DNA sequencing of a viral genome," Science, 320: 106-109 (2008).
Huse et al, "Accuracy and quality of massively parallel DNA pyrosequencing," Genome Biology, 8: R143 (2007).
Illumina Technical Note, "Calling sequencing SNPs," (2010).
Kato et al, "Analysis of accumulated T cell clonotypes in patients with systemic lupus erythematosus," Arthritis & Rheumatism, 43(12): 2712-2721 (2000).
Kim et al, "Polony multiplex analysis of gene expression (PMAGE) in mouse hypertrophic cardiomyopathy," Science, 316: 1481-1484 (2007)(including supplemental materials).
Kneba et al, "Analysis of rearranged T-cell receptor β-chain genes by polymer ase chain reaction (PCR) DNA sequencing and automated high resolution PCR fragment analysis," Blood, 86: 3930-3937 (1995).
Li et al, "Sequence analysis of clonal immunogiohulin and T-cell receptor gene rearrangements in children with acute lymphoblastic leukemia at diagnosis and at relapse: implications for pathogenesis and for the clinical utility of PCR-based methods of minimal residual disease detection,"Blood, 102:4520-4526 (2003).
Margulies et al, "Genome sequencing in microfabricated high-density picoliter reactors," Nature, 437: 376-380 (2005).
Muraro et al, "Molecular tracking of antigen-specific T cell clones in neurological immune-mediated disorders," Brain, 126: 20-31 (2003).
Ogle et al, "Direct measurement of lymphocyte receptor dhiersity," Nucleic Acids Research, 31 (22): e139 (2003).
Packer et al, "Optimized clonotypic analysis of T-cell receptor repertoire in immune reconstitution," Experimental Hematology, 35: 516-521 (2007).
Plasilova et al, "Application of the molecular analysis of the T-cell receptor repertoire in the study of immune-mediated hematologic diseases," Hematology, 8(3): 173-181 (2003).
Polz et al, "Bias in template-to-product ratios in multitemplate PCR" Applied and Environmental Microbiology. 64(10): 3724-3730 (1998).
Qu et al, "Efficient frequency-based de novo short-read clustering for error trimming in next generation sequencing," Genome Research, 19: 1309-1315 (2009).
Quince et al, "Removing noise from pyrosequenced amplicons," BMC Bioinformatics, 12: 38 (2011).
Reinartz, et al, "Massively parallel signature sequencing (MPSS) as a tool for in-depth quantitative gene expression profiling in all organisms," Briefings in Functional Genomics and Proteomics, 1(1): 95-104 (Feb. 2002).
Robins et al, "Comprehensive assessment of T-cell receptor β chain diversity in □βT cells," Blood, 114(1): 4099-4107 (2009)(including supplemental materials).
Robins et al, "Overlap and effective size of the human CD8+ T cell receptor repertoire," Science Translational Medicine, 2(47): 47ra64 (Sep. 1, 2010).
Shendure et al, "Next-generation DNA sequencing," Nature Biotechnology 26(10): 1135-1145 (2008).
Sing et al, "A molecular comparison of T lymphocyte populations infiltrating liver and circulating in the blood of patients with chronic hepatitis B: evidence for antigen-driven selection of a public complementary-determining region 3 (CDR3) motif," Hepatology. 33(5): 1288-1298 (2001).
Sint et al, "Advances in multiplex PCR: balancing primer efficiencies and improving detection success," Methods in Ecology and Evolution 3: 898-905 (2012).
Szczepanski et al, "Comparative analysis of Ig and TCR gene rearrangements at diagnosis and at relapse of childhood precursor-B-ALL provides improved strategies for selection of stable PCR targets for monitoring of minimal residual disease," Blood, 99(7): 2315-2323 (2002).

(56) References Cited

OTHER PUBLICATIONS

Van Do Gen et al, "Design and standardization of PCR primers and protocols for detection of clonal immunoglobulin and T-cell receptor gene recombinations in suspect lymphoproliferations: Report of the BIOMED-2 concerted action BMH4-CT98-3936," Leukemia, 17: 2257-2317 (2003).
Wang, et al. High throughput sequencing reveals a complex pattern of dynamic interrelationships among human T cell subsets. Proc Natl Acad Sci USA, Jan. 26, 2010: 107(4): 1518-1523.
Warren et al, "Profiling model T-cell metagenomes with short reads," Bioinformatics, 25(4): 458-464 (2009).
Warren et al, "Exhaustive T-cell repertoire sequencing of human peripheral blood samples reveals signatures of antigen selection and a directly measured repertoire size of at least 1 million clonotypes," Genome Research, 21: 790-797 (2011).
Weinstein et al, "High throughput sequencing of the zebrafish antibody repertoire," Science, 324: 807-810 (2009).
Wlodarski et al. "Pathologic clonal cytotoxic T-cell responses: nonrandom nature of the T-cell-receptor restriction in large granular lymphocyte Leukemia," Blood, 106: 2769-2779 (2005).
Wlodarski et al, "Molecular strategies for detection and quantitation of clonal cytotoxic T-cell responsses in aplastic anemia and myclodysplastic syndrome," Blood, 108: 2632-2641 (2006).
Zhou et al, "High throughput analysis of TCR-β rearrangement and gene expression in single cells," Laboratory Investigation, 86: 314-321 (2006).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Zehentner et al. "Minimal Disease Detection and Confirmation in Hematologic Malignancies: Combining Cell Sorting with Clonality Profiling",*Clinical Chemistry*, 52(3): 430-437 (2006).
Abath et al. "Single-tubed nested PCR using immobilized internal primers", *Biotechniques*, 33(6): 1210-2, 1214 (2002).
Abbott, et al. "Design and use of signature primers to detect carry-over of amplified material", *J Virol Methods*, 46(1):51-59, Abstract Only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).
Alatrakchi et al. "T-cell clonal expansion in patients with B-cell lymphoproliferative disorders", *Journal of Immunotherapy*, 21(5):363-370 (1998).
Alexandre, D. et al. "*H. sapiens* rearranged T-cell receptor gamma chain gene, V2-JP1", GenBank accession No: X57737, NCBI, Nov. 14, 2006, 8 pages [online] [retrieved on Jun. 26, 2013] Retrieved from the internet <URL:http://www.ncbi.nlm.nih.gov/nuccore/x57737>.
Alexandre, D. et al. "*H. sapiens* rearranged T-cell receptor gamma chain gene, V3RS-J1 (hybrid joint)", GenBank accession No: X57740, NCBI, Feb. 11, 1997, 8 pages [online] [retrieved on Jun. 26, 2013] Retrieved from the internet <URL:http://www.ncbi.nlm.nih.gov/nuccore/x57740>.
Altin et al. "The role of CD45 and CD45-associated molecules in T cell activation", *Immunology and Cell Biology*, 75: 430-445 (1997).
Altman, et al. "Phenotypic analysis of antigen-specific T lymphocytes", The *Journal of Immunology*, 187(1):7-9 (2011).
Altschul, et al. "Basic local alignment search tool", *J Mol Biol.*, 215(3):403-410 (1990).
Andreasson, et al. "The human IgE-encoding transcriptome to assess antibody repertoires and repertoire evolution", *J Mol Biol.*, 362(2):212-227 (2006). Epub Aug. 14, 2006.
Arnaout. "Specificity and overlap in gene segment-defined antibody repertoires", *BMC Genomics*, 6: 148 (2005).
Arden, et al. "Human T-cell receptor variable gene segment families", *Immunogenetics*, 42(6):455-500, Abstract Only (1995).

Armand, P. et al., "Detection of circulating tumour DNA in patients with aggressive B-cell non-Hodgkin lymphoma", *Brit. J. Haematol.*, vol. 163, pp. 123-126 (2013).
Aarts et al., "Variable heavy-chain gene analysis of follicular lymphomas: subclone selection rather than clonal evolution over time", Blood, 98(1): 238-240 (2001).
Aslanzadeh. "Preventing PCR amplification carryover contamination in a clinical laboratory", *Ann Clin Lab Sci*., 34(4):389-396 (2004).
Ateya, et al. "The good, the bad, and the tiny: a review of microflow cytometry", *Anal Bioanal Chem*., 391(5): 1485-1498 (2008). doi: 10.1007/s00216-007-1827-5. Epub Jan. 29, 2008.
Babrzadeh et al. "Development on High-throughput Sequencing Technology: emPCR Titration and Barcode Design", *Stanford School of Medicine*, 2 pages (2011).
Bagnara, et al. "IgV gene intraclonal diversification and clonal evolution in B-cell chronic lymphocytic leukaemia", *British Journal of Haematology*, 133(1):50-58 (2006).
Bajor et al., "Immune activation and a 9-year ongoing complete remission following CD40 antibody therapy and metastasectomy in a patient with metastatic melanoma", Cancer Immunol Res., 2(11): 1051-1058 (2014).
Baldauf, "Phylogeny for the faint of heart: a tutorial," Trends in Genetics, 19(6): 345-351 (2003).
Barbas, et al. "Assembly of combinatorial antibody libraries on phage surfaces: the gene III site", *PNAS*, 88(18): 7978-7982, Abstract Only (1991).
Barker, et al. "A second type II restriction endonuclease from Thermus aquaticus with an unusual sequence specificity", *Nucleic Acids Res*., 12(14): 5567-5581 (1984).
Batzoglou, S. "The many faces of sequence alignment", *Briefings in Bioinformatics*, 6:6-22 (2005).
Baum and McCune et al. "Direct measurement of T-cell receptor repertoire diversity with AmpliCot", *Nat Methods*, 3(11): 895-901 (2006).
Becattini et al., "T cell immunity. Functional heterogeneity of human memory CD4+ T cell clones primed by pathogens or vaccines", Science, 347(6220): 400-406 (2015).
Becker-André and Hahlbrock. "Absolute mRNA quantification using the polymerase chain reaction (PCR). A novel approach by a PCR aided transcript titration assay (PATTY)", *Nucleic Acids Res*., 17(22): 94379446 (1989).
Becton-Dickinson, CD marker handbook. bdbiosciences.com/go/mousecdmarkers, p. 1-47 (2010).
Becton-Dickinson T-Cell Research Tools, "Novel multicolor flow cytometry tools for the study of CD4+ T-cell differentiation and plasticity", 16 pages (2009).
Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", *Blood*, 83(8):2238-2247 (1994).
Ben-Ezra, et al. Effect of fixation on the amplification of nucleic acids from paraffin-embedded material by the polymerase chain reaction, *The Journal of Histochemistry and Cytochemistry*, 39(3): 351-354 (1991).
Béné and Kaeda, "How and why minimal residual disease studies are necessary in leukemia: a review from WP10 and WP12 of the European LeukaemiaNet", *Haematologica*, 94(8):1135-1150 (2009).
Benecke. "DNA typing in forensic medicine and in criminal investigations: a current survey", *Naturwissenschaften*, 84(5): 181-188 (1997).
Benichou, J. et al., "Rep-Seq: uncovering the immunological repertoire through next-generation sequencing", *Immunology*, 135(3): 183-191 (2011).
Benichou, J. et al., "The restricted DH gene reading frame usage in the expressed human antibody repertoire is selected based upon its amino acid content", J Immunol., 190(11): 5567-77, 29 pages (2013).

(56) References Cited

OTHER PUBLICATIONS

Bereczki, et al. "Optimization of PCR amplification for B- and T-cell clonality analysis on formalin-fixed and paraffin-embedded samples", *Pathology Oncology Research*, 13(3): 209-214 (2007). Epub Oct. 7, 2007.

Berger, et al. "The clonotypic T cell receptor is a source of tumor-associated antigens in cutaneous T cell lymphoma", *Annals of the New York Academy of Sciences*, 941:106-122, Abstract Only (2001).

Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.

Berglund et al., "Genomic imbalances during transformation from follicular lymphoma to diffuse large B-cell lymphoma", Modern Pathology, 20(1): 63-75 (2007).

Bernard et al. "Color multiplexing hybridization probes using the apolipoprotein E locus as a model system for genotyping", Anal Biochem., 273(2):221-228 (1999).

Bertness, et al. "T-Cell Receptor Gene Rearrangements as Clinical Markers of Human T-Cell Lymphomas", *The New England Journal of Medicine*, 313:534-538 (1985).

Bettini et al., "Membrane association of the CD3ε signaling domain is required for optimal T cell development and function", J Immunol., 193(1): 258-267 (2014).

Berzofsky, et al. "Progress on new vaccine strategies for the immunotherapy and prevention of cancer", *J Clin Invest.*, 113(11): 1515-1525 (2004).

Biagi, et al. "Responses to human CD40 ligand/human interleukin-2 autologous cell vaccine in patients with B-cell chronic lymphocytic leukemia", *Clin Cancer Res.*, 11(19 Pt 1): 6916-6923 (2005).

Biggerstaff, et al. "Enumeration of leukocyte infiltration in solid tumors by confocal laser scanning microscopy", *BMC Immunol.*, 7:16, 13 pages (2006).

Blow, N., "PCR's next frontier," *Nature Methods*, 4(10):869-875 (2007).

Brochet et al. "IMGTN-QUEST: the highly customized and integrated system for IG and TR standardized V-J and V-D-J sequence analysis", *Nucleic Acids Research*, vol. 36, Web Server issue W503-W508 (2008).

Bonner et al. "Fluorescence activated cell sorting", Rev Sci Instrum., 43(3):404-409, Abstract Only (1972).

Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.

Bousso. "Generation of MHC-peptide tetramers: a new opportunity for dissecting T-cell immune responses", Microbes Infect., 2(4):425-429, Abstract Only (2000).

Boyce, et al. "Human regulatory T-cell isolation and measurement of function", *BD Biosciences*, pp. 1-20 (2010).

Boyd, S.D. et al., "Individual Variation in the Germline Ig Gene Repertoire Inferred from Variable Region Gene Rearrangements", *The Journal of Immunology*, 184(12): 6986-6992 (2010).

Bravo and Irizarry. "Model-Based Quality Assessment and Base-Calling for Second-Generation Sequencing Data", Biometrics, 66(3): 665-674 (2010).

Brehm-Stecher and Johnson. "Single-cell microbiology: tools, technologies, and applications", *Microbiology and Molecular Biology Reviews*, 68(3):538-559 (2004).

Brenan, C. et al., "High throughput, nanoliter quantitative PCR," *Drug Discovery Today: Technologies*, 2(3):247-253 (2005).

Brenner, et al. "In vitro cloning of complex mixtures of DNA on microbeads: physical separation of differentially expressed cDNAs", *PNAS*, 97(4): 1665-1670 (2000).

Brentjens, et al. "CD19-targeted T cells rapidly induce molecular remissions in adults with chemotherapy- refractory acute lymphoblastic leukemia", Sci Transl Med., 5(177): 177ra38 (2013). doi: 10.1126/scitranslmed.3005930.

Brisco, et al. "Determining the repertoire of IGH gene rearrangements to develop molecular markers for minimal residual disease in B-lineage acute lymphoblastic leukemia", *J Mol Diagn.*, 11(3):194-200 (2009).

Brisco, et al. "Outcome prediction in childhood acute lymphoblastic leukaemia by molecular quantification of residual disease at the end of induction", *Lancet*, 343:196-200 (1994).

Brockman et al, "Quality scores and SNP detection in sequencing-by-synthesis systems," Genome Research, 18: 763-770 (2008).

Brody, et al. "Active and passive immunotherapy for lymphoma: proving principles and improving results", J Clin Oncol., 29(14):1864-1875, Abstract Only (2011). doi: 10.1200/JCO.2010. 33.4623. Epub Apr. 11, 2011.

Brody, et al., "Immunotransplant for mantle cell lymphoma: Phase I/II study preliminary results", *Journal of Clinical Oncology*, ASCO Annual Meeting Abstracts Part 1, vol. 29, No. 15, 1 page (2011).

Brody, et al. "Lymphoma immunotherapy: vaccines, adoptive cell transfer and immunotransplant", *Immunotherapy*, 1(5): 809-824 (2009). doi: 10.2217/imt.09.50.

Brown, et al. "Current techniques for single-cell lysis", *J. R. Soc. Interface*, 5:S131-S138 (2008).

Brownie et al. "The elimination of primer-dimer accumulation in PCR", Nucleic Acids Research, 25(16): 3235-3241 (1997).

Brüggemann, et al. "Clinical significance of minimal residual disease quantification in adult patients with standard-risk acute lymphoblastic leukemia", Blood, 107(3):1116-1123 (2006). Epub Sep. 29, 2005.

Brüggemann, et al. "Rearranged T-cell receptor beta genes represent powerful targets for quantification of minimal residual disease in childhood and adult T-cell acute lymphoblastic leukemia", Leukemia, 18(4): 709-719 (2004).

Brüggemann, et al. "Standardized MRD quantification in European ALL trials: proceedings of the Second International Symposium on MRD assessment in Kiel, Germany, Sep. 18-20, 2008", *Leukemia*, 24(3):521-535 (2010). doi: 10.1038/leu.2009.268. Epub Dec. 24, 2009.

Buck, G.A. et al. "Design Strategies and Performance of Custom DNA Sequencing Primers", *Biotechniques*, 27(3):528-536 (1999).

Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.

Butkus, B. "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.

Bystrykh. "Generalized DNA Barcode Design Based on Hamming Codes", *PLoS ONE*, 7(5): e36852, 1-8 (2012).

Campana. "Minimal residual disease in acute lymphoblastic leukemia", *Semin Hematol.*,46(1):100-106 (2009).

Caporaso, J.G. et al. "Global patterns of 16S rRNA diversity at a depth of millions of sequences per sample", *PNAS*, 108(Suppl. 1):4516-4522 (2010).

Carlotti, et al. "Transformation of follicular lymphoma to diffuse large B-cell lymphoma may occur by divergent evolution from a common progenitor cell or by direct evolution from the follicular lymphoma clone", *Blood*, 113(15): 3553-3557 (2009). doi: 10.1182/blood-2008-08-174839. Epub Feb. 6, 2009.

Carlson et al. "Profiling the repertoire of TCRB usage in induced and natural Treg cells", *The Journal of Immunology*, 186: 62.5, Abstract (2011).

Carlson, et al. "Immune Profiling Suggests an IGH Signaling-Dependent Subtype of Aggressive B-ALL", *Blood*, 120: 1428, Abstract (2012).

Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.

Carlson, et al. "Detection of tumor tagging clones in multiple myeloma via high throughput sequencing is robust to significant levels of SHM", Presented for the 2014 ASH Annual Meeting. Poster. 1 page. Dec. 5-9, 2014.

(56) References Cited

OTHER PUBLICATIONS

Casali, et al. "Human monoclonals from antigen-specific selection of B lymphocytes and transformation by EBV", *Science*, 234(4775): 476-479, Abstract Only (1986).

Catherwood, M.A. et al., "Improved clonality assessment in germinal centre/post germinal centre non-Hodgkin's lymphomas with high rates of somatic hypermutation", *J. Clin. Pathol.*, 60:524-528, Abstract (2007).

Chan et al. "Evaluation of Nanofluidics Technology for High-Throughput SNP Genotyping in a Clinical Setting", *The Journal of Molecular Diagnostics*, 13(3): 305-312 (2011).

Chattopadhyay, et al. "A live-cell assay to detect antigen-specific CD4+ T cells with diverse cytokine profiles", *Nat Med.*, 11(10): 1113-1117 (2005). Epub Sep. 25, 2005.

Chen et al. "A novel approach for the analysis of T-cell reconstitution by using a T-cell receptor β-based oligonucleotide microarray in hematopoietic stem cell transplantation", *Exp Hematol.*, 35(5):831-841 (2007).

Chen et al. "Identification of racehorse and sample contamination by novel 24-plex STR system", Forensic Science International: Genetics, 4:158-167 (2010).

Chen, et al. "Microfluidic cell sorter with integrated piezoelectric actuator", *Biomed Microdevices*, 11(6): 1223-1231 (2009). doi: 10.1007/s10544-009-9341-5.

Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).

Chen, et al. "Total Gene Synthesis: Novel Single-Step and Convergent Strategies Applied to the Construction of a 779 Base Pair Bacteriorhodopsis", *Gene. J. Am. Chem Soc.*, 116: 8799-8800, Abstract Only (1994).

Chiu, et al. "Non-invasive prenatal assessment of trisomy 21 by multiplexed maternal plasma DNA sequencing: large scale validity study", *BMJ*, 342:c7401, 9 pages (2011). doi: 10.1136/bmj.c7401.

Choi, et al. "Relapse in children with acute lymphoblastic leukemia involving selection of a preexisting drug-resistant subclone", *Blood*, 110(2):632-639 (2007).

Choi, et al. "Clonal evolution in B-lineage acute lymphoblastic leukemia by contemporaneous $V_H$-$V_H$ gene replacements and $V_H$-$DJ_H$ gene rearrangements", *Blood*, 87(6):2506-2512 (1996).

Churchill and Waterman. "The Accuracy of DNA Sequences: Estimating Sequence Quality", *Genomics*, 14:89-98 (1992).

Chute, et al. "Detection of immunoglobulin heavy chain gene rearrangements in classic Hodgkin lymphoma using commercially available BIOMED-2 primers", *Diagn Mol Pathol.*, 17(2): 65-72 (2008). doi: 10.1097/Pdm.0b013e318150d695.

Citri et al. "Comprehensive qPCR profiling of gene expression in single neuronal cells", *Nature Protocols*, 7(1): 118-127 (2012).

Cleary, et al. "Production of complex nucleic acid libraries using highly parallel in situ oligonucleotide synthesis", *Nat Methods*, 1(3): 241-248 (2004). Epub Nov. 18, 2004.

Clemente, et al. "Deep sequencing of the T-cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.

Conti et al. "Oral-resident natural Th17 cells and γδ T cells control opportunistic Candida albicans infections", J Exp Med., 211(10): 2075-84 (2014). doi: 10.1084/jem.20130877. Epub Sep. 8, 2014.

Cooper, et al. "BRAF inhibition is associated with increased clonality in tumorin filtrating lymphocytes", *Oncoimmunology*, 2(10):e26615 (2013). Epub Oct. 15, 2013.

Costabile, et al. "Molecular approaches in the diagnosis of primary immunodeficiency diseases", *Human Mutation*, 27(12):1163-1173 (2006).

Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.

Cronn et al. "Multiplex sequencing of plant chloroplast genomes using Solexa sequencing-by-synthesis technology", *Nucleic Acids Research*, 36(19):e122, 1-11 (2008).

Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", *The Journal of Immunology*, 172:1935-1944 (2004).

Curran-Everett, D., "Multiple comparisons: philosophies and illustrations", *Am J Physiol Regulatory Integrative Comp Physiol.*, 279:R1-R8 (2000).

Currier and Robinson. "Spectratype/immunoscope analysis of the expressed TCR repertoire", *Current Protocols in Immunology*, Supplement 38:10.28.1-10.28.24 (2000).

Dahl et al. "Multiplex amplification enabled by selective circularization of large sets of genomic DNA fragments", Nucleic Acids Res., 33(8): e71 (2005).

Damle et al. "B-cell chronic lymphocytic leukemia cells express a surface membrane phenotype of activated, antigen-experienced B lymphocytes", *Blood*, 99(11): 4087-93 (2002).

Dash, P. et al., "Paired analysis of TCR[alpha] and TCR[beta] chains at the single-cell level in mice", *Journal of Clinical Investigation*, 121(1):288-295 (2011).

Davi, et al. "Lymphocytic progenitor cell origin and clonal evolution of human B-lineage acute lymphoblastic leukemia", *Blood*, 88(2):609-621 (1996).

Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.

Davis, et al. "Interrogating the repertoire: broadening the scope of peptide-MHC multimer analysis", *Nat Rev Immunol.*, 11(8):551-558 (2011). doi: 10.1038/nri3020.

Davis, et al. "Staining of cell surface human CD4 with 2'-F-pyrimidine-containing RNA aptamers for flow cytometry", *Nucleic Acids Research*, 26(17):3915-3924 (1998).

De Bona et al. "Optimal spliced alignments of short sequence reads", *Bioinformatics*, 9(Suppl 10):07, 2 pages (2008).

de Haas et al., "Quantification of minimal residual disease in children with oligoclonal B-precursor acute lymphoblastic leukemia indicates that the clones that grow out during relapse already have the slowest rate of reduction during induction therapy", Leukemia, 15: 134-140 (2001).

Dean, et al. "Rapid amplification of plasmid and phage DNA using Phi 29 DNA polymerase and multiply-primed rolling circle amplification", *Genome Res.*, 11(6): 1095-1099 (2001).

Dedhia, et al. "Evaluation of DNA extraction methods and real time PCR optimization on formalin-fixed paraffin-embedded tissues", *Asian Pac J Cancer Prev.*, 8(1): 55-59 (2007).

Deiman, et al. "Characteristics and applications of nucleic acid sequence-based amplification (NASBA)", *Mol Biotechnol.*, 20(2): 163-179, Abstract Only (2002).

DeKosky et al. "High-throughput sequencing of the paired human immunoglobulin heavy and light chain repertoire", *Nature Biotechnology*, 31(2): 166-169 (2013).

Delaney, et al. "Evolution and Clinical Implications of the T cell Repertoire Following Cord Blood Transplant", Biology of Blood and Marrow Transplant, vol. 19, Issue 2, S201-S202. Published Feb. 2013.

Deng et al. "Gene profiling involved in immature CD4+ T lymphocyte responsible for systemic lupus erythematosus", *Molecular Immunology*, 43:1497-1507 (2006).

DeNucci, C.C. et al. "Integrin function in T-cell homing to lymphoid and nonlymphoid sites: getting there and staying there," *Critical Reviews in Immunology*, 29(2):87-109 (2009).

Deschoolmeester, et al. "Tumor infiltrating lymphocytes: an intriguing player in the survival of colorectal cancer patients", *BMC Immunology*, 11:19, 12 pages (2010). doi: 10.1186/1471-2172-11-19.

Desmarais, et al. "Deep profiling of the mouse TCRβ CDR3 region in thymus and spleen". Oct. 2010. Poster. 1 page.

Desmarais, et al. High-throughput sequencing of memory and naïve T cell receptor repertoires at the RNA and DNA levels reveals

(56) References Cited

OTHER PUBLICATIONS differences in relative expression of expanded TCR clones. Adaptive Technologies. Seattle W A. Poster, 1 page. Presented May 5, 2012.
Desmarais and Robins. "High-throughput sequencing of memory and naïve T cell receptor repertoires at the RNA and DNA levels reveals differences in relative expression of expanded TCR clones", The Journal of Immunology, 188: 178.12 (2012).
Dictor et al. "Resolving T-cell receptor clonality in two and genotype in four multiplex polymerase chain reactions", *Haematologica*, 90(11): 1524-1532 (2005).
Diederichsen, et al. "Prognostic value of the CD4+/CD8-30 ratio of tumour infiltrating lymphocytes in colorectal cancer and HLA-DR expression on tumour cells", *Cancer Immunol Immunother.*, 52(7):423-428 (2003). Epub Apr. 15, 2003.
Diehl, et al. "BEAMing: single-molecule PCR on microparticles in water-in-oil emulsions", *Nat Methods*, 3(7):551-559, Abstract Only (2006).
Diluvio et al. "Identical TCRβ-chain rearrangements in streptococcal angina and skin lesions of patients with psoriasis vulgaris", *J Immunol.*, 176(11 ): 7104-11 (2006).
Ding, et al. "Clonal evolution in relapsed acute myeloid leukaemia revealed by whole-genome sequencing", *Nature*, 481(7382):506-510 (2012). doi: 10.1038/nature10738.
Diviacco, et al. "A novel procedure for quantitative polymerase chain reaction by coamplification of competitive templates", *Gene*, 122(2):313-320 (1992).
Do and Batzoglou. "What is the expectation maximization algorithm?", *Nature Biotechnology*, 26(8): 897-899 (2008).
Dobosy, J. et al. "RNase H-dependent PCR (rhPCR): improved specificity and single nucleotide polymorphism detection using blocked cleavable primers", *BMC Biotechnology*, 11(80):1-18 (2011).
Dou, et al. "Analysis of T cell receptor $V_β$ gene usage during the course of disease in patients with chronic hepatitis B", *Journal of Biomedical Science*, 5(6):428-434 (1998).
Dressman, et al. "Transforming single DNA molecules into fluorescent magnetic particles for detection and enumeration of genetic variations", PNAS, 100(15):8817-8822 (2003). Epub Jul. 11, 2003.
Drmanac, et al. "Human genome sequencing using unchained base reads on self-assembling DNA nanoarrays", *Science*, 327(5961):78-81 (2010). doi: 10.1126/science.1181498. Epub Nov. 5, 2009.
Droege, et al. "The Genome Sequencer FLX System—longer reads, more applications, straight forward bioinformatics and more complete data sets", *J Biotechnol.*, 136(1-2):3-10 (2008). doi: 10.1016/j.jbiotec.2008.03.021. Epub Jun. 21, 2008.
Drossman, et al. "High-speed separations of DNA sequencing reactions by capillary electrophoresis", *Anal Chem.*, 62(9): 900-903 (1990).
Du et al. "TCR spectratyping revealed T lymphocytes associated with graft-versus-host disease after allogeneic hematopoietic stem cell transplantation", *Leukemia & Lymphoma*, 48(8):1618-1627 (2007).
Duby, A.D. et al., "Human T-cell receptor aberrantly rearranged beta-chain J1.5-Dx-J2.1 gene," PNAS, GenBank accession No. M13574.1, bases 1 to 100, 4 pages (1986).
Dudgeon, et al. "The evolution of thymic lymphomas in p53 knockout mice", Genes Dev., 28(23): 2613-20 (2014). doi: 10.1101/gad.252148.114.
Dunn, et al. "Focus on TILs: Prognostic significance of tumor infiltrating lymphocytes in human glioma", *Cancer Immun.*, 7:12, 16 pages (2007).
Edd et al. "Controlled encapsulation of single cells into monodisperse picoliter drops", *Lab Chip*, 8(8):1262-1264 (2008).
Eichler, et al. "Haplotype and interspersion analysis of the FMR1 CGG repeat identifies two different mutational pathways for the origin of the fragile X syndrome", *Hum Mol Genet.*, 5(3):319-330 (1996).
Eichler, et al. "Length of uninterrupted Cgg repeats determines instability in the FMR1 gene", *Nat Genet.*, 8(1):88-94, Abstract Only (1994).
Eid et al. "Real-time DNA sequencing from single polymerase molecules", *Science*, 323(5910):133-138 (2009). doi: 10.1126/science.1162986. Epub Nov. 20, 2008.
Eis, et al. "An invasive cleavage assay for direct quantitation of specific RNAs", *Nat Biotechnol.*, 19(7):673-676, Abstract Only (2001).
Eisenstein. "Personalized, sequencing-based immune profiling spurs startups", Nat Biotechnol., 31(3):184-6 (2013). doi: 10.1038/nbt0313-184b.
Elhanati et al. "Quantifying selection in immune receptor repertoires", PNAS USA, 111(27): 9875-9880 (2014) doi: 10.1073/pnas.1409572111.
Elkord et al. "T regulatory cells in cancer: recent advances and therapeutic potential", *Expert Opinion on Biological Therapy*, 10(11): 1573-1586 (2010).
Emerson, et al. "Correlation of TCR diversity with immune reconstitution after cord blood transplant", Presented at the American Society of Clinical Oncology's annual meeting. May, 2012. Poster. 1 page.
Emerson et al. "Defining the Alloreactive T Cell Repertoire Using High-Throughput Sequencing of Mixed Lymphocyte Reaction Culture", *PLoS One*, 9(11): e111943 (2014).
Emerson, R.O. et al. "High-throughput sequencing of T-cell receptors reveals a homogeneous repertoire of tumour-infiltrating lymphocytes in ovarian cancer", *Journal of Pathology*, 231: 433-440 (2013).
Emerson, et al. "CD4+ and CD8+ T cell β antigen receptors have different and predictable V and J gene usage and CDR3 lengths", Presented at the Annual Meeting of The American Association of Immunologists 2012 in Boston, MA May, 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-40 (2013). doi: 10.4049/jimmunol.1300622. Epub Oct. 25, 2013.
Erlich, et al. "Alta-Cyclic: a self-optimizing base caller for next-generation sequencing", *Nat Methods.*, 5(8): 679-682 (2008). doi: 10.1038/nmeth.1230. Epub Jul. 6, 2008.
European Application No. 09764927.1, Notice of Opposition dated Oct. 14, 2014, Reference# 547-7.
European Application No. 09764927.1, Notice of Opposition dated Oct. 14, 2014, Reference# BRO-0001EP.
European Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", *Lung Cancer*, 59(1): 32-40 (2008).
European Application No. 10732172.1, Extended European Search Report dated May 29, 2012, 5 pages.
European Patent Application No. 12856834.2, Extended European Search Report dated Jul. 7, 2015, 8 pages.
European Patent Application No. 13195379.6, European Search Report and Opinion dated Mar. 13, 2014, 6 pages.
European Patent Application No. 11777704.5, European Search Report dated Jul. 26, 2013, 6 pages.
European Patent Application No. 12841014.9, Extended European Search Report dated May 4, 2015, 11 pages.
European Patent Application No. 12844825.5, Extended European Search Report dated Jun. 22, 2015, 6 pages.
European Patent Application No. 12859772.1, Extended European Search Report dated Sep. 2, 2015, 7 pages.
European Patent Application No. 12856015.8, Extended European Search Report dated Sep. 28, 2015, 7 pages.

(56) References Cited

OTHER PUBLICATIONS

European Patent Application No. 13804085.2, Extended European Search Report dated Nov. 16, 2015, 10 pages.
European Patent Application No. 13775514.6, Extended European Search Report dated Dec. 1, 2015, 12 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
Ewing and Green, "Base-calling of automated sequencer traces using Phred. I. Accuracy Assessment," Genome Research, 8: 175-185 (1998).
Faham, M. et al. "Deep-sequencing approach for minimal residual disease detection in acute lymphoblastic leukemia", *Blood*, 120(26): 5173-5180 (2012).
Felsenstein, et al. "Evolutionary Trees from DNA Sequences: A Maximum Likelihood Approach", J Mol Evol, 17:368-376 (1981).
Ferradini et al. "Analysis of T Cell Receptor Variability in Tumor-infiltrating Lymphocytes from a Human Regressive Melanoma", *J. Clin. Invest.*, pp. 1183-190 (1993).
Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.
Fisher et al. "The Relation Between the Number of Species and the Number of Individuals in a Random Sample of an Animal Population", *Journal of Animal Ecology*, 12(1): 42-58 (1943).
Flaherty et al. "Ultrasensitive detection of rare mutations using next-generation targeted resequencing", *Nucleic Acids Research*, 40(1): e2, 12 pages (2012).
Flicek and Birney, "Sense from sequence reads: methods for alignment and assembly," Nature Methods Supplement, 6(11s): S6-S12 (2009).
Frampton, et al. "Development and validation of a clinical cancer genomic profiling test based on massively parallel DNA sequencing", *Nat Biotechnol.*, 31(11): 1023-1031 (2013). doi: 10.1038/nbt.2696. Epub Oct. 20, 2013.
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", *Biotechniques*, 6(1): 112-125 (1999).
Fridman, et al. "Prognostic and predictive impact of intra- and peritumoral immune infiltrates", *Cancer Research*, 71(17): 5601-5605 (2011). doi: 10.1158/0008-5472.CAN-11-1316. Epub Aug. 16, 2011.
Fritz et al. "Alterations in the spinal cord T cell repertoire during relapsing experimental autoimmune encephalomyelitis," *J Immunol*, 164:6662-6668 (2000).
Fuller, et al. "The challenges of sequencing by synthesis", *Nat Biotechnol.*, 7(11): 1013-23 (2009) (Abstract only). doi: 10.1038/nbt.1585. Epub Nov. 6, 2009.
Furmanski, et al. "Public T cell receptor β-chains are not advantaged during positive selection", *The Journal of Immunology*, 180(2): 1029-39 (2008).
Gauss, et al. "Mechanistic constraints on diversity in human V(D)J recombination", *Mol Cell Biol.*, 16(1):258-269 (1996).
Gawad, et al. "Massive evolution of the immunoglobulin heavy chain locus in children with B precursor acute lymphoblastic leukemia", *Blood*, 120(22):4407-4417 (2012). doi: 10.1182/blood-2012-05-429811. Epub Aug. 28, 2012.
Gerlinger and Swanton. "How Darwinian models inform therapeutic failure initiated by clonal heterogeneity in cancer medicine", *British Journal of Cancer*, 103(8):1139-1143 (2010). doi: 10.1038/sj.bjc.6605912. Epub Sep. 28, 2010.
Gerlinger, M. et al. "Ultra deep T cell receptor sequencing reveals the complexity and intratumour heterogeneity of T cell clones in renal cell carcinomas", *Journal of Pathology*, 231:424-432 (2013).

Germano, et al. "Clonality profile in relapsed precursor-B-ALL children by GeneScan and sequencing analyses. Consequences on minimal residual disease monitoring", *Leukemia*, 17(8):1573-1582 (2003).
Giannoni, et al. Allelic exclusion and peripheral reconstitution by TCR transgenic T cells arising from transduced human hematopoietic stem/progenitor cells, Mol Ther., 21(5):1044-54 (2013). doi: 10.1038/mt.2013.8. Epub Feb. 5, 2013.
Giga—Roche 454 FLX technology how it works. Fiche technique du Centre Interdisciplinaire de Genoproteomique Appliquee (Universite de Liege, Belgique). Accessed Oct. 15, 2014.
Gilbert, et al. "The isolation of nucleic acids from fixed, paraffin-embedded tissues-which methods are useful when?", *PLoS One*, 2(6):e537, 12 pages (2007).
Giuggio, et al. "Evolution of the intrahepatic T cell repertoire during chronic hepatitis C virus infection", *Viral Immunology*, 18(1):179-189 (2005).
Godelaine, et al. "Polyclonal CTL responses observed in melanoma patients vaccinated with dendritic cells pulsed with a MAGE-3.A1 peptide", *J Immunol.*, 171(9):4893-4897 (2003).
Golembowski, et al. "Clonal evolution in a primary cutaneous follicle center B cell lymphoma revealed by single cell analysis in sequential biopsies", *Immunobiology*, 201(5):631-644 (2000).
Gomes, et al. "Single-tube nested PCR using immobilized internal primers for the identification of dengue virus serotypes", *J Virol Methods.*, 145(1):76-9 (2007). Epub Jun. 15, 2007.
Gonzalez, S.F., et al. "Trafficking of B Cell Antigen in Lymph Nodes", *Ann. Rev. Immunol.*, 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", *J Immunol.*, 152(10):5109-5119 (1994).
Gottenberg, et al. "Markers of B-lymphocyte activation are elevated in patients with early rheumatoid arthritis and correlated with disease activity in the ESPOIR cohort", *Arthritis Res Ther.*, 11(4): R114 (2009). doi: 10.1186/ar2773. Epub Jul. 23, 2009.
Gratama and Kern. "Flow cytometric enumeration of antigen-specific T lymphocytes", *Cytometry A*, 58(1): 79-86 (2004).
Gratama, et al. "Measuring antigen-specific immune responses", 2008 update. *Cytometry A.*, 73(11): 971-974 (2008). doi: 10.1002/cyto.a.20655.
Green, et al. "Clonal diversity of Ig and T-cell-receptor gene rearrangements identifies a subset of childhood B-precursor acute lymphoblastic leukemia with increased risk of relapse", *Blood*, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", *Nature*, 446(7132): 153-158 (2007).
Gribben, JG. "Stem cell transplantation in chronic lymphocytic leukemia", *Biol. Blood Marrow Transplant.*, 15(1 Suppl): 53-58 (2009). doi: 10.1016/j.bbmt.2008.10.022.
Grupp, et al. "Chimeric antigen receptor-modified T cells for acute lymphoid leukemia", N Engl J Med., 368(16):1509-18 (2013). doi: 10.1056/NEJMoa1215134. Epub Mar. 25, 2013.
Grupp, et al. "Adoptive transfer of autologous T cells improves T-cell repertoire diversity and long-term B-cell function in pediatric patients with neuroblastoma", Clin Cancer Res., 18(24):6732-41 (2012). doi: 10.1158/1078-0432.CCR-12-1432. Epub Oct. 23, 2012.
Gulliksen, et al. "Real-time nucleic acid sequence-based amplification in nanoliter volumes", *Anal Chem.*, 76(1): 9-14, Abstract Only (2004).
Gunderson et al. "Decoding Randomly Ordered DNA Arrays", *Genome Research*, 14: 870-877 (2004).

(56) References Cited

OTHER PUBLICATIONS

Guo, et al. "Sequence changes at the V-D junction of the $V_H1$ heavy chain of anti-phosphocholine antibodies alter binding to and protection against *Streptococcus pneumoniae*", *Int Immunol.*, 9(5):665-677 (1997).

Gupta, Pushpendra K. "Single-molecule DNA sequencing technologies for future genomics research", *Trends Biotechnol.*, 26(11): 602-611 (2008). doi: 10.1016/j.tibtech.2008.07.003. Epub Aug. 21, 2008.

Gurrieri, et al. "Chronic lymphocytic leukemia B cells can undergo somatic hypermutation and intraclonal immunoglobulin $V_HDJ_H$ gene diversification", J Exp Med., 196(5):629-639 (2002).

Hadrup, et al. "Parallel detection of antigen-specific T-cell responses by multidimensional encoding of MHC multimers", *Nat Methods*, 6(7): 520-526 (2009) (Abstract Only). doi: 10.1038/nmeth.1345. Epub Jun. 21, 2009.

Halldórsdóttir, et al. "Application of BIOMED-2 clonality assays to formalin-fixed paraffin embedded follicular lymphoma specimens: superior performance of the IGK assays compared to IGH for suboptimal specimens", *Leukemia & Lymphoma*, 48(7): 1338-1343 (2007).

Hanahan, et al. "Hallmarks of cancer: the next generation", *Cell*, 144(5): 646-674 (2011). doi: 10.1016/j.cell.2011.02.013.

Harismendy et al. "Evaluation of next generation sequencing platforms for population targeted sequencing studies", *Genome Biology*, 10:R32, 13 pages (2009).

Hathcock, et al. "ATM influences the efficiency of TCRβ rearrangement, subsequent TCRβ-dependent T cell development, and generation of the pre-selection TCRβ CDR3 repertoire", *PLoS One*, 8(4):e62188 (2013). doi: 10.1371/journal.pone.0062188. Print 2013.

Hawkins, et al. "Whole genome amplification—applications and advances", *Curr Opin Biotechnol.*, 13(1): 65-67 (2002).

He, et al. "IgH gene rearrangements as plasma biomarkers in Non-Hodgkin's lymphoma patients", *Oncotarget*, 2(3): 178-185 (2011).

Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_I=10&hq_v=2357e2f0b3. Accessed Apr. 6, 2011.

Heger. "Roche's 454 Eyes Immune Repertoire Sequencing as Key Application for Long- Read Platform". Feb. 2, 2010. 4 pages. http://www.genomeweb.com/print/932624.

Hill, et al. "Using ecological diversity measures with bacterial communities", *FEMS Microbiol Ecol.*, 43(1):1-11 (2003). doi: 10.1111/j.1574-6941.2003.tb01040.x.

Hirohata, et al. "Regulation of human B cell function by sulfasalazine and its metabolites", *Int Immunopharmacol.*, 2(5): 631-640, Abstract Only (2002).

Hodges, E. et al. "Diagnostic role of tests for T cell receptor (TCR) genes", *J Clin Pathol.*, 56(1): 1-11 (2003).

Holder and Lewis. "Phylogeny estimation: traditional and bayesian approaches", Nat Rev Genet., 4(4): 275-84 (2009).

Holt. "Q &A: BC Cancer agency's Robert Holt on sequencing the immune repertoire in immune reconstitution," Genome Web (www.genomeweb.com) Jun. 30, 2009.

Holt and Jones. "The new paradigm of flow cell sequencing", *Genome Research*, 18:839-846 (2008).

Hoogenboom, et al. "Multi-subunit proteins on the surface of filamentous phage: methodologies for displaying antibody (Fab) heavy and light chains", *Nucleic Acids Res.*, 19(15): 4133-4137 (1991).

Hoogendoorn, et al. "Primary allogeneic T-cell responses against mantle cell lymphoma antigen-presenting cells for adoptive immunotherapy after stem cell transplantation", *Clin Cancer Res.*, 11(14): 5310-5318 (2005).

Hoos, et al. "Improved endpoints for cancer immunotherapy trials", *J Natl Cancer Inst.*, 102(18): 1388-1397 (2010). doi: 10.1093/jnci/djq310. Epub Sep. 8, 2010.

Hoover and Lubkowski. "DNAWorks: an automated method for designing oligonucleotides for PCR-based gene synthesis", *Nucleic Acids Res.*, 30(10): e43, 7 pages (2002).

Hosono, et al. "Unbiased whole-genome amplification directly from clinical samples", *Genome Res.*, 13(5): 954-964 (2003). Epub Apr. 14, 2003.

Hoven, et al. "Detection and isolation of antigen-specific B cells by the fluorescence activated cell sorter (FACS)", *J Immunol Methods*, 117(2): 275-284, Abstract Only, 2 pages (1989).

Howe, et al. "T cell receptor clonotype analysis of T cell responses: Diagnostic application of a clonotypic database", *Blood*, 102:Abstract 3918 (2003).

Huang, et al. "Isolation of cell-free DNA from maternal plasma using manual and automated systems", *Methods Mol Biol.*, 444: 203-208, Abstract Only (2008). doi: 10.1007/978-1-59745-066-9_15.

Huh, et al. "Microfluidics for flow cytometric analysis of cells and particles", *Physiol Meas.*, 26(3): R73-98, Abstract Only (2005). Epub Feb. 1, 2005.

Huijsmans, et al. "Comparative analysis of four methods to extract DNA from paraffin-embedded tissues: effect on downstream molecular applications", *BMC Res Notes*, 3:239, 9 pages (2010). doi: 10.1186/1756-0500-3-239.

Huse, et al. "Generation of a large combinatorial library of the immunoglobulin repertoire in phage lambda", *Science*, 246(4935): 1275-1281, Abstract Only (1989).

Hwang, H.Y. et al. "Identification of a Commonly used CDR3 Region of Infiltrating T Cells Expressing Vβ13 and Vβ15 Derived from Psoriasis Patients", *The Journal of Investigative Dermatology*, 120(3):359-364 (2003).

Iancu, et al. "Profile of a serial killer: cellular and molecular approaches to study individual cytotoxic T-cells following therapeutic vaccination", *J Biomed Biotechnol.*, 2011: 452606 (2011). doi: 10.1155/2011/452606. Epub Nov. 14, 2010.

Iijima et al. "A local macrophage chemokine network sustains protective tissue-resident memory CD4 T cells", Science, 346(6205): 93-8 (2014). doi: 10.1126/science.1257530. Epub Aug. 28, 2014.

Illumina. Genome analyzer pipeline software version 1.0 user guide. Part #1004759, 176 pages (2008).

Illumina. Data Sheet: Sequencing. Genomic Sequencing. Pub. No. 770.2008-016 Reference states: "Current as of Jan. 30, 2009", 6 pages (2010).

Illumina. Data Sheet, "TruSeq™ exome enrichment kit", 5 pages (2011).

Illumina Systems & Software, Technology Spotlight, DNA Sequencing with Solexa® Technology, Illumina, Inc., Pub. No. 770-2007-002, 4 pages (2007).

Illumina. TruSeq Sample Preparation Kit and Data Sheet. Illumina, Inc., San Diego, CA, 4 pages (2011).

Ishii et al. "Isolation and expression profiling of genes upregulated in the peripheral blood cells of systemic lupus erythematosus patients," *DNA Research*, 12:429-439 (2005).

Jacobi et al. "Activated memory B cell subsets correlate with disease activity in systemic lupus erythematosus: delineation by expression of CD27, IgD, and CD95", *Arthritis & Rheumatism*, 58(6):1762-1773 (2008).

Jacobi et al. "Correlation between circulating $CD27^{high}$ plasma cells and disease activity in patients with systemic lupus erythematosus" *Arthritis & Rheumatism*, 48(5):1332-1342 (2003).

Jaffe, et al. "Classification of lymphoid neoplasms: the microscope as a tool for disease discovery", *Blood*, 112(12): 4384-4399 (2008). doi: 10.1182/blood-2008-07-077982.

Jalla, et al. "Enumeration of lymphocyte subsets using flow cytometry: Effect of storage before and after staining in a developing country setting", *Indian J Clin Biochem.*, 19(2): 95-99 (2004). doi: 10.1007/B F02894264.

Jena, et al. "Amplification of genes, single transcripts and cDNA libraries from one cell and direct sequence analysis of amplified products derived from one molecule", *J. Immunol. Methods*, 190:199-213 (1996).

(56) References Cited

OTHER PUBLICATIONS

Jochems and Schlom. "Tumor-infiltrating immune cells and prognosis: the potential link between conventional cancer therapy and immunity", *Exp Biol Med* (Maywood), 236(5): 567-579 (2011). doi: 10.1258/ebm.2011.011007. Epub Apr. 12, 2011.

Johnson et al. "Polysaccharide A from the capsule of Bacteroides fragilis induces clonal CD4+ T cell expansion", J Biol Chem., 290(8): 5007-14 (2015). doi: 10.1074/jbc.M114.621771. Epub Dec. 24, 2014.

Jones, et al. "Human autoimmunity after lymphocyte depletion is caused by homeostatic T -cell proliferation", Proc Natl Acad Sci USA, 110(50) :20200-5 (2013). doi: 10.1073/pnas.1313654110. Epub Nov. 26, 2013.

Jung, et al. "Unraveling V(D)J recombination; insights into gene regulation", *Cell*, 116(2): 299-311 (2004).

Jurkat, Clone 6-1 (ATCC TIB-152) Webpage retrievable from the ATCC under http: /www.lgcstandards-atcc.org/Products/ All MB-152. aspx#characteristics. Accessed Oct. 14, 2014.

Kalinina, O. et al. "Nanoliter scale PCR with TaqMan detection", *Nucleic Acids Research*, 25(10):1999-2004 (1997).

Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt. 2012.06.005. Epub Jun. 12, 2012.

Katz, S.C. et al. "T Cell Infiltrate Predicts Long-Term Survival Following Resection of Colorectal Cancer Liver Metastases," Ann. Surg. Oncol., 16:2524-2530 (2009).

Kedzierska, et al. "Tracking phenotypically and functionally distinct T cell subsets via T cell repertoire diversity", *Mol Immunol.*, 45(3): 607-618 (2008). Epub Aug. 24, 2007.

Kehrl, J.H. et al. "Chemoattractant Receptor Signaling and Its Role in Lymphocyte Motility and Trafficking", *Current Topics in Microbiology and Immunology*, 334:107-127 (2009).

Kim, et al. "An efficient and reliable DNA extraction method for preimplantation genetic diagnosis: a comparison of allele drop out and amplification rates using different single cell lysis methods", *Fertility and Sterility*, 92: 814-818 (2009).

Kircher, et al. "Improved base calling for the Illumina Genome Analyzer using machine learning strategies", *Genome Biol.*, 10(8): R83, 9 pages (2009). doi: 10.1186/gb-2009-10-8-r83. Epub Aug. 14, 2009.

Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.

Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.

Kita, et al. "T cell receptor clonotypes in skin lesions from patients with systemic lupus erythematosus", *Journal of Investigative Dermatology*,110(1): 41-6 (1988).

Klarenbeek, P.L. et al. "Human T-cell memory consists mainly of unexpanded clones", *Immunology Letters*, 133: 42-48 (2010).

Klebanoff, et al. "Therapeutic cancer vaccines: are we there yet?", *Immunol Rev.*, 239(1): 27-44 (2011). doi: 10.1111/j.1600-065X. 2010.00979.x.

Klenerman, et al. "Tracking T cells with tetramers: new tales from new tools", *Nat Rev Immunol.*, 2(4):263-272 (2002).

Kneba, et al. "Characterization of clone-specific rearrangement T-cell receptor gamma-chain genes in lymphomas and leukemias by the polymerase chain reaction and DNA sequencing", *Blood*, 84(2):574-581 (1994).

Kobari, et al. "T cells accumulating in the inflamed joints of a spontaneous murine model of rheumatoid arthritis become restricted to common clonotypes during disease progression", *Int Immunol.*, 16(1):131-138 (2004).

Koboldt et al., "VarScan: variant detection in massively parallel sequencing of individual and pooled samples", Bioinformatics, 25(17): 2283-2285 (2009).

Koch, et al. "Tumor infiltrating T lymphocytes in colorectal cancer: Tumor-selective activation and cytotoxic activity in situ," *Ann Surg.*, 244(6): 986-992; discussion 992-993 (2006).

Kojima et al. "PCR amplification from single DNA molecules on magnetic beads in emulsion: application for high-throughput screening of transcription factor targets", *Nucleic Acids Research*, 33: 17, e150, 9 pages (2005).

Kohlmann, et al. "Integration of next-generation sequencing into clinical practice: are we there yet?", *Semin Oncol.*, 39(1): 26-36, Abstract Only (2012). doi: 10.1053/j.seminoncol.2011.11.008.

Kou, et al. "T-Cell receptor Vbeta repertoire CDR3 length diversity differs within CD45RA and CD45RO T-cell subsets in healthy and human immunodeficiency virus-infected children", *Clin Diagn Lab Immunol.*, 7(6):953-9 (2000).

Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).

Krueger, et al. "Large scale loss of data in low-diversity illumina sequencing libraries can be recovered by deferred cluster calling", *PLoS One*, 6(1): e16607, 7 pages (2011). doi: 10.1371/journal.pone. 0016607.

Ku, et al. "Exome sequencing: dual role as a discovery and diagnostic tool", *Ann Neurol.*, 71(1):5-14, Abstract Only (2012). doi: 10.1002/ana.22647.

Kumar, et al. "PEG-labeled nucleotides and nanopore detection for single molecule DNA sequencing by synthesis", *Sci Rep.*, 2:684, 8 pages (2012). Epub Sep. 21, 2012.

Kwak, et al. "Induction of immune responses in patients with B-cell lymphoma against the surface-immunoglobulin idiotype expressed by their tumors", *N Engl J Med.*, 327(17):1209-1215 (1992).

Kyu et al. "Frequencies of human influenza-specific antibody secreting cells or plasmablasts post vaccination from fresh and frozen peripheral blood mononuclear cells", *Journal of Immunological Methods*, 340: 42-47 (2009).

Ladányi, A., et al. "Prognostic impact of B-cell density in cutaneous melanoma", *Cancer Immunol. Immunother*, 60(12): 1729-1738 (2011).

Ladetto, et al., "Next-generation sequencing and real-time quantitative PCR for minimal residual disease (MRD) detection using the immunoglobulin heavy chain variable region: a methodical comparison in acute lymphoblastic leukemia (ALL), mantle cell lymphoma (MCL) and multiple myeloma (MM)", *Blood*, vol. 120 , No. 21, Abstract 788 (Conference Abstract), Entire Abstract (2012).

Ladetto, M. et al. "Real-time polymerase chain reaction in multiple myeloma: Quantitative analysis of tumor contamination of stem cell harvests", *Experimental Hematology*, 30:529-536 (2002).

Ladetto, M. et al. "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).

Landwehr-Kenzel, et al. "Novel GMP-compatible protocol employing an allogeneic B cell bank for clonal expansion of allospecific natural regulatory T cells", Am J Transplant., 14(3):594-606 (2014). doi: 10.1111/ajt.12629. Epub Jan. 27, 2014.

Langerak, et al. "Immunoglobulin/T-cell receptor clonality diagnostics", *Expert Opin. Med. Diagn.*, 1(3):451-461 (2007).

Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).

Laplaud et al. "Blood T-cell receptor β chain transcriptome in multiple sclerosis. Characterization of the T cells with altered CDR3 length distribution", *Brain*, 127:981-995 (2004).

Laplaud et al. "Serial blood T cell repertoire alterations in multiple sclerosis patients; correlation with clinical and MRI parameters", *Journal of Neuroimmunology*, 177(1-2):151-160 (2006).

Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).

Lazareva-Ulitsky et al, "On the quality of tree-based protein classification," Bioinformatics, 21(9): 1876-1890 (2005).

(56) References Cited

OTHER PUBLICATIONS

Lee, et al. "Characterization of circulating T cells specific for tumor-associated antigens in melanoma patients", Nat Med., 5(6): 677-685, Abstract Only (1999).
Lee, et al. "Prognostic implications of type and density of tumour-infiltrating lymphocytes in gastric cancer", Br J Cancer, 99(10): 1704-1711 (2008). doi: 10.1038/sj.bjc.6604738. Epub Oct. 21, 2008.
Lefranc. "IMGT, the international ImMunoGeneTics database", Nucleic Acids Res., 31(1):307-310 (2003).
Leiden, J.M. et al. "The Complete Primary Structure of the T -Cell Receptor Genes From an Alloreactive Cytotoxic Human T-Lymphocyte Clone", Immunogenetics, 24(1): 17-23 (1986).
Leisner, et al. "One-pot, mix-and-read peptide-MHC tetramers", PLoS One, 3(2):e1678, 11 pages (2008). doi: 10.1371/journal.pone.0001678.
Leary, et al. "Development of personalized tumor biomarkers using massively parallel sequencing", Sci Transl Med., 2(20): 20ra14 (2010). doi: 10.1126/scitranslmed.3000702.
Leone, et al. "Molecular beacon probes combined with amplification by NASBA enable homogeneous, real-time detection of RNA", Nucleic Acids Research, 26(9): 2150-2155 (1998).
Lepore, et al. "Parallel T -cell cloning and deep sequencing of human MAIT cells reveal stable oligoclonal TCRβ repertoire", Nat Commun., 5:3866 (and Corrigendum) (2014). doi: 10.1038/ncomms4866.
Leproust, et al. "Synthesis of high-quality libraries of long (150mer) oligonucleotides by a novel depurination controlled process", Nucleic Acids Res., 38(8): 2522-2540 (2010). doi: 10.1093/nar/gkq163. Epub Mar. 22, 2010.
Lessin, et al. "Molecular diagnosis of cutaneous T-cell lymphoma: polymerase chain reaction amplification of T-cell antigen receptor beta-chain gene rearrangements", J Invest Dermatol., 96(3): 299-302 (1991).
Leventhal et al. "Immune reconstitution/immunocompetence in recipients of kidney plus hematopoietic stem/facilitating cell transplants", Transplantation, 99(2): 288-98 (2015). doi: 10.1097/TP.0000000000000605.
Li, et al. "Utilization of Ig heavy chain variable, diversity, and joining gene segments in children with B-lineage acute lymphoblastic leukemia: implications for the mechanisms of VDJ recombination and for pathogenesis", Blood, 103(12):4602-4609 (2004).
Li, et al. "An improved one-tube RT-PCR protocol for analyzing single-cell gene expression in individual mammalian cells", Anal. Bioanal. Chem., 397: 1853-1859 (2010).
Li, et al. "β cell-specific CD4+ T cell clonotypes in peripheral blood and the pancreatic islets are distinct", J Immunol. , 183(11): 7585-7591 (2009). doi: 10.4049/jimmunol.0901587. Epub Nov. 16, 2009.
Li, et al. "Clonal rearrangements in childhood and adult precursor B acute lymphoblastic leukemia: a comparative polymerase chain reaction study using multiple sets of primers", Eur J Haematol., 63(4):211-218 (1999).
Li, et al. "Detailed clonality analysis of relapsing precursor B acute lymphoblastic leukemia: implications for minimal residual disease detection", Leukemia Research, 25:1033-1045 (2001).
Li et al, "Mapping short DNA sequencing reads and calling variants using mapping quality scores," Genome Research, 18: 1851-1858 (2008).
Liedtke, et al. "A comparison of methods for RNA extraction from lymphocytes for RT-PCR", PCR Methods and Applications, 4(3): 185-187 (1994).
Lin, et al. "Multiplex genotype determination at a large number of gene loci", Proc Natl Acad Sci USA, 93(6): 2582-2587 (1996).
Liu, et al. "CD127 expression inversely correlates with FoxP3 and suppressive function of human CD4+ T reg cells", J Exp Med., 203(7): 1701-1711 (2006). Epub Jul. 3, 2006.
Lo, et al. "T cell immunodominance is dictated by the positively selecting self-peptide", Elife, 3:e01457 (2014). doi: 10.7554/eLife.01457. Epub Jan. 14, 2014.
Logan, et al., "High-throughput immunoglobulin gene sequencing quantifies minimal residual disease in CLL with 10e-6 sensitivity and strongly predicts relapse after allogeneic hematopoietic cell transplantation", Blood, vol. 118 (21), Abstract 2542 (2011).
Logan, A.C. et al. "High-throughput VDJ sequencing for quantification of minimal residual disease in chronic lymphocytic leukemia and immune reconstitution assessment", PNAS, 108(52): 21194-21199 (2011).
Logan, et al., "Massively parallel immunoglobulin gene sequencing provides ultra-sensitive minimal residual disease detection and predicts post-transplant relapse in acute lymphoblastic leukemia by three to six months", Blood, vol. 118 (21), Abstract 4104 (2011).
Lord et al. "T-cell receptor sequencing reveals the clonal diversity and overlap of colonic effector and FOXP3+ T cells in ulcerative colitis", Inflamm Bowel Dis., 21(1):19-30 (2015). doi: 10.1097/MIB.0000000000000242.
Lossius et al. "High-throughput sequencing of TCR repertoires in multiple sclerosis reveals intrathecal enrichment of EBV-reactive CD8+ T cells", Eur J Immunol., 44(11): 3439-52 (2014). doi: 10.1002/eji.201444662. Epub Sep. 16, 2014.
Lossos, et al. "Transformation of follicular lymphoma to diffuse large-cell lymphoma: alternative patterns with increased or decreased expression of c-myc and its regulated genes", PNAS, 99(13): 8886-8891 (2002). Epub Jun. 19, 2002.
Lovisa, et al. "IGH and IGK gene rearrangements as PCR targets for pediatric Burkitt's lymphoma and mature B-ALL MRD analysis", Lab Invest., 89(10):1182-1186 (2009).
Lowe, T., et al. "A computer program for selection of oligonucleotide primers for polymerase chain reactions," Nucleic Acids Research, 18(7):1757-1761 (1990).
Lowman, et al. "Monovalent phage display: a method for selecting variant proteins from random libraries", Methods: A Companion to Methods in Enzymology, 3: 205-216, Abstract Only (1991).
Lyamichev, et al. "Polymorphism identification and quantitative detection of genomic DNA by invasive cleavage of oligonucleotide probes", Nat Biotechnol., 17(3): 292-396 (1999).
Luo et al. "Analysis of the interindividual conservation of T cell receptor α- and β-chain variable regions gene in the peripheral blood of patients with systemic lupus erythematosus", Clinical & Experimental Immunology, 154(3):316-324 (2008).
Mackay, et al. "Real-time PCR in virology", Nucleic Acids Res., 30(6): 1292-305 (2002).
Mahmoud, S.M.A. et al. "Tumor-Infiltrating CD8+ Lymphocytes Predict Clinical Outcome in Breast Cancer", Journal of Clinical Oncology, 29(15): 1949-1955 (2011).
Maldonado, et al. "Intramuscular therapeutic vaccination targeting HPV16 induces T cell responses that localize in mucosal lesions", Sci Transl Med., 6(221): 221ra13 (2014). doi: 10.1126/scitranslmed.3007323.
Malyguine, et al. "ELISPOT Assay for Monitoring Cytotoxic T Lymphocytes (CTL) Activity in Cancer Vaccine Clinical Trials", Cells, 1(2): 111-126 (2012). doi: 10.3390/cells1020111.
Manion et al., "Reducing Error in Next Generation Sequencing Data with NextGENe Software's Condensation Tool™", Mar. 2009, pp. 1-3. XP055226038.
Manrao, et al. "Reading DNA at single-nucleotide resolution with a mutant MspA nanopore and phi29 DNA polymerase", Nat Biotechnol., 30(4): 349-353 (2012). doi: 10.1038/nbt.2171.
Mar et al. "Inferring steady state single-cell gene expression distributions from analysis of mesoscopic samples", Genome Biology, 7(12): R119, 12 pages (2006).
Mardis. "Next-generation DNA sequencing methods", Annu. Rev. Genomics Hum. Genet., 9:387-402 (2008). doi: 10.1146/annurev.genom.9.081307.164359.
Marelli-Berg, F.M., et al. "Memory T-cell trafficking: new directions for busy commuters", Immunology, 130:158-165 (2010).
Marrero, et al. "High-throughput sequencing of islet-infiltrating memory CD4+ T cells reveals a similar pattern ofTCR Vβ usage in prediabetic and diabetic NOD mice", PLoS One, 8(10):e76546 (2013). doi: 10.1371/journal.pone.0076546. eCollection 2013.

(56) References Cited

OTHER PUBLICATIONS

Martin-Jimenez, et al. "Molecular characterization of heavy chain immunoglobulin gene rearrangements in Waldenström's macroglobulinemia and IgM monoclonal gammopathy of undetermined significance", Haematologica, 92(5): 635-642 (2007).
Mary et al. "Analysis of gene expression at the single-cell level using microdroplet-based microfluidic technology", Biomicrofluidics, 5: 024109-1-024109-10 (2011).
Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).
Mato et al. "Correlation of clonal T cell expansion with disease activity in systemic lupus erythematosus", Int Immunol., 9(4):547-554 (1997).
Matolcsy, et al. "Clonal evolution of B cells in transformation from low- to high-grade lymphoma", Eur. J. Immunol., 29(4):1253-1264 (1999).
Matsubara, et al. "Microchamber array based DNA quantification and specific sequence detection from a single copy via PCR in nanoliter volumes", Biosens Bioelectron, 20(8): 1482-1490, Abstract Only (2005).
Matsumoto et al. "CDR3 spectratyping analysis of the TCR repertoire in Myasthenia Gravis", The Journal of Immunology, 176:5100-5107 (2006).
Matsumoto et al. "Complementarity-determining region 3 spectratyping analysis of the TCR repertoire in multiple sclerosis", The Journal of Immunology, 170:4846-4853 (2003).
Mattoo et al. "De novo oligoclonal expansions of circulating plasmablasts in active and relapsing IgG4-related disease", J Allergy Clin Immunol., 134(3):679-87 (2014). doi: 10.1016/j.jaci.2014.03.034. Epub May 6, 2014.
Mazor et al. "Antibody internalization studied using a novel IgG binding toxin fusion", Journal of Immunological Methods, 321: 41-59 (2007).
Mazumder, et al., "Detection of multiple myeloma cells in peripheral blood using high-throughput sequencing assay" Blood, vol. 120, No. 21, Abstract 321 (Conference Abstract), Entire Abstract (2012).
McGoldrick, et al. "Cytomegalovirus-specific T cells are primed early after cord blood transplant but fail to control virus in vivo", Blood, 121(14): 2796-803 (2013). doi: 10.1182/blood-2012-09-453720. Epub Feb. 14, 2013.
Mei et al. "Blood-borne human plasma cells in steady state are derived from mucosal immune responses", Blood, 113(11): 2461-2469 (2009).
Meijer et al. "Isolation of Human Antibody Repertoires with Preservation of the Natural Heavy and Light Chain Pairing", J. Mol. Biol., 358: 764-772 (2006).
Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.
Meier et al. "Simultaneous evaluation of T-cell and B-cell clonality, t(11;14) and t(14;18), in a single reaction by a four-color multiplex polymerase chain reaction assay and automated High-Resolution fragment analysis", American Journal of Pathology, 159(6): 2031-2043 (2001).
Meier, et al. "The influence of different stimulation conditions on the assessment of antigen-induced CD154 expression on CD4+ T cells", Cytometry A., (11):1035-1042 (2008). doi: 10.1002/cyto.a.20640.
Meleshko, et al. "Rearrangements of IgH, TCRD and TCRG genes as clonality marker of childhood acute lymphoblastic leukemia", Experimental Oncology, 27(4):319-324 (2005).
Menezes et al. "A public T cell clonotype within a heterogeneous autoreactive repertoire is dominant in driving EAE", J Clin Invest, 117(8):2176-2185 (2007).

Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", Nature Reviews, Genetics, 11:31-46 (2010).
Miceli and Parnes. "The roles of CD4 and CD8 in T cell activation", Seminars in Immunology, 3(3): 133-141 (1991). Abstract only.
Michalek, et al. "Detection and long-term in vivo monitoring of individual tumor-specific T cell clones in patients with metastatic melanoma", J Immunol., 178(11):6789-6795 (2007).
Michalek, et al. "Identification and monitoring of graft-versus-host specific T-cell clone in stem cell transplantation", The Lancet, 361(9364): 1183-1185 (2003).
Miller, et al., "Assembly algorithms for next-generation sequencing data", Genomics, 95(6): 315-327 (2010).
Miltenyi, et al. "High gradient magnetic cell separation with MACS", Cytometry, 11(2): 231-238 (1990).
Mitra, et al. "Fluorescent in situ sequencing on polymerase colonies", Anal Biochem., 320(1): 55-65, Abstract Only (2003).
Mittelstadl, et al. "Thymocyte responsiveness to endogenous glucocorticoids is required for immunological fitness", J Clin Invest., 122(7):2384-94 (2012). doi: 10.1172/JCI63067. Epub Jun. 1, 2012.
Miyashita, et al. "N-Methyl substituted 2',4'- BNANC: a highly nuclease-resistant nucleic acid analogue with high-affinity RNA selective hybridization", Chem Commun (CAMB), (36): 3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", Clin Diagn Lab Immunol., 10(6): 1043-1050 (2003).
Molloy, et al. "Soluble T cell receptors: novel immunotherapies", Curr Opin Pharmacol., 5(4): 438-443 (2005) (Abstract Only).
Moody, et al. "Antigen-specific B cell detection reagents: use and quality control", Cytometry A., 73(11): 10861092 (2008). doi: 10.1002/cyto.a.20599.
Morgan, et al. "Cancer regression in patients after transfer of genetically engineered lymphocytes", Science, 314(5796): 126-129 (2006). Epub Aug. 31, 2006.
Morozova et al. "Applications of New Sequencing Technologies for Transcriptome Analysis", Annu. Rev. Genomics Hum. Genet., 10: 135-151 (2009).
Morrissy et al. "Next-generation tag sequencing for cancer gene expression profiling", Genome Research, 19: 1825-1835 (2009).
Moss, et al. "The human T cell receptor in health and disease", Annu. Rev. Immunol., 10:71-96 (1992).
Moura, et al. "Alterations on peripheral blood B-cell subpopulations in very early arthritis patients", Rheumatology (Oxford), 49(6): 1082-1092 (2010). doi: 10.1093/rheumatology/keq029. Epub Mar. 7, 2010.
Mueller, et al. "Human Treg responses allow sustained recombinant adeno-associated virus-mediated transgene expression", J Clin Invest., 123(12): 5310-8 (2013). doi: 10.1172/JCI70314. Epub Nov. 15, 2013.
Muraro, et al. "T cell repertoire following autologous stem cell transplantation for multiple sclerosis", J Clin Invest., 124(3): 1168-72 (2014). doi: 10.1172/JCI71691. Epub Feb. 17, 2014.
Murugan, et al. "Statistical inference of the generation probability of T-cell receptors from sequence repertoires", PNAS, 109(40): 16161-16166 (2012). doi: 10.1073/pnas.1212755109. Epub Sep. 17, 2012.
Naito, et al. "CD8+ T cells infiltrated within cancer cell nests as a prognostic factor in human colorectal cancer", Cancer Research, 58(16): 3491-3494 (1998).
Nakano, et al. "Single-molecule PCR using water-in-oil emulsion", J Biotechnol., 102(2): 117-124, Abstract Only (2003).
Nardi, et al. "Quantitative monitoring by polymerase colony assay of known mutations resistant to ABL kinase inhibitors", Oncogene, 27(6):775-782 (2008). Epub Aug. 6, 2007, 1-8.
Navarrete, et al. "Upfront immunization with autologous recombinant idiotype Fab fragment without prior cytoreduction in indolent

(56) References Cited

OTHER PUBLICATIONS

B-cell lymphoma", *Blood*, 117(5): 1483-1491 (2011). doi: 10.1182/blood-2010-06-292342. Epub Nov. 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Neller, et al. "High frequency of herpesvirus-specific clonotypes in the human T cell repertoire can remain stable over decades with minimal turnover", J Virol., 87(1): 697-700 (2013). doi: 10.1128/NI.02180-12. Epub Oct. 17, 2012.

Nelson. "CD20+ B cells: the other tumor-infiltrating lymphocytes", *The Journal of Immunology*, 185(9): 49774982 (2010). doi: 10.4049/jimmunol.1001323.

Newman, et al. "Identification of an antigen-specific B cell population", *J Immunol Methods*, 272(1-2): 177-187, Abstract Only (2003).

Nie, et al. "Optical detection of single molecules", *Annu. Rev. Biophys. Biomol. Struct.*, 26: 567-596 (1997).

Nielsen, et al. "Peptide nucleic acid (PNA). A DNA mimic with a pseudopeptide backbone", *Chem. Soc. Rev.*, 26:73-78, Abstract Only (1997).

Nolan, T. et al. "Quantification of mRNA using real-time RT-PCR", *Nature Protocols*, 1(3):1559-1582 (2006).

Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Nucleis product webpage, "Exonuclease I-Shrimp alkaline phosphatase clean up of PCR products," (Published on webpage 2013) Downloaded Dec. 15, 2015.

Oble, et al. "Focus on TILs: prognostic significance of tumor infiltrating lymphocytes in human melanoma", *Cancer Immunity*, 9: 3, 20 pages (2009).

O'Brian et al., "Sorting out mix-ups. The provenance of tissue sections may be confirmed by PCR using microsatellite markers", Am. J. Clin. Pathol., 106(6): 758-764 (1996). (Abstract Only).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ohtani. "Focus on TILs: prognostic significance of tumor infiltrating lymphocytes in human colorectal cancer", *Cancer Immunity*, 7: 4, 9 pages (2007).

Okajima et al. "Analysis of T cell receptor Vβ diversity in peripheral CD4+ and CD8+ T lymphocytes in patients with autoimmune thyroid diseases", *Clinical & Experimental Immunology*, 155:166-172 (2008).

Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.

Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

Pagès, Franck. Tumor-associated immune parameters for personalized patient care. Sci Transl Med., 5(214):214fs42 (2013). doi: 10.1126/scitranslmed.3007942.

Palmowski, et al. "The use of HLA class I tetramers to design a vaccination strategy for melanoma patients", *Immunol Rev.*, 188: 155-163 (2002) (Abstract Only).

Palomaki, et al. "DNA sequencing of maternal plasma reliably identifies trisomy 18 and trisomy 13 as well as Down syndrome: an international collaborative study", *Genet Med.*, 14(3): 296-305 (2012). doi: 10.1038/gim.2011.73. Epub Feb. 2, 2012.

Pan, et al. "A new FACS approach isolates hESC derived endoderm using transcription factors", *PLoS One*, 6(3): e17536, 9 pages (2011). doi: 10.1371/journal.pone.0017536.

Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).

Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.

Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.

Paszkiewicz et al, "De novo assembly of short sequence reads," Briefings in Bioinformatics, 11(5): 457-472 (2010).

Payne, et al. "Peripheral blood mononuclear cells of patients with breast cancer can be reprogrammed to enhance anti-HER-2/neu reactivity and overcome myeloid-derived suppressor cells", Breast Cancer Res Treat., 142(1):45-57 (2013). doi: 10.1007/s10549-013-2733-5. Epub Oct. 25, 2013.

Peet. "The Measurement of Species Diversity", *Annual Review of Ecology and Systematics*, 5: 285-307, Abstract Only (1974).

Petrosino, et al. "Metagenomic pyrosequencing and microbial identification", *Clin Chem.*, 55(5): 856-866 (2009). doi: 10.1373/clinchem.2008.107565. Epub Mar. 5, 2009.

PCT/US2009/006053, International Search Report dated Jun. 15, 2010, 6 pages.

PCT/US2009/006053, Written Opinion dated Jun. 15, 2010, 4 pages.

PCT/US2009/006053, International Preliminary Report on Patentability dated May 10, 2011, 5 pages.

PCT/US2010/037477, International Search Report and Written Opinion dated Sep. 24, 2010, 10 pages.

PCT/US2010/037477, International Preliminary Report on Patentability dated Jan. 4, 2012, 7 pages.

PCT/US2011/000791, International Search Report and Written Opinion dated Sep. 22, 2011, 13 pages.

PCT/US2011/000791, International Preliminary Report on Patentability dated Nov. 6, 2012, 10 pages.

PCT/US2011/049012, International Search Report and Written Opinion dated Apr. 10, 2012, 9 pages.

PCT/US2011/049012, International Preliminary Report on Patentability dated Feb. 26, 2013, 5 pages.

PCT/US2012/058989, International Search Report and Written Opinion dated Mar. 29, 2013, 12 pages.

PCT/US2012/058989, International Preliminary Report on Patentability dated Apr. 15, 2014, 8 pages.

PCT/US2012/061977, International Preliminary Report on Patentability dated May 6, 2014, 7 pages.

PCT/US2012/068617, International Preliminary Report on Patentability dated Jun. 10, 2014, 6 pages.

PCT/US2012/070674, International Search Report and Written Opinion dated Feb. 22, 2013, 8 pages.

PCT/US2012/070674, International Preliminary Report on Patentability dated Aug. 5, 2014, 6 pages.

PCT/US2013/043420, International Search Report and Written Opinion dated Oct. 25, 2013, 8 pages.

PCT/US2013/043420, International Preliminary Report on Patentability dated May 19, 2015, 7 pages.

PCT/US2013/065493, International Search Report and Written Opinion dated Jan. 20, 2014, 14 pages.

PCT/US2013/065493, International Preliminary Report on Patentability dated Apr. 21, 2015, 10 pages.

PCT/US2013/065509, International Search Report and Written Opinion dated Jan. 20, 2014, 9 pages.

PCT/US2013/065509, International Preliminary Report on Patentability dated Apr. 21, 2015, 6 pages.

PCT/US2013/065757, International Search Report and Written Opinion dated Jan. 21, 2014, 10 pages.

(56) References Cited

OTHER PUBLICATIONS

PCT/US2013/065757, International Preliminary Report on Patentability dated Apr. 28, 2015, 6 pages.
PCT/US2013/037258, International Search Report and Written Opinion dated Aug. 19, 2013, 8 pages.
PCT/US2013/037258, International Preliminary Report on Patentability dated Oct. 21, 2014, 6 pages.
PCT/US2014/017416, International Search Report dated May 12, 2014, 9 pages.
PCT/US2014/017416, Written Opinion dated May 12, 2014, 9 pages.
PCT/US2014/017416, International Preliminary Report on Patentability dated Aug. 25, 2015, 10 pages.
PCT/US2014/030859, International Search Report and Written Opinion dated Jul. 18, 2014, 14 pages.
PCT/US2014/030859, International Preliminary Report on Patentability dated Sep. 15, 2015, 8 pages.
PCT/US2014/047909, International Search Report dated Nov. 17, 2014.
PCT/US2014/047909, Written Opinion dated Nov. 17, 2014, 9 pages.
PCT/US2015/010904, International Search Report dated May 6, 2015, 4 pages.
PCT/US2015/010904, Written Opinion dated May 6, 2015, 4 pages.
PCT/US2015/018967, International Search Report and Written Opinion dated Jul. 30, 2015, 17 pages.
PCT/US2015/019029, International Search Report and Written Opinion dated Sep. 15, 2015, 19 pages.
Pekin, D. et al. "Quantitative and sensitive detection of rare mutations using droplet-based microfluidics", Lab Chip, 11(3): 2156-2166 (2011).
Pels et al. "Clonal evolution as pathogenetic mechanism in relapse of primary CNS lymphoma", Neurology, 63(1):167-169 (2004).
Pira et al. "Human naive CD4 T-cell clones specific for HIV envelope persist for years in vivo in the absence of antigenic challenge", J Acquir Immune Defic Syndr., 40(2):132-139 (2005).
Polstra, et al. "Development of real-time NASBA assays with molecular beacon detection to quantify mRNA coding for HHV-8 lytic and latent genes", BMC Infect Dis., 2: 18 (2002). Epub Sep. 4, 2002.
Pop and Salzberg. "Bioinformatics challenges of new sequencing technology", NIH, Trends Genet., 24(3): 142-149 (2008).
Pourmand, et al. "Direct electrical detection of DNA synthesis",PNAS, 103(17): 6466-6470 (2006). Epub Apr. 13, 2006.
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Poschke et al. "A phase I clinical trial combining dendritic cell vaccination with adoptive T cell transfer in patients with stage IV melanoma", Cancer Immunol Immunother., 63(10): 1061-71 (2014). doi: 10.1007/s00262-014-1575-2. Epub Jul. 4, 2014.
Prabakaran et al. "454 antibody sequencing—error characterization and correction", BMC Research Notes, 4: 404 (2011).
Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant., 13(11): 3010-20 (2013). doi: 10.1111/ajt.12433. Epub Sep. 18, 2013.
Quick. SOLiD System—a next-gen DNA sequencing platform announced, Gizmag online magazine, http://www.mizmag.com/go/8248, pp. 1-5, Oct. 2007.
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", Semin Cancer Biol., 20(4): 254-260 (2010). doi: 10.1016/j.semcancer. 2010.06.002. Epub Jul. 1, 2010.

Ray, et al. "Single cell multiplex PCR amplification of five dystrophin gene exons combined with gender determination", Molecular Human Reproduction, 7(5): 489-494 (2001).
Reddy, et al. "Monoclonal antibodies isolated without screening by analyzing the variable-gene repertoire of plasma cells", Nature Biotechnology, 28(9): 965-969 (2010). doi: 10.1038/nbt.1673. Epub Aug. 29, 2010.
Reddy and Georgiou. "Systems analysis of adaptive immunity by utilization of high-throughput technologies", Current Opinion in Biotechnology, 22(4): 584-589 (2011).
Ria, et al. "Collagen-specific T-cell repertoire in blood and synovial fluid varies with disease activity in early rheumatoid arthritis", Arthritis Res Ther., 10(6):R135, 18 pages (2008). Epub Nov. 17, 2008.
Rickinson and Moss. "Human cytotoxic T lymphocyte responses to Epstein-Barr virus infection", Annu Rev Immunol., 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", Lancet, 364:355-364 (2004).
Robert, et al. "CTLA4 blockade broadens the peripheral T -cell receptor repertoire", Clin Cancer Res., 20(9):2424-32 (2014). doi: 10.1158/1078-0432.CCR-13/2648. Epub Feb. 28, 2014.
Robins, H. et al. "Ultra-sensitive detection of rare T cell clones", Journal of Immunological Methods, 375(1-2): 14-19 (2012).
Robins, et al. "CD4+ and CD8+ T cell β antigen receptors have different and predictable V and J gene usage and CDR3 lengths", J. Immunol., 188: 115.10, Abstract (2012).
Robins et al. "Detecting and monitoring lymphoma with high-throughput sequencing" Oncotarget, 2:287-288 (2011).
Robins, H. et al. "Digital Genomic Quantification of Tumor Infiltrating Lymphocytes", Science Translational Medicine, 5:214ra169, 19 pages, Supplementary Materials (2013).
Robins, et al. "Effects of aging on the human adaptive immune system revealed by high-throughput DNA sequencing of T cell receptors", J Immunol., 188: 47.16, Abstract (2012).
Robins, et al. "High-throughput sequencing of T -cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", Curr Opin Immunol., 25(5): 646-652 (2013). doi: 10.1016/j.coi.2013.09.017. Epub Oct. 16, 2013.
Robins, et al. "Overlap of the human CD8+ T cell receptor repertoire." Oct. 2010. Poster. 1 page.
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Robins, H. et al. "The Computational Detection of Functional Nucleotide Sequence Motifs in the Coding Regions of Organisms", Exp Biol Med, 233(6): 665-673 (2008).
Ronaghi, et al. "A sequencing method based on real-time pyrophosphate", Science, 281(5375): 363, 365, 5 pages (1998).
Rosenberg, S.A. et al. "New Approach to the Adoptive Immunotherapy of Cancer with Tumor-Infiltrating Lymphocytes", Science, 233(4770): 1318-1321 (1986).
Rosenquist, et al. "Clonal evolution as judged by immunoglobulin heavy chain gene rearrangements in relapsing precursor-B acute lymphoblastic leukemia", Eur J Haematol., 63(3):171-179 (1999).
Rothberg, et al. "An integrated semiconductor device enabling non-optical genome sequencing", Nature, 475(7356): 348-352 (2011). doi: 10.1038/nature10242.

(56) References Cited

OTHER PUBLICATIONS

Rothberg et al. "The development and impact of 454 sequencing", *Nature Biotechnology*, 26(10): 1117-1124 (2008).
Rougemont, et al. "Probabilistic base calling of Solexa sequencing data", *BMC Bioinformatics*, 9:431, 12 pages (2008).
Rozen, S. et al. "Primer3 on the WWW for General Users and for Biologist Programmers", *Methods in Molecular Biology, Bioinformatics Methods and Protocols*, 132:365-386 (2000).
Ryan et al. "Clonal evolution of lymphoblastoid cell lines", *Laboratory Investigation*, 86(11):1193-1200 (2006). Epub Oct. 2, 2006.
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex lmmunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santalucia, Jr., J. "Physical Principles and Visual-OMP Software for Optimal PCR Design," *Methods in Molecular Biology*, 402(PCR Primer Design):3-33, 40 pages (2007).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sartorius Stedim Biotech product brochure, "Primer removal after a PCR reaction with Vivacon® 2", (2010).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).
Schlissel, M.S. et al. "Leukemia and lymphoma: a cost of doing business for adaptive immunity", *Genes Dev.*, 20(12): 1539-1544 (2006).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone. 002731 0.
Schøller et al. "Analysis of T cell receptor αβ variability in lymphocytes infiltrating melanoma primary tumours and metastatic lesions", *Cancer Immunol lmmunother*. 39(4):239-248 (1994).
Schreiber et al. "Cancer immunoediting: integrating immunity's roles in cancer suppression and promotion", *Science*, 331(6024): 1565-1570 (2011). doi: 10.1126/science.1203486.
Schwab et al. "CD8+ T-cell clones dominate brain infiltrates in Rasmussen encephalitis and persist in the periphery", *Brain*, 132:1236-1246 (2009).
Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.
Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).
Sehouli et al. "Epigenetic quantification of tumor-infiltrating T-lymphocytes" *Epigenetics*, 6(2): 236-246 (2011). Epub Feb. 1, 2011.
Seitz, et al. "Reconstitution of paired T cell receptor α- and β-chains from microdissected single cells of human inflammatory tissues", *PNAS*, 103: 12057-12062 (2006).

Seo, et al. "Four-color DNA sequencing by synthesis on a chip using photocleavable fluorescent nucleotides", *PNAS*, 102(17): 5926-5931 (2005). Epub Apr. 13, 2005.
Sequenta and iRepertoire Join Forces on Blood Cancer Testing. Business Wire. Aug. 8, 2013. http://www.businesswire.com/news/home/20130808005363/en/SequentaiRepertoire-Join-Forces-Blo . . . .#.VGTT9WdOyUk. 2 pages.
Sfanos et al. "Human Prostate-Infiltrating CD8+ T Lymphocytes are Oligoclonal and Pd-1+", *The Prostate*, 69(15): 1694-1703 (2009).
Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.
Shen et al. "Comparing platforms for *C. elegans* mutant identification using high-throughput whole-genome sequencing", *PLoS One*, 3(12):e4012, 6 pages (2008).
Shendure, et al. "Accurate multiplex polony sequencing of an evolved bacterial genome", *Science*, 309(5741): 1728-1732, Abstract Only (2005). Epub Aug. 4, 2005.
Shendure, et al. "Advanced sequencing technologies: methods and goals", *Nat Rev Genet.*, 5(5): 335-344 (2004).
Sherwood, et al. "New Technologies for Measurements of Tumor Infiltrating Lymphocytes", Presented Nov. 7, 2012 Moscone Center, Exhibit Halls ABC.
Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymphocytes", *The Journal of Heart and Lung Transplant*, 31: 996-1002 (2012).
Shumaker, et al. "Mutation detection by solid phase primer extension", *Hum Mutat.*, 7(4): 346-354, Abstract Only (1996).
Sia, et al. "Microfluidic devices fabricated in poly(dimethylsiloxane) for biological studies", *Electrophoresis*, 24(21): 3563-3576, Abstract Only (2003).
Sims, et al. "Fluorogenic DNA sequencing in PDMS microreactors", *Nat Methods*, 8(7): 575-580 (2011). doi: 10.1038/nmeth.1629.
Sims, et al. "MHC-peptide tetramers for the analysis of antigen-specific T cells", *Expert Rev Vaccines*, 9(7): 765-774 (2010). doi: 10.1586/erv.10.66.
Singapore Application No. 11201403212R, Written Opinion dated Mar. 27, 2015, 12 pges.
Singapore Application No. 11201407888R, Written Opinion dated Aug. 14, 2015, 12 pages.
Singapore Application No. 11201500313Y, Search Report and Written Opinion dated Dec. 9, 2015, 11 pages.
Skulina et al. "Multiple Sclerosis: Brain-infiltrating CD8+ T cells persist as clonal expansions in the cerebrospinal fluid and blood", *PNAS*, 101(8):2428-2433 (2004).
Slightom, J.L. et al. "*Homo sapiens* germline beta T-cell receptor locus", NCBI Accession No. L36092 NCBI, 254 pages (2009) Retrieved from the Internet: <URL:http://www.ncbi.nlm.nih.gov/nuccore/L36092>.
Smith, et al. "Comparison of biosequences", *Advances in Applied Mathematics*, 2: 482-489 (1981).
Smith et al. "Rapid generation of fully human monoclonal antibodies specific to a vaccinating antigen", *Nature Protocols*, 4(3): 372-384 and CORRIGENDA (2009).
Smith et al. "Rapid whole-genome mutational profiling using next-generation sequencing technologies", *Genome Research*, 18: 1638-1642 (2008).
Smith et al, "Using quality scores and longer reads improves accuracy of Solexa read mapping," BMC Bioinformatics, 9: 128 (2008).
Sobrino, et al. "SNPs in forensic genetics: a review on SNP typing methodologies", *Forensic Sci Int.*, 154(2-3): 181-194, Abstract Only (2005). Epub Jan. 11, 2005.
Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].

(56) References Cited

OTHER PUBLICATIONS

Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).
Srinivasan et al. "Effect of fixatives and tissue processing on the content and integrity of nucleic acids", *Am J Pathol.*, 161(6): 1961-1971 (2002).
Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.
Standard Sequencing Primers, Max Planck Genome Center Cologne, Jan. 15, 2011, 2 pages, downloaded from https://genomecentre.mpipz.mpg.de/SeqOrderDB/export/sequencing-primers.html.
Stanley. Essentials of Immunology & Serology, Delmar, Thomson Learning, Chapter 7, T cells, p. 95 (2002).
Steenbergen, et al. "Distinct ongoing Ig heavy chain rearrangement processes in childhood B-precursor acute lymphoblastic leukemia", *Blood*, 82(2):581-589 (1993).
Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).
Stein and Nombela-Arrieta. "Chemokine control of lymphocyte trafficking: a general overview", *Immunology*, 116(10):1-12 (2005).
Steinmetz, O.M. et al. "Chemokines and B cells in renal inflammation and allograft rejection", *Frontiers in Bioscience (Schol. Ed.)*, 1:13-22 (2009).
Stemmer, et al. "Single-step assembly of a gene and entire plasmid from large numbers of oligodeoxyribonucleotides", *Gene*, 164(1): 49-53 (1995).
Steward et al. "A polymerase chain reaction study of the stability of Ig heavy-chain and T-cell receptor delta gene rearrangements between presentation and relapse of childhood B-lineage acute lymphoblastic leukemia", *Blood*, 83(5):1355-1362 (1994).
Stewart and Schwartz. "Immunoglobulin V regions and the B cell", *Blood*, 83(7): 1717-1730 (1994).
Stickler, et al. "An in vitro human cell-based assay to rank the relative immunogenicity of proteins", *Toxicol Sci.*, 77(2): 280-289 (2004). Epub Dec. 22, 2003.
Straten, Per thor, et al. "T-cell clonotypes in cancer", *Journal of Translational Medicine*, 2(1): 11, 10 pages (2004).
Stratton. "Exploring the genomes of cancer cells: progress and promise", *Science*, 331(6024): 1553-1558 (2011). doi: 10.1126/science.1204040.
Striebich, et al. "Selective Accumulation of Related CD41 T Cell Clones in the Synovial Fluid of Patients with Rheumatoid Arthritis", *J Immunol.*, 161(8): 4428-36 (1998).
Struyk et al. "T cell receptors in rheumatoid arthritis", *Arthritis & Rheumatism*, 38(5):577-589 (1995).
Sumida et al. "T cell receptor repertoire of infiltrating T cells in lips of Sjögren's syndrome patients", *J Clin Invest.*, 89:681-685 (1992).
Sumida et al. "T cell receptor Vα repertoire of infiltrating T cells in labial salivary glands from patients with Sjögren's syndrome", *J Rheumatol.*, 21:1655-1661 (1994).
Swarup and Rajeswari. "Circulating (cell-free) nucleic acids--a promising, non-invasive tool for early detection of several human diseases", *FEBS Letters*, 581(5): 795-799 (2007). Epub Feb. 2, 2007.
Szczepanski et al. "Why and how to quantify minimal residual disease in acute lymphoblastic leukemia'?", *Leukemia*, 21(4):622-626 (2007). Epub Feb. 15, 2007.
Szereday et al., "Somatic Mutation of the 5' Noncoding Region of the BCL-6 Gene Is Associated with Intraclonal Diversity and Clonal Selection in Histological Transformation of Follicular Lymphoma", *The American Journal of Pathology*, 156(3): 1017-1024 (2000).
Tackenberg et al. "Clonal expansions of CD4+ β helper T cells in autoimmune myasthenia gravis", *European Journal of Immunology*, 37(3):849-863 (2007).

Tajiri et al. "Cell-microarray analysis of antigen-specific B-cells: single cell analysis of antigen receptor expression and specificity", *Cytometry Part A*, 71A: 961-967 (2007).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion Is not Integral to Plasma Cell Differentiation as Revealed by Xbp-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
ten Bosch et al. "Keeping Up With the Next Generation Massively Parallel Sequencing in Clinical Diagnostics", *Journal of Molecular Diagnostics*, 10(6): 484-492 (2008).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Toinoven et al. "Islet-associated T-cell receptor-β CDR sequence repertoire in prediabetic NOD mice reveals antigen-driven T-cell expansion and shared usage of Vβ Jβ TCR chains", Mol Immunol., 64(1):127-35 (2015). doi: 10.1016/j.molimm.2014.11.009. Epub Dec. 3, 2014.
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes a γ Protein Expressed on the Majority of CD3+ T Cell Receptor -a/fr Circulating Lymphocytes", *J. Exp. Med.*, 167:694-699 (1988).
Tsai et al. "Discovery of rare mutations in populations: TILLING by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Tumeh et al. "PD-1 blockade induces responses by inhibiting adaptive immune resistance", Nature, 515: 568-571 (2014). doi:10.1038/nature13954.
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 27, 2011 for UK application No. GB1105068.9.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).

(56) References Cited

OTHER PUBLICATIONS

Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Urquhart, et al. "Rate-controlled delivery systems in drug and hormone research", *Annu Rev Pharmacol Toxicol.*, 24: 199-236, Abstract Only (1984).
Van Der Velden, V.H.J., et al. "Optimization of PCR-based minimal residual disease diagnostics for childhood acute lymphoblastic leukemia in a multi-center setting," *Leukemia*, 21:706-713 (2007).
Vanderborght, et al. "Dynamic T cell receptor clonotype changes in synovial tissue of patients with early rheumatoid arthritis: effects of treatment with cyclosporin A (Neoral)", *J Rheumatol.*, 29(3): 416-426 (2002).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8+ T Cell Responses to Cytomegalovirus and EBV[1]", *The Journal of Immunology*, 181:7853-7862 (2008).
Venturi, V. et al. "The molecular basis for public T-cell responses?", *Nature Reviews*, 8:231-238 (2008).
Verhagen, O.J.H.M., et al. "Application of germline IGH probes in real-time quantitative PCR for the detection of minimal residual disease in acute lymphoblastic leukemia", *Leukemia*, 14:1426-1435 (2000).
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Vogelstein and Kinzler. "Digital PCR," *Genetics, PNAS*, 96:9236-9241 (1999).
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.
Wang, et al. "Balanced-PCR amplification allows unbiased identification of genomic copy changes in minute cell and tissue samples", *Nucleic Acids Research*, 32(9): e76, 10 pages (2004).
Wang, et al. "HIV integration site selection: Analysis by massively parallel pyrosequencing reveals association with epigenetic modifications", Genome Research, 17(8): 1186-1194 (2007). Epub Jun. 1, 2007.
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Wang, X. et al. "Quantitative Measurement of Pathogen Specific Human Memory T Cell Repertoire Diversity using a CDR3 B-Specific Microarray", *BMC Genomics*, 8(329): 1-13 (2007).
Ward and Marelli-Berg. "Mechanisms of chemokine and antigen-dependent T-lymphocyte navigation", *Biochem. J.*, 418:13-27 (2009).
Weinstein, J.A. et al. "High-Throughput Sequencing of the Zebrafish Antibody Repertoire", *Science*, 324(5928): 807-810, Supporting/Supplementary Materials (2009).
Weiss et al. "Clonal Rearrangements of T-Cell Receptor Genes in Mycosis Fungoides and Dermatopathic Lymphadenopathy", *The New England Journal of Medicine*, 313(9):539-544 (1985).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).

Wells, et al. "Strategies for preimplantation genetic diagnosis of single gene disorders by DNA amplification", *Prenatal Diagnosis*, 18(13):1389-1401 (1998).
Weng, Wen-Kai et al., "Graft-Versus-Lymphoma Effect After Non-Myeloablative Allogeneic Transplant Induces Molecular Remission Assessed by High-Throughput Sequencing of T Cell Receptor in Patients with Advanced Stage Mycosis Fungoides and Sezary Syndrome", Blood, vol. 118. No. 21. Nov. 2011 (Nov. 2011). p. 1346. XP055213326. & 53rd Annual Meeting and Exposition of the American-Society-of-Hematology (ASH); San Diego. CA. USA; Dec. 10-13, 2011.
Weng, et al. "Minimal residual disease monitoring with high-throughput sequencing of T cell receptors in cutaneous T cell lymphoma", Sci Transl Med., 5(214):214ra171 (2013). doi: 10.1126/scitranslmed.3007420.
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).
Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneo detection using molecular beacons", Nucleic Acids Res., 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Williams, et al. "Amplification of complex gene libraries by emulsion PCR", *Nat Methods*, 3(7): 545-550 (2006).
Wolda. "Similarity Indices, Sample Size and Diversity", *Oecologia* (Berl), 50:296-302 (1981).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Wrammert et al. "Rapid cloning of high-affinity human monoclonal antibodies against influenza virus", *Nature*, 453: 667-672 (2008).
Wu, et al. "High-throughput sequencing detects minimal residual disease in acute T lymphoblastic leukemia", Sci Transl Med., 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, et al., "Detection of Minimal Residual Disease in B Lymphoblastic Leukemia by High-Throughput Sequencing of IGH", Clin Cancer Res., 20(17): 4540-8 (2014). Published OnlineFirst Jun. 26, 2014; doi: 10.1158/1078-0432.CCR-13/3231.
Wu, Y-C. et al. "High-throughput immunoglobulin repertoire analysis distinguishes between human IgM memory and switched memory B-cell populations", *Blood Journal*, 116(7): 1070-1078, 22 pages (2010).
Wu et al. "Focused Evolution of HIV-1 Neutralizing Antibodies Revealed by Structures and Deep Sequencing", *Science*, 333: 1593-1602 (2011).

(56) References Cited

OTHER PUBLICATIONS

Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Xiong, et al. "Chemical gene synthesis: strategies, softwares, error corrections, and applications", *FEMS Microbiol Rev.*, 32(3): 522-540 (2008). doi: 10.1111/j.1574-6976.2008.00109.x. Epub Apr. 2, 2008.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Yan et al. "Emergence of a STAT3 Mutated NK Clone in LGL Leukemia", Leuk Res Rep., 4(1):4-7 (2014). doi: 10.1016/j.lrr.2014.12.001. eCollection 2015.
Yao, et al. "Analysis of the CDR3 length repertoire and the diversity of TCRα chain in human peripheral blood T Lymphocytes", Cell Mol Immunol., 4(3): 215-220 (2007).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yassai, M.B. et al. "A clonotype nomenclature for T cell receptors", *Immunogenetics*, 61:493-502 (2009).
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).
Zagnoni, et al. "Droplet Microfluidics for High-throughput Analysis of Cells and Particles", *Methods in Cell Biology*, Chapter 2, 102: 23-48 (2011).
Zaliova, et al. "Quantification of fusion transcript reveals a subgroup with distinct biological properties and predicts relapse in BCR/ABL-positive ALL: implications for residual disease monitoring", *Leukemia*, 23(5):944-951 (2009).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhong, Q. et al. "Multiplex digital PCR: breaking the one target per color barrier of quantitative PCR", Lab Chip, 11:2167-2174 (2011).
Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.
Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.
Zimmerman and Mannhalter. "Technical aspects of quantitative competitive PCR", *Biotechniques*, 21: 268-279 (1996).
Andersen, N.S. et al., "Failure of immunologic purging in mantle cell lymphoma assessed by polymerase chain reaction detection of minimal residual disease." Blood, 90(10): 4212-4221 (1997).
European Patent Application No. 13847123.0, Extended European Search Report dated May 31, 2016, 9 pages.
European Patent Application No. 13848896.0, Extended European Search Report dated Jun. 7, 2016, 10 pages.
European Patent Application No. 13846484.7, Extended European Search Report dated May 20, 2016, 5 pages.
Ferrero, et al., "Minimal residual disease detection in lymphoma and multiple myeloma: impact on therapeutic paradigms." Hematological Oncology, 29(4): 167-176 (2011).
Kurokawa et al., "Complementarity determining region-III is a useful molecular marker for the evaluation of minimal residual disease in mantle cell lymphoma." British Journal of Haematology, 98(2): 408-412 (1997).
Pott, C., "Minimal residual disease detection in mantle cell lymphoma: technical aspects and clinical relevance." Seminars in Hematology, 48(3): 172-184 (2011).
Pott, C., "Structure of Bcl-1 and IgH-CDR3 rearrangements as clonal markers in mantle cell lymphomas." Leukemia, 12(10): 1630-1637 (1998).
Davies et al., "Transformation of follicular lymphoma to diffuse large B-cell lymphoma proceeds by distinct oncogenic mechanisms", Br J Haematol., 136(2):286-93 (2007).
PCT/US2012/061977, International Search Report and Written Opinion dated Feb. 25, 2013, 11 pages.
Brody, J.D., "Immunotransplant for mantle cell lymphoma: Phase I/II study preliminary results." International Conference & Exhibition on Cell Science & Stem Cell Research, J Cell Sci Ther (2011); 2(4): 96.
European Patent Application No. 14754622.0, Partial Supplementary European Search Report dated Sep. 29, 2016, 7 pages.
European Patent Application No. 14754622.0, Extended European Search Report dated Jan. 12, 2017, 12 pages.
Faham, M.C., et al. "Increased T Cell Receptor Clonotype Sharing Among Ankylosing Spondylitis Patients Revealed by Deep Repertoire Sequence Analysis." Arthritis & Rheumatism (2011), Abstract 1339, 63(10)Supplement: S524, 3 pages.
NCBI Blast search; SEQ ID No. 1 vs protein database; accessed Oct. 20, 2016, 15 pages.
NCBI Blast search; SEQ ID No. 2 vs protein database; accessed Oct. 20, 2016, 21 pages.
Pott, Christiane, et al. "Molecular remission is an independent predictor of clinical outcome in patients with mantle cell lymphoma after combined immunochemotherapy: a European MCL intergroup study." Blood (2010); 115.16: 3215-3223.
Chinese Patent Application No. 201510054401.X, Search Report dated Jul. 14, 2016, 2 pages.
Treviño, M.A., et al., "CD8+ T cells oligoclonally expanded in synovial fluid at onset of spondyloarthropathy selectively proliferate in response to self-antigens: characterization of cell specificities in nonclonal populations." Journal of Rheumatology (2004); 31(10): 1962-1972.
Winchester, Robert, et al. "Circulating activated and effector memory T cells are associated with calcification and clonal expansions in bicuspid and tricuspid valves of calcific aortic stenosis." The Journal of Immunology (2011); 187.2: 1006-1014.
Woodsworth, Daniel J., et al., "Sequence analysis of T-cell repertoires in health and disease." Genome Medicine (2013); 5: 98, 13 pages.

* cited by examiner

| ID | TCRB CDR3 Sequence | % | Vgene | J gene | SEQ ID NO: |
|---|---|---|---|---|---|
| PT 50 | TGTGCCAGCAGTTACTCCGCCGAAAATGAAAAACT | 99.5 | 6 | TRBJ1-4 | 774 |
| PT 44 | TGTGCCAGCAGCCCCGGTCGCAGCCAAGTGTCTGGGGCCAACGTCCT | 99.4 | 11 | TRBJ2-6 | 775 |
| PT 63 | TGTGCCAGCAGTTACTCGCGCTCCGAACCTAATGAGCA | 99.4 | 6 | TRBJ2-1 | 776 |
| PT 39 | TGTGCCAGCAGCTTAAGCGGGTACCTTAAAGAGACCCA | 98.9 | TRBV7-9 | TRBJ2-5 | 777 |
| PT 48 | TGCGCCAGCACCCCGAGAGGAGAGCGGGAGCCAGATACGCA | 98.8 | TRBV5-1 | TRBJ2-3 | 778 |
| PT 53 | TGCAGTGCTAGAGGGCCTATGTTCCGGGACCGATCCTCCTACGAGCA | 98.6 | TRBV20-1 | TRBJ2-7 | 779 |
| PT 7 | TGTGCCAGCAGCAAGATTTTACAGGTGCAGATTCTGGGGCCAACGTCCT | 98.5 | TRBV4-2 | TRBJ2-6 | 780 |
| PT 8 | TGTGCCAGCAGTGAATTGAAAGACGAGAAGGGTGGTTTTTTTGCCACTGAAGC | 98.5 | 2 | TRBJ1-1 | 781 |
| PT 9 | TGCGCCAGCAGCCAAGATAGAGAGCGGGAGGATCGCACAGATACGCA | 98.5 | TRBV4-1 | TRBJ2-3 | 782 |
| PT 52 | TGTCCAGTCATTACCCA | 97.3 | TRBV3-1 | TRBJ2-5 | 783 |
| PT 4 | TGTGCCAGCAGTTTATTAGGAGAGGAGACCCA | 96.2 | TRBV28 | TRBJ2-5 | 784 |
| PT 6 | TGTGCCAGCAGCTTTTGTCTGTCTGGGGCCAACGTCCT | 96 | TRBV5-4 | TRBJ2-6 | 785 |
| PT 51 | TGTGCCAGCAGTGAATACACAGGGGAAGC | 94.9 | TRBV2 | TRBJ1-1 | 786 |
| PT 59 | TGTGCCAGCAGCCTATTTACTAAAAGGGGTTGTTTGGATGAGCA | 93.6 | 7 | TRBJ2-1 | 787 |
| PT 49 | TGTGCCAGCAGTTTTCGAACTCTTTCCCCCGGGGGCGCAATTCGGCCCAAAAACATTCA | 93.4 | 12 | TRBJ2-4 | 788 |
| PT 41 | TGTGCCAGCAGTTCCACAGATACGCA | 92.9 | TRBV28 | TRBJ2-3 | 789 |

Fig. 4A

| ID | TCRB CDR3 Sequence | % | Vgene | J gene | SEQ ID NO: |
|---|---|---|---|---|---|
| PT 15 | TGTGCCAGCAGCCCTGACAGGGGACGAGCCTGGAAACAC | 90.5 | TRBV7-3 | TRBJ1-3 | 790 |
| PT 32 | TGTGCCAGCAGCCCACGGGCGGATAAAGATGAAAAACT | 89.1 | TRBV9 | TRBJ1-4 | 791 |
| PT 14 | TGTGCCAGCAGTTTGAACACAAACCGGCAGTGGGCGCGAGCTAACTATGGCTA | 88.7 | 5 | TRBJ1-2 | 792 |
| PT 1 | TGTGCCAGCATTATTTTAGGGTACCCTAAACTATGGCTA | 87.1 | TRBV2 | TRBJ1-2 | 793 |
| PT 66 | TGTGCCAGCAGTTACTCGCGCTCCGAACCTAATGAGCA | 86.9 | 6 | TRBJ2-1 | 794 |
| PT 65 | TGCAGTGCTAGAGATCTACTCCCCCTGGGGGGGACGCGTGGAAACACCAT | 84.0 | TRBV20-1 | TRBJ1-3 | 795 |
| PT 5 | TGTGCCAGTAGTCACCCTCACACAGATACGCA | 82.8 | TRBV19 | TRBJ2-3 | 796 |
| PT 2 | TGTGCCAGCAGTTACATTTCAGGCTTAACTATGGCTA | 80.9 | 6 | TRBJ2-7 | 797 |
| PT 36 | TGTGCCAGCAGTTTAATAACAGTTCTTCTCGGGGAGCT | 77.5 | 12 | TRBJ2-2 | 798 |
| PT 40 | TGTGCCAGCAGTGAAGGCGGGAGAGCGCTTGGGAGCA | 70.9 | TRBV2 | TRBJ2-1 | 799 |
| PT 61 | TGCAGTGCTAGAGAGGGTAAGAGACCCA | 62.6 | TRBV20-1 | TRBJ2-5 | 800 |
| PT 58 | TGTGCCAGCAGTTCCTATGACAGGGGATCCATTCAGCCCCA | 58.6 | 6 | TRBJ1-5 | 801 |
| PT 47 | TGTGCCAGCAGTGATGAAAGGCGGGGCTCCTACAATGAGCA | 58.4 | TRBV2 | TRBJ2-1 | 802 |
| PT 30 | TGTGCCAGCAGTCTAACCGGACAGCGGTATAATGAAAAACT | 49 | TRBV27 | TRBJ1-4 | 803 |
| PT 33 | TGTGCCAGCAGCTTATGGGAAACCGGGGAGCT | 39 | TRBV11-2 | TRBJ2-2 | 804 |

Fig. 4B

| TCRB V/J SET 1 | | TCRB V/J SET 2 | | TCRB V/J SET 3 | |
|---|---|---|---|---|---|
| SEQ ID NO:V | SEQ ID NO:J | SEQ ID NO:V | SEQ ID NO:J | SEQ ID NO:V | SEQ ID NO:J |
| 2921 | 2989 | 2921 | 2990 | 2921 | 2991 |
| 2922 | 2990 | 2922 | 2991 | 2922 | 2992 |
| 2923 | 2991 | 2923 | 2992 | 2923 | 2993 |
| 2924 | 2992 | 2924 | 2993 | 2924 | 2994 |
| 2925 | 2993 | 2925 | 2994 | 2925 | 2995 |
| 2926 | 2994 | 2926 | 2995 | 2926 | 2996 |
| 2927 | 2995 | 2927 | 2996 | 2927 | 2997 |
| 2928 | 2996 | 2928 | 2997 | 2928 | 2998 |
| 2929 | 2997 | 2929 | 2998 | 2929 | 2999 |
| 2930 | 2998 | 2930 | 2999 | 2930 | 3000 |
| 2931 | 2999 | 2931 | 3000 | 2931 | 3001 |
| 2932 | 3000 | 2932 | 3001 | 2932 | 2989 |
| 2933 | 3001 | 2933 | 2989 | 2933 | 2990 |
| 2934 | 2989 | 2934 | 2990 | 2934 | 2991 |
| 2935 | 2990 | 2935 | 2991 | 2935 | 2992 |
| 2936 | 2991 | 2936 | 2992 | 2936 | 2993 |
| 2937 | 2992 | 2937 | 2993 | 2937 | 2994 |
| 2938 | 2993 | 2938 | 2994 | 2938 | 2995 |
| 2939 | 2994 | 2939 | 2995 | 2939 | 2996 |
| 2940 | 2995 | 2940 | 2996 | 2940 | 2997 |
| 2941 | 2996 | 2941 | 2997 | 2941 | 2998 |
| 2942 | 2997 | 2942 | 2998 | 2942 | 2999 |
| 2943 | 2998 | 2943 | 2999 | 2943 | 3000 |
| 2944 | 2999 | 2944 | 3000 | 2944 | 3001 |
| 2945 | 3000 | 2945 | 3001 | 2945 | 2989 |
| 2946 | 3001 | 2946 | 2989 | 2946 | 2990 |
| 2947 | 2989 | 2947 | 2990 | 2947 | 2991 |

Fig. 9A

| TCRB V/J SET 1 | | TCRB V/J SET 2 | | TCRB V/J SET 3 | |
|---|---|---|---|---|---|
| SEQ ID NO:V | SEQ ID NO:J | SEQ ID NO:V | SEQ ID NO:J | SEQ ID NO:V | SEQ ID NO:J |
| 2948 | 2990 | 2948 | 2991 | 2948 | 2992 |
| 2949 | 2991 | 2949 | 2992 | 2949 | 2993 |
| 2950 | 2992 | 2950 | 2993 | 2950 | 2994 |
| 2951 | 2993 | 2951 | 2994 | 2951 | 2995 |
| 2952 | 2994 | 2952 | 2995 | 2952 | 2996 |
| 2953 | 2995 | 2953 | 2996 | 2953 | 2997 |
| 2954 | 2996 | 2954 | 2997 | 2954 | 2998 |
| 2955 | 2997 | 2955 | 2998 | 2955 | 2999 |
| 2956 | 2998 | 2956 | 2999 | 2956 | 3000 |
| 2957 | 2999 | 2957 | 3000 | 2957 | 3001 |
| 2958 | 3000 | 2958 | 3001 | 2958 | 2989 |
| 2959 | 3001 | 2959 | 2989 | 2959 | 2990 |
| 2960 | 2989 | 2960 | 2990 | 2960 | 2991 |
| 2961 | 2990 | 2961 | 2991 | 2961 | 2992 |
| 2962 | 2991 | 2962 | 2992 | 2962 | 2993 |
| 2963 | 2992 | 2963 | 2993 | 2963 | 2994 |
| 2964 | 2993 | 2964 | 2994 | 2964 | 2995 |
| 2965 | 2994 | 2965 | 2995 | 2965 | 2996 |
| 2966 | 2995 | 2966 | 2996 | 2966 | 2997 |
| 2967 | 2996 | 2967 | 2997 | 2967 | 2998 |
| 2968 | 2997 | 2968 | 2998 | 2968 | 2999 |
| 2969 | 2998 | 2969 | 2999 | 2969 | 3000 |
| 2970 | 2999 | 2970 | 3000 | 2970 | 3001 |
| 2971 | 3000 | 2971 | 3001 | 2971 | 2989 |
| 2972 | 3001 | 2972 | 2989 | 2972 | 2990 |
| 2973 | 2989 | 2973 | 2990 | 2973 | 2991 |
| 2974 | 2990 | 2974 | 2991 | 2974 | 2992 |
| 2975 | 2991 | 2975 | 2992 | 2975 | 2993 |
| 2976 | 2992 | 2976 | 2993 | 2976 | 2994 |
| 2977 | 2993 | 2977 | 2994 | 2977 | 2995 |
| 2978 | 2994 | 2978 | 2995 | 2978 | 2996 |

Fig. 9B

| TCRB V/J SET 1 | | | TCRB V/J SET 2 | | | TCRB V/J SET 3 | |
|---|---|---|---|---|---|---|---|
| SEQ ID NO:V | SEQ ID NO:J | | SEQ ID NO:V | SEQ ID NO:J | | SEQ ID NO:V | SEQ ID NO:J |
| 2979 | 2995 | | 2979 | 2996 | | 2979 | 2997 |
| 2980 | 2996 | | 2980 | 2997 | | 2980 | 2998 |
| 2981 | 2997 | | 2981 | 2998 | | 2981 | 2999 |
| 2982 | 2998 | | 2982 | 2999 | | 2982 | 3000 |
| 2983 | 2999 | | 2983 | 3000 | | 2983 | 3001 |
| 2984 | 3000 | | 2984 | 3001 | | 2984 | 2989 |
| 2985 | 3001 | | 2985 | 2989 | | 2985 | 2990 |
| 2986 | 2989 | | 2986 | 2990 | | 2986 | 2991 |
| 2987 | 2990 | | 2987 | 2991 | | 2987 | 2992 |
| 2988 | 2991 | | 2988 | 2992 | | 2988 | 2993 |

| TCRB V/J SET 4 | | | TCRB V/J SET 5 | | | TCRB V/J SET 6 | |
|---|---|---|---|---|---|---|---|
| SEQ ID NO:V | SEQ ID NO:J | | SEQ ID NO:V | SEQ ID NO:J | | SEQ ID NO:V | SEQ ID NO:J |
| 2921 | 2992 | | 2921 | 2993 | | 2921 | 2994 |
| 2922 | 2993 | | 2922 | 2994 | | 2922 | 2995 |
| 2923 | 2994 | | 2923 | 2995 | | 2923 | 2996 |
| 2924 | 2995 | | 2924 | 2996 | | 2924 | 2997 |
| 2925 | 2996 | | 2925 | 2997 | | 2925 | 2998 |
| 2926 | 2997 | | 2926 | 2998 | | 2926 | 2999 |
| 2927 | 2998 | | 2927 | 2999 | | 2927 | 3000 |
| 2928 | 2999 | | 2928 | 3000 | | 2928 | 3001 |
| 2929 | 3000 | | 2929 | 3001 | | 2929 | 2989 |
| 2930 | 3001 | | 2930 | 2989 | | 2930 | 2990 |
| 2931 | 2989 | | 2931 | 2990 | | 2931 | 2991 |
| 2932 | 2990 | | 2932 | 2991 | | 2932 | 2992 |
| 2933 | 2991 | | 2933 | 2992 | | 2933 | 2993 |
| 2934 | 2992 | | 2934 | 2993 | | 2934 | 2994 |
| 2935 | 2993 | | 2935 | 2994 | | 2935 | 2995 |
| 2936 | 2994 | | 2936 | 2995 | | 2936 | 2996 |
| 2937 | 2995 | | 2937 | 2996 | | 2937 | 2997 |

Fig. 9C

| TCRB V/J SET 4 | | TCRB V/J SET 5 | | TCRB V/J SET 6 | |
|---|---|---|---|---|---|
| SEQ ID NO:V | SEQ ID NO:J | SEQ ID NO:V | SEQ ID NO:J | SEQ ID NO:V | SEQ ID NO:J |
| 2938 | 2996 | 2938 | 2997 | 2938 | 2998 |
| 2939 | 2997 | 2939 | 2998 | 2939 | 2999 |
| 2940 | 2998 | 2940 | 2999 | 2940 | 3000 |
| 2941 | 2999 | 2941 | 3000 | 2941 | 3001 |
| 2942 | 3000 | 2942 | 3001 | 2942 | 2989 |
| 2943 | 3001 | 2943 | 2989 | 2943 | 2990 |
| 2944 | 2989 | 2944 | 2990 | 2944 | 2991 |
| 2945 | 2990 | 2945 | 2991 | 2945 | 2992 |
| 2946 | 2991 | 2946 | 2992 | 2946 | 2993 |
| 2947 | 2992 | 2947 | 2993 | 2947 | 2994 |
| 2948 | 2993 | 2948 | 2994 | 2948 | 2995 |
| 2949 | 2994 | 2949 | 2995 | 2949 | 2996 |
| 2950 | 2995 | 2950 | 2996 | 2950 | 2997 |
| 2951 | 2996 | 2951 | 2997 | 2951 | 2998 |
| 2952 | 2997 | 2952 | 2998 | 2952 | 2999 |
| 2953 | 2998 | 2953 | 2999 | 2953 | 3000 |
| 2954 | 2999 | 2954 | 3000 | 2954 | 3001 |
| 2955 | 3000 | 2955 | 3001 | 2955 | 2989 |
| 2956 | 3001 | 2956 | 2989 | 2956 | 2990 |
| 2957 | 2989 | 2957 | 2990 | 2957 | 2991 |
| 2958 | 2990 | 2958 | 2991 | 2958 | 2992 |
| 2959 | 2991 | 2959 | 2992 | 2959 | 2993 |
| 2960 | 2992 | 2960 | 2993 | 2960 | 2994 |
| 2961 | 2993 | 2961 | 2994 | 2961 | 2995 |
| 2962 | 2994 | 2962 | 2995 | 2962 | 2996 |
| 2963 | 2995 | 2963 | 2996 | 2963 | 2997 |
| 2964 | 2996 | 2964 | 2997 | 2964 | 2998 |
| 2965 | 2997 | 2965 | 2998 | 2965 | 2999 |
| 2966 | 2998 | 2966 | 2999 | 2966 | 3000 |
| 2967 | 2999 | 2967 | 3000 | 2967 | 3001 |
| 2968 | 3000 | 2968 | 3001 | 2968 | 2989 |

Fig. 9D

| TCRB V/J SET 4 | | TCRB V/J SET 5 | | TCRB V/J SET 6 | |
|---|---|---|---|---|---|
| SEQ ID NO:V | SEQ ID NO:J | SEQ ID NO:V | SEQ ID NO:J | SEQ ID NO:V | SEQ ID NO:J |
| 2969 | 3001 | 2969 | 2989 | 2969 | 2990 |
| 2970 | 2989 | 2970 | 2990 | 2970 | 2991 |
| 2971 | 2990 | 2971 | 2991 | 2971 | 2992 |
| 2972 | 2991 | 2972 | 2992 | 2972 | 2993 |
| 2973 | 2992 | 2973 | 2993 | 2973 | 2994 |
| 2974 | 2993 | 2974 | 2994 | 2974 | 2995 |
| 2975 | 2994 | 2975 | 2995 | 2975 | 2996 |
| 2976 | 2995 | 2976 | 2996 | 2976 | 2997 |
| 2977 | 2996 | 2977 | 2997 | 2977 | 2998 |
| 2978 | 2997 | 2978 | 2998 | 2978 | 2999 |
| 2979 | 2998 | 2979 | 2999 | 2979 | 3000 |
| 2980 | 2999 | 2980 | 3000 | 2980 | 3001 |
| 2981 | 3000 | 2981 | 3001 | 2981 | 2989 |
| 2982 | 3001 | 2982 | 2989 | 2982 | 2990 |
| 2983 | 2989 | 2983 | 2990 | 2983 | 2991 |
| 2984 | 2990 | 2984 | 2991 | 2984 | 2992 |
| 2985 | 2991 | 2985 | 2992 | 2985 | 2993 |
| 2986 | 2992 | 2986 | 2993 | 2986 | 2994 |
| 2987 | 2993 | 2987 | 2994 | 2987 | 2995 |
| 2988 | 2994 | 2988 | 2995 | 2988 | 2996 |

| TCRB V/J SET 7 | | TCRB V/J SET 8 | | TCRB V/J SET 9 | |
|---|---|---|---|---|---|
| SEQ ID NO:V | SEQ ID NO:J | SEQ ID NO:V | SEQ ID NO:J | SEQ ID NO:V | SEQ ID NO:J |
| 2921 | 2995 | 2921 | 2996 | 2921 | 2997 |
| 2922 | 2996 | 2922 | 2997 | 2922 | 2998 |
| 2923 | 2997 | 2923 | 2998 | 2923 | 2999 |
| 2924 | 2998 | 2924 | 2999 | 2924 | 3000 |
| 2925 | 2999 | 2925 | 3000 | 2925 | 3001 |
| 2926 | 3000 | 2926 | 3001 | 2926 | 2989 |
| 2927 | 3001 | 2927 | 2989 | 2927 | 2990 |

Fig. 9E

| TCRB V/J SET 7 | | TCRB V/J SET 8 | | TCRB V/J SET 9 | |
|---|---|---|---|---|---|
| SEQ ID NO:V | SEQ ID NO:J | SEQ ID NO:V | SEQ ID NO:J | SEQ ID NO:V | SEQ ID NO:J |
| 2928 | 2989 | 2928 | 2990 | 2928 | 2991 |
| 2929 | 2990 | 2929 | 2991 | 2929 | 2992 |
| 2930 | 2991 | 2930 | 2992 | 2930 | 2993 |
| 2931 | 2992 | 2931 | 2993 | 2931 | 2994 |
| 2932 | 2993 | 2932 | 2994 | 2932 | 2995 |
| 2933 | 2994 | 2933 | 2995 | 2933 | 2996 |
| 2934 | 2995 | 2934 | 2996 | 2934 | 2997 |
| 2935 | 2996 | 2935 | 2997 | 2935 | 2998 |
| 2936 | 2997 | 2936 | 2998 | 2936 | 2999 |
| 2937 | 2998 | 2937 | 2999 | 2937 | 3000 |
| 2938 | 2999 | 2938 | 3000 | 2938 | 3001 |
| 2939 | 3000 | 2939 | 3001 | 2939 | 2989 |
| 2940 | 3001 | 2940 | 2989 | 2940 | 2990 |
| 2941 | 2989 | 2941 | 2990 | 2941 | 2991 |
| 2942 | 2990 | 2942 | 2991 | 2942 | 2992 |
| 2943 | 2991 | 2943 | 2992 | 2943 | 2993 |
| 2944 | 2992 | 2944 | 2993 | 2944 | 2994 |
| 2945 | 2993 | 2945 | 2994 | 2945 | 2995 |
| 2946 | 2994 | 2946 | 2995 | 2946 | 2996 |
| 2947 | 2995 | 2947 | 2996 | 2947 | 2997 |
| 2948 | 2996 | 2948 | 2997 | 2948 | 2998 |
| 2949 | 2997 | 2949 | 2998 | 2949 | 2999 |
| 2950 | 2998 | 2950 | 2999 | 2950 | 3000 |
| 2951 | 2999 | 2951 | 3000 | 2951 | 3001 |
| 2952 | 3000 | 2952 | 3001 | 2952 | 2989 |
| 2953 | 3001 | 2953 | 2989 | 2953 | 2990 |
| 2954 | 2989 | 2954 | 2990 | 2954 | 2991 |
| 2955 | 2990 | 2955 | 2991 | 2955 | 2992 |
| 2956 | 2991 | 2956 | 2992 | 2956 | 2993 |
| 2957 | 2992 | 2957 | 2993 | 2957 | 2994 |
| 2958 | 2993 | 2958 | 2994 | 2958 | 2995 |

Fig. 9F

| TCRB V/J SET 7 | | TCRB V/J SET 8 | | TCRB V/J SET 9 | |
|---|---|---|---|---|---|
| SEQ ID NO:V | SEQ ID NO:J | SEQ ID NO:V | SEQ ID NO:J | SEQ ID NO:V | SEQ ID NO:J |
| 2959 | 2994 | 2959 | 2995 | 2959 | 2996 |
| 2960 | 2995 | 2960 | 2996 | 2960 | 2997 |
| 2961 | 2996 | 2961 | 2997 | 2961 | 2998 |
| 2962 | 2997 | 2962 | 2998 | 2962 | 2999 |
| 2963 | 2998 | 2963 | 2999 | 2963 | 3000 |
| 2964 | 2999 | 2964 | 3000 | 2964 | 3001 |
| 2965 | 3000 | 2965 | 3001 | 2965 | 2989 |
| 2966 | 3001 | 2966 | 2989 | 2966 | 2990 |
| 2967 | 2989 | 2967 | 2990 | 2967 | 2991 |
| 2968 | 2990 | 2968 | 2991 | 2968 | 2992 |
| 2969 | 2991 | 2969 | 2992 | 2969 | 2993 |
| 2970 | 2992 | 2970 | 2993 | 2970 | 2994 |
| 2971 | 2993 | 2971 | 2994 | 2971 | 2995 |
| 2972 | 2994 | 2972 | 2995 | 2972 | 2996 |
| 2973 | 2995 | 2973 | 2996 | 2973 | 2997 |
| 2974 | 2996 | 2974 | 2997 | 2974 | 2998 |
| 2975 | 2997 | 2975 | 2998 | 2975 | 2999 |
| 2976 | 2998 | 2976 | 2999 | 2976 | 3000 |
| 2977 | 2999 | 2977 | 3000 | 2977 | 3001 |
| 2978 | 3000 | 2978 | 3001 | 2978 | 2989 |
| 2979 | 3001 | 2979 | 2989 | 2979 | 2990 |
| 2980 | 2989 | 2980 | 2990 | 2980 | 2991 |
| 2981 | 2990 | 2981 | 2991 | 2981 | 2992 |
| 2982 | 2991 | 2982 | 2992 | 2982 | 2993 |
| 2983 | 2992 | 2983 | 2993 | 2983 | 2994 |
| 2984 | 2993 | 2984 | 2994 | 2984 | 2995 |
| 2985 | 2994 | 2985 | 2995 | 2985 | 2996 |
| 2986 | 2995 | 2986 | 2996 | 2986 | 2997 |
| 2987 | 2996 | 2987 | 2997 | 2987 | 2998 |
| 2988 | 2997 | 2988 | 2998 | 2988 | 2999 |

Fig. 9G

| TCRB V/J SET 10 | | TCRB V/J SET 11 | | TCRB V/J SET 12 | |
|---|---|---|---|---|---|
| SEQ ID NO:V | SEQ ID NO:J | SEQ ID NO:V | SEQ ID NO:J | SEQ ID NO:V | SEQ ID NO:J |
| 2921 | 2998 | 2921 | 2999 | 2921 | 3000 |
| 2922 | 2999 | 2922 | 3000 | 2922 | 3001 |
| 2923 | 3000 | 2923 | 3001 | 2923 | 2989 |
| 2924 | 3001 | 2924 | 2989 | 2924 | 2990 |
| 2925 | 2989 | 2925 | 2990 | 2925 | 2991 |
| 2926 | 2990 | 2926 | 2991 | 2926 | 2992 |
| 2927 | 2991 | 2927 | 2992 | 2927 | 2993 |
| 2928 | 2992 | 2928 | 2993 | 2928 | 2994 |
| 2929 | 2993 | 2929 | 2994 | 2929 | 2995 |
| 2930 | 2994 | 2930 | 2995 | 2930 | 2996 |
| 2931 | 2995 | 2931 | 2996 | 2931 | 2997 |
| 2932 | 2996 | 2932 | 2997 | 2932 | 2998 |
| 2933 | 2997 | 2933 | 2998 | 2933 | 2999 |
| 2934 | 2998 | 2934 | 2999 | 2934 | 3000 |
| 2935 | 2999 | 2935 | 3000 | 2935 | 3001 |
| 2936 | 3000 | 2936 | 3001 | 2936 | 2989 |
| 2937 | 3001 | 2937 | 2989 | 2937 | 2990 |
| 2938 | 2989 | 2938 | 2990 | 2938 | 2991 |
| 2939 | 2990 | 2939 | 2991 | 2939 | 2992 |
| 2940 | 2991 | 2940 | 2992 | 2940 | 2993 |
| 2941 | 2992 | 2941 | 2993 | 2941 | 2994 |
| 2942 | 2993 | 2942 | 2994 | 2942 | 2995 |
| 2943 | 2994 | 2943 | 2995 | 2943 | 2996 |
| 2944 | 2995 | 2944 | 2996 | 2944 | 2997 |
| 2945 | 2996 | 2945 | 2997 | 2945 | 2998 |
| 2946 | 2997 | 2946 | 2998 | 2946 | 2999 |
| 2947 | 2998 | 2947 | 2999 | 2947 | 3000 |
| 2948 | 2999 | 2948 | 3000 | 2948 | 3001 |
| 2949 | 3000 | 2949 | 3001 | 2949 | 2989 |
| 2950 | 3001 | 2950 | 2989 | 2950 | 2990 |

Fig. 9H

| TCRB V/J SET 10 | | TCRB V/J SET 11 | | TCRB V/J SET 12 | |
|---|---|---|---|---|---|
| SEQ ID NO:V | SEQ ID NO:J | SEQ ID NO:V | SEQ ID NO:J | SEQ ID NO:V | SEQ ID NO:J |
| 2951 | 2989 | 2951 | 2990 | 2951 | 2991 |
| 2952 | 2990 | 2952 | 2991 | 2952 | 2992 |
| 2953 | 2991 | 2953 | 2992 | 2953 | 2993 |
| 2954 | 2992 | 2954 | 2993 | 2954 | 2994 |
| 2955 | 2993 | 2955 | 2994 | 2955 | 2995 |
| 2956 | 2994 | 2956 | 2995 | 2956 | 2996 |
| 2957 | 2995 | 2957 | 2996 | 2957 | 2997 |
| 2958 | 2996 | 2958 | 2997 | 2958 | 2998 |
| 2959 | 2997 | 2959 | 2998 | 2959 | 2999 |
| 2960 | 2998 | 2960 | 2999 | 2960 | 3000 |
| 2961 | 2999 | 2961 | 3000 | 2961 | 3001 |
| 2962 | 3000 | 2962 | 3001 | 2962 | 2989 |
| 2963 | 3001 | 2963 | 2989 | 2963 | 2990 |
| 2964 | 2989 | 2964 | 2990 | 2964 | 2991 |
| 2965 | 2990 | 2965 | 2991 | 2965 | 2992 |
| 2966 | 2991 | 2966 | 2992 | 2966 | 2993 |
| 2967 | 2992 | 2967 | 2993 | 2967 | 2994 |
| 2968 | 2993 | 2968 | 2994 | 2968 | 2995 |
| 2969 | 2994 | 2969 | 2995 | 2969 | 2996 |
| 2970 | 2995 | 2970 | 2996 | 2970 | 2997 |
| 2971 | 2996 | 2971 | 2997 | 2971 | 2998 |
| 2972 | 2997 | 2972 | 2998 | 2972 | 2999 |
| 2973 | 2998 | 2973 | 2999 | 2973 | 3000 |
| 2974 | 2999 | 2974 | 3000 | 2974 | 3001 |
| 2975 | 3000 | 2975 | 3001 | 2975 | 2989 |
| 2976 | 3001 | 2976 | 2989 | 2976 | 2990 |
| 2977 | 2989 | 2977 | 2990 | 2977 | 2991 |
| 2978 | 2990 | 2978 | 2991 | 2978 | 2992 |
| 2979 | 2991 | 2979 | 2992 | 2979 | 2993 |
| 2980 | 2992 | 2980 | 2993 | 2980 | 2994 |
| 2981 | 2993 | 2981 | 2994 | 2981 | 2995 |

Fig. 9I

| TCRB V/J SET 10 | |
|---|---|
| SEQ ID NO:V | SEQ ID NO:J |
| 2982 | 2994 |
| 2983 | 2995 |
| 2984 | 2996 |
| 2985 | 2997 |
| 2986 | 2998 |
| 2987 | 2999 |
| 2988 | 3000 |

| TCRB V/J SET 11 | |
|---|---|
| SEQ ID NO:V | SEQ ID NO:J |
| 2982 | 2995 |
| 2983 | 2996 |
| 2984 | 2997 |
| 2985 | 2998 |
| 2986 | 2999 |
| 2987 | 3000 |
| 2988 | 3001 |

| TCRB V/J SET 12 | |
|---|---|
| SEQ ID NO:V | SEQ ID NO:J |
| 2982 | 2996 |
| 2983 | 2997 |
| 2984 | 2998 |
| 2985 | 2999 |
| 2986 | 3000 |
| 2987 | 3001 |
| 2988 | 2989 |

| TCRB V/J SET 13 | |
|---|---|
| SEQ ID NO:V | SEQ ID NO:J |
| 2921 | 3001 |
| 2922 | 2989 |
| 2923 | 2990 |
| 2924 | 2991 |
| 2925 | 2992 |
| 2926 | 2993 |
| 2927 | 2994 |
| 2928 | 2995 |
| 2929 | 2996 |
| 2930 | 2997 |
| 2931 | 2998 |
| 2932 | 2999 |
| 2933 | 3000 |
| 2934 | 3001 |
| 2935 | 2989 |
| 2936 | 2990 |
| 2937 | 2991 |
| 2938 | 2992 |
| 2939 | 2993 |
| 2940 | 2994 |

Fig. 9J

| TCRB V/J SET 13 | |
|---|---|
| SEQ ID NO:V | SEQ ID NO:J |
| 2941 | 2995 |
| 2942 | 2996 |
| 2943 | 2997 |
| 2944 | 2998 |
| 2945 | 2999 |
| 2946 | 3000 |
| 2947 | 3001 |
| 2948 | 2989 |
| 2949 | 2990 |
| 2950 | 2991 |
| 2951 | 2992 |
| 2952 | 2993 |
| 2953 | 2994 |
| 2954 | 2995 |
| 2955 | 2996 |
| 2956 | 2997 |
| 2957 | 2998 |
| 2958 | 2999 |
| 2959 | 3000 |
| 2960 | 3001 |
| 2961 | 2989 |
| 2962 | 2990 |
| 2963 | 2991 |
| 2964 | 2992 |
| 2965 | 2993 |
| 2966 | 2994 |
| 2967 | 2995 |
| 2968 | 2996 |
| 2969 | 2997 |
| 2970 | 2998 |
| 2971 | 2999 |

Fig. 9K

| TCRB V/J SET 13 | |
|---|---|
| SEQ ID NO:V | SEQ ID NO:J |
| 2972 | 3000 |
| 2973 | 3001 |
| 2974 | 2989 |
| 2975 | 2990 |
| 2976 | 2991 |
| 2977 | 2992 |
| 2978 | 2993 |
| 2979 | 2994 |
| 2980 | 2995 |
| 2981 | 2996 |
| 2982 | 2997 |
| 2983 | 2998 |
| 2984 | 2999 |
| 2985 | 3000 |
| 2986 | 3001 |
| 2987 | 2989 |
| 2988 | 2990 |

Fig. 9L

| TCRG V/J SET 1 | | TCRG V/J SET 2 | | TCRG V/J SET 3 | |
|---|---|---|---|---|---|
| SEQ ID NO:V | SEQ ID NO:J | SEQ ID NO:V | SEQ ID NO:J | SEQ ID NO:V | SEQ ID NO:J |
| 3002 | 3016 | 3002 | 3017 | 3002 | 3018 |
| 3003 | 3017 | 3003 | 3018 | 3003 | 3019 |
| 3004 | 3018 | 3004 | 3019 | 3004 | 3020 |
| 3005 | 3019 | 3005 | 3020 | 3005 | 3016 |
| 3006 | 3020 | 3006 | 3016 | 3006 | 3017 |
| 3007 | 3016 | 3007 | 3017 | 3007 | 3018 |
| 3008 | 3017 | 3008 | 3018 | 3008 | 3019 |
| 3009 | 3018 | 3009 | 3019 | 3009 | 3020 |
| 3010 | 3019 | 3010 | 3020 | 3010 | 3016 |
| 3011 | 3020 | 3011 | 3016 | 3011 | 3017 |
| 3012 | 3016 | 3012 | 3017 | 3012 | 3018 |
| 3013 | 3017 | 3013 | 3018 | 3013 | 3019 |
| 3014 | 3018 | 3014 | 3019 | 3014 | 3020 |
| 3015 | 3019 | 3015 | 3020 | 3015 | 3016 |

| TCRG V/J SET 4 | | TCRG V/J SET 5 | |
|---|---|---|---|
| SEQ ID NO:V | SEQ ID NO:J | SEQ ID NO:V | SEQ ID NO:J |
| 3002 | 3019 | 3002 | 3020 |
| 3003 | 3020 | 3003 | 3016 |
| 3004 | 3016 | 3004 | 3017 |
| 3005 | 3017 | 3005 | 3018 |
| 3006 | 3018 | 3006 | 3019 |
| 3007 | 3019 | 3007 | 3020 |
| 3008 | 3020 | 3008 | 3016 |
| 3009 | 3016 | 3009 | 3017 |

Fig. 10A

| TCRG V/J SET 4 | | TCRG V/J SET 5 | |
|---|---|---|---|
| SEQ ID NO:V | SEQ ID NO:J | SEQ ID NO:V | SEQ ID NO:J |
| 3010 | 3017 | 3010 | 3018 |
| 3011 | 3018 | 3011 | 3019 |
| 3012 | 3019 | 3012 | 3020 |
| 3013 | 3020 | 3013 | 3016 |
| 3014 | 3016 | 3014 | 3017 |
| 3015 | 3017 | 3015 | 3018 |

Fig. 10B

| IGH V/J SET 1 | | IGH V/J SET 2 | | IGH V/J SET 3 | |
|---|---|---|---|---|---|
| SEQ ID NO: V | SEQ ID NO: J | SEQ ID NO: V | SEQ ID NO: J | SEQ ID NO: V | SEQ ID NO: J |
| 3021 | 3148 | 3021 | 3149 | 3021 | 3150 |
| 3022 | 3149 | 3022 | 3150 | 3022 | 3151 |
| 3023 | 3150 | 3023 | 3151 | 3023 | 3152 |
| 3024 | 3151 | 3024 | 3152 | 3024 | 3153 |
| 3025 | 3152 | 3025 | 3153 | 3025 | 3154 |
| 3026 | 3153 | 3026 | 3154 | 3026 | 3155 |
| 3027 | 3154 | 3027 | 3155 | 3027 | 3156 |
| 3028 | 3155 | 3028 | 3156 | 3028 | 3148 |
| 3029 | 3156 | 3029 | 3148 | 3029 | 3149 |
| 3030 | 3148 | 3030 | 3149 | 3030 | 3150 |
| 3031 | 3149 | 3031 | 3150 | 3031 | 3151 |
| 3032 | 3150 | 3032 | 3151 | 3032 | 3152 |
| 3033 | 3151 | 3033 | 3152 | 3033 | 3153 |
| 3034 | 3152 | 3034 | 3153 | 3034 | 3154 |
| 3035 | 3153 | 3035 | 3154 | 3035 | 3155 |
| 3036 | 3154 | 3036 | 3155 | 3036 | 3156 |
| 3037 | 3155 | 3037 | 3156 | 3037 | 3148 |
| 3038 | 3156 | 3038 | 3148 | 3038 | 3149 |
| 3039 | 3148 | 3039 | 3149 | 3039 | 3150 |
| 3040 | 3149 | 3040 | 3150 | 3040 | 3151 |
| 3041 | 3150 | 3041 | 3151 | 3041 | 3152 |
| 3042 | 3151 | 3042 | 3152 | 3042 | 3153 |
| 3043 | 3152 | 3043 | 3153 | 3043 | 3154 |
| 3044 | 3153 | 3044 | 3154 | 3044 | 3155 |
| 3045 | 3154 | 3045 | 3155 | 3045 | 3156 |
| 3046 | 3155 | 3046 | 3156 | 3046 | 3148 |
| 3047 | 3156 | 3047 | 3148 | 3047 | 3149 |

Fig. 11A

| IGH V/J SET 1 | | IGH V/J SET 2 | | IGH V/J SET 3 | |
|---|---|---|---|---|---|
| SEQ ID NO: V | SEQ ID NO:J | SEQ ID NO: V | SEQ ID NO:J | SEQ ID NO: V | SEQ ID NO:J |
| 3048 | 3148 | 3048 | 3149 | 3048 | 3150 |
| 3049 | 3149 | 3049 | 3150 | 3049 | 3151 |
| 3050 | 3150 | 3050 | 3151 | 3050 | 3152 |
| 3051 | 3151 | 3051 | 3152 | 3051 | 3153 |
| 3052 | 3152 | 3052 | 3153 | 3052 | 3154 |
| 3053 | 3153 | 3053 | 3154 | 3053 | 3155 |
| 3054 | 3154 | 3054 | 3155 | 3054 | 3156 |
| 3055 | 3155 | 3055 | 3156 | 3055 | 3148 |
| 3056 | 3156 | 3056 | 3148 | 3056 | 3149 |
| 3057 | 3148 | 3057 | 3149 | 3057 | 3150 |
| 3058 | 3149 | 3058 | 3150 | 3058 | 3151 |
| 3059 | 3150 | 3059 | 3151 | 3059 | 3152 |
| 3060 | 3151 | 3060 | 3152 | 3060 | 3153 |
| 3061 | 3152 | 3061 | 3153 | 3061 | 3154 |
| 3062 | 3153 | 3062 | 3154 | 3062 | 3155 |
| 3063 | 3154 | 3063 | 3155 | 3063 | 3156 |
| 3064 | 3155 | 3064 | 3156 | 3064 | 3148 |
| 3065 | 3156 | 3065 | 3148 | 3065 | 3149 |
| 3066 | 3148 | 3066 | 3149 | 3066 | 3150 |
| 3067 | 3149 | 3067 | 3150 | 3067 | 3151 |
| 3068 | 3150 | 3068 | 3151 | 3068 | 3152 |
| 3069 | 3151 | 3069 | 3152 | 3069 | 3153 |
| 3070 | 3152 | 3070 | 3153 | 3070 | 3154 |
| 3071 | 3153 | 3071 | 3154 | 3071 | 3155 |
| 3072 | 3154 | 3072 | 3155 | 3072 | 3156 |
| 3073 | 3155 | 3073 | 3156 | 3073 | 3148 |
| 3074 | 3156 | 3074 | 3148 | 3074 | 3149 |
| 3075 | 3148 | 3075 | 3149 | 3075 | 3150 |
| 3076 | 3149 | 3076 | 3150 | 3076 | 3151 |
| 3077 | 3150 | 3077 | 3151 | 3077 | 3152 |
| 3078 | 3151 | 3078 | 3152 | 3078 | 3153 |

Fig. 11B

| IGH V/J SET 1 | | IGH V/J SET 2 | | IGH V/J SET 3 | |
|---|---|---|---|---|---|
| SEQ ID NO: V | SEQ ID NO: J | SEQ ID NO: V | SEQ ID NO: J | SEQ ID NO: V | SEQ ID NO: J |
| 3079 | 3152 | 3079 | 3153 | 3079 | 3154 |
| 3080 | 3153 | 3080 | 3154 | 3080 | 3155 |
| 3081 | 3154 | 3081 | 3155 | 3081 | 3156 |
| 3082 | 3155 | 3082 | 3156 | 3082 | 3148 |
| 3083 | 3156 | 3083 | 3148 | 3083 | 3149 |
| 3084 | 3148 | 3084 | 3149 | 3084 | 3150 |
| 3085 | 3149 | 3085 | 3150 | 3085 | 3151 |
| 3086 | 3150 | 3086 | 3151 | 3086 | 3152 |
| 3087 | 3151 | 3087 | 3152 | 3087 | 3153 |
| 3088 | 3152 | 3088 | 3153 | 3088 | 3154 |
| 3089 | 3153 | 3089 | 3154 | 3089 | 3155 |
| 3090 | 3154 | 3090 | 3155 | 3090 | 3156 |
| 3091 | 3155 | 3091 | 3156 | 3091 | 3148 |
| 3092 | 3156 | 3092 | 3148 | 3092 | 3149 |
| 3093 | 3148 | 3093 | 3149 | 3093 | 3150 |
| 3094 | 3149 | 3094 | 3150 | 3094 | 3151 |
| 3095 | 3150 | 3095 | 3151 | 3095 | 3152 |
| 3096 | 3151 | 3096 | 3152 | 3096 | 3153 |
| 3097 | 3152 | 3097 | 3153 | 3097 | 3154 |
| 3098 | 3153 | 3098 | 3154 | 3098 | 3155 |
| 3099 | 3154 | 3099 | 3155 | 3099 | 3156 |
| 3100 | 3155 | 3100 | 3156 | 3100 | 3148 |
| 3101 | 3156 | 3101 | 3148 | 3101 | 3149 |
| 3102 | 3148 | 3102 | 3149 | 3102 | 3150 |
| 3103 | 3149 | 3103 | 3150 | 3103 | 3151 |
| 3104 | 3150 | 3104 | 3151 | 3104 | 3152 |
| 3105 | 3151 | 3105 | 3152 | 3105 | 3153 |
| 3106 | 3152 | 3106 | 3153 | 3106 | 3154 |
| 3107 | 3153 | 3107 | 3154 | 3107 | 3155 |
| 3108 | 3154 | 3108 | 3155 | 3108 | 3156 |
| 3109 | 3155 | 3109 | 3156 | 3109 | 3148 |

Fig. 11C

| IGH V/J SET 1 | | IGH V/J SET 2 | | IGH V/J SET 3 | |
|---|---|---|---|---|---|
| SEQ ID NO: V | SEQ ID NO:J | SEQ ID NO: V | SEQ ID NO:J | SEQ ID NO: V | SEQ ID NO:J |
| 3110 | 3156 | 3110 | 3148 | 3110 | 3149 |
| 3111 | 3148 | 3111 | 3149 | 3111 | 3150 |
| 3112 | 3149 | 3112 | 3150 | 3112 | 3151 |
| 3113 | 3150 | 3113 | 3151 | 3113 | 3152 |
| 3114 | 3151 | 3114 | 3152 | 3114 | 3153 |
| 3115 | 3152 | 3115 | 3153 | 3115 | 3154 |
| 3116 | 3153 | 3116 | 3154 | 3116 | 3155 |
| 3117 | 3154 | 3117 | 3155 | 3117 | 3156 |
| 3118 | 3155 | 3118 | 3156 | 3118 | 3148 |
| 3119 | 3156 | 3119 | 3148 | 3119 | 3149 |
| 3120 | 3148 | 3120 | 3149 | 3120 | 3150 |
| 3121 | 3149 | 3121 | 3150 | 3121 | 3151 |
| 3122 | 3150 | 3122 | 3151 | 3122 | 3152 |
| 3123 | 3151 | 3123 | 3152 | 3123 | 3153 |
| 3124 | 3152 | 3124 | 3153 | 3124 | 3154 |
| 3125 | 3153 | 3125 | 3154 | 3125 | 3155 |
| 3126 | 3154 | 3126 | 3155 | 3126 | 3156 |
| 3127 | 3155 | 3127 | 3156 | 3127 | 3148 |
| 3128 | 3156 | 3128 | 3148 | 3128 | 3149 |
| 3129 | 3148 | 3129 | 3149 | 3129 | 3150 |
| 3130 | 3149 | 3130 | 3150 | 3130 | 3151 |
| 3131 | 3150 | 3131 | 3151 | 3131 | 3152 |
| 3132 | 3151 | 3132 | 3152 | 3132 | 3153 |
| 3133 | 3152 | 3133 | 3153 | 3133 | 3154 |
| 3134 | 3153 | 3134 | 3154 | 3134 | 3155 |
| 3135 | 3154 | 3135 | 3155 | 3135 | 3156 |
| 3136 | 3155 | 3136 | 3156 | 3136 | 3148 |
| 3137 | 3156 | 3137 | 3148 | 3137 | 3149 |
| 3138 | 3148 | 3138 | 3149 | 3138 | 3150 |
| 3139 | 3149 | 3139 | 3150 | 3139 | 3151 |
| 3140 | 3150 | 3140 | 3151 | 3140 | 3152 |

Fig. 11D

| IGH V/J SET 1 | | IGH V/J SET 2 | | IGH V/J SET 3 | |
|---|---|---|---|---|---|
| SEQ ID NO: V | SEQ ID NO:J | SEQ ID NO: V | SEQ ID NO:J | SEQ ID NO: V | SEQ ID NO:J |
| 3141 | 3151 | 3141 | 3152 | 3141 | 3153 |
| 3142 | 3152 | 3142 | 3153 | 3142 | 3154 |
| 3143 | 3153 | 3143 | 3154 | 3143 | 3155 |
| 3144 | 3154 | 3144 | 3155 | 3144 | 3156 |
| 3145 | 3155 | 3145 | 3156 | 3145 | 3148 |
| 3146 | 3156 | 3146 | 3148 | 3146 | 3149 |
| 3147 | 3148 | 3147 | 3149 | 3147 | 3150 |

| IGH V/J SET 4 | | IGH V/J SET 5 | | IGH V/J SET 6 | |
|---|---|---|---|---|---|
| SEQ ID NO: V | SEQ ID NO:J | SEQ ID NO: V | SEQ ID NO:J | SEQ ID NO: V | SEQ ID NO:J |
| 3021 | 3151 | 3021 | 3152 | 3021 | 3153 |
| 3022 | 3152 | 3022 | 3153 | 3022 | 3154 |
| 3023 | 3153 | 3023 | 3154 | 3023 | 3155 |
| 3024 | 3154 | 3024 | 3155 | 3024 | 3156 |
| 3025 | 3155 | 3025 | 3156 | 3025 | 3148 |
| 3026 | 3156 | 3026 | 3148 | 3026 | 3149 |
| 3027 | 3148 | 3027 | 3149 | 3027 | 3150 |
| 3028 | 3149 | 3028 | 3150 | 3028 | 3151 |
| 3029 | 3150 | 3029 | 3151 | 3029 | 3152 |
| 3030 | 3151 | 3030 | 3152 | 3030 | 3153 |
| 3031 | 3152 | 3031 | 3153 | 3031 | 3154 |
| 3032 | 3153 | 3032 | 3154 | 3032 | 3155 |
| 3033 | 3154 | 3033 | 3155 | 3033 | 3156 |
| 3034 | 3155 | 3034 | 3156 | 3034 | 3148 |
| 3035 | 3156 | 3035 | 3148 | 3035 | 3149 |
| 3036 | 3148 | 3036 | 3149 | 3036 | 3150 |
| 3037 | 3149 | 3037 | 3150 | 3037 | 3151 |
| 3038 | 3150 | 3038 | 3151 | 3038 | 3152 |
| 3039 | 3151 | 3039 | 3152 | 3039 | 3153 |
| 3040 | 3152 | 3040 | 3153 | 3040 | 3154 |

Fig. 11E

| IGH V/J SET 4 | | IGH V/J SET 5 | | IGH V/J SET 6 | |
|---|---|---|---|---|---|
| SEQ ID NO: V | SEQ ID NO: J | SEQ ID NO: V | SEQ ID NO: J | SEQ ID NO: V | SEQ ID NO: J |
| 3041 | 3153 | 3041 | 3154 | 3041 | 3155 |
| 3042 | 3154 | 3042 | 3155 | 3042 | 3156 |
| 3043 | 3155 | 3043 | 3156 | 3043 | 3148 |
| 3044 | 3156 | 3044 | 3148 | 3044 | 3149 |
| 3045 | 3148 | 3045 | 3149 | 3045 | 3150 |
| 3046 | 3149 | 3046 | 3150 | 3046 | 3151 |
| 3047 | 3150 | 3047 | 3151 | 3047 | 3152 |
| 3048 | 3151 | 3048 | 3152 | 3048 | 3153 |
| 3049 | 3152 | 3049 | 3153 | 3049 | 3154 |
| 3050 | 3153 | 3050 | 3154 | 3050 | 3155 |
| 3051 | 3154 | 3051 | 3155 | 3051 | 3156 |
| 3052 | 3155 | 3052 | 3156 | 3052 | 3148 |
| 3053 | 3156 | 3053 | 3148 | 3053 | 3149 |
| 3054 | 3148 | 3054 | 3149 | 3054 | 3150 |
| 3055 | 3149 | 3055 | 3150 | 3055 | 3151 |
| 3056 | 3150 | 3056 | 3151 | 3056 | 3152 |
| 3057 | 3151 | 3057 | 3152 | 3057 | 3153 |
| 3058 | 3152 | 3058 | 3153 | 3058 | 3154 |
| 3059 | 3153 | 3059 | 3154 | 3059 | 3155 |
| 3060 | 3154 | 3060 | 3155 | 3060 | 3156 |
| 3061 | 3155 | 3061 | 3156 | 3061 | 3148 |
| 3062 | 3156 | 3062 | 3148 | 3062 | 3149 |
| 3063 | 3148 | 3063 | 3149 | 3063 | 3150 |
| 3064 | 3149 | 3064 | 3150 | 3064 | 3151 |
| 3065 | 3150 | 3065 | 3151 | 3065 | 3152 |
| 3066 | 3151 | 3066 | 3152 | 3066 | 3153 |
| 3067 | 3152 | 3067 | 3153 | 3067 | 3154 |
| 3068 | 3153 | 3068 | 3154 | 3068 | 3155 |
| 3069 | 3154 | 3069 | 3155 | 3069 | 3156 |
| 3070 | 3155 | 3070 | 3156 | 3070 | 3148 |
| 3071 | 3156 | 3071 | 3148 | 3071 | 3149 |

Fig. 11F

| IGH V/J SET 4 | | IGH V/J SET 5 | | IGH V/J SET 6 | |
|---|---|---|---|---|---|
| SEQ ID NO: V | SEQ ID NO:J | SEQ ID NO: V | SEQ ID NO:J | SEQ ID NO: V | SEQ ID NO:J |
| 3072 | 3148 | 3072 | 3149 | 3072 | 3150 |
| 3073 | 3149 | 3073 | 3150 | 3073 | 3151 |
| 3074 | 3150 | 3074 | 3151 | 3074 | 3152 |
| 3075 | 3151 | 3075 | 3152 | 3075 | 3153 |
| 3076 | 3152 | 3076 | 3153 | 3076 | 3154 |
| 3077 | 3153 | 3077 | 3154 | 3077 | 3155 |
| 3078 | 3154 | 3078 | 3155 | 3078 | 3156 |
| 3079 | 3155 | 3079 | 3156 | 3079 | 3148 |
| 3080 | 3156 | 3080 | 3148 | 3080 | 3149 |
| 3081 | 3148 | 3081 | 3149 | 3081 | 3150 |
| 3082 | 3149 | 3082 | 3150 | 3082 | 3151 |
| 3083 | 3150 | 3083 | 3151 | 3083 | 3152 |
| 3084 | 3151 | 3084 | 3152 | 3084 | 3153 |
| 3085 | 3152 | 3085 | 3153 | 3085 | 3154 |
| 3086 | 3153 | 3086 | 3154 | 3086 | 3155 |
| 3087 | 3154 | 3087 | 3155 | 3087 | 3156 |
| 3088 | 3155 | 3088 | 3156 | 3088 | 3148 |
| 3089 | 3156 | 3089 | 3148 | 3089 | 3149 |
| 3090 | 3148 | 3090 | 3149 | 3090 | 3150 |
| 3091 | 3149 | 3091 | 3150 | 3091 | 3151 |
| 3092 | 3150 | 3092 | 3151 | 3092 | 3152 |
| 3093 | 3151 | 3093 | 3152 | 3093 | 3153 |
| 3094 | 3152 | 3094 | 3153 | 3094 | 3154 |
| 3095 | 3153 | 3095 | 3154 | 3095 | 3155 |
| 3096 | 3154 | 3096 | 3155 | 3096 | 3156 |
| 3097 | 3155 | 3097 | 3156 | 3097 | 3148 |
| 3098 | 3156 | 3098 | 3148 | 3098 | 3149 |
| 3099 | 3148 | 3099 | 3149 | 3099 | 3150 |
| 3100 | 3149 | 3100 | 3150 | 3100 | 3151 |
| 3101 | 3150 | 3101 | 3151 | 3101 | 3152 |
| 3102 | 3151 | 3102 | 3152 | 3102 | 3153 |

Fig. 11G

| IGH V/J SET 4 | | IGH V/J SET 5 | | IGH V/J SET 6 | |
|---|---|---|---|---|---|
| SEQ ID NO: V | SEQ ID NO: J | SEQ ID NO: V | SEQ ID NO: J | SEQ ID NO: V | SEQ ID NO: J |
| 3103 | 3152 | 3103 | 3153 | 3103 | 3154 |
| 3104 | 3153 | 3104 | 3154 | 3104 | 3155 |
| 3105 | 3154 | 3105 | 3155 | 3105 | 3156 |
| 3106 | 3155 | 3106 | 3156 | 3106 | 3148 |
| 3107 | 3156 | 3107 | 3148 | 3107 | 3149 |
| 3108 | 3148 | 3108 | 3149 | 3108 | 3150 |
| 3109 | 3149 | 3109 | 3150 | 3109 | 3151 |
| 3110 | 3150 | 3110 | 3151 | 3110 | 3152 |
| 3111 | 3151 | 3111 | 3152 | 3111 | 3153 |
| 3112 | 3152 | 3112 | 3153 | 3112 | 3154 |
| 3113 | 3153 | 3113 | 3154 | 3113 | 3155 |
| 3114 | 3154 | 3114 | 3155 | 3114 | 3156 |
| 3115 | 3155 | 3115 | 3156 | 3115 | 3148 |
| 3116 | 3156 | 3116 | 3148 | 3116 | 3149 |
| 3117 | 3148 | 3117 | 3149 | 3117 | 3150 |
| 3118 | 3149 | 3118 | 3150 | 3118 | 3151 |
| 3119 | 3150 | 3119 | 3151 | 3119 | 3152 |
| 3120 | 3151 | 3120 | 3152 | 3120 | 3153 |
| 3121 | 3152 | 3121 | 3153 | 3121 | 3154 |
| 3122 | 3153 | 3122 | 3154 | 3122 | 3155 |
| 3123 | 3154 | 3123 | 3155 | 3123 | 3156 |
| 3124 | 3155 | 3124 | 3156 | 3124 | 3148 |
| 3125 | 3156 | 3125 | 3148 | 3125 | 3149 |
| 3126 | 3148 | 3126 | 3149 | 3126 | 3150 |
| 3127 | 3149 | 3127 | 3150 | 3127 | 3151 |
| 3128 | 3150 | 3128 | 3151 | 3128 | 3152 |
| 3129 | 3151 | 3129 | 3152 | 3129 | 3153 |
| 3130 | 3152 | 3130 | 3153 | 3130 | 3154 |
| 3131 | 3153 | 3131 | 3154 | 3131 | 3155 |
| 3132 | 3154 | 3132 | 3155 | 3132 | 3156 |
| 3133 | 3155 | 3133 | 3156 | 3133 | 3148 |

Fig. 11H

| IGH V/J SET 4 | | IGH V/J SET 5 | | IGH V/J SET 6 | |
|---|---|---|---|---|---|
| SEQ ID NO: V | SEQ ID NO: J | SEQ ID NO: V | SEQ ID NO: J | SEQ ID NO: V | SEQ ID NO: J |
| 3134 | 3156 | 3134 | 3148 | 3134 | 3149 |
| 3135 | 3148 | 3135 | 3149 | 3135 | 3150 |
| 3136 | 3149 | 3136 | 3150 | 3136 | 3151 |
| 3137 | 3150 | 3137 | 3151 | 3137 | 3152 |
| 3138 | 3151 | 3138 | 3152 | 3138 | 3153 |
| 3139 | 3152 | 3139 | 3153 | 3139 | 3154 |
| 3140 | 3153 | 3140 | 3154 | 3140 | 3155 |
| 3141 | 3154 | 3141 | 3155 | 3141 | 3156 |
| 3142 | 3155 | 3142 | 3156 | 3142 | 3148 |
| 3143 | 3156 | 3143 | 3148 | 3143 | 3149 |
| 3144 | 3148 | 3144 | 3149 | 3144 | 3150 |
| 3145 | 3149 | 3145 | 3150 | 3145 | 3151 |
| 3146 | 3150 | 3146 | 3151 | 3146 | 3152 |
| 3147 | 3151 | 3147 | 3152 | 3147 | 3153 |

| IGH V/J SET 7 | | IGH V/J SET 8 | | IGH V/J SET 9 | |
|---|---|---|---|---|---|
| SEQ ID NO: V | SEQ ID NO: J | SEQ ID NO: V | SEQ ID NO: J | SEQ ID NO: V | SEQ ID NO: J |
| 3021 | 3154 | 3021 | 3155 | 3021 | 3156 |
| 3022 | 3155 | 3022 | 3156 | 3022 | 3148 |
| 3023 | 3156 | 3023 | 3148 | 3023 | 3149 |
| 3024 | 3148 | 3024 | 3149 | 3024 | 3150 |
| 3025 | 3149 | 3025 | 3150 | 3025 | 3151 |
| 3026 | 3150 | 3026 | 3151 | 3026 | 3152 |
| 3027 | 3151 | 3027 | 3152 | 3027 | 3153 |
| 3028 | 3152 | 3028 | 3153 | 3028 | 3154 |
| 3029 | 3153 | 3029 | 3154 | 3029 | 3155 |
| 3030 | 3154 | 3030 | 3155 | 3030 | 3156 |
| 3031 | 3155 | 3031 | 3156 | 3031 | 3148 |
| 3032 | 3156 | 3032 | 3148 | 3032 | 3149 |
| 3033 | 3148 | 3033 | 3149 | 3033 | 3150 |

Fig. 11I

| IGH V/J SET 7 | | IGH V/J SET 8 | | IGH V/J SET 9 | |
|---|---|---|---|---|---|
| SEQ ID NO: V | SEQ ID NO: J | SEQ ID NO: V | SEQ ID NO: J | SEQ ID NO: V | SEQ ID NO: J |
| 3034 | 3149 | 3034 | 3150 | 3034 | 3151 |
| 3035 | 3150 | 3035 | 3151 | 3035 | 3152 |
| 3036 | 3151 | 3036 | 3152 | 3036 | 3153 |
| 3037 | 3152 | 3037 | 3153 | 3037 | 3154 |
| 3038 | 3153 | 3038 | 3154 | 3038 | 3155 |
| 3039 | 3154 | 3039 | 3155 | 3039 | 3156 |
| 3040 | 3155 | 3040 | 3156 | 3040 | 3148 |
| 3041 | 3156 | 3041 | 3148 | 3041 | 3149 |
| 3042 | 3148 | 3042 | 3149 | 3042 | 3150 |
| 3043 | 3149 | 3043 | 3150 | 3043 | 3151 |
| 3044 | 3150 | 3044 | 3151 | 3044 | 3152 |
| 3045 | 3151 | 3045 | 3152 | 3045 | 3153 |
| 3046 | 3152 | 3046 | 3153 | 3046 | 3154 |
| 3047 | 3153 | 3047 | 3154 | 3047 | 3155 |
| 3048 | 3154 | 3048 | 3155 | 3048 | 3156 |
| 3049 | 3155 | 3049 | 3156 | 3049 | 3148 |
| 3050 | 3156 | 3050 | 3148 | 3050 | 3149 |
| 3051 | 3148 | 3051 | 3149 | 3051 | 3150 |
| 3052 | 3149 | 3052 | 3150 | 3052 | 3151 |
| 3053 | 3150 | 3053 | 3151 | 3053 | 3152 |
| 3054 | 3151 | 3054 | 3152 | 3054 | 3153 |
| 3055 | 3152 | 3055 | 3153 | 3055 | 3154 |
| 3056 | 3153 | 3056 | 3154 | 3056 | 3155 |
| 3057 | 3154 | 3057 | 3155 | 3057 | 3156 |
| 3058 | 3155 | 3058 | 3156 | 3058 | 3148 |
| 3059 | 3156 | 3059 | 3148 | 3059 | 3149 |
| 3060 | 3148 | 3060 | 3149 | 3060 | 3150 |
| 3061 | 3149 | 3061 | 3150 | 3061 | 3151 |
| 3062 | 3150 | 3062 | 3151 | 3062 | 3152 |
| 3063 | 3151 | 3063 | 3152 | 3063 | 3153 |
| 3064 | 3152 | 3064 | 3153 | 3064 | 3154 |

Fig. 11J

| IGH V/J SET 7 | | IGH V/J SET 8 | | IGH V/J SET 9 | |
| --- | --- | --- | --- | --- | --- |
| SEQ ID NO: V | SEQ ID NO: J | SEQ ID NO: V | SEQ ID NO: J | SEQ ID NO: V | SEQ ID NO: J |
| 3065 | 3153 | 3065 | 3154 | 3065 | 3155 |
| 3066 | 3154 | 3066 | 3155 | 3066 | 3156 |
| 3067 | 3155 | 3067 | 3156 | 3067 | 3148 |
| 3068 | 3156 | 3068 | 3148 | 3068 | 3149 |
| 3069 | 3148 | 3069 | 3149 | 3069 | 3150 |
| 3070 | 3149 | 3070 | 3150 | 3070 | 3151 |
| 3071 | 3150 | 3071 | 3151 | 3071 | 3152 |
| 3072 | 3151 | 3072 | 3152 | 3072 | 3153 |
| 3073 | 3152 | 3073 | 3153 | 3073 | 3154 |
| 3074 | 3153 | 3074 | 3154 | 3074 | 3155 |
| 3075 | 3154 | 3075 | 3155 | 3075 | 3156 |
| 3076 | 3155 | 3076 | 3156 | 3076 | 3148 |
| 3077 | 3156 | 3077 | 3148 | 3077 | 3149 |
| 3078 | 3148 | 3078 | 3149 | 3078 | 3150 |
| 3079 | 3149 | 3079 | 3150 | 3079 | 3151 |
| 3080 | 3150 | 3080 | 3151 | 3080 | 3152 |
| 3081 | 3151 | 3081 | 3152 | 3081 | 3153 |
| 3082 | 3152 | 3082 | 3153 | 3082 | 3154 |
| 3083 | 3153 | 3083 | 3154 | 3083 | 3155 |
| 3084 | 3154 | 3084 | 3155 | 3084 | 3156 |
| 3085 | 3155 | 3085 | 3156 | 3085 | 3148 |
| 3086 | 3156 | 3086 | 3148 | 3086 | 3149 |
| 3087 | 3148 | 3087 | 3149 | 3087 | 3150 |
| 3088 | 3149 | 3088 | 3150 | 3088 | 3151 |
| 3089 | 3150 | 3089 | 3151 | 3089 | 3152 |
| 3090 | 3151 | 3090 | 3152 | 3090 | 3153 |
| 3091 | 3152 | 3091 | 3153 | 3091 | 3154 |
| 3092 | 3153 | 3092 | 3154 | 3092 | 3155 |
| 3093 | 3154 | 3093 | 3155 | 3093 | 3156 |
| 3094 | 3155 | 3094 | 3156 | 3094 | 3148 |
| 3095 | 3156 | 3095 | 3148 | 3095 | 3149 |

Fig. 11K

| IGH V/J SET 7 | | IGH V/J SET 8 | | IGH V/J SET 9 | |
|---|---|---|---|---|---|
| SEQ ID NO: V | SEQ ID NO:J | SEQ ID NO: V | SEQ ID NO:J | SEQ ID NO: V | SEQ ID NO:J |
| 3096 | 3148 | 3096 | 3149 | 3096 | 3150 |
| 3097 | 3149 | 3097 | 3150 | 3097 | 3151 |
| 3098 | 3150 | 3098 | 3151 | 3098 | 3152 |
| 3099 | 3151 | 3099 | 3152 | 3099 | 3153 |
| 3100 | 3152 | 3100 | 3153 | 3100 | 3154 |
| 3101 | 3153 | 3101 | 3154 | 3101 | 3155 |
| 3102 | 3154 | 3102 | 3155 | 3102 | 3156 |
| 3103 | 3155 | 3103 | 3156 | 3103 | 3148 |
| 3104 | 3156 | 3104 | 3148 | 3104 | 3149 |
| 3105 | 3148 | 3105 | 3149 | 3105 | 3150 |
| 3106 | 3149 | 3106 | 3150 | 3106 | 3151 |
| 3107 | 3150 | 3107 | 3151 | 3107 | 3152 |
| 3108 | 3151 | 3108 | 3152 | 3108 | 3153 |
| 3109 | 3152 | 3109 | 3153 | 3109 | 3154 |
| 3110 | 3153 | 3110 | 3154 | 3110 | 3155 |
| 3111 | 3154 | 3111 | 3155 | 3111 | 3156 |
| 3112 | 3155 | 3112 | 3156 | 3112 | 3148 |
| 3113 | 3156 | 3113 | 3148 | 3113 | 3149 |
| 3114 | 3148 | 3114 | 3149 | 3114 | 3150 |
| 3115 | 3149 | 3115 | 3150 | 3115 | 3151 |
| 3116 | 3150 | 3116 | 3151 | 3116 | 3152 |
| 3117 | 3151 | 3117 | 3152 | 3117 | 3153 |
| 3118 | 3152 | 3118 | 3153 | 3118 | 3154 |
| 3119 | 3153 | 3119 | 3154 | 3119 | 3155 |
| 3120 | 3154 | 3120 | 3155 | 3120 | 3156 |
| 3121 | 3155 | 3121 | 3156 | 3121 | 3148 |
| 3122 | 3156 | 3122 | 3148 | 3122 | 3149 |
| 3123 | 3148 | 3123 | 3149 | 3123 | 3150 |
| 3124 | 3149 | 3124 | 3150 | 3124 | 3151 |
| 3125 | 3150 | 3125 | 3151 | 3125 | 3152 |
| 3126 | 3151 | 3126 | 3152 | 3126 | 3153 |

Fig. 11L

| IGH V/J SET 7 | | IGH V/J SET 8 | | IGH V/J SET 9 | |
|---|---|---|---|---|---|
| SEQ ID NO: V | SEQ ID NO: J | SEQ ID NO: V | SEQ ID NO: J | SEQ ID NO: V | SEQ ID NO: J |
| 3127 | 3152 | 3127 | 3153 | 3127 | 3154 |
| 3128 | 3153 | 3128 | 3154 | 3128 | 3155 |
| 3129 | 3154 | 3129 | 3155 | 3129 | 3156 |
| 3130 | 3155 | 3130 | 3156 | 3130 | 3148 |
| 3131 | 3156 | 3131 | 3148 | 3131 | 3149 |
| 3132 | 3148 | 3132 | 3149 | 3132 | 3150 |
| 3133 | 3149 | 3133 | 3150 | 3133 | 3151 |
| 3134 | 3150 | 3134 | 3151 | 3134 | 3152 |
| 3135 | 3151 | 3135 | 3152 | 3135 | 3153 |
| 3136 | 3152 | 3136 | 3153 | 3136 | 3154 |
| 3137 | 3153 | 3137 | 3154 | 3137 | 3155 |
| 3138 | 3154 | 3138 | 3155 | 3138 | 3156 |
| 3139 | 3155 | 3139 | 3156 | 3139 | 3148 |
| 3140 | 3156 | 3140 | 3148 | 3140 | 3149 |
| 3141 | 3148 | 3141 | 3149 | 3141 | 3150 |
| 3142 | 3149 | 3142 | 3150 | 3142 | 3151 |
| 3143 | 3150 | 3143 | 3151 | 3143 | 3152 |
| 3144 | 3151 | 3144 | 3152 | 3144 | 3153 |
| 3145 | 3152 | 3145 | 3153 | 3145 | 3154 |
| 3146 | 3153 | 3146 | 3154 | 3146 | 3155 |
| 3147 | 3154 | 3147 | 3155 | 3147 | 3156 |

Fig. 11M

DIAGNOSIS OF LYMPHOID MALIGNANCIES AND MINIMAL RESIDUAL DISEASE DETECTION

CROSS REFERENCE TO RELATED APPLICATION

This application claims the benefit under 35 U.S.C. 119(e) of U.S. Provisional Patent Application Nos. 61/569,118 filed Dec. 9, 2011; 61/644,294, filed May 8, 2012; and 61/726,489, filed Nov. 14, 2012, each of which prior applications is incorporated herein by reference in its entirety.

SEQUENCE LISTING

The instant application contains a Sequence Listing which has been submitted via EFS-Web and is hereby incorporated by reference in its entirety. Said ASCII copy, created on Mar. 28, 2013, is named 22448US_CRF_sequencelisting.txt, and is 4,203,178 bytes in size.

BACKGROUND

Technical Field

The present disclosure relates generally to the highly sensitive quantification of the relative representation of adaptive immune cells having a particular T cell receptor (TCR) or immunoglobulin (Ig) encoding gene rearrangement (e.g., clonotype), in samples obtained from a subject prior to and/or following therapeutic treatment. Determination of the relative frequencies of such clonotypes can be used to diagnose certain lymphoid hematologic malignancies and other disorders. Also, determination of the relative frequencies of such clonotypes following therapeutic treatment provides exquisitely sensitive detection of minimal residual disease (MRD).

Description of the Related Art

The adaptive immune system protects higher organisms against infections and other pathological events that may be attributable to foreign substances, using adaptive immune receptors, the antigen-specific recognition proteins that are expressed by hematopoietic cells of the lymphoid lineage and that are capable of distinguishing self from non-self molecules in the host. These lymphocytes may be found in the circulation and tissues of a host, and their recirculation between blood and the lymphatics has been described, including their extravasation via lymph node high endothelial venules, as well as at sites of infection, inflammation, tissue injury and other clinical insults. (See, e.g., Stein et al., 2005 *Immunol.* 116:1-12; DeNucci et al., 2009 *Crit. Rev. Immunol.* 29:87-109; Marelli-Berg et al., 2010 *Immunol.* 130:158; Ward et al., 2009 *Biochem. J.* 418:13; Gonzalez et al., 2011 *Ann. Rev. Immunol.* 29:215; Kehrl et al., 2009 *Curr. Top. Microb. Immunol.* 334:107; Steinmetz et al., 2009 *Front. Biosci.* (Schol. Ed.) 1:13.)

Accordingly, the dynamic nature of movement by lymphocytes throughout a host organism is reflected in changes in the qualitative (e.g., antigen-specificity of the clonally expressed adaptive immune receptor (immunoglobulin or T cell receptor), T cell versus B cell, T helper ($T_h$) cell versus T regulatory ($T_{reg}$) cell, effector T cell versus memory T cell, etc.) and quantitative distribution of lymphocytes among tissues, as a function of changes in host immune status.

The adaptive immune system employs several strategies to generate a repertoire of T- and B-cell antigen receptors with sufficient diversity to recognize the universe of potential pathogens. B lymphocytes mature to express antibodies (immunoglobulins, Igs or Igs, also referred to as B cell receptors, BCR) that occur as heterodimers of a heavy (H) a light (L) chain polypeptide, while T lymphocytes express heterodimeric T cell receptors (TCR). The ability of T cells to recognize the universe of antigens associated with various cancers or infectious organisms is conferred by its T cell antigen receptor (TCR), which is a heterodimer comprising an α (alpha) chain and a β (beta) chain, or a γ (gamma) and a δ (delta) chain. The proteins which make up these chains are encoded by DNA, which employs a unique mechanism for generating the tremendous diversity of the TCR. This multi-subunit immune recognition receptor associates with the CD3 complex and binds to peptides presented by the major histocompatibility complex (MHC) class I and II proteins on the surface of antigen-presenting cells (APCs). Binding of TCR to the antigenic peptide on the APC is a central event in T cell activation, which occurs at an immunological synapse at the point of contact between the T cell and the APC.

Each TCR peptide contains variable complementarity determining regions (CDRs), as well as framework regions (FRs) and a constant region. The sequence diversity of αβ T cells is largely determined by the amino acid sequence of the third complementarity-determining region (CDR3) loops of the α and β chain variable domains, which diversity is a result of recombination between variable ($V_\beta$), diversity ($D_\beta$), and joining ($J_\beta$) gene segments in the β chain locus, and between analogous $V_\alpha$ and $J_\alpha$ gene segments in the α chain locus, respectively. The existence of multiple such gene segments in the TCR α and β chain loci allows for a large number of distinct CDR3 sequences to be encoded. CDR3 sequence diversity is further increased by independent addition and deletion of nucleotides at the $V_\beta$-$D_\beta$, $D_\beta$-$J_\beta$, and $V_\alpha$-$J_\alpha$ junctions during the process of TCR gene rearrangement. In this respect, immunocompetence is reflected in the diversity of TCRs.

The γδ TCR is distinctive from the αβ TCR in that it encodes a receptor that interacts closely with the innate immune system. TCRγδ, is expressed early in development, has specialized anatomical distribution, has unique pathogen and small-molecule specificities, and has a broad spectrum of innate and adaptive cellular interactions. A biased pattern of TCRγ V and J segment expression is established early in ontogeny as the restricted subsets of TCRγδ cells populate the mouth, skin, gut, vagina, and lungs prenatally. Consequently, the diverse TCRγ repertoire in adult tissues is the result of extensive peripheral expansion following stimulation by environmental exposure to pathogens and toxic molecules.

Igs (BCR) expressed by B cells are proteins consisting of four polypeptide chains, two heavy chains (H chains) and two light chains (L chains), forming an $H_2L_2$ structure. Each pair of H and L chains contains a hypervariable domain, consisting of a $V_L$ and a $V_H$ region, and a constant domain. The H chains of Igs are of several types, μ, δ, γ, α, and β. The diversity of Igs within an individual is mainly determined by the hypervariable domain. Similar to the TCR, the V domain of Ig H chains is created by the combinatorial joining of the $V_H$, $D_H$, and $J_H$ gene segments. Hypervariable domain sequence diversity is further increased by independent addition and deletion of nucleotides at the $V_H$-$D_H$, $D_H$-$J_H$, and $V_H$-$J_H$ junctions during the process of Ig gene rearrangement. In this respect, immunocompetence is reflected in the diversity of Igs.

Quantitative characterization of adaptive immune cells based on the presence in such cells of functionally rearranged Ig and TCR encoding genes that direct productive expression of adaptive immune receptors has been achieved using biological samples from which adaptive immune cells can be readily isolated in significant numbers, such as blood, lymph or other biological fluids. In these samples, adaptive immune cells occur as particles in fluid suspension. See, e.g., US 2010/0330571; see also, e.g., Murphy, *Janeway's Immunobiology* (8$^{th}$ Ed.), 2011 Garland Science, NY, Appendix I, pp. 717-762.

Acute T-cell lymphoblastic leukemia/lymphoma (T-ALL) is an aggressive, immature, malignant T-cell neoplasm that affects both adult and pediatric patients. While there has been significant progress in treating these patients with improvements in achieving durable responses, it remains clear that a subset of these patients are inadequately treated and frequently present with disease relapse, while others may be over-treated due to an inability to sufficiently individualize clinical treatment. Several studies have confirmed the importance of assessing the potential presence of minimal residual disease (MRD) following a treatment regimen, to aid in predicting clinical outcomes of patients (1-3). For example, patients who demonstrate an early response to therapy, and who fail to exhibit sustained achievement of MRD, fare significantly better than those who do not (3).

Similarly, acute B-cell lymphoblastic leukemia/lymphoma (B-ALL) is an aggressive immature malignant B-cell neoplasm that affects adult and pediatric patients. While significant progress has been made to increase the number of patients who achieve durable long-term remission, a subset of patients relapses. As in T-ALL, multiple studies have confirmed that the presence and frequency of minimal residual disease are both important prognostic markers in B-ALL. In addition, several of these studies also support the use of these data to inform and individualize therapy (e.g., Yamaji et al., 2010 *Pediatr. Blood Canc.* 55(7):1287-95; Bhojwani et al., 2009 *Clin. Lymphoma Myeloma* 9 (Suppl. 3):S222-30.

Current clinical strategies for assessment of minimal residual disease include multi-parameteric flow cytometry (mpFC) and quantitative PCR-based methods using patient-specific primers (4, 5). mpFC typically permits detection of cells potentially responsible for recurrent/persistent disease with a sensitivity of on the order of $10^{-4}$ to $10^{-6}$ nucleated cells. However, interpretation of these data is operator- and laboratory-dependent, and consequently limited by poor standardization. Furthermore, variable expression of leukemic antigens in the post-therapy setting confounds MRD detection by mpFC (6).

By comparison, molecular-based methods for detection of minimal residual disease can achieve relatively increased sensitivity, on the order of $10^{-5}$ to $10^{-6}$ cells (7, 8). However, the previous configurations of these molecular assays, principally real-time quantitative PCR-based (RT-qPCR) assays using patient-specific primers that target adaptive immune receptor (e.g., T-cell receptor (TCR) or immunoglobulin (Ig)) variable region junctional sequences, or patient-specific translocations, are complex and challenging to implement in a uniform matter (7). For instance, these approaches require the production and use of individualized, patient-specific oligonucleotide probes for each patient, which is laborious, costly and time-consuming, and incompatible with the timeframe in which clinical decisions must be made.

High-throughput sequencing (HTS) is an emerging technology that can provide insight into the complexity of the adaptive immune response through the analysis of lymphoid receptor gene rearrangement (9). Studies using this technology have challenged understanding in the art of the extent of lymphocyte diversity occurring within, and shared by, individuals (9, 10), and have provided mechanistic insight into the early molecular genetic events critical for the T-cell lineage maturation (11). Recently, high-throughput sequencing of lymphoid cell adaptive immune receptor genes has been used to monitor lymphocyte diversity after adoptive immunotherapy with chimeric antigen receptor-modified T cells for the treatment of chemotherapy-refractory chronic lymphocytic leukemia (12). Separately, high-throughput sequencing of lymphoid cell adaptive immune receptor genes has been used for monitoring disease in B lymphoproliferative disorders (13). HTS has exhibited the ability to identify rare T cell clones (one T cell in 100,000) with high accuracy and reproducibility (14).

Clearly there is a need for improved sensitivity and specificity in the diagnosis of lymphoid hematological malignancies and other conditions that are reflected in the heterogeneity and relative frequencies of occurrence of particular unique adaptive immune receptors, and in the ability to detect minimal residual disease (MRD). The presently described embodiments address these needs and provide other related advantages.

BRIEF SUMMARY

According to certain embodiments of the invention described herein, there is provided a method for diagnosing a lymphoid hematological malignancy in a subject prior to therapy, and for detecting minimal residual disease for the lymphoid hematological malignancy in the subject after therapy, the method comprising: (I) for each of (i) one or a plurality of biological samples that each comprise a plurality of lymphoid hematopoietic cells and that are each obtained from the subject at one or more timepoints prior to therapy, and (ii) one or a plurality of biological samples that each comprise a plurality of lymphoidhematopoietic cells and that are each obtained from the subject at one or more timepoints after therapy, (a) amplifying DNA extracted from the biological sample in a multiplex polymerase chain reaction (PCR) that comprises: (i) a plurality of V-segment oligonucleotide primers that are each independently capable of specifically hybridizing to at least one polynucleotide encoding a human T cell receptor (TCR) V-region polypeptide, wherein each V-segment primer comprises a nucleotide sequence of at least 15 contiguous nucleotides that is complementary to at least one functional TCR Vγ-encoding or TCR Vβ-encoding gene segment and wherein the plurality of V-segment primers specifically hybridize to substantially all functional TCR Vγ-encoding or TCR Vβ-encoding gene segments that are present in the sample, and (ii) a plurality of J-segment oligonucleotide primers that are each independently capable of specifically hybridizing to at least one polynucleotide encoding a human T cell receptor (TCR) J-region polypeptide, wherein each J-segment primer comprises a nucleotide sequence of at least 15 contiguous nucleotides that is complementary to at least one functional TCR Jγ-encoding or TCR Jβ-encoding gene segment and wherein the plurality of J-segment primers specifically hybridize to substantially all functional TCR Jγ-encoding or TCR Jβ-encoding gene segments that are present in the sample, wherein the V-segment and J-segment primers are capable of promoting amplification in said multiplex polymerase chain reaction (PCR) of substantially all rearranged TCRγ CDR3-encoding regions or substantially all TCRβ CDR3-encoding regions in the sample to produce a multiplicity of amplified rearranged DNA molecules from a population of T cells in the sample, said multiplicity of amplified rearranged DNA molecules being sufficient to quantify diversity of the TCRγ CDR3-encoding region or TCRγ CDR3-encoding region in the population of T cells, and wherein each amplified rearranged DNA molecule in the multiplicity of amplified rearranged DNA molecules is less than 600 nucleotides in length; and (b) sequencing said multiplicity of amplified rearranged DNA molecules to determine, for each unique rearranged DNA molecule in said multiplicity of amplified rearranged DNA molecules, (i) a rearranged DNA sequence and (ii) a relative frequency of occurrence of the rearranged DNA sequence; and (II) comparing (i) the relative frequency of occurrence for each unique rearranged DNA sequence from said one or a plurality of biological samples that are each obtained from the subject at one or more timepoints prior to therapy, to (ii) the relative frequency of occurrence for each unique rearranged DNA sequence from said one or a plurality of biological samples that are each obtained from the subject at one or more timepoints after therapy, wherein (A) presence, in a sample obtained from the subject prior to therapy, of at least one unique rearranged DNA sequence that has a relative frequency of at least 15% of rearranged TCRγ CDR3-encoding regions or rearranged TCRβ CDR3-encoding regions is diagnostic for a clonal lymphoid hematological malignancy in the subject prior to therapy, and wherein (B) presence, in a sample obtained from the subject after therapy, of said at least one unique rearranged DNA sequence that is diagnostic for the clonal lymphoid hematological malignancy at a relative frequency of at least one in $10^5$ TCR CDR3-encoding regions, indicates minimal residual disease for the lymphoid hematological malignancy.

In certain further embodiments each functional TCR or Ig V-encoding gene segment comprises a V gene recombination signal sequence (RSS) and each functional TCR or Ig J-encoding gene segment comprises a J gene RSS, and wherein each amplified rearranged DNA molecule comprises (i) at least 10, 20, 30 or 40 contiguous nucleotides of a sense strand of the TCR or Ig V-encoding gene segment, said at least 10, 20, 30 or 40 contiguous nucleotides being situated 5' to the V gene RSS and (ii) at least 10, 20 or 30 contiguous nucleotides of a sense strand of the TCR or Ig J-encoding gene segment, said at least 10, 20 or 30 contiguous nucleotides being situated 3' to the J gene RSS.

In certain embodiments the plurality of V-segment oligonucleotide primers and the plurality of J-segment oligonucleotide primers comprise at least one of (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351. In certain embodiments either or both of: (i) the V-segment oligonucleotide primers comprise one or a plurality of oligonucleotides that exhibit at least 90% sequence identity to one or more of the nucleotide sequences set forth in SEQ ID NOS:5579-5630, 5644-5779, 5799-5816, 6124-6127, and 6222-6273, and (ii) the J-segment primers comprise one or a plurality of oligonucleotides that exhibit at least 90% sequence identity to one or more of the nucleotide sequences set forth in SEQ ID NOS:5631-5643, 5780-5798, 6212-6215, and 6274-6286.

In certain other embodiments there is provided a method for diagnosing a lymphoid hematological malignancy in a subject, comprising (I) for each of (i) one or a plurality of biological samples that are obtained from the subject and that each comprise a plurality of lymphoid hematopoietic cells, (a) amplifying DNA extracted from the biological sample in a multiplex polymerase chain reaction (PCR) that comprises: (i) a plurality of V-segment oligonucleotide primers that are each independently capable of specifically hybridizing to at least one polynucleotide encoding a human T cell receptor (TCR) V-region polypeptide, wherein each V-segment primer comprises a nucleotide sequence of at least 15 contiguous nucleotides that is complementary to at least one functional TCR Vγ-encoding or TCR Vβ-encoding gene segment and wherein the plurality of V-segment primers specifically hybridize to substantially all functional TCR Vγ-encoding or TCR Vβ-encoding gene segments that are present in the sample, and (ii) a plurality of J-segment oligonucleotide primers that are each independently capable of specifically hybridizing to at least one polynucleotide encoding a human T cell receptor (TCR) J-region polypeptide, wherein each J-segment primer comprises a nucleotide sequence of at least 15 contiguous nucleotides that is complementary to at least one functional TCR Jγ-encoding or TCR Jβ-encoding gene segment and wherein the plurality of J-segment primers specifically hybridize to substantially all functional TCR Jγ-encoding or TCR Jβ-encoding gene segments that are present in the sample, wherein the V-segment and J-segment primers are capable of promoting amplification in said multiplex polymerase chain reaction (PCR) of substantially all rearranged TCRγ CDR3-encoding regions or substantially all TCRβ CDR3-encoding regions in the sample to produce a multiplicity of amplified rearranged DNA molecules from a population of T cells in the sample, said multiplicity of amplified rearranged DNA molecules being sufficient to quantify diversity of the TCRγ CDR3-encoding region or TCRγ CDR3-encoding region in the population of T cells, and wherein each amplified rearranged DNA molecule in the multiplicity of amplified rearranged DNA molecules is less than 600 nucleotides in length; and (b) sequencing said multiplicity of amplified rearranged DNA molecules to determine, for each unique rearranged DNA molecule in said multiplicity of amplified rearranged DNA molecules, (i) a rearranged DNA sequence and (ii) a relative frequency of occurrence of the rearranged DNA sequence; and (II) determining the relative frequency of occurrence for each unique rearranged DNA sequence from said one or a plurality of biological samples that are each obtained from the subject, wherein (A) presence, in a sample obtained from the subject, of at least one unique rearranged DNA sequence that has a relative frequency of at least 15% of rearranged TCRγ CDR3-encoding regions or rearranged TCRβ CDR3-encoding regions is diagnostic for a clonal lymphoid hematological malignancy in the subject, wherein (B) presence, in a sample obtained from the subject, of said at least one unique rearranged DNA sequence that is diagnostic for the clonal lymphoid hematological malignancy at a relative frequency of at least one in $10^5$ TCR CDR3-encoding regions, indicates minimal residual disease for the lymphoid hematological malignancy, and wherein (C) absence from the sample obtained from the subject of at least one unique rearranged DNA sequence that has a relative frequency of at least 15% of rearranged TCRγ CDR3-encoding regions or rearranged TCRβ CDR3-encoding regions indicates the subject should be evaluated for early thymic-precursor immunophenotype.

In certain embodiments each functional TCR or Ig V-encoding gene segment comprises a V gene recombination signal sequence (RSS) and each functional TCR or Ig J-encoding gene segment comprises a J gene RSS, and wherein each amplified rearranged DNA molecule comprises (i) at least 10, 20, 30 or 40 contiguous nucleotides of a sense strand of the TCR or Ig V-encoding gene segment, said at least 10, 20, 30 or 40 contiguous nucleotides being situated 5' to the V gene RSS and (ii) at least 10, 20 or 30 contiguous nucleotides of a sense strand of the TCR or Ig J-encoding gene segment, said at least 10, 20 or 30 contiguous nucleotides being situated 3' to the J gene RSS. In certain embodiments the plurality of V-segment oligonucleotide primers and the plurality of J-segment oligonucleotide primers comprise at least one of (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351. In certain embodiments either or both of (i) the V-segment oligonucleotide primers comprise one or a plurality of oligonucleotides that exhibit at least 90% sequence identity to one or more of the nucleotide sequences set forth in SEQ ID NOS:5579-5630, 5644-5779, 5799-5816, 6124-6127, and 6222-6273, and (ii) the J-segment primers comprise one or a plurality of oligonucleotides that exhibit at least 90% sequence identity to one or more of the nucleotide sequences set forth in SEQ ID NOS:5631-5643, 5780-5798, 6212-6215, and 6274-6286.

Turning to another embodiment there is provided a method for detecting minimal residual disease for a lymphoid hematological malignancy in a subject after therapy, the method comprising: (I) for each of (i) one or a plurality of biological samples that each comprise a plurality of lymphoid hematopoietic cells and that are each obtained from the subject at one or more timepoints prior to therapy, and (ii) one or a plurality of biological samples that each comprise a plurality of lymphoid hematopoietic cells and that are each obtained from the subject at one or more timepoints after therapy, (a) amplifying DNA extracted from the biological sample in a multiplex polymerase chain reaction (PCR) that comprises: (i) a plurality of V-segment oligonucleotide primers that are each independently capable of specifically hybridizing to at least one polynucleotide encoding a human T cell receptor (TCR) V-region polypeptide, wherein each V-segment primer comprises a nucleotide sequence of at least 15 contiguous nucleotides that is complementary to at least one functional TCR Vγ-encoding or TCR Vβ-encoding gene segment and wherein the plurality of V-segment primers specifically hybridize to substantially all functional TCR Vγ-encoding or TCR Vβ-encoding gene segments that are present in the sample, and (ii) a plurality of J-segment oligonucleotide primers that are each independently capable of specifically hybridizing to at least one polynucleotide encoding a human T cell receptor (TCR) J-region polypeptide, wherein each J-segment primer comprises a nucleotide sequence of at least 15 contiguous nucleotides that is complementary to at least one functional TCR Jγ-encoding or TCR Jβ-encoding gene segment and wherein the plurality of J-segment primers specifically hybridize to substantially all functional TCR Jγ-encoding or TCR Jβ-encoding gene segments that are present in the sample, wherein the V-segment and J-segment primers are capable of promoting amplification in said multiplex polymerase chain reaction (PCR) of substantially all rearranged TCRγ CDR3-encoding regions or substantially all TCRβ CDR3-encoding regions in the sample to produce a multiplicity of amplified rearranged DNA molecules from a population of T cells in the sample, said multiplicity of amplified rearranged DNA molecules being sufficient to quantify diversity of the TCRγ CDR3-encoding region or TCRγ CDR3-encoding region in the population of T cells, and wherein each amplified rearranged DNA molecule in the multiplicity of amplified rearranged DNA molecules is less than 600 nucleotides in length; and (b) sequencing said multiplicity of amplified rearranged DNA molecules to determine, for each unique rearranged DNA molecule in said multiplicity of amplified rearranged DNA molecules, (i) a rearranged DNA sequence and (ii) a relative frequency of occurrence of the rearranged DNA sequence; and (II) comparing (i) the relative frequency of occurrence for each unique rearranged DNA sequence from said one or a plurality of biological samples that are each obtained from the subject at one or more timepoints prior to therapy, to (ii) the relative frequency of occurrence for each unique rearranged DNA sequence from said one or a plurality of biological samples that are each obtained from the subject at one or more timepoints after therapy, wherein (A) presence, in a sample obtained from the subject prior to therapy, of at least one unique rearranged DNA sequence that has a relative frequency of at least 15% of rearranged TCRγ CDR3-encoding regions or rearranged TCRβ CDR3-encoding regions is diagnostic for a clonal lymphoid hematological malignancy in the subject prior to therapy, and wherein (B) presence, in a sample obtained from the subject after therapy, of said at least one unique rearranged DNA sequence that is diagnostic for the clonal lymphoid hematological malignancy at a relative frequency of at least one in $10^6$ or of at least one in $10^5$ TCR CDR3-encoding regions, indicates minimal residual disease for the lymphoid hematological malignancy.

In certain embodiments each functional TCR or Ig V-encoding gene segment comprises a V gene recombination signal sequence (RSS) and each functional TCR or Ig J-encoding gene segment comprises a J gene RSS, and wherein each amplified rearranged DNA molecule comprises (i) at least 10, 20, 30 or 40 contiguous nucleotides of a sense strand of the TCR or Ig V-encoding gene segment, said at least 10, 20, 30 or 40 contiguous nucleotides being situated 5' to the V gene RSS and (ii) at least 10, 20 or 30 contiguous nucleotides of a sense strand of the TCR or Ig J-encoding gene segment, said at least 10, 20 or 30 contiguous nucleotides being situated 3' to the J gene RSS. In certain embodiments the plurality of V-segment oligonucleotide primers and the plurality of J-segment oligonucleotide primers comprise at least one of (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351. In certain embodiments either or both of (i) the V-segment oligonucleotide primers comprise one or a plurality of oligonucleotides that exhibit at least 90% sequence identity to one or more of the nucleotide sequences set forth in SEQ ID NOS:5579-5630, 5644-5779, 5799-5816, 6124-6127, and 6222-6273, and (ii) the J-segment primers comprise one or a plurality of oligonucleotides that exhibit at least 90% sequence identity to one or more of the nucleotide sequences set forth in SEQ ID NOS:5631-5643, 5780-5798, 6212-6215, and 6274-6286.

In another embodiment of the present invention there is provided a method for diagnosing a lymphoid hematological malignancy in a subject prior to therapy, and for detecting minimal residual disease for the lymphoid hematological malignancy in the subject after therapy, the method comprising (I) for each of (i) one or a plurality of biological samples that each comprise a plurality of lymphoid hematopoietic cells and that are each obtained from the subject at one or more timepoints prior to therapy, and (ii) one or a plurality of biological samples that each comprise a plurality of lymphoid hematopoietic cells and that are each obtained from the subject at one or more timepoints after therapy, (a) amplifying DNA extracted from the biological sample in a multiplex polymerase chain reaction (PCR) that comprises: (i) a plurality of V-segment oligonucleotide primers that are each independently capable of specifically hybridizing to at least one polynucleotide encoding a human T cell receptor (TCR) V-region polypeptide or a human immunoglobulin (Ig) V-region polypeptide, wherein each V-segment primer comprises a nucleotide sequence of at least 15 contiguous nucleotides that is complementary to at least one functional TCR V region-encoding or Ig V region-encoding gene segment and wherein the plurality of V-segment primers specifically hybridize to substantially all functional TCR V-encoding or Ig V-encoding gene segments that are present in the sample, and (ii) a plurality of J-segment oligonucleotide primers that are each independently capable of specifically hybridizing to at least one polynucleotide encoding a human T cell receptor (TCR) J-region polypeptide or a human Ig J-region polypeptide, wherein each J-segment primer comprises a nucleotide sequence of at least 15 contiguous nucleotides that is complementary to at least one functional TCR J-encoding or Ig J-encoding gene segment and wherein the plurality of J-segment primers specifically hybridize to substantially all functional TCR J-encoding or Ig J-encoding gene segments that are present in the sample, wherein the V-segment and J-segment primers are capable of promoting amplification in said multiplex polymerase chain reaction (PCR) of substantially all rearranged TCR CDR3-encoding regions or substantially all Ig CDR3-encoding regions in the sample to produce a multiplicity of amplified rearranged DNA molecules from a population of lymphoid cells in the sample, said multiplicity of amplified rearranged DNA molecules being sufficient to quantify diversity of the TCR CDR3-encoding region or Ig CDR3-encoding region in the population of lymphoid cells, and wherein each amplified rearranged DNA molecule in the multiplicity of amplified rearranged DNA molecules is less than 600 nucleotides in length; and (b) sequencing said multiplicity of amplified rearranged DNA molecules to determine, for each unique rearranged DNA molecule in said multiplicity of amplified rearranged DNA molecules, (i) a rearranged DNA sequence and (ii) a relative frequency of occurrence of the rearranged DNA sequence; and (II) comparing (i) the relative frequency of occurrence for each unique rearranged DNA sequence from said one or a plurality of biological samples that are each obtained from the subject at one or more timepoints prior to therapy, to (ii) the relative frequency of occurrence for each unique rearranged DNA sequence from said one or a plurality of biological samples that are each obtained from the subject at one or more timepoints after therapy, wherein (A) presence, in a sample obtained from the subject prior to therapy, of at least one unique rearranged DNA sequence that has a relative frequency of at least 15%, 16%, 17%, 18%, 19%, 20%, 21%, 22%, 23%, 24%, 25%, 26%, 27%, 28%, 29% or 30% of rearranged TCR CDR3-encoding regions or rearranged Ig CDR3-encoding regions is diagnostic for a clonal lymphoid hematological malignancy in the subject prior to therapy, and wherein (B) presence, in a sample obtained from the subject after therapy, of at least one unique rearranged DNA sequence that is diagnostic for the clonal lymphoid hematological malignancy at a relative frequency of at least one in $10^5$ TCR or Ig CDR3-encoding regions, indicates minimal residual disease for the lymphoid hematological malignancy.

In certain embodiments each functional TCR or Ig V-encoding gene segment comprises a V gene recombination signal sequence (RSS) and each functional TCR or Ig J-encoding gene segment comprises a J gene RSS, and wherein each amplified rearranged DNA molecule comprises (i) at least 10, 20, 30 or 40 contiguous nucleotides of a sense strand of the TCR or Ig V-encoding gene segment, said at least 10, 20, 30 or 40 contiguous nucleotides being situated 5' to the V gene RSS and (ii) at least 10, 20 or 30 contiguous nucleotides of a sense strand of the TCR or Ig J-encoding gene segment, said at least 10, 20 or 30 contiguous nucleotides being situated 3' to the J gene RSS. In certain embodiments the rearranged TCR or Ig CDR3-encoding regions are selected from rearranged TCRα CDR3-encoding regions, TCRβ CDR3-encoding regions, TCRγ CDR3-encoding regions, TCRδ, CDR3-encoding regions, IgH CDR3-encoding regions, Igκ CDR3-encoding regions, and Igλ CDR3-encoding regions. In certain embodiments the plurality of V-segment oligonucleotide primers and the plurality of J-segment oligonucleotide primers comprise at least one of (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351. In certain embodiments either or both of (i) the V-segment oligonucleotide primers comprise one or a plurality of oligonucleotides that exhibit at least 90% sequence identity to one or more of the nucleotide sequences set forth in SEQ ID NOS:5579-5630, 5644-5779, 5799-5816, 5833-6211, and 6222-6273, and (ii) the J-segment primers comprise one or a plurality of oligonucleotides that exhibit at least 90% sequence identity to one or more of the nucleotide sequences set forth in SEQ ID NOS:5631-5643, 5780-5798, 5817-5832, 6212-6221, and 6274-6286.

In certain embodiments of the above described methods, either or both of (i) the V-segment oligonucleotide primers comprise one or a plurality of oligonucleotides that exhibit at least 90% sequence identity to one or more of: (1) the nucleotide sequences set forth in SEQ ID NOS:5579-5630, (2) the nucleotide sequences set forth in SEQ ID NOS:5644-5779, (3) the nucleotide sequences set forth in SEQ ID NOS:5799-5816, (4) the nucleotide sequences set forth in SEQ ID NOS:5833-6123, (5) the nucleotide sequences set forth in SEQ ID NOS:6124-6127, (6) the nucleotide sequences set forth in SEQ ID NOS:6128-6211, (7) the nucleotide sequences set forth in SEQ ID NOS:6222-6273, and (8) the nucleotide sequences set forth in SEQ ID NOS:6287-6351; and (ii) the J-segment primers comprise one or a plurality of oligonucleotides that exhibit at least 90% sequence identity to one or more of: (1) the nucleotide sequences set forth in SEQ ID NOS:5631-5643, (2) the nucleotide sequences set forth in SEQ ID NOS:5780-5792, (3) the nucleotide sequences set forth in SEQ ID NOS:5793-

5798, (4) the nucleotide sequences set forth in SEQ ID NOS:5817-5832, (5) the nucleotide sequences set forth in SEQ ID NOS:6212-6215, (6) the nucleotide sequences set forth in SEQ ID NOS:6216-6221, and (7) the nucleotide sequences set forth in SEQ ID NOS:6274-6286.

In certain embodiments of the above described methods, the lymphoid hematological malignancy is selected from acute T-cell lymphoblastic leukemia (T-ALL), acute B-cell lymphoblastic leukemia (B-ALL), multiple myeloma, plasmacytoma, macroglobulinemia, chronic lymphocytic leukemia (CLL), acute lymphoblastic leukemia (ALL), multiple myeloma, plasmacytoma, macroglobulinemia, chronic lymphocytic leukemia (CLL), Hodgkins lymphoma, non-Hodgkins lymphoma, cutaneous T-cell lymphoma, mantle cell lymphoma, peripheral T-cell lymphoma, hairy cell leukemia, T prolymphocytic lymphoma, angioimmunoblastic T-cell lymphoma, T lymphoblastic leukemia/lymphoma, peripheral T-cell lymphoma, adult T cell leukemia/lymphoma, mycosis fungoides, Sezary syndrome, T lymphoblastic leukemia, myeloproliferative neoplasm and myelodysplastic syndrome.

In certain embodiments of the above described methods the multiplex PCR further comprises a template composition for amplification factor determination in which a known number of each of a plurality of template oligonucleotides having a unique oligonucleotide sequence is present, the template composition comprising a plurality of template oligonucleotides having a plurality of oligonucleotide sequences of general formula: 5'-U1-B1-V-B2-R-B3-J-B4-U2-3' [I] wherein: (a) V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of oligonucleotide sequences V comprises a unique oligonucleotide sequence; (b) J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of oligonucleotide sequences J comprises a unique oligonucleotide sequence; (c) U1 is either nothing or comprises an oligonucleotide having a sequence that is selected from (i) a first universal adaptor oligonucleotide sequence, and (ii) a first sequencing platform-specific oligonucleotide sequence that is linked to and positioned 5' to a first universal adaptor oligonucleotide sequence; (d) U2 is either nothing or comprises an oligonucleotide having a sequence that is selected from (i) a second universal adaptor oligonucleotide sequence, and (ii) a second sequencing platform-specific oligonucleotide sequence that is linked to and positioned 5' to a second universal adaptor oligonucleotide sequence; (e) B1, B2, B3, and B4 are each independently either nothing or each comprises an oligonucleotide B that comprises an oligonucleotide barcode sequence of 3, 4, 5, 6, 7, 8, 9, 10, 11, 12, 13, 14, 15, 16, 17, 18, 19, 20, 21, 22, 23, 24 or 25, contiguous nucleotides, wherein in each of the plurality of oligonucleotide sequences B comprises a unique oligonucleotide sequence that uniquely identifies, as a paired combination, (i) the unique V oligonucleotide sequence of (a) and (ii) the unique J oligonucleotide sequence of (b); (f) R is either nothing or comprises a restriction enzyme recognition site that comprises an oligonucleotide sequence that is absent from (a)-(e), and wherein: (g) at least one of: (i) the plurality of template oligonucleotides comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51-100, 101-200, 201-300, 301-400, 401-500, 501-600, 601-700, 701-800, 801-900, 901-1000, 1001-1100, 1101-1200, 1201-1300, 1301-1400, 1401-1500, 1501-1600, 1601-1700, 1701-2000, or 2001-2500 unique oligonucleotide sequences, (ii) the plurality of template oligonucleotides comprises at least one template oligonucleotide having an oligonucleotide sequence of general formula (I) to which each V-segment oligonucleotide primer can specifically hybridize and at least one template oligonucleotide having an oligonucleotide sequence of general formula (I) to which each J-segment oligonucleotide primer can specifically hybridize, or (iii) the plurality of template oligonucleotides comprises at least a or at least b unique oligonucleotide sequences, whichever is larger, where a is the number of unique adaptive immune receptor V region-encoding gene segments in the subject and b is the number of unique adaptive immune receptor J region-encoding gene segments in the subject, and the composition comprises at least one template oligonucleotide for each unique V polynucleotide and at least one template oligonucleotide for each unique J polynucleotide; said method further comprising quantifying rearranged DNA molecules encoding one or a plurality of adaptive immune receptors in the DNA extracted from the biological sample by the steps of: (1) quantitatively sequencing all or a sufficient portion of each of said amplified template DNA molecules and each of said amplified rearranged DNA molecules to quantify (a) a template product number of amplified template DNA molecules which contain at least one oligonucleotide barcode sequence, and (b) a rearranged product number of amplified rearranged DNA molecules which lack an oligonucleotide barcode sequence; (2) calculating an amplification factor by dividing the template product number of (1)(a) by the known number of each of the plurality of template oligonucleotides having a unique oligonucleotide sequence; and (3) dividing the rearranged product number of (1)(b) by the amplification factor calculated in (2) to quantify unique adaptive immune receptor encoding DNA molecules in the sample.

In certain further embodiments, in the template composition for amplification factor determination, all template oligonucleotides in the plurality of template oligonucleotides are of substantially identical length. In certain embodiments each primer in the oligonucleotide amplification primer set is capable of specifically hybridizing to at least one template oligonucleotide in the plurality of oligonucleotides of the template composition. In certain embodiments each template oligonucleotide in the plurality of template oligonucleotides further comprises a stop codon between V and B2. In certain embodiments, in the template composition for amplification factor determination, each template oligonucleotide in the plurality of template oligonucleotides is present in a substantially equimolar amount. In certain embodiments the adaptive immune receptor is selected from TCRB, TCRG, TCRA, TCRD, IGH, IGK, and IGL, wherein (i) the V polynucleotide of (a) encodes, respectively, a TCRB, TCRG, TCRA, TCRD, IGH, IGK, or IGL receptor V-region polypeptide, and (ii) the J polynucleotide of (b) encodes, respectively, a TCRB, TCRG, TCRA, TCRD, IGH, IGK, or IGL receptor J-region polypeptide.

In certain embodiments the oligonucleotide amplification primer set is capable of amplifying productively rearranged DNA encoding one or a plurality of adaptive immune receptors, wherein in said step (A) of amplifying, the oligonucleotide amplification primer set does not include any oligonucleotide primers that specifically hybridize to a V-region pseudogene or orphon or to a J-region pseudogene or orphon. In certain embodiments the plurality of template oligonucleotides have a plurality of sequences of general formula (I) that is selected from: (1) the plurality of oligonucleotide sequences of general formula (I) in which polynucleotides V and J have the TCRB V and J sequences set forth in at least one set of 68 TCRB V and J SEQ ID NOS, respectively, as set forth in FIG. 9 as TCRB V/J set 1, TCRB V/J set 2, TCRB V/J set 3, TCRB V/J set 4, TCRB V/J set 5, TCRB V/J set 6, TCRB V/J set 7, TCRB V/J set 8, TCRB V/J set 9, TCRB V/J set 10, TCRB V/J set 11, TCRB V/J set 12 and TCRB V/J set 13; (2) the plurality of oligonucleotide sequences of general formula (I) in which polynucleotides V and J have the TCRG V and J sequences set forth in at least one set of 14 TCRG V and J SEQ ID NOS, respectively, as set forth in FIG. 10 as TCRG V/J set 1, TCRG V/J set 2, TCRG V/J set 3, TCRG V/J set 4 and TCRG V/J set 5; (3) the plurality of oligonucleotide sequences of general formula (I) in which polynucleotides V and J have the IGH V and J sequences set forth in at least one set of 127 IGH V and J SEQ ID NOS, respectively, as set forth in FIG. 11 as IGH V/J set 1, IGH V/J set 2, IGH V/J set 3, IGH V/J set 4, IGH V/J set 5, IGH V/J set 6, IGH V/J set 7, IGH V/J set 8 and IGH V/J set 9; (4) the plurality of oligonucleotide sequences of general formula (I) as set forth in SEQ ID NOS:3157-4014; (5) the plurality of oligonucleotide sequences of general formula (I) as set forth in SEQ ID NOS:4015-4084; and (6) the plurality of oligonucleotide sequences of general formula (I) as set forth in SEQ ID NOS:4085-5200.

In certain embodiments of the above described methods, the plurality of V-segment and J-segment oligonucleotide primers is capable of amplifying productively rearranged DNA encoding one or a plurality of adaptive immune receptors, and in said step (a) of amplifying, the V-segment and J-segment oligonucleotide primers do not include any oligonucleotide primers that specifically hybridize to a V-region pseudogene or orphon or to a J-region pseudogene or orphon.

Accordingly in certain embodiments of certain of the above described methods, the method further comprises quantifying rearranged DNA molecules encoding one or a plurality of adaptive immune receptors in DNA extracted from each biological sample that comprises DNA from lymphoid cells of the subject, each adaptive immune receptor comprising a variable region and a joining region, said step of quantifying comprising: (A) amplifying DNA in a multiplex polymerase chain reaction (PCR) that comprises: (1) DNA from the biological sample that comprises lymphoid cells of the subject, (2) an oligonucleotide amplification primer set that is capable of amplifying rearranged DNA encoding one or a plurality of adaptive immune receptors in the DNA from the biological sample, the primer set comprising: (a) in substantially equimolar amounts, a plurality of V-segment oligonucleotide primers that are each independently capable of specifically hybridizing to at least one polynucleotide encoding an adaptive immune receptor V-region polypeptide or to the complement thereof, wherein each V-segment primer comprises a nucleotide sequence of at least 15 contiguous nucleotides that is complementary to at least one functional adaptive immune receptor V region-encoding gene segment and wherein the plurality of V-segment primers specifically hybridize to substantially all functional adaptive immune receptor V region-encoding gene segments that are present in the template composition, and (b) in substantially equimolar amounts, a plurality of J-segment oligonucleotide primers that are each independently capable of specifically hybridizing to at least one polynucleotide encoding an adaptive immune receptor J-region polypeptide or to the complement thereof, wherein each J-segment primer comprises a nucleotide sequence of at least 15 contiguous nucleotides that is complementary to at least one functional adaptive immune receptor J region-encoding gene segment and wherein the plurality of J-segment primers specifically hybridize to substantially all functional adaptive immune receptor J region-encoding gene segments that are present in the template composition, wherein the V-segment and J-segment oligonucleotide primers are capable of promoting amplification in said multiplex polymerase chain reaction (PCR) of (i) substantially all template oligonucleotides in the template composition to produce a multiplicity of amplified template DNA molecules, said multiplicity of amplified template DNA molecules being sufficient to quantify diversity of the template oligonucleotides in the template composition, and (ii) substantially all rearranged DNA molecules encoding adaptive immune receptors in the biological sample to produce a multiplicity of amplified rearranged DNA molecules, said multiplicity of amplified rearranged DNA molecules being sufficient to quantify diversity of the rearranged DNA molecules in the DNA from the biological sample, and wherein each amplified DNA molecule in the multiplicity of amplified template DNA molecules and in the multiplicity of amplified rearranged DNA molecules is less than 1000, 900, 800, 700, 600, 500, 400, 300, 200, 100, 90, 80 or 70 nucleotides in length, and (3) a template composition for amplification factor determination in which a known number of each of a plurality of template oligonucleotides having a unique oligonucleotide sequence is present, the template composition comprising: a plurality of template oligonucleotides having a plurality of oligonucleotide sequences of general formula: 5'-U1-B1-V-B2-R-B3-J-B4-U2-3' [I] wherein: (a) V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of oligonucleotide sequences V comprises a unique oligonucleotide sequence; (b) J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of oligonucleotide sequences J comprises a unique oligonucleotide sequence; (c) U1 is either nothing or comprises an oligonucleotide having a sequence that is selected from (i) a first universal adaptor oligonucleotide sequence, and (ii) a first sequencing platform-specific oligonucleotide sequence that is linked to and positioned 5' to a first universal adaptor oligonucleotide sequence; (d) U2 is either nothing or comprises an oligonucleotide having a sequence that is selected from (i) a second universal adaptor oligonucleotide sequence, and (ii) a second sequencing platform-specific oligonucleotide sequence that is linked to and positioned 5' to a second universal adaptor oligonucleotide sequence; (e) B1, B2, B3, and B4 are each independently either nothing or each comprises an oligonucleotide B that comprises an oligonucleotide barcode sequence of 3, 4, 5, 6, 7, 8, 9, 10, 11, 12, 13, 14, 15, 16, 17, 18, 19, 20, 21, 22, 23, 24 or 25, contiguous nucleotides, wherein in each of the plurality of oligonucleotide sequences B comprises a unique oligonucleotide sequence that uniquely identifies, as a paired combination, (i) the unique V oligonucleotide sequence of (a) and (ii) the unique J oligonucleotide sequence of (b); (f) R is either nothing or comprises a restriction enzyme recognition site that comprises an oligonucleotide sequence that is absent from (a)-(e), and wherein: (g) at least one of: (i) the plurality of template oligonucleotides comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51-100, 101-200, 201-300, 301-400, 401-500, 501-600, 601-700, 701-800, 801-900, 901-1000, 1001-1100, 1101-1200, 1201-1300, 1301-1400, 1401-1500, 1501-1600, 1601-1700, 1701-2000, or 2001-2500 unique oligonucleotide sequences, (ii) the plurality of template oligonucleotides comprises at least one template oligonucleotide having an oligonucleotide sequence of general formula (I) to which each V-segment oligonucleotide primer can specifically hybridize and at least one template oligonucleotide having an oligonucleotide sequence of general formula (I) to which each J-segment oligonucleotide primer can specifically hybridize, or (iii) the plurality of template oligonucleotides comprises at least a or at least b unique oligonucleotide sequences, whichever is larger, where a is the number of unique adaptive immune receptor V region-encoding gene segments in the subject and b is the number of unique adaptive immune receptor J region-encoding gene segments in the subject, and the composition comprises at least one template oligonucleotide for each unique V polynucleotide and at least one template oligonucleotide for each unique J polynucleotide; (B) quantitatively sequencing all or a sufficient portion of each of said amplified template DNA molecules and each of said amplified rearranged DNA molecules to quantify (i) a template product number of amplified template DNA molecules which contain at least one oligonucleotide barcode sequence, and (ii) a rearranged product number of amplified rearranged DNA molecules which lack an oligonucleotide barcode sequence; (C) calculating an amplification factor by dividing the template product number of (B)(i) by the known number of each of the plurality of template oligonucleotides having a unique oligonucleotide sequence of (A)(2); and (D) dividing the rearranged product number of (B)(ii) by the amplification factor calculated in (C) to quantify unique adaptive immune receptor encoding DNA molecules in the sample.

In certain further embodiments, in the template composition for amplification factor determination, all template oligonucleotides in the plurality of template oligonucleotides are of substantially identical length. In certain other further embodiments, each primer in the oligonucleotide amplification primer set is capable of specifically hybridizing to at least one template oligonucleotide in the plurality of oligonucleotides of the template composition. In certain other further embodiments, each template oligonucleotide in the plurality of template oligonucleotides further comprises a stop codon between V and B2. In certain other further embodiments, in the template composition for amplification factor determination, each template oligonucleotide in the plurality of template oligonucleotides is present in a substantially equimolar amount. In certain other further embodiments the adaptive immune receptor is selected from TCRB, TCRG, TCRA, TCRD, IGH, IGK, and IGL, wherein (i) the V polynucleotide of (a) encodes, respectively, a TCRB, TCRG, TCRA, TCRD, IGH, IGK, or IGL receptor V-region polypeptide, and (ii) the J polynucleotide of (b) encodes, respectively, a TCRB, TCRG, TCRA, TCRD, IGH, IGK, or IGL receptor J-region polypeptide. In certain other further embodiments the oligonucleotide amplification primer set is capable of amplifying productively rearranged DNA encoding one or a plurality of adaptive immune receptors, and wherein in said step (A) of amplifying, the oligonucleotide amplification primer set does not include any oligonucleotide primers that specifically hybridize to a V-region pseudogene or orphon or to a J-region pseudogene or orphon. In certain other further embodiments the plurality of template oligonucleotides have a plurality of sequences of general formula (I) that is selected from: (1) the plurality of oligonucleotide sequences of general formula (I) in which polynucleotides V and J have the TCRB V and J sequences set forth in at least one set of 68 TCRB V and J SEQ ID NOS, respectively, as set forth in FIG. 9 as TCRB V/J set 1, TCRB V/J set 2, TCRB V/J set 3, TCRB V/J set 4, TCRB V/J set 5, TCRB V/J set 6, TCRB V/J set 7, TCRB V/J set 8, TCRB V/J set 9, TCRB V/J set 10, TCRB V/J set 11, TCRB V/J set 12 and TCRB V/J set 13; (2) the plurality of oligonucleotide sequences of general formula (I) in which polynucleotides V and J have the TCRG V and J sequences set forth in at least one set of 14 TCRG V and J SEQ ID NOS, respectively, as set forth in FIG. 10 as TCRG V/J set 1, TCRG V/J set 2, TCRG V/J set 3, TCRG V/J set 4 and TCRG V/J set 5; (3) the plurality of oligonucleotide sequences of general formula (I) in which polynucleotides V and J have the IGH V and J sequences set forth in at least one set of 127 IGH V and J SEQ ID NOS, respectively, as set forth in FIG. 11 as IGH V/J set 1, IGH V/J set 2, IGH V/J set 3, IGH V/J set 4, IGH V/J set 5, IGH V/J set 6, IGH V/J set 7, IGH V/J set 8 and IGH V/J set 9; (4) the plurality of oligonucleotide sequences of general formula (I) as set forth in SEQ ID NOS:3157-4014; (5) the plurality of oligonucleotide sequences of general formula (I) as set forth in SEQ ID NOS:4015-4084; and (6) the plurality of oligonucleotide sequences of general formula (I) as set forth in SEQ ID NOS:4085-5200.

Turning to another embodiment there is provided a method comprising receiving a dataset comprising sequencing data for a plurality of amplicons obtained from a first sample comprising rearranged DNA sequences from a rearranged T cell receptor (TCR) complementarity determining region 3 (CDR3)-encoding region, the first sample obtained from a subject; determining from the dataset: a presence of at least one unique rearranged DNA sequence indicative of a clonal lymphoid hematological malignancy in the first sample, and a relative frequency of occurrence of the at least one unique rearranged DNA sequence in the first sample; and comparing the relative frequency of occurrence of the at least one unique rearranged DNA sequence in the first sample with a relative frequency of occurrence of the unique rearranged DNA sequence in a second sample, wherein a relative frequency of occurrence of the at least one unique rearranged DNA sequence of at least 1 in $10^5$ TCR CDR-3 encoding regions is diagnostic of minimal residual disease for lymphoid hematological malignancy in the subject.

In certain embodiments the first sample comprises T cells. In certain embodiments the second sample comprises T cells. In certain embodiments the first sample comprises a plurality of lymphoid hematopoietic cells obtained from the subject at a time following treatment for the lymphoid hematological malignancy. In certain embodiments the second sample comprises a plurality of lymphoid hematopoietic cells obtained from the subject at a time point prior to treatment. In certain embodiments the step of determining from the dataset a presence of at least one unique rearranged DNA sequence indicative of a clonal lymphoid hematological malignancy in the first sample comprises identifying a clonal sequence that has a relative frequency of at least 15% of rearranged TCRγ CDR3-encoding regions or rearranged TCRβ CDR3-encoding regions. In certain embodiments the dataset is obtained by amplifying by a multiplex polymerase chain reaction (PCR) a plurality of gene segments of a rearranged TCRγ CDR3-encoding region or a rearranged TCRβ CDR3-encoding region, each gene segment comprising a variable (V)-region and a joining (J)-region, using a plurality of V-segment oligonucleotide primers, each V-segment oligonucleotide primer capable of hybridizing to one or more TCR V-region polynucleotides of the gene segments; a plurality of J-segment oligonucleotide primers, each J-segment primer capable of hybridizing to one or more TCR J-region polynucleotides of the gene segments; wherein the plurality of V-segment oligonucleotide primers and J-segment oligonucleotide primers promote amplification of the TCRγ CDR3-encoding regions or the TCRβ CDR3-encoding regions in the first sample to produce a plurality of amplicons; and sequencing the plurality of amplicons to determine a nucleotide sequence for each of the plurality of amplicons.

In a further embodiment the TCR V-region polynucleotide encodes a TCR Vγ polypeptide or a TCR Vβ polypeptide. In another further embodiment the TCR J-region polynucleotide encodes a TCR Jγ polynucleotide or a TCR Jβ polypeptide. In another further embodiment each of the plurality of V-segment oligonucleotide primers comprises a nucleotide sequence of at least 15 contiguous nucleotides. In certain embodiments the nucleotide sequence is complementary to a functional TCR Vγ encoding gene segment or a functional TCR Vβ encoding gene segment. In certain embodiments the functional TCR Vγ encoding gene segment or the functional TCR Vβ encoding gene segment comprises a V gene recombination signal sequence (RSS). In certain embodiments each of the plurality of J-segment oligonucleotide primers comprises a nucleotide sequence of at least 15 contiguous nucleotides. In certain embodiments the nucleotide sequence is complementary to a functional TCR Jγ encoding gene segment or a functional TCR Jβ encoding gene segment. In certain further embodiments the functional TCR Jγ encoding gene segment or the functional TCR Jβ encoding gene segment comprises a J gene RSS.

According to certain embodiments the plurality of V-segment oligonucleotide primers are complementary to at least 10, 20, 30, or 40 contiguous nucleotides of a TCR V-encoding gene segment. In a further embodiment the at least 10, 20, 30, or 40 contiguous nucleotides are situated 5' to a V gene RSS. In certain other embodiments the plurality of J-segment oligonucleotide primers are complementary to at least 10, 20, or 30 contiguous nucleotides of a TCR J-encoding gene segment. In certain further embodiments the at least 10, 20, or 30 contiguous nucleotides of a TCR J-encoding gene segment are situated 3' to the J gene RSS.

In another embodiment the step of amplifying comprises amplifying substantially all of the gene segments comprising rearranged TCRγ CDR3-encoding regions or rearranged TCRβ CDR3-encoding regions in the first sample. In another embodiment the plurality of V-segment oligonucleotide primers hybridize to substantially all functional TCR Vγ encoding gene segments or TCR Vβ encoding gene segments in the first sample. In another embodiment the plurality of J-segment oligonucleotide primers hybridize to substantially all functional TCR Jγ encoding gene segments or TCR Jβ encoding gene segments in the first sample. In another embodiment the plurality of amplicons is sufficient to quantify diversity of the TCRγ CDR3-encoding regions or TCRβ CDR3-encoding region in the first sample. In another embodiment each sequenced amplicon is less than 600 nucleotides in length. In another embodiment the plurality of V-segment oligonucleotide primers and the plurality of J-segment oligonucleotide primers are selected from: (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351.

In another embodiment one or more of the V-segment oligonucleotide primers comprise a nucleotide sequence comprising at least 90% sequence identity to the nucleotide sequence of SEQ ID NOs:5579-5630, 5644-5779, 5799-5816, 6124-6127, or 6222-6273. In another embodiment one or more of the J-segment oligonucleotide primers comprise a nucleotide sequence comprising at least 90% sequence identity to the nucleotide sequence of SEQ ID NOs:5631-5643, 5780-5798, 6212-6215, or 6274-6286. In another embodiment one or more of the V-segment oligonucleotide primers comprise a nucleotide sequence comprising at least 90% sequence identity to the nucleotide sequence of SEQ ID NOs:5579-5630, 5644-5779, 5799-5816, 6124-6127, or 6222-6273 and wherein one or more of the J-segment oligonucleotide primers comprise a nucleotide sequence comprising at least 90% sequence identity to the nucleotide sequence of SEQ ID NOs:5631-5643, 5780-5798, 6212-6215, or 6274-6286.

In another embodiment there is provided a method comprising: receiving a dataset comprising sequencing data for a plurality of amplicons obtained from a first sample comprising rearranged DNA sequences of a rearranged T cell receptor (TCR) complementarity determining region 3 (CDR3)-encoding region, the first sample obtained from a subject; determining from the dataset a relative frequency of occurrence of each unique sequenced amplicon; and determining whether the subject has a clonal lymphoid hematological malignancy based on a presence or an absence of at least one unique rearranged DNA sequence having a relative frequency of occurrence that exceeds 15% of rearranged TCR CDR3-encoding regions in the first sample, wherein a relative frequency of occurrence of the at least one unique rearranged DNA sequence that exceeds 15% is diagnostic for a clonal lymphoid hematological malignancy in the subject. In a further embodiment the relative frequency of occurrence of the at least one unique rearranged gene sequence is at least 16%, 17%, 18%, 19%, 20%, 21%, 22%, 23%, 24%, 25%, 26%, 27%, 28%, 29% or 30% of TCRγ CDR3-encoding regions or rearranged TCRβ CDR3-encoding regions in the sample. In another embodiment the method further comprises determining an absence from the sample of at least one unique rearranged DNA sequence that has a relative frequency of at least 15% of rearranged TCRγ CDR3-encoding regions or rearranged TCRβ CDR3-encoding regions. In certain embodiments the step of determining indicates that the subject should be evaluated for an early thymic-precursor immunophenotype.

In certain embodiments the dataset is obtained by amplifying by a multiplex polymerase chain reaction (PCR) a plurality of gene segments of a rearranged TCRγ CDR3-encoding region or a rearranged TCRβ CDR3-encoding region, each gene segment comprising a variable (V)-region and a joining (J)-region, using: a plurality of V-segment oligonucleotide primers, each V-segment oligonucleotide primer capable of hybridizing to one or more TCR V-region polynucleotides of the gene segments; a plurality of J-segment oligonucleotide primers, each J-segment primer capable of hybridizing to one or more TCR J-region polynucleotides of the gene segments; wherein the plurality of V-segment oligonucleotide primers and J-segment oligonucleotide primers promote amplification of the rearranged TCRγ CDR3-encoding regions or the rearranged TCRβ CDR3-encoding regions in the sample to produce a plurality of amplicons; and sequencing the plurality of amplicons to determine a nucleotide sequence for each of the plurality of amplicons. In certain further embodiments the plurality of V-segment oligonucleotide primers and the plurality of J-segment oligonucleotide primers are selected from: (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351. In certain other further embodiments, one or more of the V-segment oligonucleotide primers comprise a nucleotide sequence comprising at least 90% sequence identity to the nucleotide sequence of SEQ ID NOs:5579-5630, 5644-5779, 5799-5816, 6124-6127, or 6222-6273.

According to a related embodiment, one or more of the J-segment oligonucleotide primers comprise a nucleotide sequence comprising at least 90% sequence identity to the nucleotide sequence of SEQ ID NOs:5631-5643, 5780-5798, 6212-6215, or 6274-6286. In another embodiment one or more of the V-segment oligonucleotide primers comprise a nucleotide sequence comprising at least 90% sequence identity to the nucleotide sequence of SEQ ID NOs:5579-5630, 5644-5779, 5799-5816, 6124-6127, or 6222-6273 and wherein one or more of the J-segment oligonucleotide primers comprise a nucleotide sequence comprising at least 90% sequence identity to the nucleotide sequence of SEQ ID NOs:5631-5643, 5780-5798, 6212-6215, or 6274-6286.

According to another embodiment there is provided a method comprising receiving a dataset comprising sequencing data for a plurality of amplicons obtained from a first sample comprising rearranged DNA sequences of a rearranged T cell receptor (TCR) complementarity determining region 3 (CDR3)-encoding region or an immunoglobulin (Ig) CDR3-encoding region, the first sample obtained from a subject; determining from the dataset: a presence of at least one unique rearranged DNA sequence indicative of a clonal lymphoid hematological malignancy in the first sample, and a relative frequency of occurrence of the at least one unique rearranged DNA sequence in the first sample; determining whether the subject has minimal residual disease by comparing the relative frequency of occurrence of the at least one unique rearranged DNA sequence in the sample with a relative frequency of occurrence of the unique rearranged DNA sequence in a second sample, wherein a relative frequency of occurrence of at least 1 in $10^5$ TCR CDR-3 or Ig CDR-3 encoding regions in the first sample is diagnostic of minimal residual disease for lymphoid hematological malignancy. In a further embodiment the dataset is obtained by amplifying by a multiplex polymerase chain reaction (PCR) a plurality of gene segments of rearranged T cell receptor (TCR) complementarity determining region 3 (CDR3)-encoding regions or Immunoglobulin (Ig) CDR3-encoding regions, each gene segment comprising a variable (V)-region and a joining (J)-region, using: a plurality of V-segment oligonucleotide primers, each V-segment oligonucleotide primer capable of hybridizing to one or more TCR V-region polynucleotides or one or more Ig V-region polynucleotides; a plurality of J-segment oligonucleotide primers, each J-segment primer capable of hybridizing to one or more TCR J-region polynucleotides or one or more Ig J-region polynucleotides of the gene segments; wherein the plurality of V-segment oligonucleotide primers and J-segment oligonucleotide primers promote amplification of the TCR CDR3-encoding regions or the Ig CDR3-encoding regions in the first sample to produce a plurality of amplicons; and sequencing the plurality of amplicons to determine a nucleotide sequence for each of the plurality of amplicons.

In one embodiment the TCR V-region polynucleotide encodes a TCR V-region polypeptide or an Ig V-region polypeptide. In one embodiment the TCR J-region polynucleotide encodes a TCR J-region polynucleotide or a Ig J-region polypeptide. In another embodiment the plurality of V-segment oligonucleotide primers and the plurality of J-segment oligonucleotide primers are selected from: (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351. In another embodiment one or more of the V-segment oligonucleotide primers comprise a nucleotide sequence comprising at least 90% sequence identity to the nucleotide sequence of SEQ ID NOs:5579-5630, 5644-5779, 5799-5816, 6124-6127, or 6222-6273. In another embodiment one or more of the J-segment oligonucleotide primers comprise a nucleotide sequence comprising at least 90% sequence identity to the nucleotide sequence of SEQ ID NOs:5631-5643, 5780-5798, 6212-6215, or 6274-6286. In another embodiment one or more of the V-segment oligonucleotide primers comprise a nucleotide sequence comprising at least 90% sequence identity to the nucleotide sequence of SEQ ID NOs:5579-5630, 5644-5779, 5799-5816, 6124-6127, or 6222-6273 and wherein one or more of the J-segment oligonucleotide primers comprise a nucleotide sequence comprising at least 90% sequence identity to the nucleotide sequence of SEQ ID NOs:5631-5643, 5780-5798, 6212-6215, or 6274-6286.

According to certain further embodiments of the above described methods, the lymphoid hematological malignancy is selected from: acute T-cell lymphoblastic leukemia (T-ALL), acute B-cell lymphoblastic leukemia (B-ALL), multiple myeloma, plasmacytoma, macroglobulinemia, chronic lymphocytic leukemia (CLL), acute lymphoblastic leukemia (ALL), multiple myeloma, plasmacytoma, macroglobulinemia, chronic lymphocytic leukemia (CLL), Hodgkins lymphoma, non-Hodgkins lymphoma, cutaneous T-cell lymphoma, mantle cell lymphoma, peripheral T-cell lymphoma, hairy cell leukemia, T prolymphocytic lymphoma, angioimmunoblastic T-cell lymphoma, T lymphoblastic leukemia/lymphoma, peripheral T-cell lymphoma, adult T cell leukemia/lymphoma, mycosis fungoides, Sezary syndrome, T lymphoblastic leukemia, myeloproliferative neoplasm, and myelodysplastic syndrome.

In certain embodiments of the above described methods, the method further comprises: receiving a second dataset comprising sequencing data for standardizing amplification efficiencies of a plurality of primer sets, the second data set comprising sequencing data for a plurality of template amplicons. In certain further embodiments the second dataset is obtained by amplifying by multiplex PCR a plurality of unique template oligonucleotides to produce a plurality of unique template amplicons, each unique template oligonucleotide having a known concentration of molecules and a unique barcode sequence, and the plurality of primer sets comprising a plurality of V-segment oligonucleotide primers and a plurality of J-segment oligonucleotide primers; and quantitatively sequencing the plurality of unique template amplicons. In one embodiment the method further comprises adjusting the concentration of one or more V-segment oligonucleotide primers and one or more J-segment oligonucleotide primers to reduce biased amplification of TCR or Ig encoding gene segments in the first sample. In certain embodiments, amplifying by multiplex PCR of a plurality of unique template oligonucleotides comprises using equimolar concentrations of V-segment oligonucleotide primers and J-segment oligonucleotide primers. In certain embodiments the plurality of V-segment oligonucleotide primers and the plurality of J-segment oligonucleotide primers are selected from: (1) the sequences set forth in SEQ ID NOs:5579-5643, (2) the sequences set forth in SEQ ID NOs:5644-5792, (3) the sequences set forth in SEQ ID NOs:5793-5816, (4) the sequences set forth in SEQ ID NOs:5817-6123, (5) the sequences set forth in SEQ ID NOs:6124-6127 and 6212-6215, (6) the sequences set forth in SEQ ID NOs:6128-6211 and 6216-6221, (7) the sequences set forth in SEQ ID NOs:6222-6286, and (8) the sequences set forth in SEQ ID NOs:6222-6351.

In another embodiment the above described method further comprises: quantifying based on the first dataset and the second dataset: (a) a template product number of template amplicons that contain at least one oligonucleotide barcode sequence, and (b) a rearranged product number of sequenced amplicons that lack an oligonucleotide barcode sequence; calculating an amplification factor by dividing the template product number by the known number of each of the plurality of unique template oligonucleotides; and determining a number of unique rearranged TCR or Ig encoding sequences in the first sample by dividing the rearranged product number by the amplification factor. In one embodiment the method further comprises determining the number of unique T cell genomes or B cell genomes in the first sample.

According to certain related embodiments the plurality of unique template oligonucleotides comprise a general formula: 5'-U1-B1-V-B2-R-B3-J-B4-U2-3' (Formula I), wherein V comprises a polynucleotide comprising at least 20, 30, 60, 90, 120, 150, 180, or 210, and not more than 1000, 900, 800, 700, 600 or 500 contiguous nucleotides of a V-region encoding gene sequence, or a complement thereof, and wherein V comprises a unique oligonucleotide sequence, wherein J is a polynucleotide comprising at least 15-30, 31-60, 61-90, 91-120, or 120-150, and not more than 600, 500, 400, 300 or 200 contiguous nucleotides of a J-region encoding gene sequence, or a complement thereof, and wherein J comprises a unique oligonucleotide sequence, wherein U1 is either nothing or comprises an oligonucleotide having a sequence that is selected from (i) a first universal adaptor oligonucleotide sequence, and (ii) a first sequencing platform-specific oligonucleotide sequence that is linked to and positioned 5' to a first universal adaptor oligonucleotide sequence, wherein U2 is either nothing or comprises an oligonucleotide having a sequence that is selected from (i) a second universal adaptor oligonucleotide sequence, and (ii) a second sequencing platform-specific oligonucleotide sequence that is linked to and positioned 5' to a second universal adaptor oligonucleotide sequence, wherein B1, B2, B3, and B4 are each independently nothing or each comprises an oligonucleotide B that comprises an oligonucleotide barcode sequence of 3-25 contiguous nucleotides, wherein in each of the plurality of oligonucleotide sequences B comprises a unique oligonucleotide sequence that uniquely identifies, as a paired combination, a unique V oligonucleotide sequence and a unique J oligonucleotide sequence, and wherein R is either nothing or comprises a restriction enzyme recognition site that comprises an oligonucleotide sequence not found in the template oligonucleotide.

These and other aspects of the herein described invention embodiments will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE SEVERAL VIEWS OF THE DRAWINGS

FIG. 1A shows T-cell clonality as detected at day 0 using multi-parametric flow cytometry (mpFC) and high-throughput sequencing (HTS) of amplified and rearranged TCRβ CDR3-encoding DNA regions. Samples with a clonal population were identified by TCRB sequencing. Data are plotted as frequency of the clonal sequence in the total T cell population. FIG. 1B shows minimal residual disease (MRD) detection at day 29 in samples from patients that exhibited an identifiable clonal TCRβ rearrangement at day 0.

FIG. 4 (FIG. 4A-4B) shows clonal TCRB gene sequences characterized in Day 0 (pre-treatment) samples by high-throughput sequencing (HTS) of amplified and rearranged TCRβ CDR3-encoding DNA regions. TCRB (TCRβ) CDR3 sequences are shown for typical T-ALL cases. 31 of 43 (72.1%) pre-treatment samples had a detectable clonal TCRB sequence; at least 27 also had a clonal TCRG (TCRγ)

sequence. Shown are TCRB CDR3 sequences with nucleotide insertions (single underline) and D gene (double underline) regions highlighted.

Figure 5:
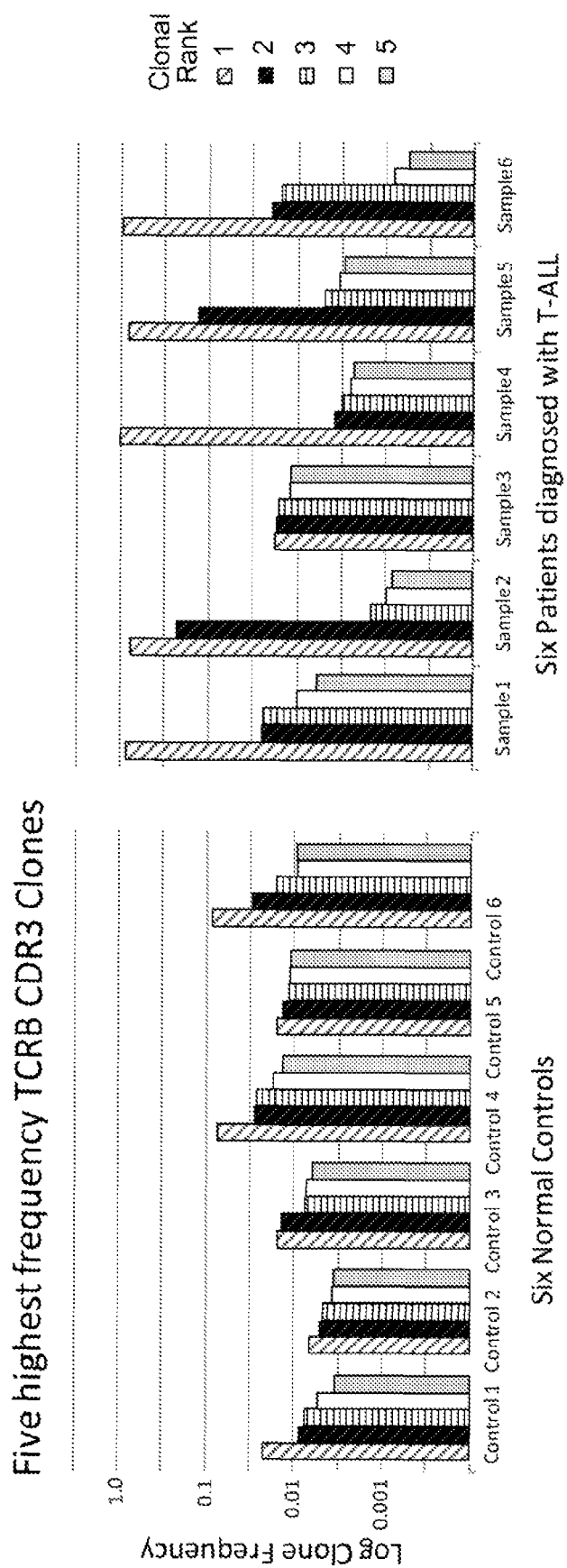

FIG. 5 shows a comparison of the normal and T-ALL clonal TCRB repertoires by the relative frequency of occurrence of the five highest frequency TCRB clones based on TCRB sequences identified by HTS in blood samples from six normal healthy control subjects (left) and six diagnosed T-ALL cases (right).

Figure 6:
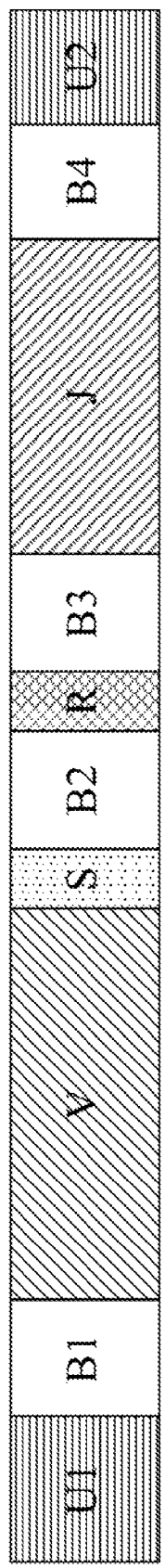

FIG. 6 shows a schematic diagram of an exemplary synthetic template oligonucleotide for use in determining an amplification factor for estimating the number of rearranged adaptive immune receptor (TCR or BCR) encoding sequences in a sample. U1, U2, universal adaptor oligonucleotides; B1-4, barcode oligonucleotides; V, variable region oligonucleotide; J, joining region oligonucleotide; R, restriction enzyme recognition site; S, optional stop codon.

Figure 7:
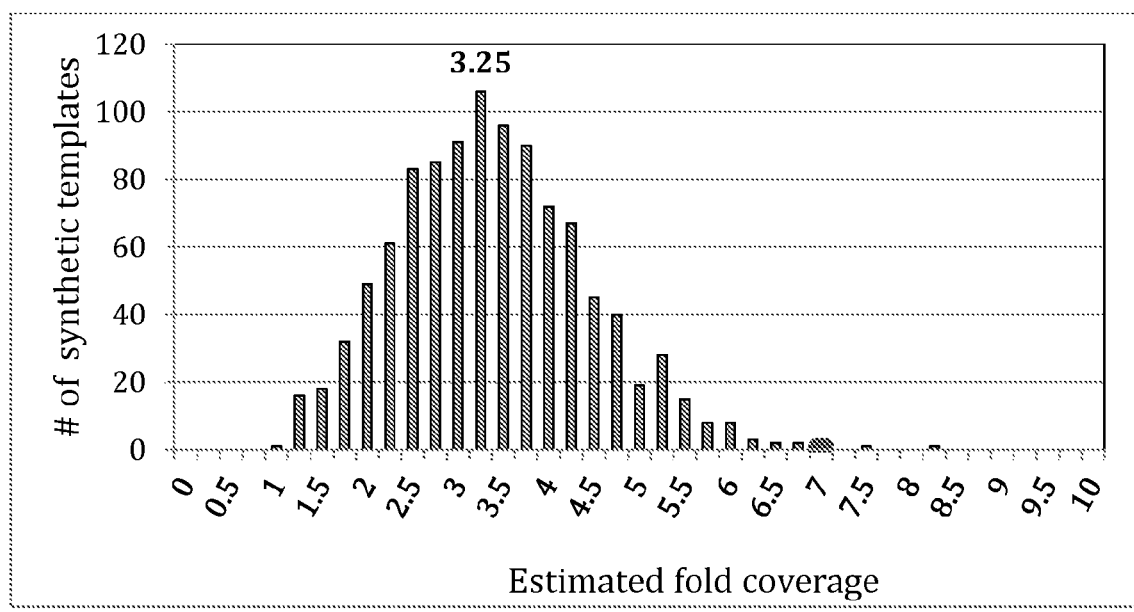

FIG. 7 shows the results of calculating an amplification factor for each VJ pair in a template composition that was added to a multiplexed PCR amplification of IGH sequences, and then averaging the amplification factor across all synthetic templates to estimate fold sequence coverage across all synthetic template molecules. Each bar represents the aggregate number of synthetic molecules with the same estimated fold sequence coverage. The median estimated fold sequence coverage was 3.25.

Figure 8:
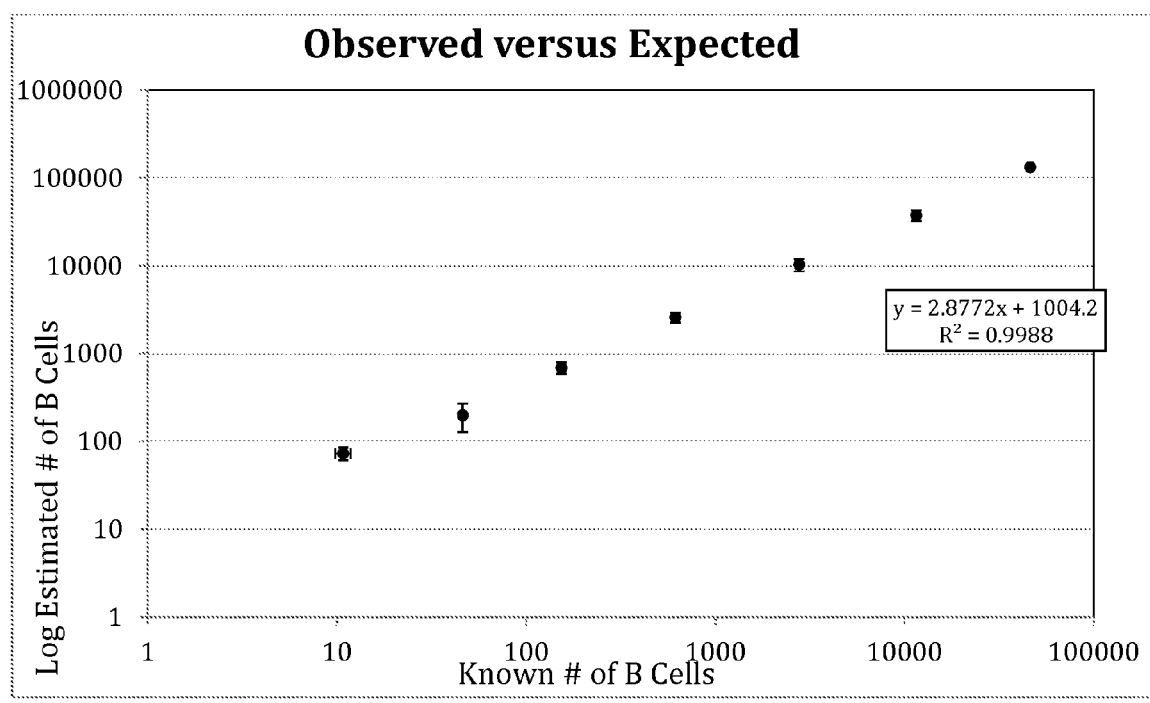

FIG. 8 shows a plot of the numbers of B cells that were estimated by multiplexed PCR using a synthetic template composition and an amplification factor calculated as described herein, versus the known numbers of B cells used as a source of natural DNA templates. Constant amounts of total DNA, of which a varied proportion was DNA from B cells, were added to multiplexed PCR reactions. In addition, approximately 5,000 synthetic template oligonucleotide molecules of general formula (I) (approximately 4-5 molecules of each sequence) were spiked into each reaction. The number of B cell genomes present in the DNA added to each PCR reaction, as estimated by the amplification of the synthetic template oligonucleotide molecules, is represented on the Y axis. On the X axis is shown the actual amount of DNA added to each PCR reaction. The correlation between actual and expected values was $r2=0.9988$.

FIG. 9 (FIG. 9A-9L) shows exemplary TCRB V/J sets (68 V+13 J) for use in template compositions that comprise a plurality of oligonucleotide sequences of general formula 5'-U1-B1-V-B2-R-B3-J-B4-U2-3' [I], for use in determining an amplification factor when amplifying rearranged DNA encoding one or a plurality of human T cell receptor β (TCRB) chain polypeptides.

FIG. 10 (FIG. 10A-10B) shows exemplary TCRG V/J sets (14 V+5 J) for use in template compositions that comprise a plurality of oligonucleotide sequences of general formula 5'-U1-B1-V-B2-R-B3-J-B4-U2-3' [I], for use in determining an amplification factor when amplifying rearranged DNA encoding one or a plurality of human T cell receptor γ (TCRG) chain polypeptides.

FIG. 11 (FIG. 11A-11M) shows exemplary IGH V/J sets (127 V+9 J) for use in template compositions that comprise a plurality of oligonucleotide sequences of general formula 5'-U1-B1-V-B2-R-B3-J-B4-U2-3' [I], for use in determining an amplification factor when amplifying rearranged DNA encoding one or a plurality of human immunoglobulin heavy (IGH) chain polypeptides.

Figure 12:
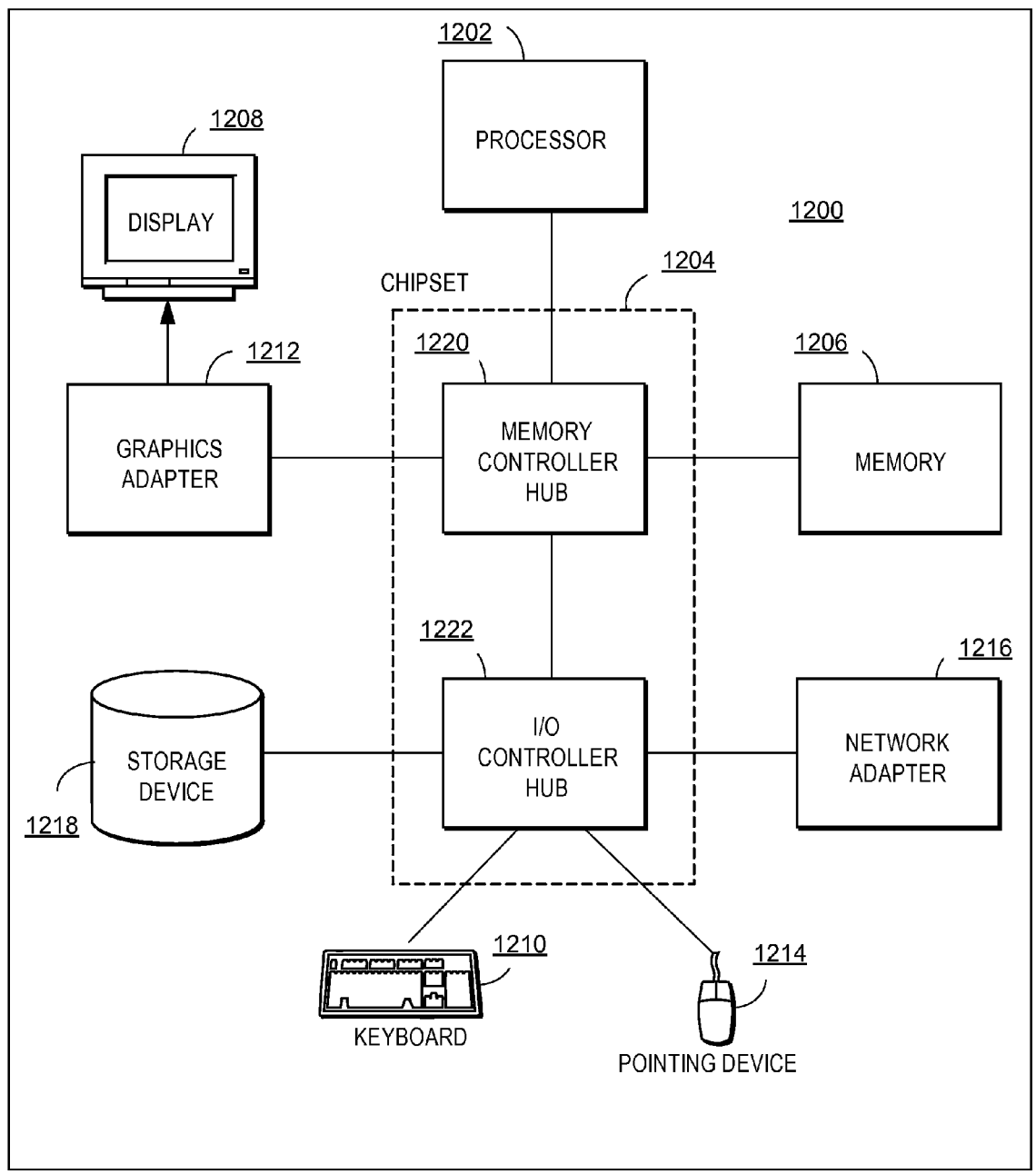

FIG. 12 is a high-level block diagram illustrating a functional view of a typical computer system for use in methods according to certain embodiments of the invention.

BRIEF DESCRIPTION OF THE SEQUENCES

SEQ ID NOS:1-871 are TCRB template oligonucleotide sequences of a template composition for amplification factor determination.

SEQ ID NOS:872-1560 are TCRB template oligonucleotide sequences of a template composition for amplification factor determination.

SEQ ID NOS:1561-1630 are TCRG template oligonucleotide sequences of a template composition for amplification factor determination.

SEQ ID NOS:1631-1695 are oligonucleotide primer sequences for TCRB amplification (TCRB-J, SEQ ID NOS: 1631-1643; TCRB-V, SEQ ID NOS:1644-1695).

SEQ ID NOS:1696-1709 are oligonucleotide primer sequences for DNA sequencing.

SEQ ID NOS:1710-1731 are oligonucleotide adaptor sequences.

SEQ ID NOS:1732-1745 are oligonucleotide primer sequences for TCRG amplification (TCRG-V, SEQ ID NOS: 1732-1741; TCRG-J, SEQ ID NOS:1742-1745).

SEQ ID NOS:1746-1747 are oligonucleotide adaptor sequences.

SEQ ID NO:1748 is an exemplary oligonucleotide barcode sequence.

SEQ ID NO:1749 is an exemplary V polynucleotide sequence.

SEQ ID NO:1750 is an exemplary J polynucleotide sequence.

SEQ ID NOS:1751-1752 are Illumina Nextera™ adaptor oligonucleotide sequences.

SEQ ID NOS:1753-1804 are oligonucleotide primer sequences for TCRB amplification.

SEQ ID NOS:1805-2920 are IGH template oligonucleotide sequences of a template composition for amplification factor determination.

SEQ ID NOS:2921-2988 are TCRB V polynucleotide sequences for use in a template composition for amplification factor determination.

SEQ ID NOS:2989-3001 are TCRB J polynucleotide sequences for use in a template composition for amplification factor determination.

SEQ ID NOS:3002-3015 are TCRG V polynucleotide sequences for use in a template composition for amplification factor determination.

SEQ ID NOS:3016-3020 are TCRG J polynucleotide sequences for use in a template composition for amplification factor determination.

SEQ ID NOS:3021-3147 are IGH V polynucleotide sequences for use in a template composition for amplification factor determination.

SEQ ID NOS:3148-3156 are IGH J polynucleotide sequences for use in a template composition for amplification factor determination.

SEQ ID NOS:3157-4014 are TCRB template oligonucleotide sequences of a template composition for amplification factor determination.

SEQ ID NOS:4015-4084 are TCRG template oligonucleotide sequences of a template composition for amplification factor determination.

SEQ ID NOS:4085-5200 are IGH template oligonucleotide sequences of a template composition for amplification factor determination.

SEQ ID NOS:5201-5286 are oligonucleotide forward primers for IGH amplification.

SEQ ID NOS:5287-5293 are oligonucleotide reverse primers for IGH amplification.

SEQ ID NOS:5294-5386 are oligonucleotide primer sequences for IGH amplification (IGH-V, SEQ ID NOS: 5294-5379; IGH-J, SEQ ID NOS:5380-5386).

SEQ ID NOS:5387-5578 are oligonucleotide sequences for adaptor tailing primers.

SEQ ID NOS:5579-6382 are oligonucleotide primer sequences for amplification of adaptive immune receptor encoding sequences.

SEQ ID NOS:6383-6388 are exemplary oligonucleotide primers for amplifying control ("housekeeping") gene sequences.

DETAILED DESCRIPTION

The present invention provides, in certain embodiments and as described herein, surprisingly advantageous methods for diagnosing diseases or disorders of lymphoid cells (e.g., T lymphocytes and/or B lymphocytes, including cells of any developmental, differentiative or maturational stage of the lymphoid lineage of hematopoietic cells) such as lymphoid hematological malignancies or other lymphoproliferative disorders, and for detecting minimal residual disease (MRD) in subjects following treatment for such conditions. These and related embodiments are directed in pertinent part to the use of recently developed high-throughput sequencing (HTS) methodologies for the qualitative and quantitative characterization of rearranged DNA sequences of genes that encode adaptive immune receptors such as T-cell receptors (TCR) or B-cell immunoglobulins (Ig).

Multiplexed amplification and high throughput sequencing of rearranged TCR and BCR (IG) encoding DNA sequences are described, for example, in Robins et al., 2009 *Blood* 114, 4099; Robins et al., 2010 *Sci. Translat. Med.* 2:47ra64; Robins et al., 2011 *J. Immunol. Meth. doi:* 10.1016/j.jim.2011.09. 001; Sherwood et al. 2011 *Sci. Translat. Med.* 3:90ra61; U.S. application Ser. No. 13/217, 126 (US Pub. No. 2012/0058902), U.S. application Ser. No. 12/794,507 (US Pub. No. 2010/0330571), WO/2010/ 151416, WO/2011/106738 (PCT/US2011/026373), WO2012/027503 (PCT/US2011/049012), U.S. Application No. 61/550,311, and U.S. Application No. 61/569,118; accordingly these disclosures are incorporated by reference and may be adapted for use according to the embodiments described herein.

Certain present embodiments may usefully benefit clinical management in lymphoid disorders such as lymphoid hematological malignancies or other lymphoproliferative disorders, for example, T-cell acute lymphoblastic leukemia/ lymphoma (T-ALL), by facilitating disease diagnosis and/or by permitting the assessment of minimal residual disease in patients following treatment. As described herein, high-throughput sequencing of T-cell receptor gene loci offers significant advantages over the prior state-of-the-art assessment of MRD by nine-color, multi-parametric flow cytometry (mpFC), including by providing easier standardization of test assay methodologies.

For instance, the present methods provide advantages in one or more of sensitivity, specificity, time, cost, reagent preparation, instrumentation set-up and calibration, overcoming unreliability of prior methods due to dependence on subjective operator manipulations, and other factors, when compared either to mpFC or to patient-specific molecular approaches for MRD testing. As described herein in the Examples, the present methods unexpectedly permitted MRD detection with comparable or greater sensitivity than mpFC, as well as surprising detection of MRD in patient samples for which mpFC failed to identify MRD. In addition, the present HTS methodologies identified T-ALL cases exhibiting early thymic precursor (ETP)-like properties. ETP/T-ALL cases described herein lacked a clonal TCRB gene rearrangement at diagnosis, as identified using the herein described methods. In view of the aggressive clinical course of ETP/T-ALL, improved disease management and other unprecedented advantages associated with early classification of ETP/T-ALL are thus provided by certain embodiments that are herein disclosed.

According to certain of the present embodiments, the ability to qualitatively (e.g., by identifying unique sequences of rearranged TCR or Ig CDR3-encoding gene regions in a sample) and quantitatively (e.g., by determining the relative frequency of occurrence of any given unique rearranged TCR or Ig CDR3-encoding DNA sequence as a proportion of the total number of TCR or Ig encoding sequences in the sample) characterize the diversity of adaptive immune receptors provides the means for diagnosing diseases of lymphoid cells (e.g., a lymphoid hematological malignancy), and also provides means for detecting the presence of minimal residual disease (MRD) in a subject during and following treatment.

Illustrative and non-limiting examples of diseases of lymphoid cells for which the presently disclosed invention embodiments may usefully aid in diagnosis and/or MRD detection include lymphoid hematological malignancies such as acute lymphoblastic leukemia (ALL), multiple myeloma, plasmacytoma, macroglobulinemia, chronic lymphocytic leukemia (CLL), other lymphomas and leukemias including Hodgkins and non-Hodgkins lymphoma, cutaneous T-cell lymphoma, mantle cell lymphoma, peripheral T-cell lymphoma, hairy cell leukemia, T prolymphocytic lymphoma, angioimmunoblastic T-cell lymphoma, T lymphoblastic leukemia/lymphoma, peripheral T-cell lymphoma—not otherwise specified, adult T cell leukemia/ lymphoma, mycosis fungoides, Sezary syndrome, T lymphoblastic leukemia and any other cancer involving T cells or B cells; and may also include other lymphoproliferative disorders, including myeloproliferative neoplasms, myelodysplastic syndrome, and others.

The detection of MRD can play a significant role not only in monitoring a patient's response to therapy, but also in the accurate diagnosis of the underlying cause of major clinical signs. MRD typically refers to the presence of malignant cells (usually in reference to leukemic cells) that are not detectable on the basis of cellular morphology. Several studies have shown that quantitative detection of MRD in lymphoid malignancies predicts clinical outcome. (Szczepanski T, et al., *Lancet Oncol* 2001; 2:409-17; van Dongen J J, et al., *Lancet* 1998; 352:1731-8; Bruggemann M, et al., *Acta Haematol* 2004; 112:111-9; Cave H, et al., *N Engl J Med* 1998; 339:591-8; Coustan-Smith E, et al., *Blood* 2000; 96:2691-6; Coustan-Smith E, et al., *Blood* 2002; 100:52-8; Wells D A, et al., *Am J Clin Pathol* 1998; 110:84-94; Radich J, et al., *Biol Blood Marrow Transplant* 1995; 1:24-31; Bahloul M, et al., *Best Pract Res Clin Haematol* 2005; 18:97-111; Hoshino A, et al., *Tohoku J Exp Med.* 2004; 203:155-64; Ciudad J, et al., *Br J Haematol* 1999; 104:695-705; Lucio P, et al., *Leukemia* 1999; 13:419-27.) Certain contemplated embodiments that relate to diagnosis, for example, may include detecting MRD in lymphomas by first performing high throughput sequencing (HTS) as described herein of DNA encoding one or more adaptive immune receptors (e.g., TCR or Ig) in a sample containing lymphoid cells obtained from lymph or lymph nodes, peripheral blood or other tissues, to identify one or more TCR or Ig clonal sequences, and may then further involve tracking the frequency of occurrence of such TCR or Ig clonal sequences in blood samples at one or more subsequent time points.

Monitoring the response of a cancer patient to a therapeutic treatment on the basis of tumor load quantification (e.g., by MRD detection) may assist in the assessment of a relative risk of relapse, and can also be used to identify patients who may benefit from therapy reduction, therapy intensification, reduction of immunosuppression for graft-versus-leukemia effect after a stem cell transplant, or adoptive T cell therapy. (Bradfield S M, et al., *Leukemia* 2004; 18:1156-8.) Minimal disease may also be encountered in diagnostic situations. For example, low levels of monoclonal B cells in patients presenting clinically with cytopenia may raise suspicions for a diagnosis of myelodysplastic syndrome. (Wells et al., *Blood* 2003; 102:394-403.) Minimal disease detection is also encountered in staging of lymphoma, which may involve the detection of low levels of tumor cells against a background of normal cells. The detection of minimal disease as described herein (e.g., as MRD detection in lymphoid cancer patients following treatment) need not be limited to monitoring the effects of treatment, but may also find uses in diagnostic settings where no reference population is available for comparison.

According to certain embodiments there is thus provided a method for detecting minimal residual disease which comprises amplifying DNA extracted from a first sample (e.g., bone marrow, lymph or blood, depending on the type of cancer) obtained from the patient in a multiplex polymerase chain reaction (PCR) using V and J segment primer sets as described herein and in one or more of Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. application Ser. No. 13/217, 126 (US Pub. No. 2012/0058902), U.S. application Ser. No. 12/794,507 (US Pub. No. 2010/0330571), WO/2010/151416, WO/2011/106738 (PCT/U52011/026373), WO2012/027503 (PCT/US2011/049012), U.S. Application No. 61/550,311, and U.S. Application No. 61/569,118, wherein the first sample is taken at a first time point before or during a therapeutic treatment, and wherein the first sample comprises a population of T or B cells, wherein the V-segment and J-segment primers permit amplification of substantially all combinations of the functional V and J segments of a rearranged TCR or Ig locus in the multiplex PCR to produce a multiplicity of amplified DNA molecules each comprising a TCR or Ig CDR3-encoding region; measuring a relative frequency of uniquely rearranged TCR CDR3-encoding regions, thereby identifying the uniquely rearranged TCR CDR3-encoding region of one or more malignant T cell clones; amplifying with the V-segment primers and the J-segment primers DNA extracted from a second sample from the patient, in a multiplex polymerase chain reaction (PCR), wherein the second sample is taken at a later time point than the first sample and wherein the second sample comprises a population of T or B cells, measuring the relative frequency of the uniquely rearranged TCR or Ig CDR3-encoding region of the one or more malignant T or B cell clones in the second sample; wherein the presence of the uniquely rearranged TCR or Ig CDR3-encoding region of the one or more malignant T or B cell clones in the second sample indicates the presence of minimal residual disease.

In certain embodiments, the presence of the uniquely rearranged CDR3-encoding region of the one or more malignant clones in the second sample at a relative frequency of greater than $10^{-6}$ TCR CDR3-encoding regions indicates the presence of minimal residual disease. In certain other embodiments the relative frequency may be greater than $9 \times 10^{-6}$, $8 \times 10^{-6}$, $7 \times 10^{-6}$, $6 \times 10^{-6}$, $5 \times 10^{-6}$, $4 \times 10^{-6}$, $3 \times 10^{-6}$, $2 \times 10^{-6}$, or $1 \times 10^{-6}$, $9 \times 10^{-4}$, $8 \times 10^{-4}$, $7 \times 10^{-4}$, $6 \times 10^{-4}$, $5 \times 10^{-4}$, $4 \times 10^{4}$, $3 \times 10^{-4}$, $2 \times 10^{4}$, or $1 \times 10^{-4}$.

The present methods may, additionally or alternatively, be used to diagnose a disorder affecting lymphoid cells such as a lymphoid hematological malignancy, for example a malignant disease associated with specific B or T cell clones, where at least one specific malignant clonotype can be identified in a patient. A clonotype may be detected by the presence in DNA extracted from a sample of at least one rearranged DNA molecule encoding a TCR or Ig CDR3 and having a unique DNA sequence, where the relative frequency of occurrence of the unique rearranged DNA sequence is determined by quantifying adaptive immune receptor diversity according to the methods described herein (including those incorporated by reference).

Preferably and in certain embodiments, detection of at least one unique rearranged CDR3-encoding DNA sequence having a relative frequency of at least 15% of the frequency of occurrence of all detectable rearranged CDR3-encoding sequences for a particular adaptive immune receptor polypeptide (e.g., TCRα, TCRβ, TCRγ, TCRδ, IgVH or IgVL) indicates presence of a malignancy-associated clonotype. In certain other embodiments, detection of at least one unique rearranged CDR3-encoding DNA sequence having a relative frequency of at least 16%, 17%, 18%, 19%, 20%, 21%, 22%, 23%, 24%, 25%, 26%, 27%, 28%, 29% or 30% of the frequency of occurrence of all detectable rearranged CDR3-encoding sequences for a particular adaptive immune receptor polypeptide, indicates presence of a malignancy-associated clonotype.

In certain other embodiments, a clonotype that is diagnostic for a clonal lymphoid hematological malignancy is identified by first determining a standard value $R_c$ (±standard deviation, SD) for the relative frequency of occurrence of the most abundant detectable unique rearranged CDR3-encoding sequence for a particular adaptive immune receptor polypeptide (e.g., TCRα, TCRβ, TCRγ, TCRδ, IgVH or IgVL) in a sample from one or more appropriately matched normal, healthy control subjects. Next, $R_x$ (±SD), the relative frequency of occurrence of detectable rearranged CDR3-encoding sequences for the particular adaptive immune receptor polypeptide in a sample from a subject known to have or suspected of having a lymphoid hematological malignancy, is determined. The sample may be obtained from the subject before, during or after treatment such as therapeutic treatment aimed at the lymphoid malignancy. A clonal lymphoid hematological malignancy may be regarded as being present, according to certain independent embodiments contemplated herein, when Rx is at least 2.5, 3.0, 3.25, 3.5, 3.75, 4.0, 4.25, 4.5, 4.75 or 5.0 standard deviations higher than Rc. For a sample obtained during or after treatment, Rx may thus be used as an indicator of MRD. Accordingly, a malignant clonotype may be identified in these and related embodiments by the presence, at a statistically significant relative level, of a clonotype in the population of uniquely rearranged CDR3-encoding regions that have been amplified and sequenced using the methods herein.

Certain presently disclosed embodiments advantageously permit determination of the number of adaptive immune cells (e.g., T or B lymphocytes) in a sample that contains lymphoid cells and that may also contain non-lymphoid cells, where DNA is extracted from the sample for use as a source of templates for multiplexed DNA amplification according to the present methods. In these and related embodiments, which are described in greater detail elsewhere herein, an artificial template composition for amplification factor determination is included in (or "spiked" in) the multiplexed amplification reaction. Quantitative sequencing of the amplification products of the template composition (which products are identifiable by virtue of unique oligonucleotide barcode sequences contained therein) permits calculation of an amplification factor that is a characteristic of the particular multiplexed amplification reaction (e.g., templates, amplification primers, reaction conditions, etc.) that has been performed. The amplification factor may then be used to calculate, from the quantitative sequencing data, the quantity of unique adaptive immune receptor encoding DNA molecules (e.g., lymphoid cell genomes that contain rearranged adaptive immune receptor encoding DNA) in the sample.

These and related embodiments thus further comprise quantifying rearranged DNA molecules encoding one or a plurality of adaptive immune receptors in DNA extracted from biological samples that comprise DNA from lymphoid cells of a subject as provided herein, by performing the steps of amplifying in the presence of a known quantity of the template composition for amplification factor determination; quantitatively sequencing amplification products of rearranged adaptive immune receptor encoding DNA in the sample and of the template composition; calculating an amplification factor; and dividing the number of amplified rearranged products of the rearranged adaptive immune receptor encoding DNA by the amplification factor to quantify the unique adaptive immune receptor encoding DNA molecules that are present in the sample.

Samples and Subjects

The subject or biological source, from which a test biological sample may be obtained, may be a human or non-human animal, or a transgenic or cloned or tissue-engineered (including through the use of stem cells) organism. In certain preferred embodiments of the invention, the subject or biological source may be known to have, or may be suspected of having or being at risk for having, a lymphoid hematopoietic cancer or other malignant condition, or an autoimmune disease, or an inflammatory condition, and in certain preferred embodiments of the invention the subject or biological source may be known to be free of a risk or presence of such disease.

Certain preferred embodiments contemplate a subject or biological source that is a human subject such as a patient that has been diagnosed as having or being at risk for developing or acquiring cancer according to art-accepted clinical diagnostic criteria, such as those of the U.S. National Cancer Institute (Bethesda, MD., USA) or as described in *DeVita, Hellman, and Rosenberg's Cancer: Principles and Practice of Oncology* (2008, Lippincott, Williams and Wilkins, Philadelphia/Ovid, N.Y.); Pizzo and Poplack, *Principles and Practice of Pediatric Oncology* (Fourth edition, 2001, Lippincott, Williams and Wilkins, Philadelphia/Ovid, N.Y.); Vogelstein and Kinzler, *The Genetic Basis of Human Cancer* (Second edition, 2002, McGraw Hill Professional, New York); Dancey et al. (2009 *Semin. Oncol.* 36 Suppl. 3:S46); certain embodiments contemplate a human subject that is known to be free of a risk for having, developing or acquiring cancer by such criteria.

Certain other embodiments contemplate a non-human subject or biological source, for example a non-human primate such as a macaque, chimpanzee, gorilla, vervet, orangutan, baboon or other non-human primate, including such non-human subjects that may be known to the art as preclinical models, including preclinical models for solid tumors and/or other cancers. Certain other embodiments contemplate a non-human subject that is a mammal, for example, a mouse, rat, rabbit, pig, sheep, horse, bovine, goat, gerbil, hamster, guinea pig or other mammal; many such mammals may be subjects that are known to the art as preclinical models for certain diseases or disorders, including lymphoid hematopoietic malignancies and/or other cancers (e.g., Li et al., 2011 *Dis. Model. Mech.* 4:311; von Euler et al., 2011 *Vet. Comp. Oncol.* 9:1; Goldstein et al., 2010 *Expert Rev. Hematol.* 3:301; Diamond et al., 2009 *J. Bone Min. Res.* 24:1150; Macor et al., 2008 *Curr. Pharm. Des.* 14:2023; Talmadge et al., 2007 *Am. J. Pathol.* 170:793; Kerbel, 2003 *Canc. Biol. Therap.* 2(4 Suppl 1):S134; Man et al., 2007 *Canc. Met. Rev.* 26:737; Cespedes et al., 2006 *Clin. Transl. Oncol.* 8:318). The range of embodiments is not intended to be so limited, however, such that there are also contemplated other embodiments in which the subject or biological source may be a non-mammalian vertebrate, for example, another higher vertebrate, or an avian, amphibian or reptilian species, or another subject or biological source.

As also noted elsewhere herein, art-accepted clinical diagnostic criteria have been established for these and other cancer types, such as those promulgated by the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, N.Y.); Pizzo and Poplack, *Principles and Practice of Pediatric Oncology* (Fourth edition, 2001, Lippincott, Williams and Wilkins, Philadelphia/Ovid, N.Y.); and Vogelstein and Kinzler, *The Genetic Basis of Human Cancer* (Second edition, 2002, McGraw Hill Professional, New York). Other non-limiting examples of typing and characterization of particular cancers are described, e.g., in Ignatiadis et al. (2008 *Pathobiol.* 75:104); Kunz (2008 *Curr. Drug Discov. Technol.* 5:9); and Auman et al. (2008 *Drug Metab. Rev.* 40:303).

Biological samples may be provided by obtaining a blood sample, biopsy specimen, tissue explant, organ culture, biological fluid or any other tissue or cell preparation from a subject or a biological source. B cells and T cells can thus be obtained from a biological sample, such as from a variety of tissue and biological fluid samples including bone marrow, thymus, lymph glands, lymph nodes, peripheral tissues and blood, but peripheral blood is most easily accessed. Any peripheral tissue can be sampled for the presence of B and T cells and is therefore contemplated for use in the methods described herein. Tissues and biological fluids from which adaptive immune cells may be obtained include, but are not limited to skin, epithelial tissues, colon, spleen, a mucosal secretion, oral mucosa, intestinal mucosa, vaginal mucosa or a vaginal secretion, cervical tissue, ganglia, saliva, cerebrospinal fluid (CSF), bone marrow, cord blood, serum, serosal fluid, plasma, lymph, urine, ascites fluid, pleural fluid, pericardial fluid, peritoneal fluid, abdominal fluid, culture medium, conditioned culture medium or lavage fluid. In certain embodiments, adaptive immune cells (e.g., hematopoietic cells of lymphoid lineage such as T cells and B cells) may be isolated from an apheresis sample. Peripheral blood samples may be obtained by phlebotomy from subjects. Peripheral blood mononuclear cells (PBMC) are isolated by techniques known to those of skill in the art, e.g., by Ficoll-Hypaque® density gradient separation. In certain embodiments, whole PBMCs are used for analysis.

In certain related embodiments, preparations that comprise predominantly lymphocytes (e.g., T and B cells) or that comprise predominantly T cells or predominantly B cells, including preparations in which cells of a lymphoid hematological malignancy are present, may be prepared for use as a biological sample as provided herein, according to established, art-accepted methodologies. In other related embodiments, specific subpopulations of T or B cells may be isolated prior to analysis using the methods described herein. Various methods and commercially available kits for isolating different subpopulations of T and B cells are known in the art and include, but are not limited to, subset selection immunomagnetic bead separation or flow immunocytometric cell sorting using antibodies specific for one or more of any of a variety of known T and B cell surface markers. Illustrative markers include, but are not limited to, one or a combination of CD2, CD3, CD4, CD8, CD14, CD19, CD20, CD25, CD28, CD45RO, CD45RA, CD54, CD62, CD62L, CDw137 (41BB), CD154, GITR, FoxP3, CD54, and CD28. For example, and as is known to the skilled person, cell surface markers, such as CD2, CD3, CD4, CD8, CD14, CD19, CD20, CD45RA, and CD45RO may be used to determine T, B, and monocyte lineages and subpopulations in flow cytometry. Similarly, forward light-scatter, side-scatter, and/or cell surface markers such as CD25, CD62L, CD54, CD137, CD154 may be used to determine activation state and functional properties of cells.

Illustrative combinations useful in certain of the methods described herein may include CD8$^+$CD45RO$^+$ (memory cytotoxic T cells), CD4$^+$CD45RO$^+$ (memory T helper), CD8$^+$CD45RO$^-$ (CD8$^+$CD62L$^+$CD45RA$^+$ (naïve-like cytotoxic T cells); CD4$^+$CD25$^+$CD62L$^{hi}$GITR$^+$FoxP3$^+$ (regulatory T cells). Illustrative antibodies for use in immunomagnetic cell separations or flow immunocytometric cell sorting include fluorescently labeled anti-human antibodies, e.g., CD4 FITC (clone M-T466, Miltenyi Biotec), CD8 PE (clone RPA-T8, BD Biosciences), CD45RO ECD (clone UCHL-1, Beckman Coulter), and CD45RO APC (clone UCHL-1, BD Biosciences). Staining of total PBMCs may be done with the appropriate combination of antibodies, followed by washing cells before analysis. Lymphocyte subsets can be isolated by fluorescence activated cell sorting (FACS), e.g., by a BD FACSAria™ cell-sorting system (BD Biosciences) and by analyzing results with FlowJo™ software (Treestar Inc.), and also by conceptually similar methods involving specific antibodies immobilized to surfaces or beads.

For nucleic acid extraction, total genomic DNA may be extracted from cells using methods known in the art and/or commercially available kits, e.g., by using the QIAamp® DNA blood Mini Kit (QIAGEN®). The approximate mass of a single haploid genome is 3 pg. Preferably, at least 25,000 to 250,000 cells, for example, at least 50,000 to 125,000 cells, or at least 75,000 to 150,000 cells, or at least 100,000 to 200,000 cells, are used for analysis, i.e., about 0.15 to 1.5 μg, or for instance, 0.6 to 1.2 μg DNA from diploid T or B cells. The number of T or B cells present in a sample may vary considerably when the sample is obtained from a patient having a lymphoid hematological malignancy such as acute T-cell lymphoblastic leukemia (T-ALL). Using PBMCs from a normal healthy adult human as a source, the number of T cells can be estimated to be about 30% of total cells; the number of B cells can also be estimated to be about 10% of total cells in a PBMC preparation.

Adaptive Immune Cell Receptors

The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MHC class I and class II ligands, which bind to the TCR, are also immunoglobulin superfamily proteins but are specialized for antigen presentation, with a highly polymorphic peptide binding site which enables them to present a diverse array of short peptide fragments at the APC cell surface.

The extracellular portions of native heterodimeric αβ and γδ TCRs consist of two polypeptides each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. CDR3 of αβ TCRs interact with the peptide presented by MHC, and CDRs 1 and 2 of αβ TCRs interact with the peptide and the MHC. The diversity of TCR sequences is generated via somatic rearrangement of linked variable (V), diversity (D), joining (J), and constant genes.

The Ig and TCR gene loci contain many different variable (V), diversity (D), and joining (J) gene segments, which are subjected to rearrangement processes during early lymphoid differentiation. Ig and TCR V, D and J gene segment sequences are known in the art and are available in public databases such as GENBANK. Non-limiting examples of TCRB V region gene segment sequences are set forth in the sequence listing at SEQ ID NOS:5579-5630, 5644-5779, 6222-6273 and 6287-6351, and examples of TCRB J region segment sequences are set forth in SEQ ID NOS:5631-5643, 5780-5792 and 6274-6286. Exemplary TCRG J region gene segment sequences are set forth in SEQ ID NOs:5793-5798 and 6212-6215. Exemplary TCRG V region gene segment sequences are set forth in SEQ ID NOs:5799-5816 and 6124-6127. Exemplary IgH J region gene segment sequences are set forth in SEQ ID NOs:5817-5832 and 6216-6221; exemplary IgH V region gene segment sequences are set forth in SEQ ID NOs:5833-6123 and 6128-6211.

The V-D-J rearrangements are mediated via a recombinase enzyme complex in which the RAG1 and RAG2 proteins play a key role by recognizing and cutting the DNA at the recombination signal sequences (RSS), which are located downstream of the V gene segments, at both sides of the D gene segments, and upstream of the J gene segments. Inappropriate RSS reduce or even completely prevent rearrangement. The recombination signal sequence (RSS) consists of two conserved sequences (heptamer, 5'-CACAGTG-3', and nonamer, 5'-ACAAAAACC-3'), separated by a spacer of either 12+/−1 bp ("12-signal") or 23+/−1 bp ("23-signal"). A number of nucleotide positions have been identified as important for recombination including the CA dinucleotide at position one and two of the heptamer, and a C at heptamer position three has also been shown to be strongly preferred as well as an A nucleotide at positions 5, 6, 7 of the nonamer. (Ramsden et. al 1994 *Nucl. Ac. Res.* 22:1785; Akamatsu et. al. 1994 *J. Immunol.* 153:4520; Hesse et. al. 1989 *Genes Dev.* 3:1053). Mutations of other nucleotides have minimal or inconsistent effects. The spacer, although more variable, also has an impact on recombination, and single-nucleotide replacements have been shown to significantly impact recombination efficiency (Fanning et. al. 1996 *Cell. Immunol. Immumnopath.* 79:1, Larijani et. al 1999 *Nucl. Ac. Res.* 27:2304; Nadel et. al. 1998 *J. Immunol.* 161:6068; Nadel et al., 1998 *J. Exp. Med.* 187:1495). Criteria have been described for identifying RSS polynucleotide sequences having significantly different recombination efficiencies (Ramsden et. al 1994 *Nucl. Ac. Res.* 22:1785;

Akamatsu et. al. 1994 *J. Immunol.* 153:4520; Hesse et. al. 1989 *Genes Dev.* 3:1053, and Lee et al., 2003 *PLoS* 1(1):E1).

The rearrangement process generally starts with a D to J rearrangement followed by a V to D-J rearrangement in the case of Ig heavy chain (IgH), TCR beta (TCRB), and TCR delta (TCRD) genes or concerns direct V to J rearrangements in case of Ig kappa (IgK), Ig lambda (IgL), TCR alpha (TCRA), and TCR gamma (TCRG) genes. The sequences between rearranging gene segments are generally deleted in the form of a circular excision product, also called TCR excision circle (TREC) or B cell receptor excision circle (BREC).

The many different combinations of V, D, and J gene segments represent the so-called combinatorial repertoire, which is estimated to be ~$2 \times 10^6$ for Ig molecules, ~$3 \times 10^6$ for TCRO and ~$5 \times 10^3$ for TCRγδ molecules. At the junction sites of the V, D, and J gene segments, deletion and random insertion of nucleotides occurs during the rearrangement process, resulting in highly diverse junctional regions, which significantly contribute to the total repertoire of Ig and TCR molecules, estimated to be >$10^{12}$.

Mature B-lymphocytes further extend their Ig repertoire upon antigen recognition in follicle centers via somatic hypermutation, a process, leading to affinity maturation of the Ig molecules. The somatic hypermutation process focuses on the V- (D-) J exon of IgH and Ig light chain genes and concerns single nucleotide mutations and sometimes also insertions or deletions of nucleotides. Somatically-mutated Ig genes are also found in mature B-cell malignancies of follicular or post-follicular origin.

In certain preferred embodiments described herein, V-segment and J-segment primers may be employed in a PCR reaction to amplify rearranged TCR or Ig CDR3-encoding DNA regions in a test biological sample, wherein each functional TCR or Ig V-encoding gene segment comprises a V gene recombination signal sequence (RSS) and each functional TCR or Ig J-encoding gene segment comprises a J gene RSS. In these and related embodiments, each amplified rearranged DNA molecule may comprise (i) at least about 10, 20, 30 or 40 contiguous nucleotides of a sense strand of the TCR or Ig V-encoding gene segment, with the at least about 10, 20, 30 or 40 contiguous nucleotides being situated 5' to the V gene RSS and/or each amplified rearranged DNA molecule may comprise (ii) at least about 10, 20 or 30 contiguous nucleotides of a sense strand of the TCR or Ig J-encoding gene segment, with the at least about 10, 20 or 30 contiguous nucleotides being situated 3' to the J gene RSS. In certain preferred embodiments, each amplified TCR or Ig CDR3-encoding region is present in an amplified rearranged DNA molecule that is less than 600 nucleotides in length. Without wishing to be bound by theory, these design features for amplifying CDR3-encoding V-J junctional regions permit V-segment primer hybridization to substantially all functional TCR or Ig V-encoding gene segments, and also permit J-segment primer hybridization to substantially all functional TCR or Ig J-encoding segments, and also permit amplification of CDR3-encoding regions that are amenable to sequencing by the herein described HTS platforms while including adequate sequence information to identify all possible V-D-J and V-J combinations.

Multiplex Quantitative PCR

As described herein and in view of Robins et al., 2009 *Blood* 114, 4099; Robins et al., 2010 *Sci. Translat. Med.* 2:47ra64; Robins et al., 2011 *J. Immunol. Meth.* doi: 10.1016/j.jim.2011.09. 001; Sherwood et al. 2011 *Sci. Translat. Med.* 3:90ra61; U.S. application Ser. No. 13/217, 126 (US Pub. No. 2012/0058902), U.S. application Ser. No. 12/794,507 (US Pub. No. 2010/0330571), WO/2010/151416, WO/2011/106738 (PCT/US2011/026373), WO2012/027503 (PCT/US2011/049012), U.S. Application No. 61/550,311, and U.S. Application No. 61/569,118, there is provided a method for quantifying the relative representation of adaptive immune cell DNA in DNA from a test biological sample, and thus for determining the relative frequency of occurrence for each unique rearranged TCR or Ig encoding DNA sequence in a sample that contains lymphoid cells. According to certain preferred embodiments the method involves a multiplex PCR method using a set of forward primers that specifically hybridize to the V segments and a set of reverse primers that specifically hybridize to the J segments where the multiplex PCR reaction allows amplification of all the possible VJ (and VDJ) combinations within a given population of T or B cells.

DNA or RNA may be extracted from cells in a sample, such as a sample of blood or lymph or other sample from a subject known to have or suspected of having a lymphoid hematological malignancy, using standard methods or commercially available kits known in the art. A multiplex PCR system may be used to amplify rearranged adaptive immune cell receptor loci from genomic DNA, preferably from a CDR3 region. In certain embodiments, the CDR3 region is amplified from a TCRα, TCRβ, TCRγ or TCRδ CDR3 region or similarly from an IgH or IgL (lambda or kappa) locus. Compositions are provided that comprise a plurality of V-segment and J-segment primers that are capable of promoting amplification in a multiplex polymerase chain reaction (PCR) of substantially all productively rearranged adaptive immune receptor CDR3-encoding regions in the sample for a given class of such receptors (e.g., TCRγ, TCRβ, IgH, etc.), to produce a multiplicity of amplified rearranged DNA molecules from a population of T cells (for TCR) or B cells (for Ig) in the sample. Preferably and in certain embodiments, primers are designed so that each amplified rearranged DNA molecule in the multiplicity of amplified rearranged DNA molecules is less than 600 nucleotides in length, thereby excluding amplification products from non-rearranged adaptive immune receptor loci.

In the human genome there are currently believed to be about 70 TCR Vα and about 61 Jα gene segments, about 52 TCR Vβ, about 2 Dβ and about 13 Jβ gene segments, about 9 TCR Vγ and about 5 Jγ gene segments, and about 46 immunoglobulin heavy chain (IGH) $V_H$, about 23 $D_H$ and about 6 $J_H$ gene segments. Accordingly, where genomic sequences for these loci are known such that specific molecular probes for each of them can be readily produced, it is believed according to non-limiting theory that the present compositions and methods relate to substantially all (e.g., greater than 90%, 91%, 92%, 93%, 94%, 95%, 96%, 97%, 98% or 99%) of these known and readily detectable adaptive immune receptor V-, D- and J-region encoding gene segments.

The TCR and Ig genes can generate millions of distinct proteins via somatic mutation. Because of this diversity-generating mechanism, the hypervariable complementarity determining regions (CDRs) of these genes can encode sequences that can interact with millions of ligands, and these regions are linked to a constant region that can transmit a signal to the cell indicating binding of the protein's cognate ligand. The adaptive immune system employs several strategies to generate a repertoire of T- and B-cell antigen receptors with sufficient diversity to recognize the universe of potential pathogens. In αβ and γδ T cells, which primarily recognize peptide antigens presented by MHC molecules, most of this receptor diversity is contained within the third complementarity-determining region (CDR3) of the T cell receptor (TCR) α and β chains (or γ and δ chains).

The assay technology uses two pools of primers to provide for a highly multiplexed PCR reaction. The first, "forward" pool (e.g., by way of illustration and not limitation, V-segment oligonucleotide primers described herein may in certain preferred embodiments be used as "forward" primers when J-segment oligonucleotide primers are used as "reverse" primers according to commonly used PCR terminology, but the skilled person will appreciate that in certain other embodiments J-segment primers may be regarded as "forward" primers when used with V-segment "reverse" primers) includes an oligonucleotide primer that is specific to (e.g., having a nucleotide sequence complementary to a unique sequence region of) each V-region encoding segment ("V segment) in the respective TCR or Ig gene locus. In certain embodiments, primers targeting a highly conserved region are used, to simultaneously capture many V segments, thereby reducing the number of primers required in the multiplex PCR. Similarly, in certain embodiments, the "reverse" pool primers anneal to a conserved sequence in the joining ("J") segment.

Each primer may be designed so that a respective amplified DNA segment is obtained that includes a sequence portion of sufficient length to identify each J segment unambiguously based on sequence differences amongst known J-region encoding gene segments in the human genome database, and also to include a sequence portion to which a J-segment-specific primer may anneal for resequencing. This design of V- and J-segment-specific primers enables direct observation of a large fraction of the somatic rearrangements present in the adaptive immune receptor gene repertoire within an individual. This feature in turn enables rapid comparison of the TCR and/or Ig repertoires (i) in individuals having a particular disease, disorder, condition or other indication of interest (e.g., cancer, an autoimmune disease, an inflammatory disorder or other condition) with (ii) the TCR and/or Ig repertoires of control subjects who are free of such diseases, disorders conditions or indications.

The term "gene" means the segment of DNA involved in producing a polypeptide chain such as all or a portion of a TCR or Ig polypeptide (e.g., a CDR3-containing polypeptide); it includes regions preceding and following the coding region "leader and trailer" as well as intervening sequences (introns) between individual coding segments (exons), and may also include regulatory elements (e.g., promoters, enhancers, repressor binding sites and the like), and may also include recombination signal sequences (RSSs) as described herein.

The nucleic acids of the present embodiments, also referred to herein as polynucleotides, and including oligonucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes a TCR or an immunoglobulin or a region thereof (e.g., a V region, a D segment, a J region, a C region, etc.) for use according to the present embodiments may be identical to the coding sequence known in the art for any given TCR or immunoglobulin gene regions or polypeptide domains (e.g., V-region domains, CDR3 domains, etc.), or may be a different coding sequence, which, as a result of the redundancy or degeneracy of the genetic code, encodes the same TCR or immunoglobulin region or polypeptide.

In one embodiment, the present disclosure provides a plurality of V segment primers and a plurality of J segment primers, wherein the plurality of V segment primers and the plurality of J segment primers amplify substantially all combinations of the V and J segments of a rearranged immune receptor locus. By substantially all combinations is meant at least 95%, 96%, 97%, 98%, 99% or more of all the combinations of the V and J segments of a rearranged immune receptor locus. In certain embodiments, the plurality of V segment primers and the plurality of J segment primers amplify all of the combinations of the V and J segments of a rearranged immune receptor locus.

In general, a multiplex PCR system may use at least 8, 9, 10, 11, 12, 13, 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to or is complementary to a sequence corresponding to one or more V region segments. Illustrative V region primers for amplification of the TCRβ are shown in SEQ ID NOs: 5579-5630. Illustrative TCRγ V region primers are provided in SEQ ID NOs:6124-6127. Illustrative IgH V region primers are provided in SEQ ID NOs:6128-6211. V region gene segment sequences may thus be used to design V region primers. Exemplary TCRB V region gene segment sequences are set forth in the sequence listing at SEQ ID NOS:5579-5630, 5644-5779, 6222-6273 and 6287-6351. Exemplary TCRG V region gene segment sequences are set forth in SEQ ID NOs:5799-5816 and 6124-6127. Exemplary IgH V region gene segment sequences are set forth in SEQ ID NOs:5833-6123 and 6128-6211. In SEQ ID NOS: 5579-5643, in the RN2 oligonucleotides "r" represents a ribonucleotide base in the oligonucleotide sequence and "/3SpC3/" represents a 3' three-carbon spacer on the hydroxyl group, preventing polymerase extension and amplification. The DNA repair endonuclease cleaves the oligonucleotide at the ribonucleotide after hybridization to a complementary sequence, creating an unblocked hydroxyl group that can be extended by a polymerase.

The multiplex PCR system also uses at least 3, 4, 5, 6, or 7, and in certain embodiments, 8, 9, 10, 11, 12 or 13 reverse primers, in which each reverse primer specifically hybridizes to or is complementary to a sequence corresponding to one or more J region segments. Illustrative TCRβ J segment primers are provided in SEQ ID NOs:5631-5643. Illustrative TCRγ J segment primers are provided in SEQ ID NOs:6212-6215. Illustrative IgH J segment primers are provided in SEQ ID NOs:6216-6221. J region gene segment sequences may thus be used to design J region primers. Exemplary TCRB J region segment sequences are set forth in SEQ ID NOS:5631-5643, 5780-5792 and 6274-6286. Exemplary TCRG J region gene segment sequences are set forth in SEQ ID NOs:5793-5798 and 6212-6215. Exemplary IgH J region gene segment sequences are set forth in SEQ ID NOs:5817-5832 and 6216-6221. In one embodiment, there is a J segment primer for every J segment.

Oligonucleotides or polynucleotides that are capable of specifically hybridizing or annealing to a target nucleic acid sequence by nucleotide base complementarity may do so under moderate to high stringency conditions. For purposes of illustration, suitable moderate to high stringency conditions for specific PCR amplification of a target nucleic acid sequence would be between 25 and 80 PCR cycles, with each cycle consisting of a denaturation step (e.g., about 10-30 seconds (s) at greater than about 95° C.), an annealing step (e.g., about 10-30 s at about 60-68° C.), and an extension step (e.g., about 10-60 s at about 60-72° C.), optionally according to certain embodiments with the annealing and extension steps being combined to provide a two-step PCR. As would be recognized by the skilled person, other PCR reagents may be added or changed in the PCR reaction to increase specificity of primer annealing and amplification, such as altering the magnesium concentration, optionally adding DMSO, and/or the use of blocked primers, modified nucleotides, peptide-nucleic acids, and the like.

In certain embodiments, nucleic acid hybridization techniques may be used to assess hybridization specificity of the primers described herein. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

PRIMERS. According to the present disclosure, oligonucleotide primers are provided in an oligonucleotide primer set that comprises a plurality of V-segment primers and a plurality of J-segment primers, where the primer set is capable of amplifying rearranged DNA encoding adaptive immune receptors in a biological sample that comprises lymphoid cell DNA. Suitable primer sets are known in the art and disclosed herein, for example, the primer sets in U.S. application Ser. No. 13/217,126; U.S. application Ser. No. 12/794,507; PCT/US2011/026373; or PCT/US2011/049012; or the like; or those shown in Table 1. In certain embodiments the primer set is designed to include a plurality of V sequence-specific primers that includes, for each unique V region gene (including pseudogenes) in a sample, at least one primer that can specifically anneal to a unique V region sequence; and for each unique J region gene in the sample, at least one primer that can specifically anneal to a unique J region sequence.

Primer design may be achieved by routine methodologies in view of known TCR and BCR genomic sequences. Accordingly, the primer set is preferably capable of amplifying every possible V-J combination that may result from DNA rearrangements in the TCR or BCR locus. As also described below, certain embodiments contemplate primer sets in which one or more V primers may be capable of specifically annealing to a "unique" sequence that may be shared by two or more V regions but that is not common to all V regions, and/or in which in which one or more J primers may be capable of specifically annealing to a "unique" sequence that may be shared by two or more J regions but that is not common to all J regions.

In particular embodiments, oligonucleotide primers for use in the compositions and methods described herein may comprise or consist of a nucleic acid of at least about 15 nucleotides long that has the same sequence as, or is complementary to, a 15 nucleotide long contiguous sequence of the target V- or J-segment (i.e., portion of genomic polynucleotide encoding a V-region or J-region polypeptide). Longer primers, e.g., those of about 16, 17, 18, 19, 20, 21, 22, 23, 24, 25, 26, 27, 28, 29, 30, 31, 32, 33, 34, 35, 36, 37, 38, 39, 40, 45, or 50, nucleotides long that have the same sequence as, or sequence complementary to, a contiguous sequence of the target V- or J-region encoding polynucleotide segment, will also be of use in certain embodiments. All intermediate lengths of the presently described oligonucleotide primers are contemplated for use herein. As would be recognized by the skilled person, the primers may have additional sequence added (e.g., nucleotides that may not be the same as or complementary to the target V- or J-region encoding polynucleotide segment), such as restriction enzyme recognition sites, adaptor sequences for sequencing, bar code sequences, and the like (see e.g., primer sequences provided in the Tables and sequence listing herein). Therefore, the length of the primers may be longer, such as about 55, 56, 57, 58, 59, 60, 61, 62, 63, 64, 65, 66, 67, 68, 69, 70, 71, 72, 73, 74, 75, 80, 85, 90, 95, 100 or more nucleotides in length or more, depending on the specific use or need.

Also contemplated for use in certain embodiments are adaptive immune receptor V-segment or J-segment oligonucleotide primer variants that may share a high degree of sequence identity to the oligonucleotide primers for which nucleotide sequences are presented herein, including those set forth in the Sequence Listing. Thus, in these and related embodiments, adaptive immune receptor V-segment or J-segment oligonucleotide primer variants may have substantial identity to the adaptive immune receptor V-segment or J-segment oligonucleotide primer sequences disclosed herein, for example, such oligonucleotide primer variants may comprise at least 70% sequence identity, preferably at least 75%, 80%, 85%, 90%, 91%, 92%, 93%, 94%, 95%, 96%, 97%, 98%, or 99% or higher sequence identity compared to a reference polynucleotide sequence such as the oligonucleotide primer sequences disclosed herein, using the methods described herein (e.g., BLAST analysis using standard parameters). One skilled in this art will recognize that these values can be appropriately adjusted to determine corresponding ability of an oligonucleotide primer variant to anneal to an adaptive immune receptor segment-encoding polynucleotide by taking into account codon degeneracy, reading frame positioning and the like.

Typically, oligonucleotide primer variants will contain one or more substitutions, additions, deletions and/or insertions, preferably such that the annealing ability of the variant oligonucleotide is not substantially diminished relative to that of an adaptive immune receptor V-segment or J-segment oligonucleotide primer sequence that is specifically set forth herein.

Table 1 presents as a non-limiting example an oligonucleotide primer set that is capable of amplifying productively rearranged DNA encoding TCR β-chains (TCRB) in a biological sample that comprises DNA from lymphoid cells of a subject. In this primer set the J segment primers share substantial sequence homology, and therefore may cross-prime amongst more than one target J polynucleotide sequence, but the V segment primers are designed to anneal specifically to target sequences within the CDR2 region of V and are therefore unique to each V segment. An exception, however, is present in the case of several V primers where the within-family sequences of the closely related target genes are identical (e.g., V6-2 and V6-3 are identical at the nucleotide level throughout the coding sequence of the V segment, and therefore may have a single primer, TRB2V6-2/3).

It will therefore be appreciated that in certain embodiments the number of different template oligonucleotides in the template composition, and/or the number of different oligonucleotide primers in the primer set, may be advantageously reduced by designing template and/or primers to exploit certain known similarities in V and/or J sequences. Thus, in these and related embodiments, "unique" oligonucleotide sequences as described herein may include specific V polynucleotide sequences that are shared by 1, 2, 3, 4, 5, 6, 7, 8, 9, 10, 11, 12, 13, 14, 15, 16, 17, 18, 19 or 20 distinct template oligonucleotides and/or specific J polynucleotide sequences that are shared by 1, 2, 3, 4, 5, 6, 7, 8, 9, 10, 11, 12 or 13 distinct template oligonucleotides, where such templates differ in sequence from one another by other than the shared V and/or J sequences.

According to certain presently contemplated embodiments, it may be useful to decrease (e.g., reduce in a statistically significant manner) template amplification bias such as non-uniform nucleic acid amplification potential among members of a set of amplification primers that can result from unequal primer efficiencies (e.g., unequal primer utilization) only for a limited subset of all naturally occurring V and J genes. For example, in analyses of the TCR or BCR immune repertoire involved in an immune response, whether to a specific antigen, as in a vaccine, or to a tissue, as in an autoimmune disease, only the productive TCR or IG rearrangements may be of interest. In such circumstances, it may be economically advantageous to identify and correct non-uniform nucleic acid amplification potential only for those V and J segment primers that contribute to productive rearrangements of TCR or BCR encoding DNA, and to exclude efforts to correct non-uniform amplification of pseudogenes and orphons (i.e., TCR or BCR V region-encoding segments that have been duplicated onto other chromosomes).

In the human IGH locus, for instance, the ImmunoGeneTics (IMGT) database (M.-P. LeFranc, Université Montpellier, Montpellier, France; www.imgt.org) annotates 165 V segment genes, of which 26 are orphons on other chromosomes and 139 are in the IGH locus at chromosome 14. Among the 139 V segments within the IGH locus, 51 have at least one functional allele, while 6 are ORFs (open-reading frames) which are missing at least one highly conserved amino-acid residue, and 81 are pseudogenes. Pseudogenes may include V segments that contain an in-frame stop codon within the V-segment coding sequence, a frameshift between the start codon and the CDR3 encoding sequence, one or more repeat-element insertions, and deletions of critical regions, such as the first exon or the RSS. To characterize functional IGH rearrangements in a sample while avoiding the time and expense of characterizing pseudogenes and/or orphons, it is therefore contemplated to use a subset of the herein described synthetic template oligonucleotides which is designed to include only those V segments that participate in a functional rearrangement to encode a TCR or BCR, without having to synthesize or calibrate amplification primers and template oligonucleotides specific to the pseudogene sequences. Advantageous efficiencies with respect, inter alia, to time and expense are thus obtained.

TABLE 1

Exemplary Oligonucleotide Primer Set (hsTCRB PCR Primers)

| Name | Sequence | SEQ ID NO: |
|---|---|---|
| TRBJ1-1 | TTACCTACAACTGTGAGTCTGGTGCCTTGTCCAAA | 1631 |
| TRBJ1-2 | ACCTACAACGGTTAACCTGGTCCCCGAACCGAA | 1632 |
| TRBJ1-3 | ACCTACAACAGTGAGCCAACTTCCCTCTCCAAA | 1633 |
| TRBJ1-4 | CCAAGACAGAGAGCTGGGTTCCACTGCCAAA | 1634 |
| TRBJ1-5 | ACCTAGGATGGAGAGTCGAGTCCCATCACCAAA | 1635 |
| TRBJ1-6 | CTGTCACAGTGAGCCTGGTCCCGTTCCCAAA | 1636 |
| TRBJ2-1 | CGGTGAGCCGTGTCCCTGGCCCGAA | 1637 |
| TRBJ2-2 | CCAGTACGGTCAGCCTAGAGCCTTCTCCAAA | 1638 |
| TRBJ2-3 | ACTGTCAGCCGGGTGCCTGGGCCAAA | 1639 |
| TRBJ2-4 | AGAGCCGGGTCCCGGCGCCGAA | 1640 |
| TRBJ2-5 | GGAGCCGCGTGCCTGGCCCGAA | 1641 |
| TRBJ2-6 | GTCAGCCTGCTGCCGGCCCCGAA | 1642 |
| TRBJ2-7 | GTGAGCCTGGTGCCCGGCCCGAA | 1643 |
| TRB2V10-1 | AACAAAGGAGAAGTCTCAGATGGCTACAG | 1644 |
| TRB2V10-2 | GATAAAGGAGAAGTCCCCGATGGCTATGT | 1645 |
| TRB2V10-3 | GACAAAGGAGAAGTCTCAGATGGCTATAG | 1646 |
| TRB2V6-2/3 | GCCAAAGGAGAGGTCCCTGATGGCTACAA | 1647 |
| TRB2V6-8 | CTCTAGATTAAACACAGAGGATTTCCCAC | 1648 |
| TRB2V6-9 | AAGGAGAAGTCCCCGATGGCTACAATGTA | 1649 |
| TRB2V6-5 | AAGGAGAAGTCCCCAATGGCTACAATGTC | 1650 |
| TRB2V6-6 | GACAAAGGAGAAGTCCCGAATGGCTACAAC | 1651 |
| TRB2V6-7 | GTTCCCAATGGCTACAATGTCTCCAGATC | 1652 |
| TRB2V6-1 | GTCCCCAATGGCTACAATGTCTCCAGATT | 1653 |
| TRB2V6-4 | GTCCCTGATGGTTATAGTGTCTCCAGAGC | 1654 |
| TRB2V24-1 | ATCTCTGATGGATACAGTGTCTCTCGACA | 1655 |
| TRB2V25-1 | TTTCCTCTGAGTCAACAGTCTCCAGAATA | 1656 |
| TRB2V27 | TCCTGAAGGGTACAAAGTCTCTCGAAAAG | 1657 |
| TRB2V26 | CTCTGAGAGGTATCATGTTTCTTGAAATA | 1658 |
| TRB2V28 | TCCTGAGGGGTACAGTGTCTCTAGAGAGA | 1659 |
| TRB2V19 | TATAGCTGAAGGGTACAGCGTCTCTCGGG | 1660 |
| TRB2V4-1 | CTGAATGCCCCAACAGCTCTCTCTTAAAC | 1661 |
| TRB2V4-2/3 | CTGAATGCCCCAACAGCTCTCACTTATTC | 1662 |
| TRB2V2P | CCTGAATGCCCTGACAGCTCTCGCTTATA | 1663 |
| TRB2V3-1 | CCTAAATCTCCAGACAAAGCTCACTTAAA | 1664 |
| TRB2V3-2 | CTCACCTGACTCTCCAGACAAAGCTCAT | 1665 |
| TRB2V16 | TTCAGCTAAGTGCCTCCCAAATTCACCCT | 1666 |
| TRB2V23-1 | GATTCTCATCTCAATGCCCCAAGAACGC | 1667 |

TABLE 1-continued

Exemplary Oligonucleotide Primer Set
(hsTCRB PCR Primers)

| Name | Sequence | SEQ ID NO: |
|---|---|---|
| TRB2V18 | ATTTTCTGCTGAATTTCCCAAAGAGGGCC | 1668 |
| TRB2V17 | ATTCACAGCTGAAAGACCTAACGGAACGT | 1669 |
| TRB2V14 | TCTTAGCTGAAAGGACTGGAGGGACGTAT | 1670 |
| TRB2V2 | TTCGATGATCAATTCTCAGTTGAAAGGCC | 1671 |
| TRB2V12-1 | TTGATTCTCAGCACAGATGCCTGATGT | 1672 |
| TRB2V12-2 | GCGATTCTCAGCTGAGAGGCCTGATGG | 1673 |
| TRB2V12-3/4 | TCGATTCTCAGCTAAGATGCCTAATGC | 1674 |
| TRB2V12-5 | TTCTCAGCAGAGATGCCTGATGCAACTTTA | 1675 |
| TRB2V7-9 | GGTTCTCTGCAGAGAGGCCTAAGGGATCT | 1676 |
| TRB2V7-8 | GCTGCCCAGTGATCGCTTCTTTGCAGAAA | 1677 |
| TRB2V7-4 | GGCGGCCCAGTGGTCGGTTCTCTGCAGAG | 1678 |
| TRB2V7-6/7 | ATGATCGGTTCTCTGCAGAGAGGCCTGAGG | 1679 |
| TRB2V7-2 | AGTGATCGCTTCTCTGCAGAGAGGACTGG | 1680 |
| TRB2V7-3 | GGCTGCCCAACGATCGGTTCTTTGCAGT | 1681 |
| TRB2V7-1 | TCCCCGTGATCGGTTCTCTGCACAGAGGT | 1682 |
| TRB2V11-123 | CTAAGGATCGATTTTCTGCAGAGAGGCTC | 1683 |
| TRB2V13 | CTGATCGATTCTCAGCTCAACAGTTCAGT | 1684 |
| TRB2V5-1 | TGGTCGATTCTCAGGGCGCCAGTTCTCTA | 1685 |
| TRB2V5-3 | TAATCGATTCTCAGGGCGCCAGTTCCATG | 1686 |
| TRB2V5-4 | TCCTAGATTCTCAGGTCTCCAGTTCCCTA | 1687 |
| TRB2V5-8 | GGAAACTTCCCTCCTAGATTTTCAGGTCG | 1688 |
| TRB2V5-5 | AAGAGGAAACTTCCCTGATCGATTCTCAGC | 1689 |
| TRB2V5-6 | GGCAACTTCCCTGATCGATTCTCAGGTCA | 1690 |
| TRB2V9 | GTTCCCTGACTTGCACTCTGAACTAAAC | 1691 |
| TRB2V15 | GCCGAACACTTCTTTCTGCTTTCTTGAC | 1692 |
| TRB2V30 | GACCCCAGGACCGGCAGTTCATCCTGAGT | 1693 |
| TRB2V20-1 | ATGCAAGCCTGACCTTGTCCACTCTGACA | 1694 |
| TRB2V29-1 | CATCAGCCGCCCAAACCTAACATTCTCAA | 1695 |

In certain preferred embodiments, the V-segment and J-segment oligonucleotide primers as described herein are designed to include nucleotide sequences such that adequate information is present within the sequence of an amplification product of a rearranged adaptive immune receptor (TCR or Ig) gene to identify uniquely both the specific V and the specific J genes that give rise to the amplification product in the rearranged adaptive immune receptor locus (e.g., at least 1, 2, 3, 4, 5, 6, 7, 8, 9, 10, 11, 12, 13, 14, 15, 16, 17, 18, 19 or 20 base pairs of sequence upstream of the V gene recombination signal sequence (RSS), preferably at least about 22, 24, 26, 28, 30, 32, 34, 35, 36, 37, 38, 39 or 40 base pairs of sequence upstream of the V gene recombination signal sequence (RSS), and in certain preferred embodiments greater than 40 base pairs of sequence upstream of the V gene recombination signal sequence (RSS), and at least 1, 2, 3, 4, 5, 6, 7, 8, 9, 10, 11, 12, 13, 14, 15, 16, 17, 18, 19 or 20 base pairs downstream of the J gene RSS, preferably at least about 22, 24, 26, 28 or 30 base pairs downstream of the J gene RSS, and in certain preferred embodiments greater than 30 base pairs downstream of the J gene RSS).

This feature stands in contrast to oligonucleotide primers described in the art for amplification of TCR-encoding or Ig-encoding gene sequences, which rely primarily on the amplification reaction merely for detection of presence or absence of products of appropriate sizes for V and J segments (e.g., the presence in PCR reaction products of an amplicon of a particular size indicates presence of a V or J segment but fails to provide the sequence of the amplified PCR product and hence fails to confirm its identity, such as the common practice of spectratyping).

In certain embodiments, the primers are designed not to cross an intron/exon boundary. The forward primers in certain embodiments anneal to the V segments in a region of relatively strong sequence conservation between V segments so as to maximize the conservation of sequence among these primers. Accordingly, this minimizes the potential for differential annealing properties of each primer, and so that the amplified region between V and J primers contains sufficient TCR or Ig V sequence information to identify the specific V gene segment used. In one embodiment, the J segment primers hybridize with a conserved element of the J segment, and have similar annealing strength. In one particular embodiment, the J segment primers anneal to the same conserved framework region motif.

Oligonucleotides (e.g., primers) can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Lett.* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature.

A primer is preferably a single-stranded DNA, but in some embodiments may also include RNA. The appropriate length of a primer depends on the intended use of the primer but typically ranges from 6 to 50 nucleotides, or in certain embodiments, from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

As described herein, primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning, detection, or sequencing of the amplified product. The region of the primer which is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences which contain the target primer binding sites.

In particular embodiments, primers for use in the methods described herein comprise or consist of a nucleic acid of at least about 15 nucleotides long that has the same sequence as, or is complementary to, a 15 nucleotide long contiguous sequence of the target V or J segment. Longer primers, e.g., those of about 16, 17, 18, 19, 20, 21, 22, 23, 24, 25, 26, 27, 28, 29, 30, 31, 32, 33, 34, 35, 36, 37, 38, 39, 40, 45, or 50, nucleotides long that have the same sequence as, or sequence complementary to, a contiguous sequence of the target V or J segment, will also be of use in certain embodiments. All intermediate lengths of the aforementioned primers are contemplated for use herein. As would be recognized by the skilled person, the primers may have additional sequence added (e.g., nucleotides that may not be the same as or complementary to the target V or J segment), such as restriction enzyme recognition sites, adaptor sequences for sequencing, bar code sequences, and the like (see e.g., primer sequences provided herein and in the sequence listing). Therefore, the length of the primers may be longer, such as 55, 56, 57, 58, 59, 60, 65, 70, 75, nucleotides in length or more, depending on the specific use or need. For example, in one embodiment, the forward and reverse primers are both modified at the 5' end with the universal forward primer sequence compatible with a DNA sequencer.

Also contemplated for use in certain embodiments are adaptive immune receptor V-segment or J-segment oligonucleotide primer variants that may share a high degree of sequence identity to the oligonucleotide primers for which nucleotide sequences are presented herein, including those set forth in the Sequence Listing. Thus, in these and related embodiments, adaptive immune receptor V-segment or J-segment oligonucleotide primer variants may have substantial identity to the adaptive immune receptor V-segment or J-segment oligonucleotide primer sequences disclosed herein, for example, such oligonucleotide primer variants may comprise at least 70% sequence identity, preferably at least 75%, 80%, 85%, 90%, 91%, 92%, 93%, 94%, 95%, 96%, 97%, 98%, or 99% or higher sequence identity compared to a reference polynucleotide sequence such as the oligonucleotide primer sequences disclosed herein, using the methods described herein (e.g., BLAST analysis using standard parameters). One skilled in this art will recognize that these values can be appropriately adjusted to determine corresponding ability of an oligonucleotide primer variant to anneal to an adaptive immune receptor segment-encoding polynucleotide by taking into account codon degeneracy, reading frame positioning and the like.

Typically, oligonucleotide primer variants will contain one or more substitutions, additions, deletions and/or insertions, preferably such that the annealing ability of the variant oligonucleotide is not substantially diminished relative to that of an adaptive immune receptor V-segment or J-segment oligonucleotide primer sequence that is specifically set forth herein. As also noted elsewhere herein, in preferred embodiments adaptive immune receptor V-segment and J-segment oligonucleotide primers are designed to be capable of amplifying a rearranged TCR or IGH sequence that includes the coding region for CDR3.

According to certain embodiments contemplated herein, the primers for use in the multiplex PCR methods of the present disclosure may be functionally blocked to prevent non-specific priming of non-T or B cell sequences. For example, the primers may be blocked with chemical modifications as described in U.S. patent application publication US2010/0167353. According to certain herein disclosed embodiments, the use of such blocked primers in the present multiplex PCR reactions involves primers that may have an inactive configuration wherein DNA replication (i.e., primer extension) is blocked, and an activated configuration wherein DNA replication proceeds. The inactive configuration of the primer is present when the primer is either single-stranded, or when the primer is specifically hybridized to the target DNA sequence of interest but primer extension remains blocked by a chemical moiety that is linked at or near to the 3' end of the primer.

The activated configuration of the primer is present when the primer is hybridized to the target nucleic acid sequence of interest and is subsequently acted upon by RNase H or another cleaving agent to remove the 3' blocking group, thereby allowing an enzyme (e.g., a DNA polymerase) to catalyze primer extension in an amplification reaction. Without wishing to be bound by theory, it is believed that the kinetics of the hybridization of such primers are akin to a second order reaction, and are therefore a function of the T cell or B cell gene sequence concentration in the mixture. Blocked primers minimize non-specific reactions by requiring hybridization to the target followed by cleavage before primer extension can proceed. If a primer hybridizes incorrectly to a sequence that is related to the desired target sequence but which differs by having one or more non-complementary nucleotides that result in base-pairing mismatches, cleavage of the primer is inhibited, especially when there is a mismatch that lies at or near the cleavage site. This strategy to improve the fidelity of amplification reduces the frequency of false priming at such locations, and thereby increases the specificity of the reaction. As would be recognized by the skilled person, reaction conditions, particularly the concentration of RNase H and the time allowed for hybridization and extension in each cycle, can be optimized to maximize the difference in cleavage efficiencies between highly efficient cleavage of the primer when it is correctly hybridized to its true target sequence, and poor cleavage of the primer when there is a mismatch between the primer and the template sequence to which it may be incompletely annealed.

As described in US2010/0167353, a number of blocking groups are known in the art that can be placed at or near the 3' end of the oligonucleotide (e.g., a primer) to prevent extension. A primer or other oligonucleotide may be modified at the 3'-terminal nucleotide to prevent or inhibit initiation of DNA synthesis by, for example, the addition of a 3' deoxyribonucleotide residue (e.g., cordycepin), a 2',3'-dideoxyribonucleotide residue, non-nucleotide linkages or alkane-diol modifications (U.S. Pat. No. 5,554,516). Alkane diol modifications which can be used to inhibit or block primer extension have also been described by Wilk et al., (1990 *Nucleic Acids Res.* 18 (8):2065), and by Arnold et al. (U.S. Pat. No. 6,031,091). Additional examples of suitable blocking groups include 3' hydroxyl substitutions (e.g., 3'-phosphate, 3'-triphosphate or 3'-phosphate diesters with alcohols such as 3-hydroxypropyl), 2'3'-cyclic phosphate, 2' hydroxyl substitutions of a terminal RNA base (e.g., phosphate or sterically bulky groups such as triisopropyl silyl (TIPS) or tert-butyl dimethyl silyl (TBDMS)). 2'-alkyl silyl groups such as TIPS and TBDMS substituted at the 3'-end of an oligonucleotide are described by Laikhter et al., U.S. patent application Ser. No. 11/686,894, which is incorporated herein by reference. Bulky substituents can also be incorporated on the base of the 3'-terminal residue of the oligonucleotide to block primer extension.

In certain embodiments, the oligonucleotide may comprise a cleavage domain that is located upstream (e.g., 5' to) of the blocking group used to inhibit primer extension. As examples, the cleavage domain may be an RNase H cleavage domain, or the cleavage domain may be an RNase H2 cleavage domain comprising a single RNA residue, or the oligonucleotide may comprise replacement of the RNA base with one or more alternative nucleosides. Additional illustrative cleavage domains are described in US2010/0167353.

Thus, a multiplex PCR system may use 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, or more forward primers, wherein each forward primer is complementary to a single functional TCR or Ig V segment or a small family of functional TCR or Ig V segments, e.g., a TCR Vβ segment (see e.g., the TCRBV primers as set forth in Table 1 and in the Sequence Listing, SEQ ID NOS:1644-1695) and, for example, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, or more reverse primers, each specific to a TCR or Ig J segment, such as TCR JR segment (see e.g., the TCRBJ primers in Table 1 and in the Sequence Listing, SEQ ID NOS:1631-1643). In another embodiment, a multiplex PCR reaction may use four forward primers each specific to one or more functional TCRγ V segment and four reverse primers each specific for one or more TCRγ J segments. In another embodiment, a multiplex PCR reaction may use 84 forward primers each specific to one or more functional V segments and six reverse primers each specific for one or more J segments.

Thermal cycling conditions may follow methods of those skilled in the art. For example, using a PCR Express™ thermal cycler (Hybaid, Ashford, UK), the following cycling conditions may be used: 1 cycle at 95° C. for 15 minutes, 25 to 40 cycles at 94° C. for 30 seconds, 59° C. for 30 seconds and 72° C. for 1 minute, followed by one cycle at 72° C. for 10 minutes. As will be recognized by the skilled person, thermal cycling conditions may be optimized, for example, by modifying annealing temperatures, annealing times, number of cycles and extension times. As would be recognized by the skilled person, the amount of primer and other PCR reagents used, as well as PCR parameters (e.g., annealing temperature, extension times and cycle numbers), may be optimized to achieve desired PCR amplification efficiency.

Alternatively, in certain related embodiments also contemplated herein, "digital PCR" methods can be used to quantitate the number of target genomes in a sample, without the need for a standard curve. In digital PCR, the PCR reaction for a single sample is performed in a multitude of more than 100 microcells or droplets, such that each droplet either amplifies (e.g., generation of an amplification product provides evidence of the presence of at least one template molecule in the microcell or droplet) or fails to amplify (evidence that the template was not present in a given microcell or droplet). By simply counting the number of positive microcells, it is possible directly to count the number of target genomes that are present in an input sample.

Digital PCR methods typically use an endpoint readout, rather than a conventional quantitative PCR signal that is measured after each cycle in the thermal cycling reaction (see, e.g., Pekin et al., 2011 *Lab. Chip* 11(13):2156; Zhong et al., 2011 *Lab. Chip* 11(13):2167; Tewhey et al., 2009 *Nature Biotechnol.* 27:1025; 2010 *Nature Biotechnol.* 28:178; Vogelstein and Kinzler, 1999 *Proc. Natl. Acad. Sci. USA* 96:9236-41; Pohl and Shih, 2004 *Expert Rev. Mol. Diagn.* 4(1); 41-7, 2004). Compared with traditional PCR, dPCR has the following advantages: (1) there is no need to rely on references or standards, (2) desired precision may be achieved by increasing the total number of PCR replicates, (3) it is highly tolerant to inhibitors, (4) it is capable of analyzing complex mixtures, and (5) it provides a linear response to the number of copies present in a sample to allow for small change in the copy number to be detected. Accordingly, any of the herein described compositions (e.g., template compositions and adaptive immune receptor gene-specific oligonucleotide primer sets) and methods may be adapted for use in such digital PCR methodology, for example, the ABI QuantStudio™ 12K Flex System (Life Technologies, Carlsbad, Calif.), the QX100™ Droplet Digital™ PCR system (BioRad, Hercules, Calif.), the QuantaLife™ digital PCR system (BioRad, Hercules, Calif.) or the RainDance™ microdroplet digital PCR system (RainDance Technologies, Lexington, Mass.).

Primers can be modified at either end (5' or 3') with the following modifications: TET (tetrachlorofluorescein) or BHQ_1 (4-(2-nitro-4-toloyldiazo)-2'-methoxy-5'-methyl-azobenzene-4"-(N-ethyl)-N-ethyl-2-cyanoethyl-(N,N-diisopropyl)-phosphoramidite). Certain primers (e.g., SEQ ID NOS: 5579-5643) can include a three-carbon spacer at the 3'-end on the hydroxyl group, preventing polymerase extension and amplification. In some embodiments, the first nucleotide of the primer is modified with a 6-carboxyfluorescein. The last nucleotide of the primer can be modified with a non-fluorescent quencher. In another embodiment, the primer has a minor groove-binding chemical modification (located at the second to last position at the 3'-end of the primer).

Quantifying Rearranged TCR and Ig Encoding DNA Molecules in a Sample

According to certain embodiments described herein, the proportion of lymphoid cells in a sample that are cancerous (e.g., malignant cells) can be determined. The present disclosure, however, also contemplates embodiments in which can be calculated the number of lymphoid cancer cells in a sample, out of the total number of input cells of the sample. The present disclosure also contemplates embodiments in which can be calculated the proportion of lymphoid cancer cells in a sample, out of the total number of input cells of the sample.

Briefly and by way of non-limiting example, to calculate the number of lymphoid cancer cells out of the total number of input cells from a sample, a known number of synthetic template oligonucleotide molecules of the herein described template composition for amplification factor determination, having sequences that correspond to the V and J priming sites, can be added ("spiked" in) to each amplification reaction of the presently disclosed methods. The synthetic template oligonucleotide molecules include a set of oligonucleotides that anneal to one V primer and one J primer, in the correct orientation, and a set of barcode oligonucleotides as described herein that uniquely identify each of the distinct synthetic template molecules. As described in greater detail elsewhere herein, these synthetic template oligonucleotide molecules may also include additional barcodes, additional unique identifying sets of oligonucleotide sequences, and universal primer sequences.

According to one embodiment, there is thus provided a template composition for amplification factor determination in which a known number of each of a plurality of template oligonucleotides having a unique oligonucleotide sequence is present, the template composition comprising: a plurality of template oligonucleotides having a plurality of oligonucleotide sequences of general formula:

5'-U1-B1-V-B2-R-B3-J-B4-U2-3'     [I]

wherein: (a) V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of oligonucleotide sequences V comprises a unique oligonucleotide sequence;

(b) J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of oligonucleotide sequences J comprises a unique oligonucleotide sequence;

(c) U1 is either nothing or comprises an oligonucleotide having a sequence that is selected from (i) a first universal adaptor oligonucleotide sequence, and (ii) a first sequencing platform-specific oligonucleotide sequence that is linked to and positioned 5' to a first universal adaptor oligonucleotide sequence;

(d) U2 is either nothing or comprises an oligonucleotide having a sequence that is selected from (i) a second universal adaptor oligonucleotide sequence, and (ii) a second sequencing platform-specific oligonucleotide sequence that is linked to and positioned 5' to a second universal adaptor oligonucleotide sequence;

(e) B1, B2, B3, and B4 are each independently either nothing or each comprises an oligonucleotide B that comprises an oligonucleotide barcode sequence of 3, 4, 5, 6, 7, 8, 9, 10, 11, 12, 13, 14, 15, 16, 17, 18, 19, 20, 21, 22, 23, 24 or 25, contiguous nucleotides, wherein in each of the plurality of oligonucleotide sequences B comprises a unique oligonucleotide sequence that uniquely identifies, as a paired combination, (i) the unique V oligonucleotide sequence of (a) and (ii) the unique J oligonucleotide sequence of (b);

(f) R is either nothing or comprises a restriction enzyme recognition site that comprises an oligonucleotide sequence that is absent from (a)-(e), and wherein:

(g) at least one of: (i) the plurality of template oligonucleotides comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51-100, 101-200, 201-300, 301-400, 401-500, 501-600, 601-700, 701-800, 801-900, 901-1000, 1001-1100, 1101-1200, 1201-1300, 1301-1400, 1401-1500, 1501-1600, 1601-1700, 1701-2000, or 2001-2500 unique oligonucleotide sequences, (ii) the plurality of template oligonucleotides comprises at least one template oligonucleotide having an oligonucleotide sequence of general formula (I) to which each V-segment oligonucleotide primer can specifically hybridize and at least one template oligonucleotide having an oligonucleotide sequence of general formula (I) to which each J-segment oligonucleotide primer can specifically hybridize, or (iii) the plurality of template oligonucleotides comprises at least a or at least b unique oligonucleotide sequences, whichever is larger, where a is the number of unique adaptive immune receptor V region-encoding gene segments in the subject and b is the number of unique adaptive immune receptor J region-encoding gene segments in the subject, and the composition comprises at least one template oligonucleotide for each unique V polynucleotide and at least one template oligonucleotide for each unique J polynucleotide (FIG. 6).

Because the synthetic template oligonucleotide molecules each include a priming site for at least one of the V primers and one for the J primers, the multiplex TCR or IG amplification primers described herein also amplify these synthetic template oligonucleotide molecules when the synthetic templates are "spiked" into a multiplexed amplification reaction. The number of unique synthetic template molecules for amplification factor determination that may be added ("spiked" in) to the amplification reaction must be at least two, but may comprise a much larger number of unique sequences, for instance, enough unique species so that the template composition for amplification factor determination includes synthetic templates to which can anneal every possible pair of V and J primers.

Certain embodiments thus contemplate a template composition for amplification factor determination that comprises at least one template oligonucleotide having an oligonucleotide sequence of general formula (I) to which each V-segment oligonucleotide primer can specifically hybridize and at least one template oligonucleotide having an oligonucleotide sequence of general formula (I) to which each J-segment oligonucleotide primer can specifically hybridize.

Certain other embodiments thus contemplate a template composition for amplification factor determination that comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51-100, 101-200, 201-300, 301-400, 401-500, 501-600, 601-700, 701-800, 801-900, 901-1000, 1001-1100, 1101-1200, 1201-1300, 1301-1400, 1401-1500, 1501-1600, 1601-1700, 1701-2000, or 2001-2500 unique oligonucleotide sequences.

Certain other embodiments thus contemplate a template composition for amplification factor determination that comprises at least a or at least b unique oligonucleotide sequences, whichever is larger, where a is the number of unique adaptive immune receptor V region-encoding gene segments in the subject and b is the number of unique adaptive immune receptor J region-encoding gene segments in the subject, and the composition comprises at least one template oligonucleotide for each unique V polynucleotide and at least one template oligonucleotide for each unique J polynucleotide.

In practice, for example, if a known number of synthetic template oligonucleotide molecules, each with a unique barcode (B) tracking sequence, are added to a multiplexed amplification reaction for amplifying rearranged DNA sequences that encode an adaptive immune receptor, the amplification products of which are then quantitatively sequenced, the number of sequenced molecules can be used to calculate the number of times each input molecule was amplified. This parameter, described in greater detail below, may be referred to as the amplification factor.

In a non-limiting and exemplary simplified application, the amplification factor can be calculated as: Amplification Factor=Number of Sequenced Synthetic Template Oligonucleotide Molecules/Number of Input Synthetic Template Oligonucleotide Molecules. In other embodiments, the amplification factor can be calculated for each sequence-unique species of synthetic template oligonucleotide molecule that is included in a multiplexed amplification reaction, to obtain a distribution of amplification factors for the reaction. The median of this distribution can be used as the final amplification factor for the calculation of the number of unique adaptive immune receptor encoding DNA molecules in the sample. If the amplification factor is uniquely calculated for each type of synthetic template oligonucleotide molecule of the template composition for amplification factor determination, information about primer amplification bias (e.g., detectable statistically significant differences in the efficiencies with which different amplification primers amplify their cognate template sequences) can be obtained and used to correct for such bias that may be introduced during the multiplexed amplification reaction.

As another non-limiting example, by using (i) the amplification factor value that is determined by quantifying the amplification products of the synthetic template oligonucleotide molecules of the template composition for amplification factor determination, and (ii) the number of rearranged DNA molecules encoding adaptive immune receptors that are detected by quantitative sequencing of multiplexed amplification products, the starting number of adaptive immune cells in the sample can be calculated. This calculation is: Number of Input Cells Having Rearranged DNA Encoding Adaptive Immune Receptors=Number of Adaptive Immune Receptor Sequences/Amplification Factor. From determination in this manner of the number of input cells in the sample that have rearranged DNA encoding adaptive immune receptors, a probable count of the number of lymphoid cancer cells in the sample can be calculated.

In certain embodiments, alternatively or additionally (e.g., in parallel), the proportion of total cells in the sample that carry a rearranged adaptive immune receptor encoding DNA sequence that is associated with lymphoid cancer cells can be calculated. In these and related embodiments, the amplification reaction includes the V and J multiplex primers and also includes a set of control primers that amplify a genomic region with known and consistent copy number. Suitable target genes for these control primers include housekeeping genes, for example, HLA-DRB1, ABO, ZFXY, or other widely and constitutively expressed genes. Non-limiting examples of such primers are shown in Table 2. The control primers amplify a set region of the genome. To efficiently use sequencer flow cell space by maximizing the portion used for determining adaptive immune receptor encoding sequences and minimizing that for determining the genomic control sequences, the primers may be modified to reduce efficient PCR amplification. The genomic control primers amplification efficiency may be limited, for example, by altering the primer sequences to introduce mismatches, and/or these primers can be included in the amplification reaction at low concentration. While these modifications are not necessary, they may increase sequencing throughput. To estimate the proportion of the total cells that are cancerous lymphoid cells, the final number of target gene sequences may then be counted.

TABLE 2

Exemplary Control (Housekeeping Gene) Primers

| Target Gene | Forward Primer | SEQ ID NO: | Reverse Primer | SEQ ID NO: |
|---|---|---|---|---|
| HLA-DRB1 | GGATGATAAATAGGTGCCAAGTG | 6383 | ACTTCAATGCTGCCTGGAT | 6384 |
| ABO | AAGGACGAGGGCGATTTCTA | 6385 | TATCTGCGATTGCGTGTCTG | 6386 |
| ZFXY | TTGCATGATTTGTGGGAAGA | 6387 | TTCTGAAGGCCTGTGAAAGC | 6388 |

Further details regarding determination of amplification factor values using the herein described template composition for amplification factor determination are presented below. The template composition for amplification factor determination comprises a plurality of diverse template oligonucleotides of general formula (I) as described in greater detail herein:

$$5'\text{-}U1\text{-}B1\text{-}V\text{-}B2\text{-}R\text{-}B3\text{-}J\text{-}B4\text{-}U2\text{-}3' \qquad (I)$$

The constituent template oligonucleotides, of which the template composition is comprised, are diverse with respect to the nucleotide sequences of the individual template oligonucleotides. The individual template oligonucleotides thus may vary in nucleotide sequence considerably from one another as a function of significant sequence variability amongst the large number of possible TCR or BCR variable (V) and joining (J) region polynucleotides. Sequences of individual template oligonucleotide species may also vary from one another as a function of sequence differences in U1, U2, B (B1, B2, B3, and B4) and R oligonucleotides that are included in a particular template within the diverse plurality of templates.

In certain embodiments barcode oligonucleotides B (B1, B2, B3, and B4) may independently and optionally comprise an oligonucleotide barcode sequence, wherein the barcode sequence is selected to identify uniquely a particular paired combination of a particular unique V oligonucleotide sequence and a particular unique J oligonucleotide sequence. The relative positioning of the barcode oligonucleotides B1 and B4 and universal adaptors advantageously permits rapid identification and quantification of the amplification products of a given unique template oligonucleotide by short sequence reads and paired-end sequencing on automated DNA sequencers (e.g., Illumina HiSeq™ or Illumina MiSEQ®, or GeneAnalyzer™-2, Illumina Corp., San Diego, Calif.). In particular, these and related embodiments permit rapid high-throughput determination of specific combinations of a V and a J sequence that are present in an amplification product, thereby to characterize the relative amplification efficiency of each V-specific primer and each J-specific primer that may be present in a primer set which is capable of amplifying rearranged TCR or BCR encoding DNA in a sample. Verification of the identities and/or quantities of the amplification products may be accomplished by longer sequence reads, optionally including sequence reads that extend to B2.

In use, each template oligonucleotide in the plurality of template oligonucleotides is present in a substantially equimolar amount, which in certain preferred embodiments includes preparations in which the molar concentrations of all oligonucleotides are within 1, 2, 3, 4, 5, 6, 7, 8, 9, 10, 11, 12, 13, 14, 15, 16, 17, 18, 19, 20, 21, 22, 23, 24 or 25 percent of each other. In certain other preferred embodiments as provided herein, template oligonucleotides are regarded as being present in a substantially equimolar amount when the molar concentrations of all oligonucleotides are within one order of magnitude of each other, including preparations in which the greatest molar concentration that any given unique template oligonucleotide species may have is no more than 1000, 900, 800, 700, 600, 500, 440, 400, 350, 300, 250, 200, 150, 100, 90, 80, 70, 60, 50, 40 or 30 percent greater than the molar concentration at which is present the unique template oligonucleotide species having the lowest concentration in the composition.

In a similar manner, certain embodiments disclosed herein contemplate oligonucleotide primer sets for amplification, in which sets the component primers may be provided in substantially equimolar amounts. As also described herein, according to certain other embodiments, the concentration of one or more primers in a primer set may be adjusted deliberately so that certain primers are not present in equimolar amounts or in substantially equimolar amounts.

Preferably all templates in the template composition for amplification factor determination, which is described herein and which comprises a plurality of template oligonucleotides having diverse sequences and the general structure of general formula (I), are oligonucleotides of substantially identical length. Without wishing to be bound by theory, it is generally believed that in a nucleic acid amplification reaction such as a polymerase chain reaction (PCR), template DNA length can influence the amplification efficiency of oligonucleotide primers by affecting the kinetics of interactions between primers and template DNA molecules to which the primers anneal by specific, nucleotide sequence-directed hybridization through nucleotide base complementarity. Longer templates are generally regarded as operating less efficiently than relatively shorter templates. In certain embodiments, the presently disclosed template composition for amplification factor determination comprises a plurality of template oligonucleotides of general formula (I) as provided herein, wherein the template oligonucleotides are of an identical length or a substantially identical length that is not more than 1000, 950, 900, 850, 800, 750, 700, 650, 600, 550, 500, 450, 400, 350, 300, 250, 200, 150 or 100 nucleotides in length, including all integer values therebetween.

Accordingly, in order to reduce, remove or minimize the potential contribution to undesirable biases in oligonucleotide primer utilization during multiplexed amplification, preferred embodiments disclosed herein may employ a plurality of template oligonucleotides wherein all template oligonucleotides in the sequence-diverse plurality of template oligonucleotides are of substantially identical length. A plurality of template oligonucleotides may be of substantially identical length when all (e.g., 100%) or most (e.g., greater than 50%) such oligonucleotides in a template composition are oligonucleotides that each have the exact same number of nucleotides, or where one or more template oligonucleotides in the template composition may vary in length from one another by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 nucleotides in length. It will be appreciated from the present disclosure that even in situations where not all template oligonucleotides have exactly the same length, the herein described compositions and methods may still be employed to determine an amplification factor as described herein.

According to certain presently disclosed embodiments, (i) each template oligonucleotide of the presently described template composition is provided in a substantially equimolar amount, (ii) the oligonucleotide primer set that is capable of amplifying rearranged DNA encoding a plurality of adaptive immune receptor comprises a plurality of V-segment oligonucleotide primers that are provided in substantially equimolar amounts, (iii) the oligonucleotide primer set that is capable of amplifying rearranged DNA encoding a plurality of adaptive immune receptor comprises a plurality of J-segment oligonucleotide primers that are provided in substantially equimolar amounts, and (iv) amplification scales linearly with the number of starting templates of a given sequence.

Hence, an expected yield for the amplification product of each template can be calculated and arbitrarily assigned a theoretical uniform amplification level value of 100%. After permitting the primer sets to amplify the sequences of the template oligonucleotides in an amplification reaction, any statistically significant deviation from substantial equivalence that is observed among the relative proportions of distinct amplification products indicates that there has been bias (i.e., unequal efficiency) in primer utilization during amplification. In other words, quantitative differences in the relative amounts of different amplification products that are obtained indicate that not all primers in the primer set have amplified their respective templates with comparable efficiencies. Certain embodiments contemplate assigning a range of tolerances above and below a theoretical 100% yield, such that any amplification level value within the range of tolerances may be regarded as substantial equivalence.

In certain such embodiments, the range of amplification product yields may be regarded as substantially equivalent when the product yields are all within the same order of magnitude (e.g., differ by less than a factor of ten). In certain other such embodiments, the range of amplification product yields may be regarded as substantially equivalent when the product yields differ from one another by no more than nine-fold, eight-fold, seven-fold, six-fold, five-fold, four-fold or three-fold. In certain other embodiments, product yields that may be regarded as being within an acceptable tolerance range may be more or less than a calculated 100% yield by as much as 1, 2, 3, 4, 5, 6, 7, 8, 9, 10, 11, 12, 13, 14, 15, 16, 17, 18, 19, 20, 30, 40, 50, 60, 100, or 200%.

Because the method involves determining the nucleotide sequence of each amplification product using known techniques as part of the quantification process, the primer(s)

responsible for amplification of each unique (as defined by sequence) product can be identified and their relative amount(s) in the primer set can be adjusted (e.g., increased or decreased in a statistically significant manner) accordingly. The concentrations of excessively efficient primers in the primer set can be reduced relative to the concentrations of other primers, so that the level of specific amplification by such primers of templates in the herein described template composition is substantially equivalent to the level of amplification delivered by the majority of primers which deliver the theoretical uniform amplification level, or which deliver a level that is within the acceptable tolerance range. The concentrations of poorly efficient primers in the primer set can be increased relative to the concentrations of other primers, so that the level of specific amplification by such primers of templates in the herein described template composition is substantially equivalent to the level of amplification delivered by the majority of primers which deliver the theoretical uniform amplification level, or which deliver a level within the acceptable tolerance range.

By providing the herein described template composition as a standard with which oligonucleotide primer sets can be calibrated, and in particular embodiments, where each template oligonucleotide is present in a substantially equimolar amount so that individual primer concentrations can be adjusted to yield substantially uniform amplification of a structurally diverse array of amplification products, the present disclosure thus advantageously overcomes the above described problems associated with biases in individual primer efficiency.

Using the compositions and methods provided herein, individual primers may be identified as having a non-uniform amplification potential by virtue of their promotion of non-uniform amplification as evidenced by increased (e.g., greater in a statistically significant manner) or decreased (e.g., lower in a statistically significant manner) amplification of specific template oligonucleotides relative to the uniform amplification level, despite the presence in an amplification reaction (i) of all template oligonucleotides in substantially equimolar amounts to one another, (ii) of all V-segment primers in substantially equimolar amounts to one another, and (iii) of all J-segment primers in substantially equimolar amounts to one another.

The relative concentrations of such primers may then be decreased or increased to obtain a modified complete set of primers in which all primers are not present in substantially equimolar amounts relative to one another, to compensate, respectively, for the increased or decreased level of amplification relative to the uniform amplification level. The primer set may then be retested for its ability to amplify all sequences in the herein disclosed template composition at the uniform amplification level, or within an acceptable tolerance range.

The process of testing modified primer sets for their ability to amplify the herein disclosed template composition, in which all template oligonucleotides are provided in substantially equimolar amounts to one another, may be repeated iteratively until all products are amplified at the uniform amplification level, or within an acceptable tolerance range. By such a process using the herein disclosed template composition, the amplification efficiency of an oligonucleotide primer set may be standardized, where the primer set is capable of amplifying productively rearranged DNA encoding one or a plurality of adaptive immune receptors in a biological sample that comprises DNA from lymphoid cells of a subject.

Additionally or alternatively, according to the present disclosure it may be determined whether any particular pair of oligonucleotide amplification primers exhibits non-uniform amplification potential, such as increased or decreased amplification of the template composition relative to a uniform amplification level exhibited by a majority of the oligonucleotide amplification primers, and a normalizing adjustment factor can then be used to calculate, respectively, a proportionately decreased or increased relative frequency of occurrence of the amplification products that are promoted by each such amplification primer pair. The present template compositions thus, in certain embodiments, provide a method of correcting for non-uniform nucleic acid amplification potential among members of a set of oligonucleotide amplification primers.

Certain such embodiments may advantageously permit correction, calibration, standardization, normalization, or the like, of data that are obtained as a consequence of non-uniform amplification events. Thus, the present embodiments permit correction of data inaccuracies, such as may result from biased oligonucleotide primer utilization, without the need for iteratively adjusting the concentrations of one or more amplification primers and repeating the steps of amplifying the herein described template compositions. Advantageous efficiencies may thus be obtained where repetition of the steps of quantitatively sequencing the amplification products can be avoided. Certain other contemplated embodiments may, however, employ such an iterative approach.

Accordingly, and as described herein, there is presently provided a template composition for amplification factor determination, along with methods for using such a template composition. Also described herein are methods for correcting such non-uniform nucleic acid amplification potentials (e.g., biases) among members of the oligonucleotide primer set. These and related embodiments exploit previously unrecognized benefits that are obtained by calibrating complex oligonucleotide primer sets to compensate for undesirable amplification biases using the template composition for amplification factor determination having the features described herein, and will find uses in improving the accuracy with which specific clonotypic TCR and/or Ig encoding DNA sequences can be quantified, relative to previously described methodologies.

As also noted above and described elsewhere herein, prior to the present disclosure there existed, in certain situations, unsatisfactory and difficult-to-discern discrepancies between (i) the actual quantitative distribution of rearranged adaptive immune receptor-encoding DNA templates having unique sequences in a biological sample comprising lymphoid cell DNA from a subject, and (ii) the observed relative representation of nucleic acid amplification products of such templates that were detected, following multiplexed amplification using a complex set of oligonucleotide amplification primers designed to amplify substantially all productively rearranged adaptive immune receptor genes in the sample.

TEMPLATES. According to certain preferred embodiments there is thus provided a template composition for amplification factor determination, for use in a multiplexed nucleic acid amplification reaction with an oligonucleotide primer set that is capable of amplifying rearranged DNA (which in certain embodiments may refer to productively rearranged DNA but which in certain other embodiments need not be so limited) encoding one or a plurality of adaptive immune receptors in a biological sample that comprises DNA from lymphoid cells of a subject, the template composition comprising a plurality of template oligonucleotides of general formula (I):

5'-U1-B1-V-B2-R-B3-J-B4-U2-3'                  (I)

as provided herein. In certain preferred embodiments each template oligonucleotide in the plurality of template oligonucleotides is present in a substantially equimolar amount, which in certain embodiments and as noted above may refer to a composition in which each of the template oligonucleotides is present at an equimolar concentration or at a molar concentration that deviates from equimolar by no more than 1, 2, 3, 4, 5, 6, 7, 8, 9, 10, 11, 12, 13, 14, 15, 16, 17, 18, 19, 20, 21, 22, 23, 24, 25, 50, 60, 70, 80, 90, 100 or 200% on a molar basis, and which in certain other embodiments may refer to a composition in which all of the template oligonucleotides are present at molar concentrations that are within an order of magnitude of one another. The plurality of templates may comprise at least 100, 200, 300, 400, 500, 600, 700, 800, 900, 1000, 1100 or more discrete oligonucleotide species each having a distinct nucleotide sequence, including every intermediate integer value therebetween.

The herein disclosed template composition thus comprises a plurality of template oligonucleotides of general formula:

5'-U1-B1-V-B2-R-B3-J-B4-U2-3'                  [I]

wherein, briefly and as elaborated in greater detail elsewhere herein, according to certain preferred embodiments:

V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of template oligonucleotide sequences V comprises a unique oligonucleotide sequence;

J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of template oligonucleotide sequences J comprises a unique oligonucleotide sequence;

U1 and U2 are each either nothing or each comprise an oligonucleotide having, independently, a sequence that is selected from (i) a universal adaptor oligonucleotide sequence, and (ii) a sequencing platform-specific oligonucleotide sequence that is linked to and positioned 5' to the universal adaptor oligonucleotide sequence;

B1, B2, B3. and B4 are each independently either nothing or each comprise an oligonucleotide B that comprises an oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 contiguous nucleotides (including all integer values therebetween), wherein in each of the plurality of template oligonucleotide sequences B comprises a unique oligonucleotide sequence that uniquely identifies, or identifies as a paired combination, (i) the unique V oligonucleotide sequence of the template oligonucleotide and (ii) the unique J oligonucleotide sequence of the template oligonucleotide; and R is either nothing or comprises a restriction enzyme recognition site that comprises an oligonucleotide sequence that is absent from V, J, U1, U2, B1, B2, B3, and B4.

In certain preferred embodiments the template composition comprises at least one template oligonucleotide to which each oligonucleotide amplification primer in an amplification primer set can anneal. That is, in certain preferred embodiments the template composition comprises at least one template oligonucleotide having an oligonucleotide sequence of general formula (I) to which each V-segment oligonucleotide primer can specifically hybridize, and at least one template oligonucleotide having an oligonucleotide sequence of general formula (I) to which each J-segment oligonucleotide primer can specifically hybridize.

According to such embodiments the oligonucleotide primer set that is capable of amplifying rearranged DNA encoding one or a plurality of adaptive immune receptors comprises a plurality a of unique V-segment oligonucleotide primers and a plurality b of unique J-segment oligonucleotide primers. The plurality of a V-segment oligonucleotide primers are each independently capable of annealing or specifically hybridizing to at least one polynucleotide encoding an adaptive immune receptor V-region polypeptide or to the complement thereof, wherein each V-segment primer comprises a nucleotide sequence of at least 15 contiguous nucleotides that is complementary to at least one adaptive immune receptor V region-encoding gene segment. The plurality of b J-segment oligonucleotide primers are each independently capable of annealing or specifically hybridizing to at least one polynucleotide encoding an adaptive immune receptor J-region polypeptide or to the complement thereof, wherein each J-segment primer comprises a nucleotide sequence of at least 15 contiguous nucleotides that is complementary to at least one adaptive immune receptor J region-encoding gene segment.

Thus, in certain embodiments and as also discussed elsewhere herein, the present template composition may be used in amplification reactions with amplification primers that are designed to amplify all rearranged adaptive immune receptor encoding gene sequences, including those that are not expressed, while in certain other embodiments the template composition and amplification primers may be designed so as not to yield amplification products of rearranged genes that are not expressed (e.g., pseudogenes, orphons). It will therefore be appreciated that in certain embodiments only a subset of rearranged adaptive immune receptor encoding genes may desirably be amplified, such that suitable amplification primer subsets may be designed and employed to amplify only those rearranged V-J sequences that are of interest. In these and related embodiments, correspondingly, a herein described template composition comprising only a subset of interest of rearranged V-J rearranged sequences may be used, so long as the template composition comprises at least one template oligonucleotide to which each oligonucleotide amplification primer in an amplification primer set can anneal. The actual number of template oligonucleotides in the template composition may thus vary considerably among the contemplated embodiments, as a function of the amplification primer set that is to be used.

For example, in certain related embodiments, in the template composition the plurality of template oligonucleotides may have a plurality of sequences of general formula (I) that is selected from (1) the plurality of oligonucleotide sequences of general formula (I) in which polynucleotides V and J have the TCRB V and J sequences set forth in at least one set of 68 TCRB V and J SEQ ID NOS, respectively, as set forth in FIG. 9 as TCRB V/J set 1, TCRB V/J set 2, TCRB V/J set 3, TCRB V/J set 4, TCRB V/J set 5, TCRB V/J set 6, TCRB V/J set 7, TCRB V/J set 8, TCRB V/J set 9, TCRB V/J set 10, TCRB V/J set 11, TCRB V/J set 12 and TCRB V/J set 13; (2) the plurality of oligonucleotide sequences of general formula (I) in which polynucleotides V and J have the TCRG V and J sequences set forth in at least one set of 14 TCRG V and J SEQ ID NOS, respectively, as set forth in FIG. 10 as TCRG V/J set 1, TCRG V/J set 2, TCRG V/J set 3, TCRG V/J set 4 and TCRG V/J set 5; and (3) the plurality of oligonucleotide sequences of general formula (I) in which polynucleotides V and J have the IGH V and J sequences set forth in at least one set of 127 IGH V and J SEQ ID NOS, respectively, as set forth in FIG. 11 as IGH V/J set 1, IGH V/J set 2, IGH V/J set 3, IGH V/J set 4, IGH V/J set 5, IGH V/J set 6, IGH V/J set 7, IGH V/J set 8 and IGH V/J set 9.

In certain embodiments, V is a polynucleotide sequence that encodes at least 10-70 contiguous amino acids of an adaptive immune receptor V-region, or the complement thereof; J is a polynucleotide sequence that encodes at least 5-30 contiguous amino acids of an adaptive immune receptor J-region, or the complement thereof; U1 and U2 are each either nothing or comprise an oligonucleotide comprising a nucleotide sequence that is selected from (i) a universal adaptor oligonucleotide sequence, and (ii) a sequencing platform-specific oligonucleotide sequence that is linked to and positioned 5' to the universal adaptor oligonucleotide sequence; B1, B2, B3 and B4 are each independently either nothing or each comprise an oligonucleotide B that comprises an oligonucleotide barcode sequence of 3, 4, 5, 6, 7, 8, 9, 10, 11, 12, 13, 14, 15, 16, 17, 18, 19 or 20 contiguous nucleotides, wherein in each of the plurality of oligonucleotide sequences B comprises a unique oligonucleotide sequence that uniquely identifies, as a paired combination, (i) the unique V oligonucleotide sequence and (ii) the unique J oligonucleotide sequence; and R is either nothing or comprises a restriction enzyme recognition site that comprises an oligonucleotide sequence that is absent from V, J, U1, U2, B1, B2, B3, and B4.

A large number of adaptive immune receptor variable (V) region and joining (J) region gene sequences are known as nucleotide and/or amino acid sequences, including non-rearranged genomic DNA sequences of TCR and Ig loci, and productively rearranged DNA sequences at such loci and their encoded products, and also including pseudogenes at these loci, and also including related orphons. See, e.g., U.S. application Ser. No. 13/217,126; U.S. application Ser. No. 12/794,507; PCT/US2011/026373; PCT/US2011/049012. These and other sequences known to the art may be used according to the present disclosure for the design and production of template oligonucleotides to be included in the presently provided template composition for standardizing amplification efficiency of an oligonucleotide primer set, and for the design and production of the oligonucleotide primer set that is capable of amplifying rearranged DNA encoding TCR or Ig polypeptide chains, which rearranged DNA may be present in a biological sample comprising lymphoid cell DNA.

In formula (I), V is a polynucleotide sequence of at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400 or 450 and not more than 1000, 900, 800, 700, 600 or 500 contiguous nucleotides of an adaptive immune receptor (e.g., TCR or BCR) variable (V) region gene sequence, or the complement thereof, and in each of the plurality of oligonucleotide sequences V comprises a unique oligonucleotide sequence. Genomic sequences for TCR and BCR V region genes of humans and other species are known and available from public databases such as Genbank; V region gene sequences include polynucleotide sequences that encode the products of expressed, rearranged TCR and BCR genes and also include polynucleotide sequences of pseudogenes that have been identified in the V region loci. The diverse V polynucleotide sequences that may be incorporated into the presently disclosed templates of general formula (I) may vary widely in length, in nucleotide composition (e.g., GC content), and in actual linear polynucleotide sequence, and are known, for example, to include "hot spots" or hypervariable regions that exhibit particular sequence diversity.

The polynucleotide V in general formula (I) (or its complement) includes sequences to which members of oligonucleotide primer sets specific for TCR or BCR genes can specifically anneal. Primer sets that are capable of amplifying rearranged DNA encoding a plurality of TCR or BCR are described, for example, in U.S. application Ser. No. 13/217, 126; U.S. application Ser. No. 12/794,507; PCT/US2011/026373; or PCT/US2011/049012; or the like; or as described therein may be designed to include oligonucleotide sequences that can specifically hybridize to each unique V gene and to each J gene in a particular TCR or BCR gene locus (e.g., TCR α, β, γ or δ, or IgH μ, γ, δ, α or ε, or IgL κ or λ). For example by way of illustration and not limitation, an oligonucleotide primer of an oligonucleotide primer amplification set that is capable of amplifying rearranged DNA encoding one or a plurality of TCR or BCR may typically include a nucleotide sequence of 15, 16, 17, 18, 19, 20, 21, 22, 23, 24, 25, 26, 27, 28, 29, 30, 31, 32, 33, 34, 35, 36, 37, 38, 39 or 40 contiguous nucleotides, or more, and may specifically anneal to a complementary sequence of 15, 16, 17, 18, 19, 20, 21, 22, 23, 24, 25, 26, 27, 28, 29, 30, 31, 32, 33, 34, 35, 36, 37, 38, 39 or 40 contiguous nucleotides of a V or a J polynucleotide as provided herein. In certain embodiments the primers may comprise at least 19, 20, 21, 22, 23, 24, 25, 26, 27, 28, 29 or 30 nucleotides, and in certain embodiment the primers may comprise sequences of no more than 15, 16, 17, 18, 19, 20, 21, 22, 23, 24, 25, 26, 27, 28, 29, 30, 31, 32, 33, 34, 35, 36, 37, 38, 39 or 40 contiguous nucleotides. Primers and primer annealing sites of other lengths are also expressly contemplated, as disclosed herein.

The entire polynucleotide sequence of each polynucleotide V in general formula (I) may, but need not, consist exclusively of contiguous nucleotides from each distinct V gene. For example and according to certain embodiments, in the template composition described herein, each polynucleotide V of formula (I) need only have at least a region comprising a unique V oligonucleotide sequence that is found in one V gene and to which a single V region primer in the primer set can specifically anneal. Thus, the V polynucleotide of formula (I) may comprise all or any prescribed portion (e.g., at least 15, 20, 30, 60, 90, 120, 150, 180 or 210 contiguous nucleotides, or any integer value therebetween) of a naturally occurring V gene sequence (including a V pseudogene sequence) so long as at least one unique V oligonucleotide sequence region (the primer annealing site) is included that is not included in any other template V polynucleotide.

It may be preferred in certain embodiments that the plurality of V polynucleotides that are present in the herein described template composition have lengths that simulate the overall lengths of known, naturally occurring V gene nucleotide sequences, even where the specific nucleotide sequences differ between the template V region and any naturally occurring V gene. The V region lengths in the herein described templates may differ from the lengths of naturally occurring V gene sequences by no more than 1, 2, 3, 4, 5, 6, 7, 8, 9, 10, 11, 12, 13, 14, 15, 16, 17, 18, 19 or 20 percent.

The V polynucleotide in formula (I) may thus, in certain embodiments, comprise a nucleotide sequence having a length that is the same or similar to that of the length of a typical V gene from its start codon to its CDR3 encoding region and may, but need not, include a nucleotide sequence that encodes the CDR3 region. CDR3 encoding nucleotide sequences and sequence lengths may vary considerably and have been characterized by several different numbering schemes (e.g., Lefranc, 1999 *The Immunologist* 7:132; Kabat et al., 1991 *In: Sequences of Proteins of Immunological Interest*, NIH Publication 91-3242; Chothia et al., 1987 *J. Mol. Biol.* 196:901; Chothia et al., 1989 *Nature* 342:877; Al-Lazikani et al., 1997 *J. Mol. Biol.* 273:927; see also, e.g., Rock et al., 1994 *J. Exp. Med.* 179:323; Saada et al., 2007 *Immunol. Cell Biol.* 85:323).

Briefly, the CDR3 region typically spans the polypeptide portion extending from a highly conserved cysteine residue (encoded by the trinucleotide codon TGY; Y=T or C) in the V segment to a highly conserved phenylalanine residue (encoded by TTY) in the J segment of TCRs, or to a highly conserved tryptophan (encoded by TGG) in IGH. More than 90% of natural, productive rearrangements in the TCRB locus have a CDR3 encoding length by this criterion of between 24 and 54 nucleotides, corresponding to between 9 and 17 encoded amino acids. The CDR3 lengths of the presently disclosed synthetic template oligonucleotides should, for any given TCR or BCR locus, fall within the same range as 95% of naturally occurring rearrangements. Thus, for example, in a herein described template composition for amplification factor determination, the CDR3 encoding portion of the V polynucleotide may have a length of from 24 to 54 nucleotides, including every integer therebetween. The numbering schemes for CDR3 encoding regions described above denote the positions of the conserved cysteine, phenylalanine and tryptophan codons, and these numbering schemes may also be applied to pseudogenes in which one or more codons encoding these conserved amino acids may have been replaced with a codon encoding a different amino acid. For pseudogenes which do not use these conserved amino acids, the CDR3 length may be defined relative to the corresponding position at which the conserved residue would have been observed absent the substitution, according to one of the established CDR3 sequence position numbering schemes referenced above.

It may also be preferred, in certain embodiments, that the plurality of V polynucleotides that are present in the herein described template composition have nucleotide compositions (e.g., percentage of GC content) that simulate the overall nucleotide compositions of known, naturally occurring V gene sequences, even where the specific nucleotide sequences differ. Such template V region nucleotide compositions may differ from the nucleotide compositions of naturally occurring V gene sequences by no more than 1, 2, 3, 4, 5, 6, 7, 8, 9, 10, 11, 12, 13, 14, 15, 16, 17, 18, 19 or 20 percent. Optionally and according to certain embodiments, the V polynucleotide of the herein described template oligonucleotide includes a stop codon at or near the 3' end of V in general formula (I).

In formula (I) J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of oligonucleotide sequences J comprises a unique oligonucleotide sequence.

The polynucleotide J in general formula (I) (or its complement) includes sequences to which members of oligonucleotide primer sets specific for TCR or BCR genes can specifically anneal. Primer sets that are capable of amplifying rearranged DNA encoding a plurality of TCR or BCR are described, for example, in U.S. application Ser. No. 13/217,126; U.S. application Ser. No. 12/794,507; PCT/US2011/026373; or PCT/US2011/049012; or the like; or as described therein may be designed to include oligonucleotide sequences that can specifically hybridize to each unique V gene and to each unique J gene in a particular TCR or BCR gene locus (e.g., TCR α, β, γ or δ, or IgH μ, γ, δ, α or ε, or IgL κ or λ).

The entire polynucleotide sequence of each polynucleotide J in general formula (I) may, but need not, consist exclusively of contiguous nucleotides from each distinct J gene. For example and according to certain embodiments, in the template composition described herein, each polynucleotide J of formula (I) need only have at least a region comprising a unique J oligonucleotide sequence that is found in one J gene and to which a single V region primer in the primer set can specifically anneal. Thus, the V polynucleotide of formula (I) may comprise all or any prescribed portion (e.g., at least 15, 20, 30, 60, 90, 120, 150, 180 or 210 contiguous nucleotides, or any integer value therebetween) of a naturally occurring V gene sequence (including a V pseudogene sequence) so long as at least one unique V oligonucleotide sequence region (the primer annealing site) is included that is not included in any other template J polynucleotide.

It may be preferred in certain embodiments that the plurality of J polynucleotides that are present in the herein described template composition have lengths that simulate the overall lengths of known, naturally occurring J gene nucleotide sequences, even where the specific nucleotide sequences differ between the template J region and any naturally occurring J gene. The J region lengths in the herein described templates may differ from the lengths of naturally occurring J gene sequences by no more than 1, 2, 3, 4, 5, 6, 7, 8, 9, 10, 11, 12, 13, 14, 15, 16, 17, 18, 19 or 20 percent.

The J polynucleotide in formula (I) may thus, in certain embodiments, comprise a nucleotide sequence having a length that is the same or similar to that of the length of a typical naturally occurring J gene and may, but need not, include a nucleotide sequence that encodes the CDR3 region, as discussed above.

Genomic sequences for TCR and BCR J region genes of humans and other species are known and available from public databases such as Genbank; J region gene sequences include polynucleotide sequences that encode the products of expressed and unexpressed rearranged TCR and BCR genes. The diverse J polynucleotide sequences that may be incorporated into the presently disclosed templates of general formula (I) may vary widely in length, in nucleotide composition (e.g., GC content), and in actual linear polynucleotide sequence.

Alternatives to the V and J sequences described herein, for use in construction of the herein described template oligonucleotides and/or V-segment and J-segment oligonucleotide primers, may be selected by a skilled person based on the present disclosure using knowledge in the art regarding published gene sequences for the V- and J-encoding regions of the genes for each TCR and Ig subunit. Reference Genbank entries for human adaptive immune receptor sequences include: TCRα: (TCRA/D): NC_000014.8 (chr14:22090057.23021075); TCRβ: (TCRB): NC_000007.13 (chr7:141998851.142510972); TCRγ: (TCRG): NC_000007.13 (chr7:38279625.38407656); immunoglobulin heavy chain, IgH (IGH): NC_000014.8 (chr14: 106032614.107288051); immunoglobulin light chain-kappa, IgLκ (IGK): NC_000002.11 (chr2: 89156874.90274235); and immunoglobulin light chain-lambda, IgLλ (IGL): NC_000022.10 (chr22: 22380474.23265085). Reference Genbank entries for mouse adaptive immune receptor loci sequences include: TCRβ: (TCRB): NC_000072.5 (chr6: 40841295.41508370), and immunoglobulin heavy chain, IgH (IGH): NC_000078.5 (chr12:114496979.117248165).

Template and primer design analyses and target site selection considerations can be performed, for example, using the OLIGO primer analysis software and/or the BLASTN 2.0.5 algorithm software (Altschul et al., *Nucleic Acids Res.* 1997, 25(17):3389-402), or other similar programs available in the art.

Accordingly, based on the present disclosure and in view of these known adaptive immune receptor gene sequences and oligonucleotide design methodologies, for inclusion in the instant template oligonucleotides those skilled in the art can design a plurality of V region-specific and J region-specific polynucleotide sequences that each independently contain oligonucleotide sequences that are unique to a given V and J gene, respectively. Similarly, from the present disclosure and in view of known adaptive immune receptor sequences, those skilled in the art can also design a primer set comprising a plurality of V region-specific and J region-specific oligonucleotide primers that are each independently capable of annealing to a specific sequence that is unique to a given V and J gene, respectively, whereby the plurality of primers is capable of amplifying substantially all V genes and substantially all J genes in a given adaptive immune receptor-encoding locus (e.g., a human TCR or IgH locus). Such primer sets permit generation, in multiplexed (e.g., using multiple forward and reverse primer pairs) PCR, of amplification products that have a first end that is encoded by a rearranged V region-encoding gene segment and a second end that is encoded by a J region-encoding gene segment.

Typically and in certain embodiments, such amplification products may include a CDR3-encoding sequence although the invention is not intended to be so limited and contemplates amplification products that do not include a CDR3-encoding sequence. The primers may be preferably designed to yield amplification products having sufficient portions of V and J sequences and/or of V-J barcode (B) sequences as described herein, such that by sequencing the products (amplicons), it is possible to identify on the basis of sequences that are unique to each gene segment (i) the particular V gene, and (ii) the particular J gene in the proximity of which the V gene underwent rearrangement to yield a functional adaptive immune receptor-encoding gene. Typically, and in preferred embodiments, the PCR amplification products will not be more than 600 base pairs in size, which according to non-limiting theory will exclude amplification products from non-rearranged adaptive immune receptor genes. In certain other preferred embodiments the amplification products will not be more than 500, 400, 300, 250, 200, 150, 125, 100, 90, 80, 70, 60, 50, 40, 30 or 20 base pairs in size, such as may advantageously provide rapid, high-throughput quantification of sequence-distinct amplicons by short sequence reads.

In certain preferred embodiments, the plurality of template oligonucleotides comprises at least one template oligonucleotide having an oligonucleotide sequence of general formula (I) to which each V-segment oligonucleotide primer can hybridize, preferably specifically hybridize, and at least one template oligonucleotide having an oligonucleotide sequence of general formula (I) to which each J-segment oligonucleotide primer can hybridize, preferably specifically hybridize.

In certain embodiments the plurality of template oligonucleotides comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51-100, 101-200, 201-300, 301-400, 401-500, 501-600, 601-700, 701-800, 801-900, 901-1000, 1001-1100, 1101-1200, 1201-1300, 1301-1400, 1401-1500, 1501-1600, 1601-1700, 1701-2000, or 2001-2500 unique oligonucleotide sequences.

In certain embodiments the composition comprises at least one template oligonucleotide for each unique V polynucleotide and at least one template oligonucleotide for each unique J polynucleotide. It will be appreciated that because the template oligonucleotides have a plurality of oligonucleotide sequences of general formula (I), which includes a V polynucleotide and which also includes a J polynucleotide, that the template composition may thus comprise fewer than (a×b) unique oligonucleotide sequences, but will in certain embodiments comprise at least the larger of a or b unique oligonucleotide sequences.

Accordingly, the composition may accommodate at least one occurrence of each unique V polynucleotide sequence and at least one occurrence of each unique J polynucleotide sequence, where in some instances the at least one occurrence of a particular unique V polynucleotide will be present in the same template oligonucleotide in which may be found the at least one occurrence of a particular unique J polynucleotide. Thus, for example, "at least one template oligonucleotide for each unique V polynucleotide and at least one template oligonucleotide for each unique J polynucleotide" may in certain instances refer to a single template oligonucleotide in which one unique V polynucleotide and one unique J polynucleotide are present.

As also disclosed elsewhere herein, in certain other preferred embodiments the template composition comprises at least one template oligonucleotide to which each oligonucleotide amplification primer in an amplification primer set can anneal. Hence, the composition may comprise fewer than a or b unique sequences, for example, where an amplification primer set may not include a unique primer for every possible V and/or J sequence.

It will be noted that certain embodiments contemplate a template composition for amplification factor determination, wherein the template composition comprises a plurality of template oligonucleotides having a plurality of oligonucleotide sequences of general formula 5'-U1-B1-V-B2-R-B3-J-B4-U2-3' (I) as described herein. According to these and related embodiments and as also described elsewhere herein, the set of oligonucleotide amplification primers that is capable of amplifying productively rearranged DNA may exclude any oligonucleotide primers that specifically hybridize to a V-region pseudogene or orphon or to a J-region pseudogene or orphon. Hence, in such embodiments the template composition will desirably exclude template oligonucleotides of general formula (I) in which unique V oligonucleotide sequences and/or unique J oligonucleotide sequences are sequences that are, respectively, unique to a V-region pseudogene or orphon or to a J-region pseudogene or orphon.

An exemplary TCRB template composition comprising 858 distinct template oligonucleotides is disclosed in the Sequence Listing in SEQ ID NOS:3157-4014. Another exemplary TCRB template composition comprising 871 distinct template oligonucleotides is disclosed in the Sequence Listing in SEQ ID NOS:1-871. Another exemplary TCRB template composition comprising 689 distinct template oligonucleotides is disclosed in the Sequence Listing in SEQ ID NOS:872-1560.

An exemplary TCRG template composition comprising 70 distinct template oligonucleotides is disclosed in the Sequence Listing in SEQ ID NOS:4015-4084. An exemplary TCRG template composition comprising 70 distinct template oligonucleotides is also disclosed in the Sequence Listing in SEQ ID NOS:1561-1630.

An exemplary IGH template composition comprising 1116 distinct template oligonucleotides is disclosed in the Sequence Listing in SEQ ID NOS:4085-5200. An exemplary IGH template composition comprising 1116 distinct template oligonucleotides is also disclosed in the Sequence Listing in SEQ ID NOS:1805-2920.

Also disclosed herein are exemplary sets of V and J polynucleotides for inclusion in the herein described template oligonucleotides having a plurality of oligonucleotide sequences of general formula (I). For TCRB, the plurality of template oligonucleotides may have a plurality of oligonucleotide sequences of general formula (I) in which polynucleotides V and J have the TCRB V and J sequences set forth in at least one set of 68 TCRB V and J SEQ ID NOS, respectively, as set forth in FIG. 5 as TCRB V/J set 1, TCRB V/J set 2, TCRB V/J set 3, TCRB V/J set 4, TCRB V/J set 5, TCRB V/J set 6, TCRB V/J set 7, TCRB V/J set 8, TCRB V/J set 9, TCRB V/J set 10, TCRB V/J set 11, TCRB V/J set 12 and TCRB V/J set 13.

For TCRG, the plurality of template oligonucleotides may have a plurality of oligonucleotide sequences of general formula (I) in which polynucleotides V and J have the TCRG V and J sequences set forth in at least one set of 14 TCRG V and J SEQ ID NOS, respectively, as set forth in FIG. 6 as TCRG V/J set 1, TCRG V/J set 2, TCRG V/J set 3, TCRG V/J set 4 and TCRG V/J set 5.

For IGH, the plurality of template oligonucleotides may have a plurality of oligonucleotide sequences of general formula (I) in which polynucleotides V and J have the IGH V and J sequences set forth in at least one set of 127 IGH V and J SEQ ID NOS, respectively, as set forth in FIG. 7 as IGH V/J set 1, IGH V/J set 2, IGH V/J set 3, IGH V/J set 4, IGH V/J set 5, IGH V/J set 6, IGH V/J set 7, IGH V/J set 8 and IGH V/J set 9.

ADAPTORS. The herein described template oligonucleotides of general formula (I) also may in certain embodiments comprise first (U1) and second (U2) universal adaptor oligonucleotide sequences, or may lack either or both of U1 and U2. U1 thus may comprise either nothing or an oligonucleotide having a sequence that is selected from (i) a first universal adaptor oligonucleotide sequence, and (ii) a first sequencing platform-specific oligonucleotide sequence that is linked to and positioned 5' to a first universal adaptor oligonucleotide sequence, and U2 may comprise either nothing or an oligonucleotide having a sequence that is selected from (i) a second universal adaptor oligonucleotide sequence, and (ii) a second sequencing platform-specific oligonucleotide sequence that is linked to and positioned 5' to a second universal adaptor oligonucleotide sequence.

U1 and/or U2 may, for example, comprise universal adaptor oligonucleotide sequences and/or sequencing platform-specific oligonucleotide sequences that are specific to a single-molecule sequencing technology being employed, for example the HiSeq™ or GeneAnalyzer™-2 (GA-2) systems (Illumina, Inc., San Diego, Calif.) or another suitable sequencing suite of instrumentation, reagents and software. Inclusion of such platform-specific adaptor sequences permits direct quantitative sequencing of the presently described template composition, which comprises a plurality of different template oligonucleotides of general formula (I), using a nucleotide sequencing methodology such as the HiSeq™ or GA2 or equivalent. This feature therefore advantageously permits qualitative and quantitative characterization of the template composition.

In particular, the ability to sequence all components of the template composition directly allows for verification that each template oligonucleotide in the plurality of template oligonucleotides is present in a substantially equimolar amount. For example, a set of the presently described template oligonucleotides may be generated that have universal adaptor sequences at both ends, so that the adaptor sequences can be used to further incorporate sequencing platform-specific oligonucleotides at each end of each template.

Without wishing to be bound by theory, platform-specific oligonucleotides may be added onto the ends of such modified templates using 5' (5'-platform sequence-universal adaptor-1 sequence-3') and 3' (5'-platform sequence-universal adaptor-2 sequence-3') oligonucleotides in as little as two cycles of denaturation, annealing and extension, so that the relative representation in the template composition of each of the component template oligonucleotides is not quantitatively altered. Unique identifier sequences (e.g., barcode sequences B comprising unique V and B oligonucleotide sequences that are associated with and thus identify, respectively, individual V and J regions, as described herein) are placed adjacent to the adaptor sequences, thus permitting quantitative sequencing in short sequence reads, in order to characterize the template population by the criterion of the relative amount of each unique template sequence that is present.

Where such direct quantitative sequencing indicates that one or more particular oligonucleotides may be over- or underrepresented in a preparation of the template composition, adjustment of the template composition can be made accordingly to obtain a template composition in which all oligonucleotides are present in substantially equimolar amounts. The template composition in which all oligonucleotides are present in substantially equimolar amounts may then be used as a calibration standard for amplification primer sets, such as in the presently disclosed methods for determining and correcting non-uniform amplification potential among members of a primer set.

In addition to adaptor sequences described in the Examples and included in the exemplary template sequences in the Sequence Listing (e.g., at the 5' and 3' ends of SEQ ID NOS:1-1630), other oligonucleotide sequences that may be used as universal adaptor sequences will be known to those familiar with the art in view of the present disclosure, including selection of adaptor oligonucleotide sequences that are distinct from sequences found in other portions of the herein described templates. Non-limiting examples of additional adaptor sequences are shown in Table 3 and set forth in SEQ ID NOS:1710-1731.

TABLE 3

Exemplary Adaptor Sequences

| Adaptor(primer) name | Sequence | SEQ ID NO: |
|---|---|---|
| T7 Promoter | AATACGACTCACTATAGG | 1710 |
| T7 Terminator | GCTAGTTATTGCTCAGCGG | 1711 |
| T3 | ATTAACCCTCACTAAAGG | 1712 |
| SP6 | GATTTAGGTGACACTATAG | 1713 |
| M13F(-21) | TGTAAAACGACGGCCAGT | 1714 |
| M13F(-40) | GTTTTCCCAGTCACGAC | 1715 |
| M13R Reverse | CAGGAAACAGCTATGACC | 1716 |
| AOX1 Forward | GACTGGTTCCAATTGACAAGC | 1717 |
| AOX1 Reverse | GCAAATGGCATTCTGACATCC | 1718 |
| pGEX Forward (GST 5, pGEX 5') | GGGCTGGCAAGCCACGTTTGGTG | 1719 |
| pGEX Reverse (GST 3, pGEX 3') | CCGGGAGCTGCATGTGTCAGAGG | 1720 |
| BGH Reverse | AACTAGAAGGCACAGTCGAGGC | 1721 |
| GFP (C' terminal, CFP, YFP or BFP) | CACTCTCGGCATGGACGAGC | 1722 |
| GFP Reverse | TGGTGCAGATGAACTTCAGG | 1723 |
| GAG | GTTCGACCCCGCCTCGATCC | 1724 |
| GAG Reverse | TGACACACATTCCACAGGGTC | 1725 |
| CYC1 Reverse | GCGTGAATGTAAGCGTGAC | 1726 |
| pFastBacF | 5'-d(GGATTATTCATACCGTCCCA)-3' | 1727 |
| pFastBacR | 5'-d(CAAATGTGGTATGGCTGATT)-3' | 1728 |
| pBAD Forward | 5'-d(ATGCCATAGCATTTTTATCC)-3' | 1729 |
| pBAD Reverse | 5'-d(GATTTAATCTGTATCAGG)-3' | 1730 |
| CMV-Forward | 5'-d(CGCAAATGGGCGGTAGGCGTG)-3' | 1731 |

BARCODES. As described herein, certain embodiments contemplate designing the template oligonucleotide sequences to contain short signature sequences that permit unambiguous identification of the template sequence, and hence of at least one primer responsible for amplifying that template, without having to sequence the entire amplification product. In the herein described template oligonucleotides of general formula (I), B1, B2, B3, and B4 are each independently either nothing or each comprises an oligonucleotide B that comprises an oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 or more contiguous nucleotides (including all integer values therebetween), wherein in each of the plurality of template oligonucleotide sequences B comprises a unique oligonucleotide sequence that uniquely identifies, as a paired combination, (i) the unique V oligonucleotide sequence of the template oligonucleotide and (ii) the unique J oligonucleotide sequence of the template oligonucleotide.

Thus, for instance, template oligonucleotides having barcode identifier sequences may permit relatively short amplification product sequence reads, such as barcode sequence reads of no more than 1000, 900, 800, 700, 600, 500, 400, 300, 200, 100, 90, 80, 70, 60, 55, 50, 45, 40, 35, 30, 25, 20, 19, 18, 17, 16, 15, 14, 13, 12, 11, 10, 9, 8, 7, 6, 5, 4 or fewer nucleotides, followed by matching this barcode sequence information to the associated V and J sequences that are incorporated into the template having the barcode as part of the template design. By this approach, a large number of amplification products can be simultaneously partially sequenced by high throughput parallel sequencing, to identify primers that are responsible for amplification bias in a complex primer set.

Exemplary barcodes may comprise a first barcode oligonucleotide of 5, 6, 7, 8, 9, 10, 11, 12, 13, 14, 15 or 16 nucleotides that uniquely identifies each V polynucleotide in the template and a second barcode oligonucleotide of 5, 6, 7, 8, 9, 10, 11, 12, 13, 14, 15 or 16 nucleotides that uniquely identifies each J polynucleotide in the template, to provide barcodes of, respectively, 10, 11, 12, 13, 14, 15, 16, 17, 18, 19, 20, 21, 22, 23, 24, 25, 26, 27, 28, 29, 30, 31 or 32 nucleotides in length, but these and related embodiments are not intended to be so limited. Barcode oligonucleotides may comprise oligonucleotide sequences of any length, so long as a minimum barcode length is obtained that precludes occurrence of a given barcode sequence in two or more template oligonucleotides having otherwise distinct sequences (e.g., V and J sequences).

Thus, the minimum barcode length, to avoid such redundancy amongst the barcodes that are used to uniquely identify different V-J sequence pairings, is X nucleotides, where $4^x$ is greater than the number of distinct template species that are to be differentiated on the basis of having non-identical sequences. For example, for the set of 871 template oligonucleotides set forth herein as SEQ ID NOS: 1-871, the minimum barcode length would be five nucleotides, which would permit a theoretical total of 1024 (i.e., greater than 871) different possible pentanucleotide sequences. In practice, barcode oligonucleotide sequence read lengths may be limited only by the sequence read-length limits of the nucleotide sequencing instrument to be employed. For certain embodiments, different barcode oligonucleotides that will distinguish individual species of template oligonucleotides should have at least two nucleotide mismatches (e.g., a minimum hamming distance of 2) when aligned to maximize the number of nucleotides that match at particular positions in the barcode oligonucleotide sequences.

In preferred embodiments, for each distinct template oligonucleotide species having a unique sequence within the template composition of general formula (I), B1, B2, B3, and B4 will be identical.

The skilled artisan will be familiar with the design, synthesis, and incorporation into a larger oligonucleotide or polynucleotide construct, of oligonucleotide barcode sequences of, for instance, at least 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 70, 80, 90, 100, 200, 300, 300, 500 or more contiguous nucleotides, including all integer values therebetween. For non-limiting examples of the design and implementation of oligonucleotide barcode sequence identification strategies, see, e.g., de Carcer et al., 2011 Adv. Env. Microbiol. 77:6310; Parameswaran et al., 2007 Nucl. Ac. Res. 35(19):330; Roh et al., 2010 Trends Biotechnol. 28:291.

Typically, barcodes are placed in templates at locations where they are not found naturally, i.e., barcodes comprise nucleotide sequences that are distinct from any naturally occurring oligonucleotide sequences that may be found in the vicinity of the sequences adjacent to which the barcodes are situated (e.g., V and/or J sequences). Such barcode sequences may be included, according to certain embodiments described herein, as elements B1, B2 and/or B3 of the presently disclosed template oligonucleotide of general formula (I). Accordingly, certain of the herein described template oligonucleotides of general formula (I) may also in certain embodiments comprise one, two or all three of barcodes B1, B2 and B3, while in certain other embodiments some or all of these barcodes may be absent. In certain embodiments all barcode sequences will have identical or similar GC content (e.g., differing in GC content by no more than 20%, or by no more than 19, 18, 17, 16, 15, 14, 13, 12, 11 or 10%).

In the template compositions according to certain herein disclosed embodiments the barcode-containing element B (e.g., B1, B2, B3, and/or B4) comprises the oligonucleotide sequence that uniquely identifies a single paired V-J combination. Optionally and in certain embodiments the barcode-containing element B may also include a random nucleotide, or a random polynucleotide sequence of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 70, 80, 90, 100, 200, 300, 300, 500 or more contiguous nucleotides, situated upstream and/or downstream of the specific barcode sequence that uniquely identifies each specific paired V-J combination. When present both upstream and downstream of the specific barcode sequence, the random nucleotide or random polynucleotide sequence are independent of one another, that is, they may but need not comprise the same nucleotide or the same polynucleotide sequence.

RESTRICTION ENZYME SITES. According to certain embodiments disclosed herein, the template oligonucleotide may comprise a restriction endonuclease (RE) recognition site that is situated between the V and J sequences and does not occur elsewhere in the template oligonucleotide sequence. The RE recognition site may optionally be adjacent to a barcode site that identifies the V region sequence. The RE site may be included for any of a number of purposes, including without limitation as a structural feature that may be exploited to destroy templates selectively by contacting them with the appropriate restriction enzyme. It may be desirable to degrade the present template oligonucleotides selectively by contacting them with a suitable RE, for example, to remove template oligonucleotides from other compositions into which they may have been deliberately or accidentally introduced. Alternatively, the RE site may be usefully exploited in the course of sequencing template oligonucleotides in the template composition, and/or as a positional sequence marker in a template oligonucleotide sequence regardless of whether or not it is cleaved with a restriction enzyme. An exemplary RE site is the oligonucleotide motif GTCGAC, which is recognized by the restriction enzyme Sal I. A large number of additional restriction enzymes and their respective RE recognition site sequences are known in the art and are available commercially (e.g., New England Biolabs, Beverly, Mass.). These include, for example, EcoRI (GAATTC) and SphI (GCATGC). Those familiar with the art will appreciate that any of a variety of such RE recognition sites may be incorporated into particular embodiments of the presently disclosed template oligonucleotides.

Sequencing

Sequencing may be performed using any of a variety of available high through-put single molecule sequencing machines and systems. Illustrative sequence systems include sequence-by-synthesis systems such as the Illumina Genome Analyzer and associated instruments (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.), or other systems having similar capabilities. Sequencing is achieved using a set of sequencing oligonucleotides that hybridize to a defined region within the amplified DNA molecules. The sequencing oligonucleotides are designed such that the V- and J-encoding gene segments can be uniquely identified by the sequences that are generated, based on the present disclosure and in view of known adaptive immune receptor gene sequences that appear in publicly available databases. See, e.g., U.S. application Ser. No. 13/217,126; U.S. application Ser. No. 12/794,507; PCT/US2011/026373; or PCT/US2011/049012. Exemplary TCRB J-region sequencing primers are set forth in Table 4:

TABLE 4

TCRBJ SEQUENCING PRIMERS

| PRIMER | SEQUENCE | SEQ ID NO: |
|---|---|---|
| >Jseq1-1 | ACAACTGTGAGTCTGGTGCCTTGTCCAAAGAAA | 1696 |
| >Jseq1-2 | ACAACGGTTAACCTGGTCCCCGAACCGAAGGTG | 1697 |
| >Jseq1-3 | ACAACAGTGAGCCAACTTCCCTCTCCAAAATAT | 1698 |
| >Jseq1-4 | AAGACAGAGAGCTGGGTTCCACTGCCAAAAAAC | 1699 |
| >Jseq1-5 | AGGATGGAGAGTCGAGTCCCATCACCAAAATGC | 1700 |

TABLE 4-continued

TCRBJ SEQUENCING PRIMERS

| PRIMER | SEQUENCE | SEQ ID NO: |
|---|---|---|
| >Jseq1-6 | GTCACAGTGAGCCTGGTCCCGTTCCCAAAGTGG | 1701 |
| >Jseq2-1 | AGCACGGTGAGCCGTGTCCCTGGCCCGAAGAAC | 1702 |
| >Jseq2-2 | AGTACGGTCAGCCTAGAGCCTTCTCCAAAAAAC | 1703 |
| >Jseq2-3 | AGCACTGTCAGCCGGGTGCCTGGGCCAAAATAC | 1704 |
| >Jseq2-4 | AGCACTGAGAGCCGGGTCCCGGCGCCGAAGTAC | 1705 |
| >Jseq2-5 | AGCACCAGGAGCCGCGTGCCTGGCCCGAAGTAC | 1706 |
| >Jseq2-6 | AGCACGGTCAGCCTGCTGCCGGCCCCGAAAGTC | 1707 |
| >Jseq2-7 | GTGACCGTGAGCCTGGTGCCCGGCCCGAAGTAC | 1708 |

In certain embodiments, the amplified J-region encoding gene segments may each have a unique sequence-defined identifier tag of 2, 3, 4, 5, 6, 7, 8, 9, 10 or about 15, 20 or more nucleotides, situated at a defined position relative to a RSS site. For example, a four-base tag may be used, in the Jβ-region encoding segment of amplified TCRβ CDR3-encoding regions, at positions +11 through +14 downstream from the RSS site. However, these and related embodiments need not be so limited and also contemplate other relatively short nucleotide sequence-defined identifier tags that may be detected in J-region encoding gene segments and defined based on their positions relative to an RSS site. These may vary between different adaptive immune receptor encoding loci.

Accordingly, the sequencing oligonucleotides may hybridize adjacent to a four base tag within the amplified J-encoding gene segments at positions+11 through +14 downstream of the RSS site. For example, sequencing oligonucleotides for TCRB may be designed to anneal to a consensus nucleotide motif observed just downstream of this "tag", so that the first four bases of a sequence read will uniquely identify the J-encoding gene segment (see, e.g., WO/2012/027503).

The average length of the CDR3-encoding region, for the TCR, defined as the nucleotides encoding the TCR polypeptide between the second conserved cysteine of the V segment and the conserved phenylalanine of the J segment, is 35+/−3 nucleotides. Accordingly and in certain embodiments, PCR amplification using V-segment oligonucleotide primers with J-segment oligonucleotide primers that start from the J segment tag of a particular TCR or IgH J region (e.g., TCR Jβ, TCR Jγ or IgH JH as described herein) will nearly always capture the complete V-D-J junction in a 50 base pair read. The average length of the IgH CDR3 region, defined as the nucleotides between the conserved cysteine in the V segment and the conserved phenylalanine in the J segment, is less constrained than at the TCRβ locus, but will typically be between about 10 and about 70 nucleotides. Accordingly and in certain embodiments, PCR amplification using V-segment oligonucleotide primers with J-segment oligonucleotide primers that start from the IgH J segment tag will capture the complete V-D-J junction in a 100 base pair read.

PCR primers that anneal to and support polynucleotide extension on mismatched template sequences are referred to as promiscuous primers. In certain embodiments, the TCR and Ig J-segment reverse PCR primers may be designed to minimize overlap with the sequencing oligonucleotides, in order to minimize promiscuous priming in the context of multiplex PCR. In one embodiment, the TCR and Ig J-segment reverse primers may be anchored at the 3' end by annealing to the consensus splice site motif, with minimal overlap of the sequencing primers. Generally, the TCR and Ig V and J-segment primers may be selected to operate in PCR at consistent annealing temperatures using known sequence/primer design and analysis programs under default parameters.

For the sequencing reaction, the exemplary IGHJ sequencing primers extend three nucleotides across the conserved CAG sequences as described in WO/2012/027503.

Amplification Factor Determination

Certain embodiments contemplate use of the herein described synthetic template compositions to determine amplification factors for estimating the number of rearranged adaptive immune receptor encoding sequences in a sample. These and related embodiments may find use to quantify the number of adaptive immune receptor encoding sequences in a DNA sample that has been obtained from lymphoid cells, including lymphoid cells that are present in a mixture of cells that comprises cells in which DNA encoding an adaptive immune receptor has undergone DNA rearrangement, but where the sample also contains DNA from cells in which no such rearrangement has taken place (e.g., non-lymphoid cells, immature lymphoid and/or non-lymphoid cells, mesenchymal cells, cancer cells, etc.).

The total number of different members of a given class of adaptive immune receptors (e.g., TCRs or IGs) in a subject may be estimated by multiplexed PCR using a comprehensive V-J amplification primer set followed by quantitative sequencing of amplification products. Multiplexed amplification and high throughput sequencing of rearranged TCR and BCR (IG) encoding DNA sequences are described, for example, in Robins et al., 2009 Blood 114, 4099; Robins et al., 2010 Sci. Translat. Med. 2:47ra64; Robins et al., 2011 J. Immunol. Meth. doi:10.1016/j.jim.2011.09. 001; Sherwood et al. 2011 Sci. Translat. Med. 3:90ra61; U.S. application Ser. No. 13/217,126 (US Pub. No. 2012/0058902), U.S. application Ser. No. 12/794,507 (US Pub. No. 2010/0330571), WO/2010/151416, WO/2011/106738 (PCT/US2011/026373), WO2012/027503 (PCT/US2011/049012), U.S. Application No. 61/550,311, and U.S. Application No. 61/569,118.

This methodology typically involves sampling DNA from a subpopulation of lymphoid cells, such as lymphoid cells that are present in a blood sample, which is known also to contain nucleated cells that lack rearranged TCR or IG encoding DNA. The present compositions and methods may permit improved accuracy and precision in the determination of the number of rearranged TCR and IG encoding DNA molecules in such a sample. As described herein, for instance, by "spiking" (adding into) the DNA sample with the present template composition, an internal amplification template standard is provided for assessing the relative efficiencies across the range of oligonucleotide primers that are present in the multiplexed amplification primer set. By so assessing the amplification products of the present artificial template composition, which is added to the amplification reaction in known amounts, an amplification factor (e.g., a multiplicative, normalizing, scaling or geometric factor, etc.) can be determined for the oligonucleotide amplification primer set and can then be used to calculate the number of natural DNA templates in the sample.

As another example, these and related embodiments permit quantification of Minimal Residual Disease (MRD) in lymphoma or leukemia, by quantitative detection of rearranged TCR or IG encoding DNA in samples obtained from mixed preparations of lymphoid and non-lymphoid cells, including persistent lymphoma or leukemia cells. Prior methods determine MRD as the number of malignant cells that are detectable as a proportion of the total number of cells in a sample. In contrast, the present methods permit estimation of the total number of cells in a sample that have rearranged TCR or IG encoding DNA, so that malignant cells (e.g., those having a particular TCR or IG rearrangement, such as a clonotype) can be quantified as a proportion of such rearranged cells instead of as a proportion of all cells. By way of non-limiting theory, it is believed that because the representation of all rearranged cells in a clinical sample from a subject having or suspected of having MRD is typically very low, the present methods will dramatically improve the sensitivity with which MRD can be detected, including improving such sensitivity by increasing the signal-to-noise ratio.

Accordingly certain embodiments thus provide a method for quantifying rearranged DNA molecules encoding one or a plurality of adaptive immune receptors in a biological sample that comprises DNA from lymphoid cells of a subject, each adaptive immune receptor comprising a variable region and a joining region. Briefly, the method comprises the steps of:

(A) in a multiplexed amplification reaction using the herein described oligonucleotide amplification primer set that is capable of amplifying substantially all V-J encoding combinations for a given adaptive immune receptor, amplifying DNA from the sample to which has been added a known amount of the herein described template composition for amplification factor determination, to obtain amplification products;

(B) quantitatively sequencing the amplification products of (A) to quantify (i) template amplification products, which are amplification products of the herein described template composition and will be identifiable because they contain at least one barcode oligonucleotide sequence, and (ii) amplification products of rearranged adaptive immune receptor encoding DNA sequences in the sample, which will be identifiable because they contain specific V and J sequences but lack an oligonucleotide barcode sequence;

(C) calculating an amplification factor based on quantitative information obtained in step (B); and (D) using the amplification factor of (C) to determine, by calculation, the number of unique adaptive immune receptor encoding DNA molecules in the sample.

Without wishing to be bound by theory, according to these and related methods, the number of rearranged TCR or IG encoding DNA molecules that are sampled in a multiplexed amplification reaction is measured. To do so, a sequence coverage value, e.g., the number of output sequence reads that are determined for each input (template) molecule, is determined and averaged across the entire number of different template oligonucleotides that are present, to obtain an average sequence coverage value. By dividing (i) the number of reads that are obtained for a given sequence by (ii) the average sequence coverage value, the number of rearranged molecules that are present as templates at the start of the amplification reaction can be calculated.

Thus, for example, to calculate the sequence coverage value, a known quantity of a set of synthetic molecules of the presently disclosed template composition is added to each PCR amplification, the synthetic templates having the basic structure of formula (I) 5' U-B1-V-B2-R-(B3)-J-B4-U 3' where each V is a 300 base pair segment having a sequence that matches a TCR or IG V gene sequence and J is a 100 base pair segment having a sequence that matches a TCR or IG J gene. B2 is a unique barcode oligonucleotide sequence that uniquely identifies each VJ pair and that also differentiates amplification products of the synthetic DNA templates (which will contain the barcode sequence) from amplification products of naturally occurring biologic template DNA molecules that are contributed by the lymphoid DNA sample (which will lack the barcode sequence). In this example, B3 of formula (I) is nothing. After PCR amplification and sequencing, the numbers of each sequenced synthetic molecule (i.e., amplification products containing the barcode sequence) are counted. The sequence coverage of the synthetic molecules is then calculated based on the known number of starting synthetic template molecules used to spike the amplification reaction.

For example, a pool of 5000 synthetic, barcode-containing template molecules comprising 4-5 copies each of 1100 unique synthetic template oligonucleotide sequences (representing every possible VJ pair) may be added to the amplification reaction. If the amplification products include 50,000 sequences that match the synthetic template molecules, a sequence coverage value of 10× has been obtained and the amplification factor is 10. To estimate the number of natural VDJ-rearranged template molecules in the DNA obtained from the sample, the number of amplification products of the natural templates (i.e., amplification products that lack any barcode sequence) is then divided by the amplification factor. For added accuracy, because in this example the 5000 synthetic molecules are a complex pool of 1100 molecules representing every VJ pair, the amplification factor for every VJ pair can be individually calculated. The amplification factor can then be averaged across all of the synthetic molecules (FIG. 7). The accuracy and robustness of the method are shown in FIG. 8 and details are described below in Example 2.

Accordingly, in these embodiments the method comprises:

(A) amplifying DNA in a multiplex polymerase chain reaction (PCR) that comprises: (1) DNA from the biological sample that comprises lymphoid cells of the subject, (2) the template composition for amplification factor determination of general formula (I) as described herein, in which a known number of each of the plurality of template oligonucleotides having a unique oligonucleotide sequence is present, (3) an oligonucleotide amplification primer set that is capable of amplifying rearranged DNA encoding one or a plurality of adaptive immune receptors in the DNA from the biological sample, the primer set comprising: (a) in substantially equimolar amounts, a plurality of V-segment oligonucleotide primers that are each independently capable of specifically hybridizing to at least one polynucleotide encoding an adaptive immune receptor V-region polypeptide or to the complement thereof, wherein each V-segment primer comprises a nucleotide sequence of at least 15 contiguous nucleotides that is complementary to at least one functional adaptive immune receptor V region-encoding gene segment and wherein the plurality of V-segment primers specifically hybridize to substantially all functional adaptive immune receptor V region-encoding gene segments that are present in the template composition, and (b) in substantially equimolar amounts, a plurality of J-segment oligonucleotide primers that are each independently capable of specifically hybridizing to at least one polynucleotide encoding an adaptive immune receptor J-region polypeptide or to the complement thereof, wherein each J-segment primer comprises a nucleotide sequence of at least 15 contiguous nucleotides that is complementary to at least one functional adaptive immune receptor J region-encoding gene segment and wherein the plurality of J-segment primers specifically hybridize to substantially all functional adaptive immune receptor J region-encoding gene segments that are present in the template composition, wherein the V-segment and J-segment oligonucleotide primers are capable of promoting amplification in said multiplex polymerase chain reaction (PCR) of (i) substantially all template oligonucleotides in the template composition to produce a multiplicity of amplified template DNA molecules, said multiplicity of amplified template DNA molecules being sufficient to quantify diversity of the template oligonucleotides in the template composition, and (ii) substantially all rearranged DNA molecules encoding adaptive immune receptors in the biological sample to produce a multiplicity of amplified rearranged DNA molecules, said multiplicity of amplified rearranged DNA molecules being sufficient to quantify diversity of the rearranged DNA molecules in the DNA from the biological sample, and wherein each amplified DNA molecule in the multiplicity of amplified template DNA molecules and in the multiplicity of amplified rearranged DNA molecules is less than 1000, 900, 800, 700, 600, 500, 400, 300, 200, 100, 90, 80 or 70 nucleotides in length;

(B) quantitatively sequencing all or a sufficient portion of each of said amplified template DNA molecules and each of said amplified rearranged DNA molecules to quantify (i) a template product number of amplified template DNA molecules which contain at least one oligonucleotide barcode sequence, and (ii) a rearranged product number of amplified rearranged DNA molecules which lack an oligonucleotide barcode sequence;

(C) calculating an amplification factor by dividing the template product number of (B)(i) by the known number of each of the plurality of template oligonucleotides having a unique oligonucleotide sequence of (A)(2); and (D) dividing the rearranged product number of (B)(ii) by the amplification factor calculated in (C) to quantify unique adaptive immune receptor encoding DNA molecules in the sample.

The contemplated embodiments are not intended to be limited to the above described method, such that from the present disclosure the skilled person will appreciate variations that may be employed. An alternative approach, for example, may not use the herein described synthetic template composition as a spiked-in control template in multiplexed PCR amplification of a DNA sample that contains rearranged lymphoid cell TCR and/or IG encoding DNA as well as non-rearranged DNA. Instead, according to one such alternative, to the amplification reaction using V and J amplification primers may be added a known set of oligonucleotide amplification primers that amplify a distinct, highly conserved genomic sequence region. These genomic control primers may amplify every genome that is present in the DNA sample regardless of whether or not it contains rearranged TCR and/or IG encoding sequences, whereas the V and J primers may amplify products only from genomes with a rearranged VDJ region. The ratio between these two classes of amplification product molecules permits estimation of the total number of B cell genomes in the sample.

It is further contemplated for these and related embodiments of any of the herein described methods that such a method may further comprise sequencing the amplified adaptive immune receptor encoding DNA molecules that are produced. Compositions and methods for the sequencing of rearranged adaptive immune receptor gene sequences and for adaptive immune receptor clonotype determination are described in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. application Ser. No. 13/217,126 (US Pub. No. 2012/0058902), U.S. application Ser. No. 12/794,507 (US Pub. No. 2010/0330571), WO/2010/151416, WO/2011/106738 (PCT/US2011/026373), WO2012/027503 (PCT/US2011/049012), U.S. Application No. 61/550,311, and U.S. Application No. 61/569,118, herein incorporated by reference. Therein can also be found details regarding sequencing PCR amplification products, processing sequencing data, and uses of measurements of adaptive immune receptor diversity, all of which which may be employed for use according to the methods described herein.

According to non-limiting theory, these embodiments exploit current understanding in the art (also described above) that once an adaptive immune cell (e.g., a T or B lymphocyte) has rearranged its adaptive immune receptor-encoding (e.g., TCR or Ig) genes, its progeny cells possess the same adaptive immune receptor-encoding gene rearrangement, thus giving rise to a clonal population that can be uniquely identified by the presence therein of rearranged CDR3-encoding V- and J-gene segments that may be amplified by a specific pairwise combination of V- and J-specific oligonucleotide primers as herein disclosed.

The practice of certain embodiments of the present invention will employ, unless indicated specifically to the contrary, conventional methods in microbiology, molecular biology, biochemistry, molecular genetics, cell biology, virology and immunology techniques that are within the skill of the art, and reference to several of which is made below for the purpose of illustration. Such techniques are explained fully in the literature. See, e.g., Sambrook, et al., *Molecular Cloning: A Laboratory Manual* ($3^{rd}$ Edition, 2001); Sambrook, et al., *Molecular Cloning: A Laboratory Manual* ($2^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols* (*Methods in Molecular Biology*) (Park, Ed., $3^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Computer System

FIG. 12 is a high-level block diagram illustrating a functional view of a typical computer system 1200, according to an embodiment of the invention. Illustrated are at least one processor 1202 coupled to a bus 1204. Also coupled to the bus 1204 are a memory 1206, a storage device 1208, a keyboard 1210, a graphics adapter 1212, a pointing device 1214, and a network adapter 1216. A display 1218 is coupled to the graphics adapter 1212.

The processor 1202 may be any general-purpose processor such as an INTEL x86, SUN MICROSYSTEMS SPARC, or POWERPC compatible-CPU. The storage device 1208 is, in one embodiment, a hard disk drive but can also be any other device capable of storing data, such as a writeable compact disk (CD) or DVD, or a solid-state memory device. The memory 1206 may be, for example, firmware, read-only memory (ROM), non-volatile random access memory (NVRAM), and/or RAM, and holds instructions and data used by the processor 202. The pointing device 1214 may be a mouse, track ball, or other type of pointing device, and is used in combination with the keyboard 1210 to input data into the computer system 1200. The graphics adapter 1212 displays images and other information on the display 1218. The network adapter 1216 couples the computer system 1200 to the network.

As is known in the art, the computer system 1200 is adapted to execute computer program modules. As used herein, the term "module" refers to computer program logic and/or data for providing the specified functionality. A module can be implemented in hardware, firmware, and/or software. In one embodiment, the modules are stored on the storage device 1208, loaded into the memory 1206, and executed by the processor 1202. The various methods and steps illustrated herein may be executed by the components of the computer system 1200.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Embodiments of the invention may also relate to a computer data signal embodied in a carrier wave, where the computer data signal includes any embodiment of a computer program product or other data combination described herein. The computer data signal is a product that is presented in a tangible medium or carrier wave and modulated or otherwise encoded in the carrier wave, which is tangible, and transmitted according to any suitable transmission method.

Additionally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

Unless the context requires otherwise, throughout the present specification and claims, the word "comprise" and variations thereof, such as, "comprises" and "comprising" are to be construed in an open, inclusive sense, that is, as "including, but not limited to". By "consisting of" is meant including, and typically limited to, whatever follows the phrase "consisting of" By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

EXAMPLES

Example 1

Characterization of T Cell Clonality and MRD Detection in T-ALL Samples

In this example, paired blood samples of pediatric T-cell acute lymphoblastic leukemia (T-ALL) from 43 patients (Children's Oncology Group AALL0434) were obtained at diagnosis and at day 29 post-induction therapy. The complementarity determining region (CDR3) encoding regions of TCRB and TCRG genes were sequenced for all 86 specimens by high-throughput sequencing (HTS) using an Illumina GA2 platform (Illumina, San Diego, Calif.) as previously described (see Robins et al., *Blood*, 114(19):4099-4107, 2009; and Robins et al., *Sci Transl Med.* 3(90):90ra61, 2011). Pre-treatment samples were used to identify unique rearranged TCR CDR3-encoding DNA sequences for the leukemic clone, and post-treatment samples were assessed for the frequency of each rearranged TCR CDR3-encoding DNA sequence as a percentage of the total. The frequency of each rearranged TCR CDR3-encoding DNA sequence was also enumerated in post-treatment samples from all other patients to evaluate specificity. These results were compared to MRD results obtained by 9-color flow cytometry, per trial protocol.

Thirty-one of 43 pre-treatment samples (72.1%) had a detectable clonal T-cell population based on TCRB sequence analysis, and 27 of these also had a detectable clonal TCRG sequence. Five samples exhibited an additional unique rearranged TCRG CDR3-encoding sequence, consistent either with rearrangement of both TCRG loci or with the presence of two clonal subpopulations. Five of 12 cases without a detectable clonal TCRB gene sequence had the immunophenotype of early thymic precursor (ETP) T-ALL, consistent with their bearing only unrearranged germline TCRB and TCRG genes. No other cases were ETP. Six of the 12 cases without a detectable clonal TCRB gene sequence had the immunophenotype of near early thymic precursor (n-ETP) T-ALL. The remaining sample without a detectable clonal TCRB gene sequence, did have a detectable clonal TCRG gene sequence. By contrast, of the 31 cases in which a clonal TCRB rearrangement was identified at diagnosis, no cases were ETP, three were near-ETP, and the remaining 28 were non-ETP T-ALL immunophenotype. In this cohort, there was an association of the absence of a complete, clonal TCRB sequence in the pre-treatment sample with either ETP or near-ETP immunophenotype by mpFC (p<0.0001, Fischer's exact test).

Figure 1:
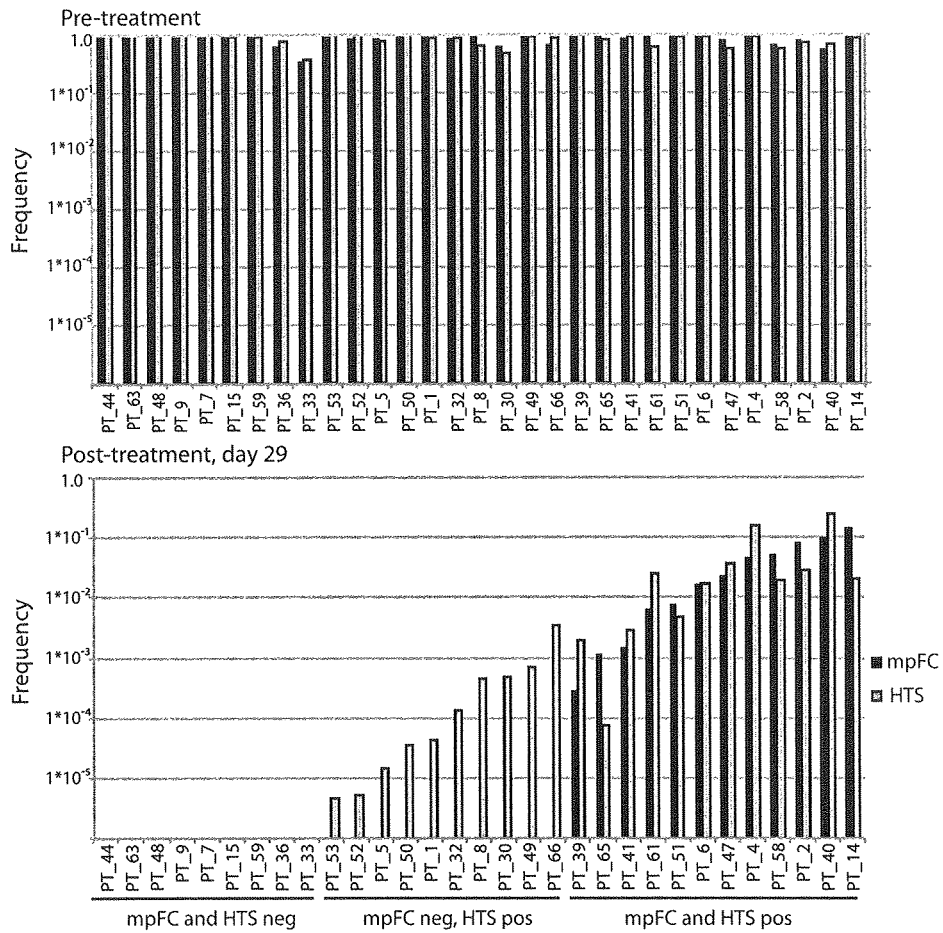
FIG. 1 (FIG. 1A-1B) depicts comparison of T-cell clonality assessment in blood samples from T-ALL patients, by high-throughput sequencing (HTS) and multi-parametric flow cytometry (mpFC), prior to treatment (Day 0) and 29 days after treatment (Day 29). Clones detected by HTS (red) were found in all 12 informative post-treatment samples that were positive for MRD by mpFC (blue), as well as at a lower level in 10 additional patients, suggesting superior sensitivity for HTS versus mpFC. Patients 39 and 52 were near-early thymic precursor (nETP) immunophenotype; all others were typical T-cell acute lymphoblastic leukemia (T-ALL).

The remaining 37 samples with a detectable clonal TCR sequence prior to treatment were used to compare mpFlow with HTS. High-throughput sequencing used to detect the patient's original clonal TCRB sequences at day 29 revealed three sub-groups of patients in this cohort: 1) those for whom MRD was not detected by either HTS or mpFC, 9 cases; 2) those for whom MRD was detected only by HTS but not mpFC, 10 cases; and 3) those in which MRD was detected by both HTS and mpFC, 12 cases (FIG. 1B). Of the ten cases for which HTS did and mpFC did not detect MRD, the MRD was 10 to 100-fold lower than for the 12 cases for which both mpFC and HTS detected MRD. These results suggested that HTS offered superior sensitivity MRD detection. The background sequence frequencies were very low (0-$10^{-5}$) in other patient post-treatment samples, being slightly higher for TCRG than for TCRB, consistent with germline sequence diversity. The strong association of ETP status with the lack of a detectable clonal TCR sequence by HTS at diagnosis also suggested the utility of TCR HTS for identifying this poor outcome subset of T-ALL.

Materials and Methods

Sample preparation. Blood (5 ml samples) was collected prior to treatment (Day 0) and 29 days following initial treatment (Day 29) from 43 individuals diagnosed with T-ALL. Collected blood was subdivided into a sample for TCR high-throughput sequencing (HTS) and a sample for mpFC flow cytometric analysis. Samples were blind-coded and submitted for HTS. All patients provided consent for the use of their samples as part of the COG trial.

Flow cytometry. Multi-parametric, 9-color flow cytometry (mpFC) was performed at the University of Washington (Seattle, Wash.) as part of the routine evaluation for MRD (17). Flow data were reviewed, with samples being classified as early-thymic precursor (ETP), or non-ETP T-ALL, as previously described (15). Cases in which the immunophenotype was similar but not sufficient to meet criteria for ETP were designated as near-ETP (nETP). Data were analyzed using Woodlist software version 2.7 (B. Wood, Univ. of Washington, Seattle, Wash.). Results are reported as lymphoblast percent of total T cells, total mononuclear cells and total cellularity for comparison with molecular studies.

High-throughput sequencing (HTS)/Sequencing CDR3 regions: TCRG and TCRB CDR3 regions were amplified and sequenced from 400 ng of Day 0 and 1200 ng of Day 29 samples, or all remaining sample of extracted DNA. Amplification and sequencing of TCRβ CDR3 regions was carried out as previously described (9) and amplification and sequencing of TCRG CDR3 regions was carried as previously described (11). The sequences for both the TCRβ and TCRγ CDR3 region were delineated according to the definition established by the International ImMunoGeneTics collaboration (18). Sequences that did not match CDR3 sequences were removed from the analysis. A standard algorithm was used to identify which V, D, and J segments contributed to each TCRβ CDR3 sequence and which V and J segments contributed to each TCRγ CDR3 sequence (18). Rearranged CDR3 sequences were classified as non-productive if insertions or deletions that resulted in frame-shifts or premature stop-codons were identified.

Identifying CDR3 sequences: Ten mL of blood were isolated from six healthy controls. Peripheral blood mononuclear cells (PBMC) were isolated, DNA extracted, and 1200 ng of extracted DNA was used to amplify TCRB sequences using the same protocol as the day 29 T-ALL samples. The frequency of the most common αβ T cell reactive clones in PBMC from these healthy individuals averaged 3% of the total repertoire with a standard deviation of 3%. Given that αβ T cells carried both rearranged TCRG and TCRB chain CDR3 encoding sequences (11), both the frequencies of the highest copy TCRB and TCRG CDR3 chains were assumed to represent the neoplastic T lymphoblasts. At day 0, samples with ten-fold higher frequency of the most common CDR3 sequences as compared to controls, >30%, were considered to be the clonal population. For samples in which the two most common TCR sequences were of comparable frequency, both sequences were considered as being the probable cancer clone. MRD at 29 days after treatment was screened by searching for CDR3 sequences that identically matched the clonal sequence identified at day 0, requiring a 60 base pair match. Both the presence and the frequency of the MRD relative to the total TCR repertoire were noted. To determine if the clonal sequence was specific, all day 29 samples were screened for the presence and frequency of all identified clonal TCR CDR3 sequences to determine cross-patient specificity.

Results

Using 43 matched-pairs of T-ALL samples derived from patients enrolled in the Children's Oncology Group AALL0434 trial (University of Washington, Seattle, Wash.), the complementarity determining regions (CDR3) of TCRB (Table 5) and TCRG (Tables 5 and 6) were sequenced by HTS using approximately 75,000 genomes on day 0 and 150,000 genomes on day 29. These day 0 sequences permitted definition, for each patient, of the unique recombined TCR gene sequences representing each patient's clonal, neoplastic T lymphoblasts (Tables 5 and 6). Normalized mpFC (blast/CD7+ cells) data are also shown in Tables 5 and 6.

TABLE 5

% of T cells that were Blasts at Day 0 and Day 29: Characterization by mpFC and HTS of TCRB

| Patient | Day 0 Blast/T cells mpFC | Day 0 TCRB HTS | Day 29 Blast/T cells by mpFC | Day29 TCRB HTS |
|---|---|---|---|---|
| PT_44 | 0.97672065 | 0.99434804 | 0 | 0 |
| PT_63 | 0.971875 | 0.99433591 | 0 | 0 |
| PT_48 | 0.98097252 | 0.98802835 | 0 | 0 |
| PT_9 | 0.97037794 | 0.98506196 | 0 | 0 |
| PT_7 | 0.9726997 | 0.98471692 | 0 | 0 |
| PT_15 | 0.97247706 | 0.96641846 | 0 | 0 |
| PT_59 | 0.92966361 | 0.93608697 | 0 | 0 |
| PT_36 | 0.63565891 | 0.77634724 | 0 | 0 |
| PT_33 | 0.36514523 | 0.38978913 | 0 | 0 |
| PT_53 | 0.96843177 | 0.98636256 | 0 | 4.6305E-06 |
| PT_52 | 0.87757202 | 0.97285037 | 0 | 5.0976E-06 |
| PT_5 | 0.88681319 | 0.80910921 | 0 | 1.4101E-05 |
| PT_50 | 0.98088531 | 0.99470926 | 0 | 3.4997E-05 |
| PT_1 | 0.93128964 | 0.86986261 | 0 | 4.4024E-05 |
| PT_32 | 0.87001287 | 0.89047715 | 0 | 0.00013614 |
| PT_8 | 0.97985901 | 0.63830248 | 0 | 0.0004481 |
| PT_30 | 0.67403315 | 0.48984069 | 0 | 0.00048091 |
| PT_49 | 0.94558522 | 0.93357269 | 0 | 0.00070619 |
| PT_66 | 0.71351351 | 0.86920201 | 0 | 0.00348305 |
| PT_39 | 1 | 0.98803323 | 0.0002907 | 0.00201475 |
| PT_65 | 0.9563795 | 0.84025047 | 0.00114679 | 7.6499E-05 |
| PT_41 | 0.90253807 | 0.92867626 | 0.00152838 | 0.00292659 |
| PT_61 | 0.93349456 | 0.62550401 | 0.00653266 | 0.02535341 |
| PT_51 | 0.95571576 | 0.94895541 | 0.00797546 | 0.0047952 |
| PT_6 | 0.98189135 | 0.95963063 | 0.01690647 | 0.01741715 |
| PT_47 | 0.83670295 | 0.58431047 | 0.02276786 | 0.03573035 |
| PT_4 | 0.99295775 | 0.96190309 | 0.04795737 | 0.1614654 |
| PT_58 | 0.68115942 | 0.58647625 | 0.05369128 | 0.01921525 |
| PT_2 | 0.81477516 | 0.74794199 | 0.08156607 | 0.02893032 |
| PT_40 | 0.5815508 | 0.70912279 | 0.0990566 | 0.2422609 |
| PT_14 | 0.91898148 | 0.88730182 | 0.14479026 | 0.02124786 |
| PT_55 | 0.98183653 | 0.12006615 | 0.43255814 | 0 |
| PT_57 | 0.95523906 | 0.02088572 | 0.6459144 | 0 |
| PT_3 | 0.98694779 | 0.01755708 | 0.00202703 | 0 |
| PT_12 | 0.89263804 | 0.01493205 | 0.05456989 | 0 |
| PT_54 | 0.97082495 | 0.09110046 | 0.069869 | 0.28020422 |
| PT_45 | 0.99296482 | 0.07754443 | 0.2345679 | 0 |
| PT_60 | 0.90118153 | 0.03709322 | 0.05792683 | 0 |
| PT_68 | 0.9874477 | 0.02719658 | 0.00849858 | 0.0424174 |
| PT_56 | 0.86721144 | 0.01765149 | 0.1245283 | 0.0053763 |
| PT_13 | 0.95947426 | 0.06090199 | 0.76954315 | 0 |
| PT_42 | 0.91920252 | 0.08504223 | 0.0019544 | 0.01346556 |
| PT_11 | 0.96177686 | 0.00694597 | 0 | 0 |
| AVG ETP | | | 0.18478833 | |
| AVG other | | | 0.01613064 | |
| AVG All | | | 0.06712017 | |

Figure 2:
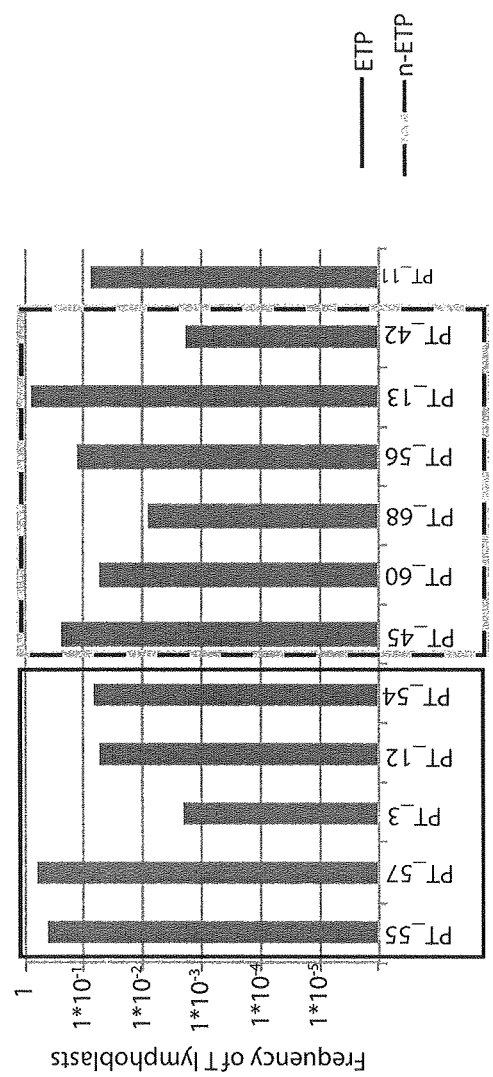
FIG. 2 shows MRD detection in early thymic precursor (ETP) or near-ETP (nETP) cases at day 29. All cases (5/5) designated early-thymic precursor ETP (yellow), and most cases (6/8) designated near-ETP (nETP, green) lacked a clonal, complete TCRB gene rearrangement at day 0, as assessed by HTS of amplified and rearranged TCRβ CDR3-encoding DNA regions. These cases, however, had MRD detectable by mpFC.
Figure 3:
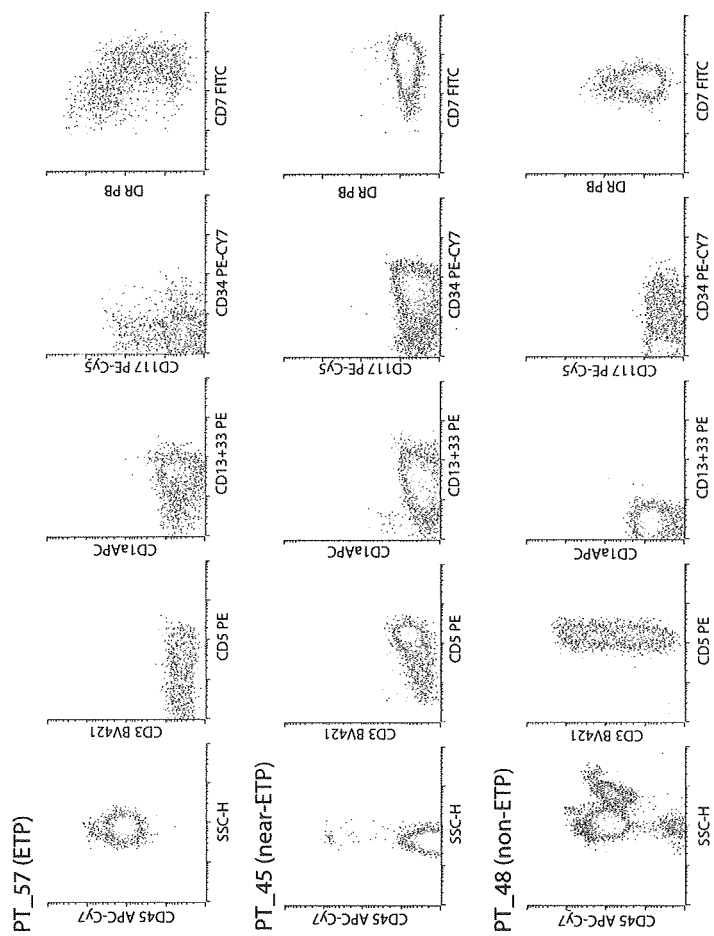
FIG. 3 shows representative T-ALL immunophenotypes as characterized by mpFC of ETP sub-type (top row), near-ETP subtype (middle row) and typical ALL/non-ETP subtype (bottom row). T lymphoblast populations are shown in teal. Reported criteria for ETP immunophenotype were used (5). Five of 43 cases had an ETP immunophenotype. Eight of 43 cases had a near-ETP immunophenotype. The other 30 cases were typical T-ALL and were neither ETP nor near-ETP.

Samples PT_13, 39, 42, 45, 56, 60 and 68 were classified as ETP.
Samples PT_3, 12, 54, 55 and 57 were classified as nETP (FIGS. 2 and 3).

TABLE 6

% of T cells that were Blasts at Day 0 and Day 29 Characterization by mpFC and HTS of TCRB/TCRG

| | Day 0 | | | Day 29 | | |
| | mpFC | HTS | | mpFC | HTS | |
| Sample | Blast/T cells | TCRB | TCRG | Blast/T cells | TCRB | TCRG |
|---|---|---|---|---|---|---|
| 1 | 0.931289641 | 0.869862606 | 52.5254048 | 0 | 4.4024E-05 | 0.03937815 |
| 2 | 0.814775161 | 0.747941989 | 82.3288372 | 0.08156607 | 0.02893032 | 4.63888072 |
| 3 | 0.986947791 | 0.017557079 | 12.3924143 | 0.00202703 | 0 | |
| 4 | 0.992957746 | 0.961903091 | 54.7257337 | 0.04795737 | 0.1614654 | 7.45339935 |
| 5 | 0.886813187 | 0.809100213 | 41.6389335 | 0 | 1.4101E-05 | 0.01490627 |
| 6 | 0.981891348 | 0.95963063 | 58.557176 | 0 | 0.01420907 | 1.25544372 |
| 7 | 0.972699697 | 0.984716924 | 0.59258927 | 0 | 0 | 0 |
| 8 | 0.979859013 | 0.638302477 | 70.6051915 | 0 | 0.0004481 | 0 |
| 9 | 0.970377937 | 0.98506196 | 50 | 0 | 0 | 0 |
| 11 | 0.96177686 | 0.006945971 | 94.6793227 | 0 | 0 | 19.9611535 |
| 12 | 0.892638037 | 0.014932055 | 4.16576441 | 0.05456989 | 0 | |
| 13 | 0.959474261 | 0.050950488 | 0.05179646 | 0.76954315 | 0 | |

TABLE 6-continued

% of T cells that were Blasts at Day 0 and Day 29
Characterization by mpFC and HTS of TCRB/TCRG

| | Day 0 | | | Day 29 | | |
|---|---|---|---|---|---|---|
| | mpFC | HTS | | mpFC | HTS | |
| Sample | Blast/T cells | TCRB | TCRG | Blast/T cells | TCRB | TCRG |
| 14 | 0.918981481 | 0.88730182 | 84.245218 | 0.14479026 | 0.0154863 | 7.92210056 |
| 15 | 0.972477064 | 0.966418465 | 80.8011935 | 0 | 0 | 0.04827268 |
| 30 | 0.67403315 | 0.489840689 | 17.1898345 | | 0.00048091 | |
| 32 | 0.87001287 | 0.863124126 | 64.0647828 | | 0.00013614 | 0.08466056 |
| 33 | 0.36514523 | 0.389789133 | 6.58138203 | | 0 | |
| 36 | 0.63565891 | 0.776347236 | 55.128848 | | 0 | |
| 39 | 1 | 0.98803323 | 78.3268267 | | 0.00201475 | 7.67E−04 |
| 40 | 0.5815508 | 0.515729332 | 35.0639536 | 0.0990566 | 0.09248403 | |
| 41 | 0.90253807 | 0.928676259 | 59.2559701 | 0.00152838 | 0.00292659 | 0.1406089 |
| 42 | 0.91920252 | 0.08504223 | ND | 0.0019544 | 0.01346556 | |
| 44 | 0.97672065 | 0.994348041 | 96.9885863 | 0 | 0 | |
| 45 | 0.99296482 | 0.077544426 | 10.8482546 | 0.2345679 | 0 | |
| 47 | 0.83670295 | 0.58431047 | 27.5213337 | 0.02276786 | 0.03573035 | |
| 48 | 0.98097252 | 0.988028346 | 12.2479173 | 0 | 0 | |
| 49 | 0.94558522 | 0.933572687 | 72.0934554 | 0 | 0.00070619 | |
| 50 | 0.98088531 | 0.994709258 | | | 3.4997E−05 | |
| 51 | 0.95571576 | 0.948955408 | 61.973728 | 0.00797546 | 0.0047952 | |
| 52 | 0.87757202 | 0.97285037 | 13.5297526 | | 5.0976E−06 | |
| 53 | 0.96843177 | 0.986362564 | 8.64156011 | | 4.6305E−06 | |
| 54 | 0.97082495 | 0.107187084 | 71.5454996 | 0.069869 | 0.08321639 | |
| 55 | 0.98183653 | 0.120066146 | 4.8143757 | 0.43255814 | 0 | |
| 56 | 0.86721144 | 0.017651493 | 33.7748913 | 0.1245283 | 0.00564494 | |
| 57 | 0.95523906 | 0.020885717 | 71.2907132 | 0.6459144 | 0.00838002 | 0.16145989 |
| 58 | 0.68115942 | 0.586476251 | 14.9081924 | 0.05369128 | 0.03701839 | 3.40390897 |
| 59 | 0.92966361 | 0.936086965 | ND | 0 | 0 | |
| 60 | 0.90118153 | 0.037093219 | ND | 0.05792683 | 0 | |
| 61 | 0.93349456 | 0.625504008 | 56.3484994 | 0.00653266 | 0.02535341 | 0.03928545 |
| 63 | 0.971875 | 0.994335907 | 76.362186 | | 0 | |
| 65 | 0.9563795 | 0.840250471 | 92.723888 | 0.00114679 | 7.6499E−05 | 0.03433687 |
| 66 | 0.71351351 | 0.869202008 | 11.7433739 | | 0.00276186 | |
| 68 | 0.9874477 | 0.024076739 | ND | 0.00849858 | 0.0424174 | |

ND; not determined.

In general, each of these clonal sequences represented at least 15% of the total T-cell repertoire of the subject at diagnosis, a proportion that was greater than three standard deviations from the mean of reactive T-cell clones in normal individuals (Table 7 and FIG. 5). At day 0, a clonal population of TCRB was readily identified in 31 of 43 cases (FIG. 1A; FIG. 4). By contrast, 12 patient samples did not have an identifiable clonal TCRB sequence at diagnosis, defined as that comprising less than 15% of total sequences. Of the 12 patients in whom no clonal TCRB sequence was identified, four had a clonal TCRG rearrangement on concurrent analysis (Table 6).

TABLE 7

Frequency of Occurrence of Highest-Frequency
Clones in Normal Control Subjects

| Healthy Control | Most Frequent Clone |
|---|---|
| AS | 2.1975 |
| BC | 0.6709 |
| CD | 1.6264 |
| HR | 7.7823 |
| JA | 1.6008 |
| RL | 8.7205 |
| Average | 3.7664 |
| SD | 3.520896205 |
| Average + 3SD | 14.32908862 |

With knowledge of the specific CDR sequences of the patient's clonal population from day 0, the ability of HTS to identify the clonal sequence at day 29 was next examined, and these findings were compared to results of mpFC that were performed as part of the current protocol at the University of Washington in the Children's Oncology Group AALL0434 trial. In light of the patient's original clonal TCRB and TCRG sequences at diagnosis, high-throughput sequencing of these patient samples at day 29 revealed three sub-groups of patients in this cohort: 1) those for whom MRD was not detected by HTS or mpFC, 9 cases; 2) those for whom MRD was detected by both HTS and mpFC, 12 cases; and 3) a subset for whom MRD was detectable by HTS, but not by mpFC, 10 cases (FIG. 1B). In general, there was approximately a 100-fold increase in the sensitivity with which MRD could be detected by the herein disclosed HTS methodology, as compared to mpFC.

Of the cases for which no clonal TCRB population was identified at day 0, further evaluation showed that these patients generally had high levels of MRD at day 29. Review of the immunophenoptype of the patients' T lymphoblasts at day 0 showed that of the 12 cases, 5 had an immunophenotype compatible with an early thymic-precursor (ETP) sub-type, whereas 7 had a near-ETP immunophenotype, in which some but not all of the immunophenotypic criteria for ETP were met (Table 5) (15). The association of higher minimal residual disease in patients with lymphoblasts of ETP immunophenotype ($x=0.1848$) versus non-ETP T-ALL (mean=0.01613, Fisher's statistic) was compatible with previous reports identifying this sub-group as having a more aggressive clinical course with increased propensity for disease relapse. Based on these data, the near-ETP group appeared in its characteristics to occupy a position along a continuum between non-ETP and ETP-subtypes of T-ALL.

To evaluate the specificity of HTS for assessment of MRD, evaluation was conducted of the frequency of occurrence of a specific TCR clonal sequence from one patient being present in the other 41 patient samples at day 29. This analysis demonstrated 15 "false positives" of 1,722 TCRG gene comparisons (=$N^2-N=42^2 42=1,722$) for TCRG and 3 "false positives" of 1,722 comparisons for TCRB. Of note, the level of these false positive clones was much lower, by one order of magnitude, as compared to true MRD positives.

Discussion

Recent data from the AIEOP-BFM-ALL 2000 study, a multi-institutional, prospective clinical trial involving 464 patients with T-ALL confirmed the importance of minimal residual disease (MRD) to categorize standard, intermediate and high-risk disease on the basis of MRD at two time points post-therapy (2). Patients with detectable MRD of greater than $10^{-3}$ cells at the second time-point, TP2 (day 78) fared poorly, such that persistent MRD at TP2 was concluded to be an important predictive factor for T-ALL relapse. Detection of this level of disease was readily within the sensitivity of the present HTS technology as shown herein, whereby determination of clonality was achieved without the laborious requirements for individualized PCR or allele-specific oligonucleotide design of prior approaches to MRD. HTS was readily scalable, less organizationally complex than prior methodologies, and readily adaptable to any clinical laboratory environment.

In the present Example, TCRG sequencing was suitable for detecting clonality in a slightly greater proportion of cases as compared to TCRB, but TCRB was also regarded as highly useful for MRD assessment due to the relatively greater germ-line diversity of TCRB relative to TCRG. In analyses of day 29 samples, clonal TCR sequences were found to be highly specific with coincidental identification of cross-patient sequences—that is, identification of the clonal sequence of one patient in the other 41 patients sequenced in this study, being generally rare. Previously described molecular protocols for MRD detection using custom-prepared, patient-specific primers (7, 8) disadvantageously did not routinely test for cross-patient specificity, as evaluation of sensitivity (e.g., % of subjects correctly identified as MRD+ by given criteria) and not specificity (e.g., % of subjects correctly identified as MRD− by given criteria) was the only requirement for the prior assays. As such, the present HTS methods also permitted identification of rare, coincidental overlap of TCR gene sequences from one patient to another. Notably, the level of these shared sequences detectable in such false-positive, cross-patient comparisons was much lower than seen in true patient MRD cases. Importantly, for T-ALL MRD, TCR gene rearrangements appeared to be stable, with limited evidence (less than 5%) for clonal evolution.

The presently described HTS methodology contributed to disease-prognostication at diagnosis for T-ALL for a subset of cases, by identifying samples in which there was no TCRB gene rearrangement at diagnosis, despite evidence for a high proportion of T lymphoblasts by mpFC. These cases tended to have either an early thymic precursor-like immunophenotype, or similar immunophenotypic characteristics that were described herein as being near-ETP like (15). An ETP subtype of T-ALL has been proposed to be derived from an immunogenetically early subset of T-cells prior to TCR gene rearrangement, although a recent study suggests such a subset may also have represented reversion from the double-positive immature T-cell state to a more immature immunophenotype (16). Comparison with flow cytometry results of MRD at day 29 showed that the 12 cases, for which no clonal TCRB sequence was identified at pre-treatment, had increased MRD at day 29, consistent with a more aggressive clinical course of these ETP-like tumors.

The utility of HTS for sequencing of lymphoid adaptive immune receptor encoding genes in T-ALL is extendable to routine clinical monitoring by HTS of lymphoid adaptive immune receptor encoding genes in acute B-cell lymphoblastic leukemia/lymphomas (B-ALL). MRD determination in B-ALL, by molecular and mpFC techniques, has been shown to be important for patient prognosis (3). B-ALL commonly shows cross-lineage (B to T) rearrangements of TCRB and/or TCRG, so the approach described herein is directly applicable to a subset of B-ALL cases (1). Similarly, HTS of immunoglobulin heavy chain gene rearrangements can also readily be performed based on the teachings provided herein.

REFERENCES

1. Flohr et al., *Leukemia* 22, 771-782 (2008).
2. Schrappe et al., *Blood* 118, 2077-2084).
3. van Dongen et al., *Lancet* 352, 1731-1738 (1998).
4. D. Campana, *Hematology Am Soc Hematol Educ Program* 2010, 7-12).
5. Campana, *Curr Hematol Malig Rep* 5, 169-176 (2010).
6. Roshal et al., *Cytometry B Clin Cytom* 78, 139-146).
7. van der Velden et al., *Leukemia* 21, 706-713 (2007).
8. van der Velden et al., *Leukemia* 21, 604-611 (2007).
9. Robins et al., *Blood* 114, 4099-4107 (2009).
10. Robins et al., *Sci Transl Med* 2, 47ra64 (2010).
11. Sherwood et al., *Sci Transl Med* 3, 90ra61 (2011).
12. Kalos et al., *Sci Transl Med* 3, 95ra73 (2011).
13. Boyd et al., *Sci Transl Med* 1, 12ra23 (2009).
14. Robins, Desmarais, Mat this, Livingston, Andriesen, Reijonen, Carlson, Nepom, Yee, Cerosaletti, Ultra-sensitive detection of rare T cell clones. *J Immunol Methods* doi:10.1016/j.jim.2011.09.001 (Sep. 10, 2011 Epub ahead of print PMID 21945395).
15. Coustan-Smith et al., *Lancet Oncol* 10, 147-156 (2009).
16. Berquam-Vrieze et al., *Blood* 118, 4646-4656).
17. Wood et al., *Arch Pathol Lab Med* 130, 680-690 (2006).
18. Yousfi Monod et al., *Bioinformatics* 20 Suppl 1, i379-385 (2004).

Example 2

Use of the Template Composition to Determine Amplification Factor

This example describes quantification of rearranged DNA molecules encoding a plurality of IG molecules, using the presently described template oligonucleotide composition as a "spiked-in" synthetic template in a multiplexed PCR amplification of a DNA sample containing B cell and fibroblast DNA.

Biological Template DNA: Eight biological samples were used as sources of template DNA, with each biological sample containing the same amount of total genomic DNA (gDNA), 300 ng, but in a different proportion of (i) DNA extracted from B cells to (ii) DNA extracted from human fibroblast cells, a cell type in which IG and TCR encoding genes do not rearrange. The samples contained either 0, 0.07, 0.3, 1, 4, 18, 75 or 300 ng B cell gDNA, with fibroblast gDNA supplying the balance of each 300 ng gDNA preparation. Four replicates of each sample were made.

Synthetic Template DNA: To each PCR reaction (below) were added 5000 molecules (4-5 molecules of each sequence) from an oligonucleotide template composition comprising a pool of 1116 synthetic IGH template oligonucleotide molecules (SEQ ID NOS:4085-5200). (An IGH template composition comprising a set of 1116 template oligonucleotides is also disclosed in the Sequence Listing as SEQ ID NOS:1805-2920.

PCR Reaction: The PCR reaction used QIAGEN Multiplex Plus™ PCR master mix (QIAGEN part number 206152, Qiagen, Valencia, Calif.), 10% Q-solution (QIAGEN), and 300 ng of biological template DNA (described above). The pooled amplification primers were added so the final reaction had an aggregate forward primer concentration of 2 µM and an aggregate reverse primer concentration of 2 µM. The forward primers (SEQ ID NOS:5201-5286) included 86 primers that had at the 3' end an approximately 20 bp segment that annealed to the IGH V segment encoding sequence and at the 5' end an approximately 20 bp universal primer pGEXf. The reverse primers (SEQ ID NOS:5287-5293) included an aggregate of J segment specific primers that at the 3' end had an approximately 20 bp segment that annealed to the IGH J segment encoding sequence and at the 5' end of the J primers was a universal primer pGEXr. The following thermal cycling conditions were used in a C100 thermal cycler (Bio-Rad Laboratories, Hercules, Calif., USA): one cycle at 95° C. for 10 minutes, 30 cycles at 94° C. for 30 seconds, 63° C. for 30 seconds, and 72° C. for one minute, followed by one cycle at 72° C. for 10 minutes. Each reaction was run in quadruplicates.

For sequencing, Illumina adapters (Illumina Inc., San Diego, Calif.), which also included a 8 bp tag and a 6 bp random set of nucleotides, were incorporated onto the ends of the PCR reaction products in a 7 cycle PCR reaction. The PCR reagents and conditions were as described above, except for the thermocycle conditions, which were: 95° C. for 5 minutes, followed by 7 cycles of 95° for 30 sec, 68° for 90 sec, and 72° for 30 sec. Following thermal cycling, the reactions were held for 10 minutes at 72° and the primers were the Illumina adaptor tailing primers (SEQ ID NOS: 5387-5578). Samples were sequenced on an Illumina MiSEQ™ sequencer using the Illumina_PE_RD2 primer.

Results. Sequence data were obtained for each sample and amplification products of synthetic templates were identified by the presence of the barcode oligonucleotide sequence. For each sample, the number of template products was divided by the number of unique synthetic template oligonucleotide sequences (1116) to arrive at a sample amplification factor. The total number of amplification products of the biological templates for each sample was then divided by the amplification factor to calculate the number of rearranged biological template molecules (e.g., VDJ recombinations) in the starting amplification reaction as an estimate of the number of unique B cell genome templates. The average values with standard deviations were plotted against the known number of rearranged biological template molecules based on B cell input (FIG. 8). In FIG. 8, the dots represent the average amplification factor and the bars represent the standard deviation across the four replicates. The use of amplification factors calculated as described herein to estimate the number of VJ-rearranged IG encoding molecules (as a proxy value for the number of B cells) yielded determinations that were consistent with known B cell numbers at least down to an input of 100 B cells. The estimated amplification factor values and the observed amplification factor were highly correlated (FIG. 8, $R^2=0.9988$).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09824179B2). An electronic copy of the "Sequence Listing" will also be available from the USPTO upon request and payment of the fee set forth in 37 CFR 1.19(b)(3).

What is claimed is:

1. A method of quantifying the number of input molecules for one or more rearranged DNA sequences identified as indicative of a clonal lymphoid hematological malignancy, comprising:
   (A) amplifying by a single multiplex polymerase chain reaction (PCR):
   (i) a plurality of gene segments from a sample comprising T cells and/or B cells to produce a plurality of sample amplicons, wherein each gene segment comprises rearranged TCRβ CDR3-encoding region or a rearranged Ig CDR3-encoding region comprising a variable (V)-region and a joining (J)-region, and wherein said single multiplex PCR amplifies substantially all rearranged TCRβ CDR3-encoding regions or substantially all rearranged Ig CDR3-encoding regions; and within the single multiplex PCR
   (ii) a known number of a plurality of template oligonucleotides each having a unique oligonucleotide sequence to produce a plurality of template amplicons wherein each of said template oligonucleotides is defined by the formula:

5'-U1-B1-V-B2-R-B3-J-B4-U2-3' wherein V comprises a polynucleotide comprising at least 20 and not more than 1000 contiguous nucleotides of a V-region encoding gene segment or a complement thereof, and wherein V comprises a unique oligonucleotide sequence;

wherein J is a polynucleotide comprising at least 15 and not more than 600 contiguous nucleotides of a J-region encoding gene sequence, or a complement thereof, and wherein J comprises a unique oligonucleotide sequence;

wherein U1 comprises an oligonucleotide having a sequence that is selected from (i) a first universal adaptor oligonucleotide sequence, and (ii) a first sequencing platform-specific oligonucleotide sequence that is linked to and positioned 5' to a first universal adaptor oligonucleotide sequence;

wherein U2 comprises an oligonucleotide having a sequence that is selected from (i) a second universal adaptor oligonucleotide sequence and (ii) a second sequencing platform-specific oligonucleotide sequence that is linked to and positioned 5' to a second universal adaptor oligonucleotide sequence;

wherein B1, B2, B3 and B4 are each independently nothing or each comprises an oligonucleotide barcode sequence, wherein each of the plurality of oligonucleotide barcode sequences comprises a unique oligonucleotide sequence that uniquely identifies, as a paired combination, a unique V oligonucleotide sequence and a unique J oligonucleotide sequence, and wherein R is either nothing or comprises a restriction enzyme recognition site that comprises an oligonucleotide sequence not found in the template oligonucleotide;

(B) sequencing by high throughput sequencing said plurality of sample amplicons and template amplicons to generate sequence reads of said substantially all rearranged TCRβ or Ig CDR3-encoding regions and said unique template oligonucleotides;

(C) counting the number of sequence reads of each unique template oligonucleotide and the number of sequence reads of each rearranged TCRβ or Ig CDR3-encoding region from the sequence reads obtained in step (B);

(D) identifying from the sequence reads of the rearranged TCRβ or Ig CDR3-encoding regions at least one rearranged TCRβ or Ig CDR3-encoding region indicative of a clonal lymphoid hematological malignancy in the sample based on the frequency of the sequence reads of the rearranged TCRβ or Ig CDR3-encoding region as compared to the remaining sequence reads;

(E) calculating an amplification factor by dividing the number of template oligonucleotides counted in (C) by the known number of each of the plurality of template oligonucleotides having a unique oligonucleotide sequence in the template composition amplified in (A)(ii); and (F) dividing the number of sequence reads counted for the at least one rearranged TCRβ or Ig CDR3-encoding regions indicative of a clonal lymphoid hematological malignancy identified in (D) and counted in (C) by the amplification factor calculated in (E) thereby quantifying the number of input molecules of one or more rearranged DNA sequences identified as indicative of a clonal lymphoid hematological malignancy.

2. The method of claim 1, wherein said clonal lymphoid hematological malignancy is selected from: acute T-cell lymphoblastic leukemia (T-ALL), acute B-cell lymphoblastic leukemia (B-ALL), multiple myeloma, plasmacytoma, macroglobulinemia, chronic lymphocytic leukemia (CLL), acute lymphoblastic leukemia (ALL), Hodgkins lymphoma, non-Hodgkins lymphoma, cutaneous T-cell lymphoma, mantle cell lymphoma, peripheral T-cell lymphoma, hairy cell leukemia, T prolymphocytic lymphoma, angioimmunoblastic T-cell lymphoma, T lymphoblastic leukemia/lymphoma, peripheral T-cell lymphoma, adult T cell leukemia/lymphoma, mycosis fungoides, Sezary syndrome, T lymphoblastic leukemia, myeloproliferative neoplasm, and myelodysplastic syndrome.

3. The method of claim 1, wherein said rearranged Ig CDR3-encoding regions are selected from a rearranged IgH CDR3-encoding, region (V-D-J), a partially rearranged IgH CDR3-encoding region (D-J), a rearranged IgK CDR3-encoding region, a deleted IgK rearrangement using the iRSS in lieu of a V segment, a deleted IgK rearrangement using the Kdel in lieu of a J segment, or a rearranged Igλ CDR3-encoding region.

4. The method of claim 3, wherein said rearranged Igκ CDR3-encoding regions comprise a non-coding iRSS sequence and a joining (1) gene segment rearrangement, or a non-coding variable (V) gene segment and the non-coding Kdel element.

5. The method of claim 1 wherein each of said template oligonucleotides comprises at least one unique barcode sequence.

6. The method of claim 5 wherein each of said template oligonucleotides comprises a V region encoding gene sequence or a complement thereof and J region encoding gene sequence or a complement thereof.

7. The method of claim 6 wherein said unique oligonucleotide barcode sequence comprises a random polynucleotide sequence of at least 6 nucleotides.

8. The method of claim 6 wherein each of said plurality of said template oligonucleotides is present in a substantially equimolar amount.

9. The method of claim 6 wherein each of said plurality of said template oligonucleotides has substantially identical lengths.

10. The method of claim 6 wherein each of said V region encoding gene sequences or a complement thereof is unique to a single V region encoding gene and wherein each of said J region encoding gene sequences or a complement thereof is unique to a single J region encoding gene.

11. The method of claim 1, wherein said at least one unique rearranged sequence identified as indicative of a clonal lymphoid hematological malignancy in said subject is identified from a sample obtained from said subject at a time prior to a treatment.

12. The method of claim 1 wherein said sample comprises at least 100,000 T cells or B cells.

13. The method of claim 1 wherein each of said plurality of template oligonucleotides comprises at least one oligonucleotide barcode that is 3-25 contiguous nucleotides in length.

14. The method of claim 1 wherein at least one rearranged TCRβ or Ig CDR3-encoding region is identified as being indicative of a hematological malignancy when it has a relative frequency of at least 15% of the total TCRβ or Ig CDR3-encoding regions counted in step (C).

15. The method of claim 1 wherein at least one rearranged TCRβ or Ig CDR3-encoding region is identified as being indicative of a hematological malignancy when it has a relative frequency of at least one in $10^5$ of the total TCRβ of Ig CDR3-encoding regions counted in step (C).

16. The method of claim 1 wherein said high throughput sequencing is sequencing by synthesis.

17. The method of claim 1 wherein the single PCR uses a plurality of V-segment oligonucleotide primers, each V-segment oligonucleotide primer capable of hybridizing to one or more TCRβ V-regions or one or more Ig V-regions of said plurality of gene segments; and a plurality of J segment oligonucleotide primers, each J-segment primer capable of hybridizing to one or more TCRβ J-regions or one or more Ig J-regions of said plurality of gene segments.

18. The method of claim 17, wherein said plurality of V segment oligonucleotide primers are complementary to at least one TCR Vβ-encoding gene segment.

19. The method of claim 17, wherein said plurality of J-segment oligonucleotide primers are complementary to at least one functional TCR Jβ-encoding gene segment.

20. The method of claim 17 wherein said plurality of said template oligonucleotides is greater than or equal to the lesser of said plurality of said V-segment oligonucleotide primers and said plurality of J-segment oligonucleotide primers.

21. The method of claim 17 wherein said template composition comprises at least one template oligonucleotide amplified by each different pair of said V-segment oligonucleotide primers and said J-segment oligonucleotide primers.

* * * * *